US012637410B2

(12) United States Patent
Dwoskin et al.

(10) Patent No.: US 12,637,410 B2
(45) **Date of Patent: *May 26, 2026**

(54) VESICULAR MONOAMINE TRANSPORTER-2 LIGANDS AND THEIR USE IN THE TREATMENT OF PSYCHOSTIMULANT ABUSE

(71) Applicant: University of Kentucky Research Foundation, Lexington, KY (US)

(72) Inventors: Linda P. Dwoskin, Lexington, KY (US); David Watt, Lexington, KY (US); Jon Thorson, Lexington, KY (US); Mark Leggas, Lexington, KY (US); Rodney Kip Guy, Lexington, KY (US); Jared Hammill, Lexington, KY (US); Stefan Kwiatkowski, Lexington, KY (US); Derong Ding, Lexington, KY (US); Guangrong Zheng, Gainesville, FL (US); Peter Anthony Crooks, Little Rock, AR (US); Na-Ra Lee, Suwon-si (KR)

(73) Assignee: University of Kentucky Research Foundation, Lexington, KY (US)

( * ) Notice: Subject to any disclaimer, the term of this patent is extended or adjusted under 35 U.S.C. 154(b) by 924 days.

This patent is subject to a terminal disclaimer.

(21) Appl. No.: 17/842,425

(22) Filed: Jun. 16, 2022

(65) Prior Publication Data

US 2022/0315523 A1 Oct. 6, 2022

Related U.S. Application Data

(63) Continuation-in-part of application No. 16/848,462, filed on Apr. 14, 2020, now Pat. No. 11,999,676, which is a continuation-in-part of application No. 15/493,836, filed on Apr. 21, 2017, now Pat. No. 10,668,030.

(60) Provisional application No. 62/325,875, filed on Apr. 21, 2016.

(51) Int. Cl.

| | |
|---|---|
| *C07C 211/53* | (2006.01) |
| *C07C 233/43* | (2006.01) |
| *C07D 209/14* | (2006.01) |
| *C07D 213/38* | (2006.01) |
| *C07D 215/12* | (2006.01) |

(52) U.S. Cl.

CPC .......... *C07C 211/53* (2013.01); *C07C 233/43* (2013.01); *C07D 209/14* (2013.01); *C07D 213/38* (2013.01); *C07D 215/12* (2013.01)

(58) Field of Classification Search

None

See application file for complete search history.

(56) References Cited

U.S. PATENT DOCUMENTS

| | | | | |
|---|---|---|---|---|
| 2,276,618 | A | 3/1942 | Kulz | |
| 4,360,511 | A | 11/1982 | Baldwin et al. | |
| 6,057,371 | A | 5/2000 | Glennon | |
| 10,668,030 | B2 * | 6/2020 | Dwoskin | A61K 31/137 |
| 11,999,676 | B2 * | 6/2024 | Dwoskin | C07D 213/38 |
| 2006/0035889 | A1 | 2/2006 | Tedford et al. | |
| 2017/0304227 | A1 | 10/2017 | Dwoskin et al. | |
| 2020/0290948 | A1 | 9/2020 | Dwoskin et al. | |
| 2022/0315523 | A1 | 10/2022 | Dwoskin et al. | |

FOREIGN PATENT DOCUMENTS

| | | | |
|---|---|---|---|
| GB | 2 088 873 | A | 6/1982 |
| JP | 52-113992 | A | 9/1977 |
| SU | 302334 | A1 | 12/1971 |
| WO | WO 91/09594 | A1 | 7/1991 |
| WO | WO 93/00313 | A2 | 1/1993 |

OTHER PUBLICATIONS

U.S. Final Office Action issued in U.S. Appl. No. 16/846,989 dated Apr. 9, 2025 (10 pages).

CAS STN Database Registry No. 14817-74-4 [Entered STN: Nov. 16, 1984]. (Year: 1984)

CAS STN Database Registry No. 1552763-03-7 [Entered STN: Feb. 23, 2014]. (Year: 2014)

Tran, J. et al., "Studies on the Structure-Activity Relationship of the Basic Amine of Phenylpiperazines as Melanocortin-4 Receptor Antagonists", Medical Chemistry, 2008, pp. 67-74, vol. 4 (8 pages).

Nickolls, S. et al., "Molecular Determinants of Melanocortin 4 Receptor Ligand Binding and MC4/MC3 Receptor Selectivity", The Journal of Pharmacology and Experimental Therapeutics, 2003, pp. 1217-1227, vol. 304, No. 3 (11 pages).

U.S. Office Action issued in U.S. Appl. No. 16/846,989 dated Feb. 16, 2023 (12 pages).

United States Non-Final Office Action issued in U.S. Appl. No. 16/848,462 dated Sep. 20, 2023 (9 pages).

Glennon et al; "Binding of Substituted and Conformationally Restricted Derivatives of N-(3-Phenyl-n-propyl)-1-phenyl-2-aminopropane at δ-Receptors", J. Med. Chem., 1991, pp. 1855-1859, vol. 34, No. 6, (5 pages).

"ChemBridge Corp catalog with an STN Entry Date", Nov. 3, 2008, (1 page).

United States Non-Final Office Action issued in U.S. Appl. No. 16/846,989 dated Oct. 3, 2023 (9 pages).

U.S. Non-Final Office Action issued in U.S. Appl. No. 16/846,989 dated Nov. 15, 2024 (12 pages).

(Continued)

*Primary Examiner* — Jeffrey S Lundgren
*Assistant Examiner* — Michael J Schmitt
(74) *Attorney, Agent, or Firm* — Crowell & Moring LLP

(57) ABSTRACT

The present invention relates to methods of treatment of a disease or pathology of the central nervous system, an eating disorder, or substance use disorder, drug dependence/abuse/addiction and withdrawal therefrom comprising administering at least one N-phenylalkyl amphetamine derivative and pharmaceutical compositions comprising at least one N-phenylalkyl amphetamine derivative to an individual in need thereof.

20 Claims, No Drawings

(56) References Cited

OTHER PUBLICATIONS

Gangadhar et al; "Phenothiazine Functional Materials for Organic Optoelectronic Applications", Phys. Chem. Chem. Phys., 2021, pp. 14969-14996, vol. 23 (28 pages).
International Search Report (PCT/ISA/220 & PCT/ISA/210) issued in PCT Apptication No. PCT/US2023/068564 dated Jan. 22, 2024 (5 pages).
Written Opinion (PCT/ISA/237) issued in PCT Appiication No. PCT/US2023/068564 dated Jan. 22, 2024 (11 pages).
Khalil, A. T., "Benzyiamides from *Salvadora persica*", Archives of Pharmacal Research, 2006, pp. 952-956, vol. 29, No. 11 (5 pages).
Lee et al., "Enantiomers of (±)GZ-888 potently and selectively inhibit vesicular monoamine transporter-2 function and methamphetamine-stimulated locomotor activity", 2016, (one (1) page).
Teng et al., "Lobeline Diplaces [$^3$H] Dihydrotetrabenazine Binding and Releases [$^3$H] Dopamine from Rat Striatal Synaptic Vesicles: Comparison with d-Amphetamine", Journal of Neurochemistry, International Society for Neurochemistry, 1998, pp. 258-265, vol. 71, No. 1, Lippincott-Raven Publishers, Philadelphia (eight (8) pages).
Teng et al., "Lobeline and Nicotine Evoke [$^3$H]Overflow from Rat Striatal Slices Preloaded with [$^3$H]Dopamine: Differential Inhibition of Synaptosomal and Vesicular [$^3$H]Dopamine Uptake[1]", The Journal of Pharmacology and Experimental Therapeutics, 1997, pp. 1432-1444, vol. 280, No. 3, The American Society for Pharmacology and Experimental Therapeutics (13 pages).
Mark et al., "An Appetitively Conditioned Taste Elicits a Preferential Increase in Mesolimbic Dopamine Release", Pharmacology Biochemistry and Behavior, 1994, pp. 651-660, vol. 48, No. 3, Elsevier Science Ltd (10 pages).
Martel et al., "Mesolimbic Dopaminergic System Activity as a Function of Food Reward: A Microdialysis Study", Pharmacology Biochemistry and Behavior, 1996, pp. 221-226, vol. 53, No. 1, Elsevier Science Inc. (six (6) pages).
Johnson et al., "Dopamine D2 receptors in addiction-like reward dysfunction and compulsive eating in obese rats", nature neuroscience, May 2010, pp. 635-641 (10 pages total), vol. 13, No. 5, Nature America, Inc. (10 pages).
Kelley, "Ventral striatal control of appetitive motivation: role in ingestive behavior and reward-related learning", Neuroscience and Biobehavioral Reviews, 2004, pp. 765-776, vol. 27, Elsevier (12 pages).
Small et al., "Feeding-induced dopamine release in dorsal striatum correlates with meal pleasantness ratings in healthy human volunteers", NeuroImage, 2003, pp. 1709-1715, vol. 19, Academic Press (seven (7) pages).
Volkow et al., "How can drug addiction help us understand obesity?" Nature Neuroscience, May 2005, pp. 555-560, vol. 8, No. 5, Nature Publishing Group (six 6) pages).
Wang et al., "The role of dopamine in motivation for food in humans: implications for obesity", Expert Opin. Ther. Targets, 2002, pp. 601-609, vol. 6, No. 5, Ashley Publications Ltd (nine (9) pages).
Yin et al., "Lesions of dorsolateral striatum preserve outcome expectancy but disrupt habit formation in instrumental learning", European Journal of Neuroscience, 2004, pp. 181-189, vol. 19, Federation of European Neuroscience Societies (nine (9) pages).
Patani et al. "Bioisosterism: A Rational Approach in Drug Design". Chem. Rev. 1996; 96:3147-3176. (Year: 1996) (30 pages).
German et al. "Regulation of the Dopamine and Vesicular Monoamine Transporters: Pharmacological Targets and Implications for Disease", Pharmacological Reviews, Oct. 2015; 67: 1005-1024. (Year: 2015) (20 pages).
Nickell et al. "The Vesicular Monoamine Transporter-2: An Important Pharmacological Target for the Discovery of Novel Therapeutics to Treat Methamphetamine Abuse", Adv Pharmacol, 2014; 69:71-106, Abstract Only. (Year: 2014) (one (1) page).
Horton et al. "GZ-293A, a Lobelane Analog, Interacts with the Vesicular Monoamine Transporter-2 to Inhibit the Effect of Methamphetamine", Journal of Neurochemistry, 2013; 127:177-186. (Year: 2013) (10 pages).
Wilmouth et al. "Oral Administration of GZ-793A, a VMAT2 Inhibitor, Decreases Methamphetamine Self-Administration in Rats", Pharmacology, Biochemistry and Behavior, 2013; 112; 29-33. (Year: 2013) (five (5) pages).
Nickell et al. "Preclinical Evaluation of JPC-077 as a Novel Treatment for Methamphetamine Abuse", Drug and Alcohol Dependence (Abstracts), 2014; 140:e160. (Year: 2014) (two (2) page).
Cao, Zheng. "Lobelane Analogs with Various Methylene Linker Lengths and Acyclic Lobelane Analogs as Potential V Pharmacotherapies to Treat Methamphetamine Abuse". (2014). Theses and Dissertations—Pharmacy. 32. Obtained from the Internet: <URL: https://uknowledge.uky.edu/pharmacy_etds/32>. (Year: 2014) (291 pages).
U.S. Office Action issued in U.S. Appl. No. 16/846,989 dated Oct. 28, 2021 (13 pages).
U.S. Final Office Action issued in U.S. Appl. No. 16/846,989 dated Mar. 13, 2024 (12 pages).
CAS STN Database Registry No. 415970-89-7 [Entered STN: May 15, 2002]. (Year:2002) (2 pages).
United States Final Office Action issued in U.S. Appl. No. 16/846,989 dated Apr. 18, 2022 (12 pages).
United States Non-Final Office Action issued in U.S. Appl. No. 16/846,989 dated Aug. 4, 2022 (15 pages).
United States Non-Final Office Action issued in U.S. Appl. No. 16/848,462 dated Apr. 28, 2022 (17 pages).
United States Final Office Action issued in U.S. Appl. No. 16/848,462 dated Nov. 3, 2022 (10 pages).

* cited by examiner

VESICULAR MONOAMINE TRANSPORTER-2 LIGANDS AND THEIR USE IN THE TREATMENT OF PSYCHOSTIMULANT ABUSE

CROSS-REFERENCE TO RELATED APPLICATIONS

The present application is a continuation-in-part of U.S. application Ser. No. 16/848,462, filed Apr. 14, 2020, which is a continuation-in-part of U.S. application Ser. No. 15/493,836, filed Apr. 21, 2017, now U.S. Pat. No. 10,668,030, which claims the benefit of U.S. Provisional Application No. 62/325,875, filed Apr. 21, 2016, all of which are herein incorporated by reference in their entireties.

FIELD OF THE INVENTION

The present invention relates to compounds of formula (I) and formula (II). The present invention further relates to pharmaceutical compositions comprising compounds of formula (I) or formula (II) and to methods of treatment of a disease or pathology of the central nervous system, an eating disorder, or substance use disorder, drug dependence/abuse/addiction and withdrawal therefrom comprising administering N-phenylalkyl amphetamine derivatives and pharmaceutical compositions containing these compounds to an individual in need thereof.

BACKGROUND OF THE INVENTION

The action of many therapeutic neuropharmacological agents involve the modulation of dopamine (DA), norepinephrine (NE) and serotonin (5-HT) release, uptake and storage within their respective terminals in the central nervous system (CNS). Most neurotransmitters are stored in synaptic vesicles, which are prominent features of nerve terminals. Sequestration into vesicles appears to be responsible for maintaining a ready supply of neurotransmitter molecules available for neuronal exocytotic release into the synaptic cleft. Vesicles also serve the role of protecting the neurotransmitter molecules from metabolic breakdown. One transport site on the vesicle membrane is the vesicular monoamine transporter-2 (VMAT2), whose role is to transport transmitters from the cytosol into the synaptic vesicle. Once the neurotransmitter is released from the terminal into the synaptic space, it interacts with postsynaptic receptors and subsequently is taken back up into the terminal via the plasma membrane transporter (e.g., DAT and/or the serotonin transporter [SERT]). Thus, transporter proteins modify the concentration of neurotransmitters in the cytosolic and vesicular storage pools, and thereby have the ability to alter subsequent neurotransmission.

SUMMARY OF THE INVENTION

The present invention provides a compound of formula (I):

(I)

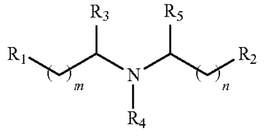

wherein m is an integer in the range from 1 to 3;

n is zero or an integer in the range from 1 to 5;

$R_1$ and $R_2$ are independently an aryl group or a heteroaryl group and which are independently unsubstituted or substituted by one or more substituents;

$R_3$ is =O, methyl; ethyl; propyl; isopropyl; hydroxymethyl; 2-hydroxyethyl; 1-hydroxyethyl; methoxymethyl; 2-methoxyethyl; 1-methoxyethyl; aminomethyl; 2-aminoethyl; 1-aminoethyl; N-methylaminomethyl; 2-N-methylaminoethyl; 1-N-methylaminoethyl; N,N-dimethylaminomethyl; 2-N,N-dimethylaminoethyl; 1-N,N-dimethylaminoethyl; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); amide ($-CONH_2$); methyl amide ($-CONHCH_3$), ethyl amide ($-CONHCH_2CH_3$); propyl amide ($-CONHCH_2CH_2CH_3$); isopropyl amide ($-CONHCH(CH_3)_2$); butylamide ($-CONHCH_2CH_2CH_2CH_3$); sec-butylamide ($-CONHCH(CH_3)(CH_2CH_3)$); tert-butylamide ($-CONHC(CH_3)_3$); dimethyl amide ($-CON(CH_3)_2$), diethyl amide ($-CON(CH_2CH_3)_2$); dipropyl amide ($-CON(CH_2CH_2CH_3)_2$); isopropyl amide ($-CON[CH(CH_3)_2]_2$); dibutylamide ($-CON(CH_2CH_2CH_2CH_3)_2$); di-sec-butylamide ($-CON[CH(CH_3)(CH_2CH_3)]_2$); di-tert-butylamide ($-CON[C(CH_3)_3]_2$); methyl, ethyl, propyl, or isopropyl substituted with one or more fluoro, chloro, bromo, or iodo; benzyl; or $-(CH_2)_a-O-(C{=}O)-CHR_6-NH_2$;

$R_4$ is a hydrogen atom; a methyl, ethyl, propyl, isopropyl, or carbonyl group; or a methyl, ethyl, propyl or isopropyl group substituted with a hydroxyaryl group; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); or benzyl ester ($-COOCH_2(C_6H_6)$); and $R_5$ is hydrogen, methyl, or =O;

$R_6$ is selected from the group consisting of methyl, ethyl, propyl, isopropyl, and $C_4$-$C_7$ straight chain or branched alkyl, wherein the methyl, ethyl, propyl, isopropyl, or $C_4$-$C_7$ straight chain or branched alkyl are unsubstituted or substituted with one or more substituents selected from the group consisting of substituted or unsubstituted aryl groups and substituted or unsubstituted heteroaryl groups;

a is an integer in the range from 1 to 5; or an enantiomer; racemate; or pharmaceutically acceptable salt thereof.

Examples of an aryl group that may be used as $R_1$ or $R_2$ are phenyl, naphthalenyl, cyclobutadienyl, cyclopentadienyl, indenyl, anthracenyl, phenanthrenyl, tirphenylenyl, fluorenyl, and pyrenyl.

Examples of a heteroaryl group that may be used as $R_1$ or $R_2$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]

isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl; and benzo[c]thiophen-1(3H)-one.

Substituents on $R_1$ and $R_2$ are independently selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); alkylsulfonyl; alkylsulfinyl; a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; ortho-, meta-, or para-substituted phenyl; ortho-, meta-, or para-substituted benzyl; ortho-, meta-, or para-substituted benzenephenyl; phenylethyl; amino; cycloalkylamino, isopropylamino; N-methylamino; N,N-dimethylamino; N-cyclopropylamino; N,N-dicyclopropylamino; N-cyclobutylamino; N,N-dicyclobutylamino; N-cyclopentylamino; N,N-dicyclopentylamino; N-cyclohexylamino; N,N-dicyclohexylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; phenyl; methylsulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl ($-S(=O)-CH_3$); ethylsulfinyl ($-S(=O)-CH_2CH_3$); propiosulfinyl ($-S(=O)-CH_2CH_2CH_3$); isopropiosulfinyl ($-S(=O)-CH(CH_3)_2$); methylsulfonyl ($-S(=O)_2-CH_3$); ethylsulfonyl ($-S(=O)_2-CH_2CH_3$); propiosulfonyl ($-S(=O)_2-CH_2CH_2CH_3$); isopropiosulfonyl ($-S(=O)_2-CH(CH_3)_2$); fluoro; chloro; bromo; iodo; trifluoromethyl; trichloromethyl; tribromomethyl; triiodomethyl; aminomethyl ($-CH_2NH_2$); vinyl; allyl; propargyl; nitro; carbamoyl; ureido ($-NH(C=O)-NH_2$); azido; isocyanate; thioisocyanate; hydroxylamino; nitrile; sulfonamide ($-S(=O)_2-NH_2$); methylsulfonamide ($-NH-S(=O)_2-CH_3$); ethylsulfonamide ($-NH_2-S(=O)_2-CH_2CH_3$); propiosulfonamide ($-NH_2-S(=O)_2-CH_2CH_2CH_3$); isopropiosulfonamide ($-NH_2-S(=O)_2-CH(CH_3)_2$); a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; and ortho-, meta-, or para-substituted benzene, wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be substituted with one or more substituents selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); amino; cycloalkylamino, isopropylamino; N-methylamino; N,N-dimethylamino; hydroxyl; methoxy; mono-, di-, or tri-fluoromethoxy; ethoxy; propoxy; isopropoxy; thiol; methylthio; ethylthio; propiothiol; isopropiothiol; fluoro; chloro; bromo; iodo; trifluoromethyl; trichloromethyl; tribromomethyl; triiodomethyl; nitro; azido; isocyanate; thioisocyanate; hydroxylamino; and nitrile; and wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be independently fused to $R_1$ or $R_2$ or linked to $R_1$ or $R_2$.

Examples of a saturated or unsaturated hydrocarbon ring that may be used as substituents on $R_1$ and $R_2$ are cyclopropyl, cyclobutyl, cyclopentyl, cyclohexyl, cycloheptyl, cyclooctyl, cyclopropenyl, cyclobutenyl, cyclobutadienyl, cyclopentenyl, cyclopentadienyl, cyclohexenyl, cyclohexadienyl, phenyl, cycloheptenyl, cycloheptadienyl, cycloheptatrienyl, cyclooctenyl, cyclooctadienyl, cyclooctatrienyl, cyclooctatetraenyl, naphthalenyl, indenyl, anthracenyl, phenanthrenyl, tirphenylenyl, fluorenyl, and pyrenyl.

Examples of a nitrogen-containing heterocyclic or heteroaryl moiety that may be used as substituents on $R_1$ and $R_2$ are pyrrolidinyl, pyrrolinyl, pyrazolidinyl, imidazolinyl, imidazolidinyl, pyrazolinyl, piperidinyl, piperazinyl, pyrrolyl, imidazolyl, pyrazolyl, pyridinyl, pyridazinyl, pyrmidinyl, pyrazinyl, indolinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, carbazolyl, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione; and 1H-benzo[d][1,2,3]triazolyl.

Examples of an oxygen-containing heterocyclic or heteroaryl moiety that may be used as substituents on $R_1$ and $R_2$ are tetrahydrofuranyl, dihydrofuranyl, tetrahydropyranyl, dihydropyranyl, furanyl, pyranyl, benzofuranyl, isobenzofuranyl, dibenzofuranyl, 2H-chromenyl, 1H-isochromenyl, 3H-isochromenyl, xanthenyl, benzofuran-2(3H)-one, and isobenzofuran-1(3H)-one.

Examples of a sulfur-containing heterocyclic or heteroaryl moiety that may be used as substituents on $R_1$ and $R_2$ are tetrahydrothiophenyl, dihydrothiophenyl, tetrahydrothiopyranyl, dihydrothiopyranyl, thiopyranyl, thiophenyl, benzo[b]thiophenyl, benzo[c]thiophenyl, benzo[b]thiophen-2(3H)-one, and benzo[c]thiophen-1(3H)-one.

Examples of a selenium-containing heterocyclic or heteroaryl moiety that may be used as substituents on $R_1$ and $R_2$ are tetrahydroselenophenyl, dihydroselenophenyl, tetrahydroselenopyranyl, dihydroselenopyranyl, selenopyranyl, selenophenyl, benzo[b]selenophenyl, benzo[c]selenophenyl, benzo[b]selenophen-2(3H)-one, and benzo[c]selenophen-1(3H)-one.

Examples of a mixed heterocyclic or heteroaryl moiety containing at least two atoms selected from the group consisting of nitrogen, oxygen, sulfur, and selenium that may be used as substituents on $R_1$ and $R_2$ are morpholinyl, thiomorpholinyl, selenomorpholinyl, 1,2-oxathiolanyl, 1,3-oxathiolanyl, 1,2-oxaselenolanyl, 1,3-oxaselenolanyl, 1,2-thiaselenolanyl, 1,3-thiaselenolanyl, oxazolidine, isoxazolidine, thiazolidine, isothiazolidine, selenazolidine, isoselenazolidine, oxazolyl, isoxazolyl, thiazolyl, isothiazolyl, selenazolyl, isoselenazolyl, benzo[d]oxazole, benzo[d]thiazole, benzo[d]selenazole, benzo[c]isoxazole, benzo[d]isoxazole, benzo[c]isothiazole, benzo[d]isothiazole, benzo[c]isoselenazole, benzo[d]isoselenazole, benzo[c][1,2,5]oxadiazole, benzo[c][1,2,5]thiadiazole, benzo[c][1,2,5]selenadiazole, oxazinyl, thiazinyl, and selenazinyl.

Examples of an aryl group that may be used as substituents on $R_6$ are phenyl, naphthalenyl, cyclobutadienyl, cyclopentadienyl, indenyl, anthracenyl, phenanthrenyl, tirphenylenyl, fluorenyl, and pyrenyl. Each of these aryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

Examples of a heteroaryl group that may be used as substituents on $R_6$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl and benzo[c]thiophen-1(3H)-one. Each of these heteroaryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

The present invention provides a pharmaceutical composition comprising a compound of formula (I) and a pharmaceutically acceptable additive:

(I)

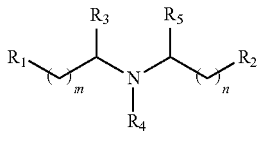

wherein m is an integer in the range from 1 to 3;

n is zero or an integer in the range from 1 to 5;

$R_1$ and $R_2$ are independently an aryl group or a heteroaryl group and which are independently unsubstituted or substituted by one or more substituents;

$R_3$ is =O, methyl; ethyl; propyl; isopropyl; hydroxymethyl; 2-hydroxyethyl; 1-hydroxyethyl; methoxymethyl; 2-methoxyethyl; 1-methoxyethyl; aminomethyl; 2-aminoethyl; 1-aminoethyl; N-methylaminomethyl; 2-N-methylaminoethyl; 1-N-methylaminoethyl; N,N-dimethylaminomethyl; 2-N,N-dimethylaminoethyl; 1-N,N-dimethylaminoethyl; carboxylate; methyl ester ($—COOCH_3$), ethyl ester ($—COOCH_2CH_3$); propyl ester ($—COOCH_2CH_2CH_3$); isopropyl ester ($—COOCH(CH_3)_2$); butylester ($—COOCH_2CH_2CH_2CH_3$); sec-butylester ($—COOCH(CH_3)(CH_2CH_3)$); tert-butylester ($—COOC(CH_3)_3$); amide ($—CONH_2$); methyl amide ($—CONHCH_3$), ethyl amide ($—CONHCH_2CH_3$); propyl amide ($—CONHCH_2CH_2CH_3$); isopropyl amide ($—CONHCH(CH_3)_2$); butylamide ($—CONHCH_2CH_2CH_2CH_3$); sec-butylamide ($—CONHCH(CH_3)(CH_2CH_3)$); tert-butylamide ($—CONHC(CH_3)_3$); dimethyl amide ($—CON(CH_3)_2$), diethyl amide ($—CON(CH_2CH_3)_2$); dipropyl amide ($—CON(CH_2CH_2CH_3)_2$); isopropyl amide ($—CON[CH(CH_3)_2]_2$); dibutylamide ($—CON(CH_2CH_2CH_2CH_3)_2$); di-sec-butylamide ($—CON[CH(CH_3)(CH_2CH_3)]_2$); di-tert-butylamide ($—CON[C(CH_3)_3]_2$); methyl, ethyl, propyl, or isopropyl substituted with one or more fluoro, chloro, bromo, or iodo; benzyl; or $—(CH_2)_a—O—(C{=}O)—CHR_6—NH_2$;

$R_4$ is a hydrogen atom; a methyl, ethyl, propyl, isopropyl, or carbonyl group; or a methyl, ethyl, propyl or isopropyl group substituted with a hydroxyaryl group; carboxylate; methyl ester ($—COOCH_3$), ethyl ester ($—COOCH_2CH_3$); propyl ester ($—COOCH_2CH_2CH_3$); isopropyl ester ($—COOCH(CH_3)_2$); butylester ($—COOCH_2CH_2CH_2CH_3$); sec-butylester ($—COOCH(CH_3)(CH_2CH_3)$); tert-butylester ($—COOC(CH_3)_3$); or benzyl ester ($—COOCH_2(C_6H_6)$); and $R_5$ is hydrogen, methyl, or =O;

$R_6$ is selected from the group consisting of methyl, ethyl, propyl, isopropyl, and $C_4$-$C_7$ straight chain or branched alkyl, wherein the methyl, ethyl, propyl, isopropyl, or $C_4$-$C_7$ straight chain or branched alkyl are unsubstituted or substituted with one or more substituents selected from the group consisting of substituted or unsubstituted aryl groups and substituted or unsubstituted heteroaryl groups;

a is an integer in the range from 1 to 5; or an enantiomer; racemate; or pharmaceutically acceptable salt thereof.

Examples of an aryl group that may be used as $R_1$ or $R_2$ are phenyl, naphthalenyl, cyclobutadienyl, cyclopentadienyl, indenyl, anthracenyl, phenanthrenyl, tirphenylenyl, fluorenyl, and pyrenyl.

Examples of a heteroaryl group that may be used as $R_1$ or $R_2$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, and benzo[c]thiophen-1(3H)-one.

Substituents on $R_1$ and $R_2$ are independently selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); alkylsulfonyl; alkylsulfinyl; a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; ortho-, meta-, or para-substituted phenyl; ortho-, meta-, or para-substituted benzyl; ortho-, meta-, or para-substituted benzenephenyl; phenylethyl; amino; cycloalkylamino, isopropylamino; N-methylamino; N,N-dimethylamino; N-cyclopropylamino; N,N-dicyclopropylamino; N-cyclobutylamino; N,N-dicyclobutylamino; N-cyclopentylamino; N,N-dicyclopentylamino; N-cyclohexylamino; N,N-dicyclohexylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; phenyl; methylsulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl ($-S(=O)-CH_3$); ethylsulfinyl ($-S(=O)-CH_2CH_3$); propiosulfinyl ($-S(=O)-CH_2CH_2CH_3$); isopropiosulfinyl ($-S(=O)-CH(CH_3)_2$); methylsulfonyl ($-S(=O)_2-CH_3$); ethylsulfonyl ($-S(=O)_2-CH_2CH_3$); propiosulfonyl ($-S(=O)_2-CH_2CH_2CH_3$); isopropiosulfonyl ($-S(=O)_2-CH(CH_3)_2$); fluoro; chloro; bromo; iodo; trifluoromethyl; trichloromethyl; tribromomethyl; triiodomethyl; aminomethyl ($-CH_2NH_2$); vinyl; allyl; propargyl; nitro; carbamoyl; ureido ($-NH(C=O)-NH_2$); azido; isocyanate; thioisocyanate; hydroxylamino; nitrile; sulfonamide ($-S(=O)_2-NH_2$); methylsulfonamide ($-NH-S(=O)_2-CH_3$); ethylsulfonamide ($-NH_2-S(=O)_2-CH_2CH_3$); propiosulfonamide ($-NH_2-S(=O)_2-CH_2CH_2CH_3$); isopropiosulfonamide ($-NH_2-S(=O)_2-CH(CH_3)_2$); a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; and ortho-, meta-, or para-substituted benzene, wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be substituted with one or more substituents selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); amino; cycloalkylamino, isopropylamino; N-methylamino; N,N-dimethylamino; hydroxyl; methoxy; mono-, di-, or tri-fluoromethoxy; ethoxy; propoxy; isopropoxy; thiol; methylthio; ethylthio; propiothiol; isopropiothiol; fluoro; chloro; bromo; iodo; trifluoromethyl; trichloromethyl; tribromomethyl; triiodomethyl; nitro; azido; isocyanate; thioisocyanate; hydroxylamino; and nitrile; and wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be independently fused to $R_1$ or $R_2$ or linked to $R_1$ or $R_2$.

Examples of a saturated or unsaturated hydrocarbon ring that may be used as substituents on $R_1$ and $R_2$ are cyclopropyl, cyclobutyl, cyclopentyl, cyclohexyl, cycloheptyl, cyclooctyl, cyclopropenyl, cyclobutenyl, cyclobutadienyl, cyclopentenyl, cyclopentadienyl, cyclohexenyl, cyclohexadienyl, phenyl, cycloheptenyl, cycloheptadienyl, cycloheptatrienyl, cyclooctenyl, cyclooctadienyl, cyclooctatrienyl, cyclooctatetraenyl, naphthalenyl, indenyl, anthracenyl, phenanthrenyl, tirphenylenyl, fluorenyl, and pyrenyl.

Examples of a nitrogen-containing heterocyclic or heteroaryl moiety that may be used as substituents on $R_1$ and $R_2$ are pyrrolidinyl, pyrrolinyl, pyrazolidinyl, imidazolinyl, imidazolidinyl, pyrazolinyl, piperidinyl, piperazinyl, pyrrolyl, imidazolyl, pyrazolyl, pyridinyl, pyridazinyl, pyrmidinyl, pyrazinyl, indolinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, carbazolyl, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, and 1H-benzo[d][1,2,3]triazolyl.

Examples of an oxygen-containing heterocyclic or heteroaryl moiety that may be used as substituents on $R_1$ and $R_2$ are tetrahydrofuranyl, dihydrofuranyl, tetrahydropyranyl, dihydropyranyl, furanyl, pyranyl, benzofuranyl, isobenzofuranyl, dibenzofuranyl, 2H-chromenyl, 1H-isochromenyl, 3H-isochromenyl, xanthenyl, benzofuran-2(3H)-one, and isobenzofuran-1(3H)-one.

Examples of a sulfur-containing heterocyclic or heteroaryl moiety that may be used as substituents on $R_1$ and $R_2$ are tetrahydrothiophenyl, dihydrothiophenyl, tetrahydrothiopyranyl, dihydrothiopyranyl, thiopyranyl, thiophenyl, benzo[b]thiophenyl, benzo[c]thiophenyl, benzo[b]thiophen-2(3H)-one, and benzo[c]thiophen-1(3H)-one.

Examples of a selenium-containing heterocyclic or heteroaryl moiety that may be used as substituents on $R_1$ and $R_2$ are tetrahydroselenophenyl, dihydroselenophenyl, tetrahydroselenopyranyl, dihydroselenopyranyl, selenopyranyl, selenophenyl, benzo[b]selenophenyl, benzo[c]selenophenyl, benzo[b]selenophen-2(3H)-one, and benzo[c]selenophen-1(3H)-one.

Examples of a mixed heterocyclic or heteroaryl moiety containing at least two atoms selected from the group consisting of nitrogen, oxygen, sulfur, and selenium that may be used as substituents on $R_1$ and $R_2$ are morpholinyl, thiomorpholinyl, selenomorpholinyl, 1,2-oxathiolanyl, 1,3-oxathiolanyl, 1,2-oxaselenolanyl, 1,3-oxaselenolanyl, 1,2-thiaselenolanyl, 1,3-thiaselenolanyl, oxazolidine, isoxazolidine, thiazolidine, isothiazolidine, selenazolidine, isoselenazolidine, oxazolyl, isoxazolyl, thiazolyl, isothiazolyl, selenazolyl, isoselenazolyl, benzo[d]oxazole, benzo[d]thiazole, benzo[d]selenazole, benzo[c]isoxazole, benzo[d]isoxazole, benzo[c]isothiazole, benzo[d]isothiazole, benzo[c]isoselenazole, benzo[d]isoselenazole, benzo[c][1,2,5]oxadiazole, benzo[c][1,2,5]thiadiazole, benzo[c][1,2,5]selenadiazole, oxazinyl, thiazinyl, and selenazinyl.

Examples of an aryl group that may be used as substituents on $R_6$ are phenyl, naphthalenyl, cyclobutadienyl, cyclopentadienyl, indenyl, anthracenyl, phenanthrenyl, tirphenylenyl, fluorenyl, and pyrenyl. Each of these aryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

Examples of a heteroaryl group that may be used as substituents on $R_6$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, and 1H-benzo[d][1,2,3]triazolyl, and benzo[c]thiophen-1(3H)-one. Each of these heteroaryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

The present invention provides a method of treating a substance use disorder, drug dependence/abuse/addiction or withdrawal from drug dependence/abuse/addiction in an individual in need thereof, wherein the method comprises the step of administering to the individual a compound of formula (I):

(I)

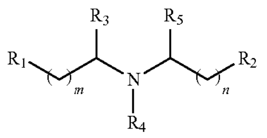

wherein m is an integer in the range from 1 to 3;

n is zero or an integer in the range from 1 to 5;

$R_1$ and $R_2$ are independently an aryl group or a heteroaryl group and which are independently unsubstituted or substituted by one or more substituents;

$R_3$ is =O, methyl; ethyl; propyl; isopropyl; hydroxymethyl; 2-hydroxyethyl; 1-hydroxyethyl; methoxymethyl; 2-methoxyethyl; 1-methoxyethyl; aminomethyl; 2-aminoethyl; 1-aminoethyl; N-methylaminomethyl; 2-N-methylaminoethyl; 1-N-methylaminoethyl; N,N-dimethylaminomethyl; 2-N,N-dimethylaminoethyl; 1-N,N-dimethylaminoethyl; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); amide ($-CONH_2$); methyl amide ($-CONHCH_3$), ethyl amide ($-CONHCH_2CH_3$); propyl amide ($-CONHCH_2CH_2CH_3$); isopropyl amide ($-CONHCH(CH_3)_2$); butylamide ($-CONHCH_2CH_2CH_2CH_3$); sec-butylamide ($-CONHCH(CH_3)(CH_2CH_3)$); tert-butylamide ($-CONHC(CH_3)_3$); dimethyl amide ($-CON(CH_3)_2$), diethyl amide ($-CON(CH_2CH_3)_2$); dipropyl amide ($-CON(CH_2CH_2CH_3)_2$); isopropyl amide ($-CON[CH(CH_3)_2]_2$); dibutylamide ($-CON(CH_2CH_2CH_2CH_3)_2$);

di-sec-butylamide ($-CON[CH(CH_3)(CH_2CH_3)]_2$); di-tert-butylamide ($-CON[C(CH_3)_3]_2$); methyl, ethyl, propyl, or isopropyl substituted with one or more fluoro, chloro, bromo, or iodo; benzyl; or $-(CH_2)_a-O-(C{=}O)-CHR_6-NH_2$;

$R_4$ is a hydrogen atom; a methyl, ethyl, propyl, isopropyl, or carbonyl group; or a methyl, ethyl, propyl or isopropyl group substituted with a hydroxyaryl group; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); or benzyl ester ($-COOCH_2(C_6H_6)$); and $R_5$ is hydrogen, methyl, or =O; $R_6$ is selected from the group consisting of methyl, ethyl, propyl, isopropyl, and $C_4$-$C_7$ straight chain or branched alkyl, wherein the methyl, ethyl, propyl, isopropyl, or $C_4$-$C_7$ straight chain or branched alkyl are unsubstituted or substituted with one or more substituents selected from the group consisting of substituted or unsubstituted aryl groups and substituted or unsubstituted heteroaryl groups;

a is an integer in the range from 1 to 5; or an enantiomer; racemate; or pharmaceutically acceptable salt thereof.

Examples of an aryl group that may be used as $R_1$ or $R_2$ are phenyl, naphthalenyl, cyclobutadienyl, cyclopentadienyl, indenyl, anthracenyl, phenanthrenyl, tirphenylenyl, fluorenyl, and pyrenyl.

Examples of a heteroaryl group that may be used as $R_1$ or $R_2$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]

isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, and benzo[c]thiophen-1(3H)-one.

Substituents on $R_1$ and $R_2$ are independently selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); alkylsulfonyl; alkylsulfinyl; a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; ortho-, meta-, or para-substituted phenyl; ortho-, meta-, or para-substituted benzyl; ortho-, meta-, or para-substituted benzenephenyl; phenylethyl; amino; cycloalkylamino, isopropylamino; N-methylamino; N,N-dimethylamino; N-cyclopropylamino; N,N-dicyclopropylamino; N-cyclobutylamino; N,N-dicyclobutylamino; N-cyclopentylamino; N,N-dicyclopentylamino; N-cyclohexylamino; N,N-dicyclohexylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; phenyl; methylsulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl ($-S(=O)-CH_3$); ethylsulfinyl ($-S(=O)-CH_2CH_3$); propiosulfinyl ($-S(=O)-CH_2CH_2CH_3$); isopropiosulfinyl ($-S(=O)-CH(CH_3)_2$); methylsulfonyl ($-S(=O)_2-CH_3$); ethylsulfonyl ($-S(=O)_2-CH_2CH_3$); propiosulfonyl ($-S(=O)_2-CH_2CH_2CH_3$); isopropiosulfonyl ($-S(=O)_2-CH(CH_3)_2$); fluoro; chloro; bromo; iodo; trifluoromethyl; trichloromethyl; tribromomethyl; triiodomethyl; aminomethyl ($-CH_2NH_2$); vinyl; allyl; propargyl; nitro; carbamoyl; ureido ($-NH(C=O)-NH_2$); azido; isocyanate; thioisocyanate; hydroxylamino; nitrile; sulfonamide ($-S(=O)_2-NH_2$); methylsulfonamide ($-NH-S(=O)_2-CH_3$); ethylsulfonamide ($-NH_2-S(=O)_2-CH_2CH_3$); propiosulfonamide ($-NH_2-S(=O)_2-CH_2CH_2CH_3$); isopropiosulfonamide ($-NH_2-S(=O)_2-CH(CH_3)_2$); a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; and ortho-, meta-, or para-substituted benzene, wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be substituted with one or more substituents selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); amino; cycloalkylamino, isopropylamino; N-methylamino; N,N-dimethylamino; hydroxyl; methoxy; mono-, di-, or tri-fluoromethoxy; ethoxy; propoxy; isopropoxy; thiol; methylthio; ethylthio; propiothiol; isopropiothiol; fluoro; chloro; bromo; iodo; trifluoromethyl; trichloromethyl; tribromomethyl; triiodomethyl; nitro; azido; isocyanate; thioisocyanate; hydroxylamino; and nitrile; and wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be independently fused to $R_1$ or $R_2$ or linked to $R_1$ or $R_2$.

Examples of a saturated or unsaturated hydrocarbon ring that may be used as substituents on $R_1$ and $R_2$ are cyclopropyl, cyclobutyl, cyclopentyl, cyclohexyl, cycloheptyl, cyclooctyl, cyclopropenyl, cyclobutenyl, cyclobutadienyl, cyclopentenyl, cyclopentadienyl, cyclohexenyl, cyclohexadienyl, phenyl, cycloheptenyl, cycloheptadienyl, cycloheptatrienyl, cyclooctenyl, cyclooctadienyl, cyclooctatrienyl, cyclooctatetraenyl, naphthalenyl, indenyl, anthracenyl, phenanthrenyl, tirphenylenyl, fluorenyl, and pyrenyl.

Examples of a nitrogen-containing heterocyclic or heteroaryl moiety that may be used as substituents on $R_1$ and $R_2$ are pyrrolidinyl, pyrrolinyl, pyrazolidinyl, imidazolinyl, imidazolidinyl, pyrazolinyl, piperidinyl, piperazinyl, pyrrolyl, imidazolyl, pyrazolyl, pyridinyl, pyridazinyl, pyrmidinyl, pyrazinyl, indolinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, carbazolyl, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, and 1H-benzo[d][1,2,3]triazolyl.

Examples of an oxygen-containing heterocyclic or heteroaryl moiety that may be used as substituents on $R_1$ and $R_2$ are tetrahydrofuranyl, dihydrofuranyl, tetrahydropyranyl, dihydropyranyl, furanyl, pyranyl, benzofuranyl, isobenzofuranyl, dibenzofuranyl, 2H-chromenyl, 1H-isochromenyl, 3H-isochromenyl, xanthenyl, benzofuran-2(3H)-one, and isobenzofuran-1(3H)-one.

Examples of a sulfur-containing heterocyclic or heteroaryl moiety that may be used as substituents on $R_1$ and $R_2$ are tetrahydrothiophenyl, dihydrothiophenyl, tetrahydrothiopyranyl, dihydrothiopyranyl, thiopyranyl, thiophenyl, benzo[b]thiophenyl, benzo[c]thiophenyl, benzo[b]thiophen-2(3H)-one, and benzo[c]thiophen-1(3H)-one.

Examples of a selenium-containing heterocyclic or heteroaryl moiety that may be used as substituents on $R_1$ and $R_2$ are tetrahydroselenophenyl, dihydroselenophenyl, tetrahydroselenopyranyl, dihydroselenopyranyl, selenopyranyl, selenophenyl, benzo[b]selenophenyl, benzo[c]selenophenyl, benzo[b]selenophen-2(3H)-one, and benzo[c]selenophen-1(3H)-one.

Examples of a mixed heterocyclic or heteroaryl moiety containing at least two atoms selected from the group consisting of nitrogen, oxygen, sulfur, and selenium that may be used as substituents on $R_1$ and $R_2$ are morpholinyl, thiomorpholinyl, selenomorpholinyl, 1,2-oxathiolanyl, 1,3-oxathiolanyl, 1,2-oxaselenolanyl, 1,3-oxaselenolanyl, 1,2-thiaselenolanyl, 1,3-thiaselenolanyl, oxazolidine, isoxazolidine, thiazolidine, isothiazolidine, selenazolidine, isoselenazolidine, oxazolyl, isoxazolyl, thiazolyl, isothiazolyl, selenazolyl, isoselenazolyl, benzo[d]oxazole, benzo[d]thiazole, benzo[d]selenazole, benzo[c]isoxazole, benzo[d]isoxazole, benzo[c]isothiazole, benzo[d]isothiazole, benzo[c]isoselenazole, benzo[d]isoselenazole, benzo[c][1,2,5]oxadiazole, benzo[c][1,2,5]thiadiazole, benzo[c][1,2,5]selenadiazole, oxazinyl, thiazinyl, and selenazinyl.

Examples of an aryl group that may be used as substituents on $R_6$ are phenyl, naphthalenyl, cyclobutadienyl, cyclopentadienyl, indenyl, anthracenyl, phenanthrenyl, tirphenylenyl, fluorenyl, and pyrenyl. Each of these aryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

Examples of a heteroaryl group that may be used as substituents on $R_6$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, benzo[c]thiophen-1(3H)-one, and 1H-benzo[d][1,2,3]triazolyl. Each of these heteroaryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

The present invention provides a compound of formula (II):

(II)

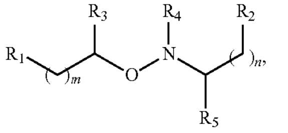

an enantiomer; racemate; or pharmaceutically acceptable salt thereof, wherein m, n, $R_1$, $R_2$, $R_3$, $R_4$, and $R_5$ are the same as those described above for formula (I).

The present invention provides a pharmaceutical composition comprising a compound of formula (II), an enantiomer; racemate; or pharmaceutically acceptable salt thereof and a pharmaceutically acceptable additive, wherein the compound of formula (II) is:

(II)

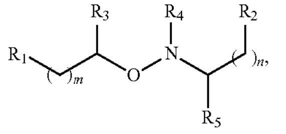

wherein m, n, $R_1$, $R_2$, $R_3$, $R_4$, and $R_5$ are the same as those described above for formula (I).

The present invention provides a method of treating a substance use disorder, drug dependence/abuse/addiction or withdrawal from drug dependence/abuse/addiction in an individual in need thereof, wherein the method comprises the step of administering to the individual a compound of formula (II):

(II)

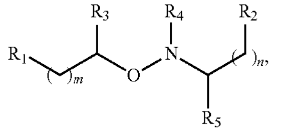

wherein m, n, $R_1$, $R_2$, $R_3$, $R_4$, and $R_5$ are the same as those described above for formula (I); or an enantiomer; racemate; or pharmaceutically acceptable salt thereof.

DETAILED DESCRIPTION OF THE INVENTION

The present invention provides a compound of formula (I):

(I)

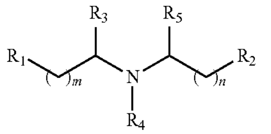

wherein m is an integer in the range from 1 to 3;

n is zero or an integer in the range from 1 to 5;

$R_1$ and $R_2$ are independently an aryl group or a heteroaryl group and which are independently unsubstituted or substituted by one or more substituents;

$R_3$ is =O, methyl; ethyl; propyl; isopropyl; hydroxymethyl; 2-hydroxyethyl; 1-hydroxyethyl; methoxymethyl; 2-methoxyethyl; 1-methoxyethyl; aminomethyl; 2-aminoethyl; 1-aminoethyl; N-methylaminomethyl; 2-N-methylaminoethyl; 1-N-methylaminoethyl; N,N-dimethylaminomethyl; 2-N,N-dimethylaminoethyl; 1-N,N-dimethylaminoethyl; carboxylate; methyl ester ($-COOCH_3$), ethyl ester ($-COOCH_2CH_3$); propyl ester ($-COOCH_2CH_2CH_3$); isopropyl ester (—$COOCH(CH_3)_2$); butylester (—$COOCH_2CH_2CH_2CH_3$); sec-butylester (—$COOCH(CH_3)(CH_2CH_3)$); tert-butylester (—$COOC(CH_3)_3$); amide (—$CONH_2$); methyl amide (—$CONHCH_3$), ethyl amide (—$CONHCH_2CH_3$); propyl amide (—$CONHCH_2CH_2CH_3$); isopropyl amide (—$CONHCH(CH_3)_2$); butylamide (—$CONHCH_2CH_2CH_2CH_3$); sec-butylamide (—$CONHCH(CH_3)(CH_2CH_3)$); tert-butylamide (—$CONHC(CH_3)_3$); dimethyl amide (—$CON(CH_3)_2$), diethyl amide (—$CON(CH_2CH_3)_2$); dipropyl amide (—$CON(CH_2CH_2CH_3)_2$); isopropyl amide (—$CON[CH(CH_3)_2]_2$); dibutylamide (—$CON(CH_2CH_2CH_2CH_3)_2$); di-sec-butylamide (—$CON[CH(CH_3)(CH_2CH_3)]_2$); di-tert-butylamide (—$CON[C(CH_3)_3]_2$); methyl, ethyl, propyl, or isopropyl substituted with one or more fluoro, chloro, bromo, or iodo; benzyl; or —$(CH_2)_a$—O—(C═O)—$CHR_6$—$NH_2$;

$R_4$ is a hydrogen atom; a methyl, ethyl, propyl, isopropyl, or carbonyl group; or a methyl, ethyl, propyl or isopropyl group substituted with a hydroxyaryl group; carboxylate; methyl ester (—$COOCH_3$), ethyl ester (—$COOCH_2CH_3$); propyl ester (—$COOCH_2CH_2CH_3$); isopropyl ester (—$COOCH(CH_3)_2$); butylester (—$COOCH_2CH_2CH_2CH_3$); sec-butylester (—$COOCH(CH_3)(CH_2CH_3)$); tert-butylester (—$COOC(CH_3)_3$); or benzyl ester (—$COOCH_2(C_6H_6)$); and $R_5$ is hydrogen, methyl, or ═O;

$R_6$ is selected from the group consisting of methyl, ethyl, propyl, isopropyl, and $C_4$-$C_7$ straight chain or branched alkyl, wherein the methyl, ethyl, propyl, isopropyl, or $C_4$-$C_7$ straight chain or branched alkyl are unsubstituted or substituted with one or more substituents selected from the group consisting of substituted or unsubstituted aryl groups and substituted or unsubstituted heteroaryl groups;

a is an integer in the range from 1 to 5; or an enantiomer; racemate; or pharmaceutically acceptable salt thereof.

Examples of an aryl group that may be used as $R_1$ or $R_2$ are phenyl, naphthalenyl, cyclobutadienyl, cyclopentadienyl, indenyl, anthracenyl, phenanthrenyl, tirphenylenyl, fluorenyl, and pyrenyl.

Examples of a heteroaryl group that may be used as $R_1$ or $R_2$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, benzo[c]thiophen-1(3H)-one.

Substituents on $R_1$ and $R_2$ are independently selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); alkylsulfonyl; alkylsulfinyl; a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; ortho-, meta-, or para-substituted phenyl; ortho-, meta-, or para-substituted benzyl; ortho-, meta-, or para-substituted benzenephenyl; phenylethyl; amino; cycloalkylamino, isopropylamino; N-methylamino; N,N-dimethylamino; N-cyclopropylamino; N,N-dicyclopropylamino; N-cyclobutylamino; N,N-dicyclobutylamino; N-cyclopentylamino; N,N-dicyclopentylamino; N-cyclohexylamino; N,N-dicyclohexylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; phenyl; methylsulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl (—S(═O)—$CH_3$); ethylsulfinyl (—S(═O)—$CH_2CH_3$); propiosulfinyl (—S(═O)—$CH_2CH_2CH_3$); isopropiosulfinyl (—S(═O)—$CH(CH_3)_2$); methylsulfonyl (—$S(═O)_2$—$CH_3$); ethylsulfonyl (—$S(═O)_2$—$CH_2CH_3$); propiosulfonyl (—$S(═O)_2$—$CH_2CH_2CH_3$); isopropiosulfonyl (—$S(═O)_2$—$CH(CH_3)_2$); fluoro; chloro; bromo; iodo; trifluoromethyl; trichloromethyl; tribromomethyl; triiodomethyl; aminomethyl (—$CH_2NH_2$); vinyl; allyl; propargyl; nitro; carbamoyl; ureido (—NH(C═O)—$NH_2$); azido; isocyanate; thioisocyanate; hydroxylamino; nitrile; sulfonamide (—$S(═O)_2$—$NH_2$); methylsulfonamide (—NH—$S(═O)_2$—$CH_3$); ethylsulfonamide (—$NH_2$—$S(═O)_2$—$CH_2CH_3$); propiosulfonamide (—$NH_2$—$S(═O)_2$—$CH_2CH_2CH_3$); isopropiosulfonamide (—$NH_2$—$S(═O)_2$—$CH(CH_3)_2$); a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; and ortho-, meta-, or para-substituted benzene, wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be substituted with one or more substituents selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); amino; cycloalkylamino, isopropylamino; N-methylamino; N,N-dimethylamino; hydroxyl; methoxy; mono-, di-, or tri-fluoromethoxy; ethoxy; propoxy; isopropoxy; thiol; methylthio; ethylthio; propiothiol; isopropiothiol; fluoro; chloro; bromo; iodo; trifluoromethyl; trichloromethyl; tribromomethyl; triiodomethyl; nitro; azido; isocyanate; thioisocyanate; hydroxylamino; and nitrile; and wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be independently fused to $R_1$ or $R_2$ or linked to $R_1$ or $R_2$.

Examples of a saturated or unsaturated hydrocarbon ring that may be used as substituents on $R_1$ and $R_2$ are cyclopropyl, cyclobutyl, cyclopentyl, cyclohexyl, cycloheptyl, cyclooctyl, cyclopropenyl, cyclobutenyl, cyclobutadienyl, cyclopentenyl, cyclopentadienyl, cyclohexenyl, cyclohexadienyl, phenyl, cycloheptenyl, cycloheptadienyl, cycloheptatrienyl, cyclooctenyl, cyclooctadienyl, cyclooctatrienyl, cyclooctatetraenyl, naphthalenyl, indenyl, anthracenyl, phenanthrenyl, tirphenylenyl, fluorenyl, and pyrenyl.

Examples of a nitrogen-containing heterocyclic or heteroaryl moiety that may be used as substituents on $R_1$ and $R_2$ are pyrrolidinyl, pyrrolinyl, pyrazolidinyl, imidazolinyl, imidazolidinyl, pyrazolinyl, piperidinyl, piperazinyl, pyrrolyl, imidazolyl, pyrazolyl, pyridinyl, pyridazinyl, pyrmidinyl, pyrazinyl, indolinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, carbazolyl, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, and 1H-benzo[d][1,2,3]triazolyl.

Examples of an oxygen-containing heterocyclic or heteroaryl moiety that may be used as substituents on $R_1$ and $R_2$ are tetrahydrofuranyl, dihydrofuranyl, tetrahydropyranyl, dihydropyranyl, furanyl, pyranyl, benzofuranyl, isobenzofuranyl, dibenzofuranyl, 2H-chromenyl, 1H-isochromenyl, 3H-isochromenyl, xanthenyl, benzofuran-2(3H)-one, and isobenzofuran-1(3H)-one.

Examples of a sulfur-containing heterocyclic or heteroaryl moiety that may be used as substituents on $R_1$ and $R_2$ are tetrahydrothiophenyl, dihydrothiophenyl, tetrahydrothiopyranyl, dihydrothiopyranyl, thiopyranyl, thiophenyl, benzo[b]thiophenyl, benzo[c]thiophenyl, benzo[b]thiophen-2(3H)-one, and benzo[c]thiophen-1(3H)-one.

Examples of a selenium-containing heterocyclic or heteroaryl moiety that may be used as substituents on $R_1$ and $R_2$ are tetrahydroselenophenyl, dihydroselenophenyl, tetrahydroselenopyranyl, dihydroselenopyranyl, selenopyranyl, selenophenyl, benzo[b]selenophenyl, benzo[c]selenophenyl, benzo[b]selenophen-2(3H)-one, and benzo[c]selenophen-1(3H)-one.

Examples of a mixed heterocyclic or heteroaryl moiety containing at least two atoms selected from the group consisting of nitrogen, oxygen, sulfur, and selenium that may be used as substituents on $R_1$ and $R_2$ are morpholinyl, thiomorpholinyl, selenomorpholinyl, 1,2-oxathiolanyl, 1,3-oxathiolanyl, 1,2-oxaselenolanyl, 1,3-oxaselenolanyl, 1,2-thiaselenolanyl, 1,3-thiaselenolanyl, oxazolidine, isoxazolidine, thiazolidine, isothiazolidine, selenazolidine, isoselenazolidine, oxazolyl, isoxazolyl, thiazolyl, isothiazolyl, selenazolyl, isoselenazolyl, benzo[d]oxazole, benzo[d]thiazole, benzo[d]selenazole, benzo[c]isoxazole, benzo[d]isoxazole, benzo[c]isothiazole, benzo[d]isothiazole, benzo[c]isoselenazole, benzo[d]isoselenazole, benzo[c][1,2,5]oxadiazole, benzo[c][1,2,5]thiadiazole, benzo[c][1,2,5]selenadiazole, oxazinyl, thiazinyl, and selenazinyl.

Examples of an aryl group that may be used as substituents on $R_6$ are phenyl, naphthalenyl, cyclobutadienyl, cyclopentadienyl, indenyl, anthracenyl, phenanthrenyl, tirphenylenyl, fluorenyl, and pyrenyl. Each of these aryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

Examples of a heteroaryl group that may be used as substituents on $R_6$ are pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, and benzo[c]thiophen-1(3H)-one. Each of these heteroaryl groups may be unsubstituted or substituted with one or more substituents selected from the group consisting of methyl, ethyl, propyl, isopropyl, and $C_4$-$C_7$ straight chain or branched alkyl substituted with one or more fluoro, chloro, bromo, iodo, hydroxy, amino, phenyl, or pyridinyl.

A further embodiment of the invention is a compound of formula (I), wherein (I)

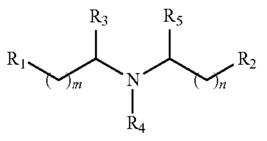

wherein m is 1;

n is 2;

$R_1$ and $R_2$ are independently an aryl group or a heteroaryl group which may be substituted by one or more substituents;

wherein substituents on $R_1$ and $R_2$ are independently selected from the group consisting of methyl; alkylsulfonyl; alkylsulfinyl; a saturated or unsaturated hydrocarbon ring; a nitrogen containing heterocyclic or heteroaryl moiety; a sulfur containing heterocyclic or heteroaryl moiety; phenyl; amino; cycloalkylamine; isopropylamino; N-methylamino; N, N-dimethylamino; ethylcarboxylate; carboxamide; N-methylcarboxamide; hydroxyl; methoxy; difluoromethoxy; thiol; fluoro; chloro; bromo; iodo; trifluoromethyl; nitro; nitrile; a saturated or unsaturated hydrocarbon ring; a nitrogen containing heterocyclic or heteroaryl moiety; and a sulfur containing heterocyclic or heteroaryl moiety, wherein one or more of the phenyl; saturated or unsaturated hydrocarbon ring; nitrogen containing heterocyclic or heteroaryl moiety; sulfur containing heterocyclic or heteroaryl moiety substituent on $R_1$ or $R_2$ may be independently fused to $R_1$ or $R_2$ or linked to $R_1$ or $R_2$;

$R_3$ is methyl, ethyl, isopropyl, hydroxymethyl, or methyl substituted with one or more fluoro; or benzyl; and $R_4$ is a hydrogen atom; a carbonyl group; or a methyl, ethyl, propyl or isopropyl group substituted with a hydroxyaryl group; and $R_5$ is hydrogen or methyl; or an enantiomer; racemate; or pharmaceutically acceptable salt thereof.

A further embodiment of the invention is a compound of formula (I), wherein: m is 1 or 2; and n is an integer from 1 to 5; or an enantiomer; racemate; or pharmaceutically acceptable salt thereof.

An further embodiment of the invention is a compound of formula (I), wherein: m is 1 or 2; and n is an integer from 1 to 5; $R_3$ is methyl, ethyl, propyl, or isopropyl; and $R_4$ is a hydrogen atom or a methyl, ethyl, propyl, or isopropyl group; or an enantiomer; racemate; or pharmaceutically acceptable salt thereof.

A further embodiment of the invention is a compound of formula (I), wherein: m is 1 or 2; and n is an integer from 1 to 5; wherein $R_3$ is methyl; and $R_4$ is a hydrogen atom or a methyl group; or an enantiomer; racemate; or pharmaceutically acceptable salt thereof.

Another embodiment of the invention is a compound of formula (I), wherein m is 1; n is 1; $R_1$ and $R_2$ are each independently a phenyl group, wherein $R_1$ and $R_2$ are each independently unsubstituted or substituted by one or more substituents selected from the group consisting of benzyl; amino; hydroxyl; methoxy; fluoro; and bromo; $R_3$ is methyl; and $R_4$ is a hydrogen atom or a methyl group; or an enantiomer; racemate; or pharmaceutically acceptable salt thereof.

Another embodiment of the invention is a compound of formula (I), wherein m is 1; n is 2; $R_1$ and $R_2$ are each independently a phenyl group, wherein $R_1$ and $R_2$ are each independently unsubstituted or substituted by one or more substituents selected from the group consisting of benzyl; amino; hydroxyl; methoxy; fluoro; and bromo; $R_3$ is methyl; and $R_4$ is a hydrogen atom or a methyl group; or an enantiomer; racemate; or pharmaceutically acceptable salt thereof.

Another embodiment of the invention is a compound of formula (I), wherein m is 2; n is 1; $R_1$ and $R_2$ are each independently a phenyl group, wherein $R_1$ and $R_2$ are each independently unsubstituted or substituted by one or more substituents selected from the group consisting of methoxy and bromo; $R_3$ is methyl; and $R_4$ is a hydrogen atom; or an enantiomer; racemate; or pharmaceutically acceptable salt thereof.

Yet another embodiment of the invention is a compound of formula (I), wherein m is 2; n is 2; $R_1$ and $R_2$ are each independently a phenyl group, wherein $R_1$ and $R_2$ are each independently unsubstituted or substituted by one or more methoxy groups; $R_3$ is methyl; and $R_4$ is a hydrogen atom or a methyl group; or an enantiomer; racemate; or pharmaceutically acceptable salt thereof.

Yet another embodiment of the invention is a compound of formula (I), wherein m is 1; n is an integer from 3 to 5; $R_1$ and $R_2$ are each independently a phenyl group, wherein $R_1$ and $R_2$ are each independently unsubstituted or substituted by one or more substituents selected from the group consisting of methoxy and bromo; $R_3$ is methyl; and $R_4$ is a hydrogen atom; or an enantiomer; racemate; or pharmaceutically acceptable salt thereof.

Yet another embodiment of the invention is a compound of formula (I), wherein m is 1; n is 2; $R_1$ is an unsubstituted phenyl group; $R_2$ is a phenyl group substituted with a methoxy group; $R_3$ is methyl; and $R_4$ is a hydrogen atom; or an enantiomer; racemate; or pharmaceutically acceptable salt thereof.

A further embodiment of the invention is a compound of formula (I), wherein m is 1 and n is 2; or an enantiomer; racemate; or pharmaceutically acceptable salt thereof.

A further embodiment of the invention is a compound of formula (I), wherein m is 1; n is 2; and $R_1$ and $R_2$ are aryl groups; or an enantiomer; racemate; or pharmaceutically acceptable salt thereof.

A further embodiment of the invention is a compound of formula (I), wherein: m is 1; n is 2; $R_1$ and $R_2$ are independently aryl or heteroaryl groups, at least one of which is independently substituted with methyl; alkylsulfonyl; alkylsulfinyl; a saturated or unsaturated hydrocarbon ring; a nitrogen containing heterocyclic or heteroaryl moiety; a sulfur containing heterocyclic or heteroaryl moiety; phenyl; amino; cycloalkylamine; isopropylamino; N-methylamino; N, N-dimethylamino; ethylcarboxylate; carboxamide; N-methylcarboxamide; hydroxyl; methoxy; difluoromethoxy; thiol; fluoro; chloro; bromo; iodo; trifluoromethyl; nitro; nitrile; a saturated or unsaturated hydrocarbon ring; a nitrogen containing heterocyclic or heteroaryl moiety; and a sulfur containing heterocyclic or heteroaryl moiety, wherein one or more of the phenyl; saturated or unsaturated hydrocarbon ring; nitrogen containing heterocyclic or heteroaryl moiety; sulfur containing heterocyclic or heteroaryl moiety substituent on $R_1$ or $R_2$ may be independently fused to $R_1$ or $R_2$ or linked to $R_1$ or $R_2$.

A further embodiment is a compound of formula (I), wherein $R_1$ is a pyridyl group; a pyrimidyl group; an unsubstituted phenyl; or a phenyl substituted with chloro, fluoro, bromo, difluoro, trifluoromethyl, methoxy, carboxamide, amino, pyridinyl, or nitro; and $R_2$ is a indolyl group; a pyridyl group; a pyrazolyl group; an imidazolyl group; a quinolinyl group; a methylpyrazolyl group; an unsubstituted phenyl; or a phenyl substituted with fluoro, chloro, bromo, iodo, trifluoromethyl, methoxy, carboxamide, methylcarboxamide, amine, aminoisopropyl, nitro, methylsulfonyl, methylsulfinyl, aminocyclobutyl, dimethylamino, ethylcarboxylate, pyrimidinyl, pyridinyl, indolyl, thiophene, or hydroxyl; or an enantiomer; racemate; or pharmaceutically acceptable salt thereof.

A further embodiment of the invention is a compound of formula (I), wherein m is 1; n is 2; $R_1$ and $R_2$ are aryl groups, at least one of which is independently substituted with amino; fluoro; a saturated or unsaturated hydrocarbon ring; or a nitrogen containing heterocyclic or heteroaryl moiety; or an enantiomer; racemate; or pharmaceutically acceptable salt thereof.

A further embodiment of the invention is a compound of formula (I), wherein m is 1; n is 2; and at least one of $R_1$ and $R_2$ is a heteroaryl group; or an enantiomer; racemate; or pharmaceutically acceptable salt thereof.

A further embodiment of the invention is a compound of formula (I), wherein m is 1; n is 2; and at least one of $R_1$ and $R_2$ is an aryl group fused with a heteroaryl group; or an enantiomer; racemate; or pharmaceutically acceptable salt thereof.

A further embodiment of the invention is a compound of formula (I), wherein m is 1; n is 2; and at least one of $R_1$ and $R_2$ is a heteroaryl group fused with one or more additional heteroaryl groups; or an enantiomer; racemate; or pharmaceutically acceptable salt thereof.

A further embodiment of the invention is a compound of formula (I), wherein m is 1; n is 2; and at least one of $R_1$ and $R_2$ is a heteroaryl group fused with an aryl group; or an enantiomer; racemate; or pharmaceutically acceptable salt thereof.

A further embodiment of the invention is a compound of formula (I), wherein at least one of $R_1$ and $R_2$ is a heteroaryl group fused with or linked to an aryl group, wherein the aryl group is substituted with an alkyl, methoxy, or carbonyl group; or at least one of $R_1$ and $R_2$ is an aryl group fused with or linked to a heteroaryl group, wherein the heteroaryl group is substituted with an alkyl, methoxy, or carbonyl group; or an enantiomer; racemate; or pharmaceutically acceptable salt thereof.

A further embodiment of the invention is a compound of formula (I), wherein m is 1; n is 2; and at least one of $R_1$ and $R_2$ is a nitrogen-containing heteroaryl group; or an enantiomer; racemate; or pharmaceutically acceptable salt thereof.

A further embodiment of the invention is a compound of formula (I), wherein m is 1; n is 2; and at least one of $R_1$ and $R_2$ is a nitrogen-containing heteroaryl group fused with a phenyl; or an enantiomer; racemate; or pharmaceutically acceptable salt thereof.

In an embodiment of formula (I), $R_5$ is hydrogen. In another embodiment of formula (I), $R_5$ is methyl.

A preferred embodiment of the invention is a compound of formula (I), (I)

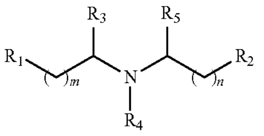

wherein: m is 1; n is 2; $R_1$ and $R_2$ are each independently an aryl group or a heteroaryl group which may be unsubstituted or substituted by one or more substitutents;

wherein the substituents on $R_1$ and $R_2$ are each independently selected from the group consisting of amino; hydroxy; thiol; carboxylate; methylcarboxylate; ethylcarboxylate; methoxy; fluoro; chloro; bromo; trifluoromethyl; nitro; sulfonamide ($-S(=O)_2-NH_2$); carboxamide; carbamoyl; ureido ($-NH(C=O)-NH_2$); a nitrogen-containing heterocyclic or heteroaryl moiety; oxygen-containing heterocyclic or heteroaryl moiety; and a mixed heterocyclic or heteroaryl moiety containing at least two atoms selected from the group consisting of nitrogen, oxygen, and sulfur;

wherein one or more of the nitrogen-containing heterocyclic or heteroaryl moiety; oxygen-containing heterocyclic or heteroaryl moiety; or mixed heterocyclic or heteroaryl moiety containing at least two atoms selected from the group consisting of nitrogen, oxygen, and sulfur on $R_1$ or $R_2$ may be independently fused to $R_1$ or $R_2$ or linked to $R_1$ or $R_2$;

wherein $R_3$ is methyl, hydroxymethyl; or methyl, ethyl, propyl, or isopropyl substituted with one or more fluoro;

$R_4$ is hydrogen; and $R_5$ is hydrogen; or an enantiomer; racemate; or pharmaceutically acceptable salt thereof.

Another preferred embodiment of the invention is a compound of formula (I), (I)

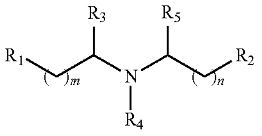

wherein:

m is 1;

n is 2;

$R_1$ and $R_2$ are each independently selected from the group consisting of phenyl, pyrrolyl, imidazolyl, pyrazolyl, thiazolyl, isothiazolyl, oxazolyl, isoxazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, furanyl, benzofuranyl, isobenzofuranyl, 2H-chromenyl, 1H-isochromenyl, 3H-isochromenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, and benzo[c]thiophen-1(3H)-one wherein $R_1$ and $R_2$ are each independently unsubstituted or substituted with one or more substitutents selected from the group consisting of methyl; ethyl; propyl; isopropyl; $C_4$-$C_7$ straight chain or branched alkyl; amino; isopropylamino; N-methylamino; N,N-dimethylamino; N-cyclopropylamino; N,N-dicyclopropylamino; N-cyclobutylamino; N,N-dicyclobutylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl ($-S(=O)-CH_3$); ethylsulfinyl ($-S(=O)-CH_2CH_3$); propiosulfinyl ($-S(=O)-CH_2CH_2CH_3$); isopropiosulfinyl ($-S(=O)-CH(CH_3)_2$); methylsulfonyl ($-S(=O)_2-CH_3$); ethylsulfonyl ($-S(=O)_2-CH_2CH_3$); propiosulfonyl ($-S(=O)_2-CH_2CH_2CH_3$); isopropiosulfonyl ($-S(=O)_2-CH(CH_3)_2$); fluoro; chloro; bromo; iodo; trifluoromethyl; trichloromethyl; tribromomethyl; triiodomethyl; aminomethyl ($-CH_2NH_2$); nitro; carbamoyl; ureido ($-NH(C=O)-NH_2$); azido; isocyanate; thioisocyanate; hydroxylamino; nitrile; sulfonamide ($-S(=O)_2-NH_2$); methylsulfonamide ($-NH-S(=O)_2-CH_3$); ethylsulfonamide ($-NH_2-S(=O)_2-CH_2CH_3$); propiosulfonamide ($-NH_2-S(=O)_2-CH_2CH_2CH_3$); and isopropiosulfonamide ($-NH_2-S(=O)_2-CH(CH_3)_2$); phenyl;

pyrrolyl; imidazolyl; pyrazolyl; thiazolyl; isothiazolyl; oxazolyl; isoxazolyl; pyridinyl; pyridazinyl; pyrmidinyl; pyrazinyl; 1H-indolyl; 3H-indolyl; 2H-isoindolyl; indolizinyl; quinolinyl; isoquinolinyl; quinoxalinyl; cinnolinyl; quinazolinyl; phthalazinyl; purinyl; indazolyl; benzimidazolyl; benzo[d]oxazole; benzo[d]thiazole; benzo[c]isoxazole; benzo[d]isoxazole; benzo[c]isothiazole; benzo[d]isothiazole; benzo[c][1,2,5]oxadiazole; benzo[c][1,2,5]thiadiazole; quinoline-2(1H)-one; isoquinoline-1(2H)-one; indolin-2-one; isoindolin-1-one; 1H-benzo[d]imidazole-2(3H)-one; furanyl; benzofuranyl; isobenzofuranyl; benzofuran-2(3H)-one; isobenzofuran-1(3H)-one; thiophenyl; benzo[b]thiophenyl; benzo[c]thiophenyl; benzo[b]thiophen-2(3H)-one; benzo[c]thiophen-1(3H)-one; and 1H-benzo[d][1,2,3]triazolyl;

$R_3$ is =O, methyl; ethyl; propyl; isopropyl; hydroxymethyl; 2-hydroxyethyl; 1-hydroxyethyl; methoxymethyl; carboxylate; methyl, ethyl, propyl, or isopropyl substituted with one or more fluoro, chloro, bromo, or iodo; benzyl; or $-(CH_2)_a-O-(C{=}O)-CHR_6-NH_2$;

$R_4$ is hydrogen; a methyl, ethyl, propyl, or isopropyl group substituted with a hydroxyaryl group; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); or benzyl ester ($-COOCH_2(C_6H_6)$);

$R_5$ is hydrogen, methyl, or =O; and $R_6$ is methyl substituted with one or more substituents selected from the group consisting of substituted aryl groups and substituted heteroaryl groups; or an enantiomer; racemate; or pharmaceutically acceptable salt thereof.

Another preferred embodiment of the invention is a compound of formula (I), (I)

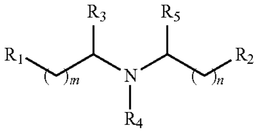

wherein:

m is 1;

n is 2;

$R_1$ is selected from the group consisting of phenyl, quinoxalinyl, and benzimidazolyl;

wherein $R_1$ is unsubstituted or substituted with one or more substitutents selected from the group consisting of fluoro; chloro; bromo; iodo; amino; carboxamide; ureido ($-NH(C{=}O)-NH_2$); and sulfonamide ($-S(=O)_2-NH_2$).

$R_2$ is selected from the group consisting of phenyl, quinoxalinyl, indazolyl, benzimidazolyl, benzo[d]oxazole, benzo[c]isoxazole, benzo[d]isoxazole, and 1H-benzo[d][1,2,3]triazolyl;

wherein $R_2$ is unsubstituted or substituted with one or more substitutents selected from the group consisting of fluoro; chloro; bromo; iodo; amino; carboxamide; ureido ($-NH(C{=}O)-NH_2$); and sulfonamide ($-S(=O)_2-NH_2$);

$R_3$ is methyl;

$R_4$ is hydrogen; and $R_5$ is hydrogen; or an enantiomer; racemate; or pharmaceutically acceptable salt thereof.

Another preferred embodiment of the invention is a compound of formula (I), (I)

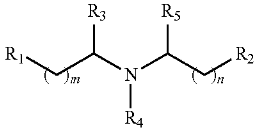

wherein:

m is 1;

n is 2;

$R_1$ is selected from the group consisting of unsubstituted quinoxalinyl, unsubstituted benzimidazolyl, or phenyl substituted with 3-fluoro, 4-fluoro, 3-chloro, 4-chloro, 3-amine, 4-amine, 3-ureido, 4-ureido, 3-carboxamide, 4-carboxamide, 3,4-difluoro, 3,4-dichloro, 3,5-difluoro, or 3,5-dichloro;

$R_2$ is selected from the group consisting of unsubstituted quinoxalinyl, unsubstituted indazolyl, unsubstituted benzimidazolyl, unsubstituted benzo[d]oxazole, unsubstituted benzo[c]isoxazole, unsubstituted benzo[d]isoxazole, unsubstituted 1H-benzo[d][1,2,3]triazolyl, and phenyl substituted with 3-fluoro, 4-fluoro, 3-chloro, 4-chloro, 3-amine, 4-amine, 3-ureido, 4-ureido, 3-carboxamide, 4-carboxamide, 3-sulfonamide, 4-sulfonamide, 3,4-difluoro, 3,4-dichloro, 3,5-difluoro, 3,5-dichloro, 3-fluoro-4-carboxamide, 3-chloro-4-carboxamide, 3-fluoro-4-sulfonamide, 3-chloro-4-sulfonamide, 3-fluoro-4-ureido, or 3-chloro-4-ureido;

$R_3$ is methyl;

$R_4$ is hydrogen; and $R_5$ is hydrogen; or an enantiomer; racemate; or pharmaceutically acceptable salt thereof.

Another preferred embodiment of the invention is a compound of formula (I), wherein m is 1; n is 2; and at least one of $R_1$ and $R_2$ is an unsubstituted phenyl; or a phenyl substituted with one or more of chloro, fluoro, bromo, difluoro, trifluoromethyl, amino, carboxamide, or nitro; or an enantiomer; racemate; or pharmaceutically acceptable salt thereof.

Another preferred embodiment of the invention is a compound of formula (I), wherein m is 1; n is 2; and at least one of $R_1$ and $R_2$ is an unsubstituted heteroaryl; or a heteroaryl substituted with trifluoromethyl; or an enantiomer; racemate; or pharmaceutically acceptable salt thereof.

Another preferred embodiment of the invention is a compound of formula (I), wherein m is 1; n is 2; and at least one of $R_1$ and $R_2$ is a phenyl fused with a nitrogen-containing heteroaryl group; or an enantiomer; racemate; or pharmaceutically acceptable salt thereof.

Another preferred embodiment of the invention is a compound of formula (I), wherein m is 1; n is 2; and at least one of $R_1$ and $R_2$ is a phenyl linked with a nitrogen-containing heteroaryl group; or an enantiomer; racemate; or pharmaceutically acceptable salt thereof.

Another preferred embodiment of the invention is a compound of formula (I), wherein m is 1; n is 2; $R_1$ is a phenyl substituted with chloro, fluoro, difluoro, or an enantiomer; racemate; or pharmaceutically acceptable salt thereof.

Another preferred embodiment of the invention is a compound of formula (I), wherein m is 1; n is 2; $R_3$ is methyl; $R_4$ is hydrogen; $R_5$ is hydrogen or an enantiomer; racemate; or pharmaceutically acceptable salt thereof.

Another preferred embodiment of the invention is a compound of formula (II),

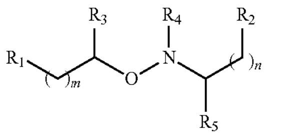

(II)

wherein m is 1 or 2;

n is 1 or 2;

$R_1$ and $R_2$ are independently an aryl group or a heteroaryl group which may be unsubstituted or substituted by one or more substituents;

wherein substituents on $R_1$ and $R_2$ are independently selected from the group consisting of methyl; alkylsulfonyl; alkylsulfinyl; a saturated or unsaturated hydrocarbon ring; a nitrogen containing heterocyclic or heteroaryl moiety; a sulfur containing heterocyclic or heteroaryl moiety; phenyl; amino; cycloalkylamine; isopropylamino; N-methylamino; N, N-dimethylamino; ethylcarboxylate; carboxamide; N-methylcarboxamide; hydroxyl; methoxy; difluoromethoxy; thiol; fluoro; chloro; bromo; iodo; trifluoromethyl; nitro; nitrile; a saturated or unsaturated hydrocarbon ring; a nitrogen containing heterocyclic or heteroaryl moiety; and a sulfur containing heterocyclic or heteroaryl moiety, wherein one or more of the phenyl; saturated or unsaturated hydrocarbon ring; nitrogen containing heterocyclic or heteroaryl moiety; sulfur containing heterocyclic or heteroaryl moiety substituent on $R_1$ or $R_2$ may be independently fused to $R_1$ or $R_2$ or linked to $R_1$ or $R_2$;

$R_3$ is methyl, ethyl, isopropyl, hydroxymethyl, or methyl substituted with one or more fluoro; or benzyl; and $R_4$ is a hydrogen atom; a carbonyl group; or a methyl, ethyl, propyl or isopropyl group substituted with a hydroxyaryl group; and $R_5$ is hydrogen or methyl; or an enantiomer; racemate; or pharmaceutically acceptable salt thereof.

Another preferred embodiment of the invention is a compound of formula (II), wherein: m is 1 or 2; n is 1 or 2; $R_1$ and $R_2$ are each independently an unsubstituted phenyl or a phenyl substituted with one or more substituents selected from the group consisting of methyl, alkylsulfonyl, alkylsulfinyl, amino, carboxamide, hydroxyl, methoxy, thiol, fluoro, chloro, bromo, iodo, nitro, and nitrile; $R_3$ is methyl; $R_4$ is hydrogen; $R_5$ is hydrogen; or an enantiomer; racemate; or pharmaceutically acceptable salt thereof.

Another preferred embodiment of the invention is a compound of formula (II), wherein: m is 1; n is 1; $R_1$ and $R_2$ are each independently an unsubstituted phenyl; $R_3$ is methyl; $R_4$ is hydrogen; $R_5$ is hydrogen; or an enantiomer; racemate; or pharmaceutically acceptable salt thereof.

Compounds of formula (I) include the following compounds:

1. m=1, n=1, $R_1$=Ph, $R_2$=Ph, $R_3$=Me, $R_4$=H, $R_5$=H
2. m=1, n=1, $R_1$=Ph, $R_2$=Ph, $R_3$=Me, $R_4$=$CH_3$, $R_5$=H
3. m=1, n=1, $R_1$=4-BrPh, $R_2$=Ph, $R_3$=Me, $R_4$=H, $R_5$=H
4. m=1, n=2, $R_1$=Ph, $R_2$=Ph, $R_3$=Me, $R_4$=H, $R_5$=H
5. R—, m=1, n=2, $R_1$=Ph, $R_2$=Ph, $R_3$=Me, $R_4$=H, $R_5$=H
6. S—, m=1, n=2, $R_1$=Ph, $R_2$=Ph, $R_3$=Me, $R_4$=H, $R_5$=H
7. m=1, n=2, $R_1$=Ph, $R_2$=Ph, $R_3$=Me, $R_4$=$CH_3$, $R_5$=H
8. m=1, n=2, $R_1$=Ph, $R_2$=4-MeOPh, $R_3$=Me, $R_4$=H, $R_5$=H
9. R—, m=1, n=2, $R_1$=Ph, $R_2$=4-MeOPh, $R_3$=Me, $R_4$=H, $R_5$=H
10. S—, m=1, n=2, $R_1$=Ph, $R_2$=4-MeOPh, $R_3$=Me, $R_4$=H, $R_5$=H
11. m=1, n=2, $R_1$=4-BrPh, $R_2$=Ph, $R_3$=Me, $R_4$=H, $R_5$=H
12. R—, m=1, n=2, $R_1$=4-BrPh, $R_2$=Ph, $R_3$=Me, $R_4$=H, $R_5$=H
13. S—, m=1, n=2, $R_1$=4-BrPh, $R_2$=Ph, $R_3$=Me, $R_4$=H, $R_5$=H
14. m=1, n=3, $R_1$=4-BrPh, $R_2$=Ph, $R_3$=Me, $R_4$=H, $R_5$=H
15. m=1, n=3, $R_1$=Ph, $R_2$=Ph, $R_3$=Me, $R_4$=H, $R_5$=H
16. m=1, n=2, $R_1$=4-BrPh, $R_2$=4-MeOPh, $R_3$=Me, $R_4$=H, $R_5$=H
17. m=1, n=4, $R_1$=Ph, $R_2$=Ph, $R_3$=Me, $R_4$=H, $R_5$=H
18. m=1, n=5, $R_1$=Ph, $R_2$=Ph, $R_2$=Me, $R_4$=H, $R_5$=H
19. m=1 n=1, $R_1$=Ph, $R_2$=PhO, $R_3$=Me, $R_4$=H, $R_5$=H
20. m=1, n=1, $R_1$=4-BrPh, $R_2$=PhO, $R_3$=Me, $R_4$=H, $R_5$=H
21. m=1, n=1, $R_1$=Ph, $R_2$=4-OHPh, $R_3$=Me, $R_4$=H, $R_5$=H
22. m=1, n=1, $R_1$=Ph, $R_2$=3,4-diBnOPh, $R_3$=Me, $R_4$=H, $R_5$=H
23. m=1, n=1, $R_1$=Ph, $R_2$=3,4-diOHPh, $R_3$=Me, $R_4$=H, $R_5$=H
24. m=1, n=1, $R_1$=4-MeOPh, $R_2$=Ph, $R_3$=Me, $R_4$=H, $R_5$=H
25. m=1, n=1, $R_1$=4-MeOPh, $R_2$=Ph, $R_3$=Me, $R_4$=$CH_3$, $R_5$=H
26. m=1, n=2, $R_1$=4-MeOPh, $R_2$=Ph, $R_3$=Me, $R_4$=H, $R_5$=H
27. R—, m=1, n=2, $R_1$=4-MeOPh, $R_2$=Ph, $R_3$=Me, $R_4$=H, $R_5$=H
28. S—, m=1, n=2, $R_1$=4-MeOPh, $R_2$=Ph, $R_3$=Me, $R_4$=H, $R_5$=H
29. m=1, n=2, $R_1$=4-MeOPh, $R_2$=4-MeOPh, $R_3$=Me, $R_4$=H, $R_5$=H
30. m=1, n=2, $R_1$=4-MeOPh, $R_2$=Ph, $R_3$=Me, $R_4$=$CH_3$, $R_5$=H
31. m=2, n=1, $R_1$=4-MeOPh, $R_2$=Ph, $R_3$=Me, $R_4$=H, $R_5$=H
32. m=2, n=2, $R_1$=4-MeOPh, $R_2$=Ph, $R_3$=Me, $R_4$=H, $R_5$=H
33. m=2, n=1, $R_1$=4-MeOPh, $R_2$=4-MeOPh, $R_3$=Me, $R_4$=H, $R_5$=H
34. m=2, n=1, $R_1$=4-MeOPh, $R_2$=4-BrPh, $R_3$=Me, $R_4$=H, $R_5$=H
35. m=1, n=1, $R_1$=4-OHPh, $R_2$=Ph, $R_3$=Me, $R_4$=H, $R_5$=H
36. m=1, n=2, $R_1$=4-OHPh, $R_2$=4-MeOPh, $R_3$=Me, $R_4$=H, $R_5$=H
37. m=1, n=2, $R_1$=4-OHPh, $R_2$=Ph, $R_3$=Me, $R_4$=H, $R_5$=H
38. m=1, n=1, $R_1$=4-FPh, $R_2$=Ph, $R_3$=Me, $R_4$=H, $R_5$=H
39. m=1, n=2, $R_1$=4-FPh, $R_2$=Ph, $R_3$=Me, $R_4$=H, $R_5$=H
40. m=1, n=2, $R_1$=4-FPh, $R_2$=4-MeOPh, $R_3$=Me, $R_4$=H, $R_5$=H
41. m=1, n=1, $R_1$=4-$NO_2$Ph, $R_2$=Ph, $R_3$=Me, $R_4$=H, $R_5$=H 42. m=1, n=2, $R_1$=4-$NO_2$Ph, $R_2$=Ph, $R_3$=Me, $R_4$=H, $R_5$=H
43. m=1, n=2, $R_1$=4-$NO_2$Ph, $R_2$=4-MeOPh, $R_3$=Me, $R_4$=H, $R_5$=H
44. m=1, n=1, $R_1$=4-$NH_2$Ph, $R_2$=Ph, $R_3$=Me, $R_4$=H, $R_5$=H
45. m=1, n=2, $R_1$=4-$NH_2$Ph, $R_2$=Ph, $R_3$=Me, $R_4$=H, $R_5$=H
46. m=1, n=2, $R_1$=3,4-diMeOPh, $R_2$=Ph, $R_3$=Me, $R_4$=H, $R_5$=H
47. m=1, n=3, $R_1$=3,4-diMeOPh, $R_2$=Ph, $R_3$=Me, $R_4$=H, $R_5$=H
48. m=2, n=1, $R_1$=Ph, $R_2$=Ph, $R_3$=Me, $R_4$=H, $R_5$=H
49. m=2, n=1, $R_1$=Ph, $R_2$=Ph, $R_3$=Me, $R_4$=H, $R_5$=H
50. m=2, n=2, $R_1$=Ph, $R_2$=Ph, $R_3$=Me, $R_4$=H, $R_5$=H
51. m=2, n=2, $R_1$=Ph, $R_2$=Ph, $R_3$=Me, $R_4$=$CH_3$, $R_5$=H
52. m=2, n=2, $R_1$=Ph, $R_2$=4-MeOPh, $R_3$=Me, $R_4$=H, $R_5$=H
53. m=2, n=2, $R_1$=4-MeOPh, $R_2$=4-MeOPh, $R_3$=Me, $R_4$=H, $R_5$=H.
54. m=1, n=2, $R_1$=4-$CF_3$Ph, $R_2$=4-$NH_2$Ph, $R_3$=Me, $R_4$=H, $R_5$=H
55. m=1, n=2, $R_1$=4-FPh, $R_2$=1H-indol-5-yl, $R_3$=Me, $R_4$=H, $R_5$=H
56. m=1, n=2, $R_1$=4-FPh, $R_2$=1H-indol-5-yl, $R_3$=Me, $R_4$=H, $R_5$=H
57. m=1, n=2, $R_1$=4-MeOPh, $R_2$=4-$NH_2$Ph, $R_3$=Me, $R_4$=H, $R_5$=H
58. m=1, n=2, $R_1$=4-MeOPh, $R_2$=4-$NO_2$Ph, $R_3$=Me, $R_4$=H, $R_5$=H
59. m=1, n=2, $R_1$=3,4-diFPh, $R_2$=4-$NO_2$Ph, $R_3$=Me, $R_4$=H, $R_5$=H
60. m=1, n=2, $R_1$=3,4-diFPh, $R_2$=4-$NH_2$Ph, $R_3$=Me, $R_4$=H, $R_5$=H
61. m=1, n=2, $R_1$=3,4-diFPh, $R_2$=4-$NH_2$Ph, $R_3$=Me, $R_4$=H, $R_5$=H
62. m=1, n=2, $R_1$=4-ClPh, $R_2$=4-$NH_2$Ph, $R_3$=Me, $R_4$=H, $R_5$=H
63. m=1, n=2, $R_1$=4-ClPh, $R_2$=4-$NH_2$Ph, $R_3$=Me, $R_4$=H, $R_5$=H
64. m=1, n=2, $R_1$=4-ClPh, $R_2$=4-$NO_2$Ph, $R_3$=Me, $R_4$=H, $R_5$=H
65. m=1, n=2, $R_1$=4-FPh, $R_2$=4-[NH(isopropyl)]Ph, $R_3$=Me, $R_4$=H, $R_5$=H
66. m=1, n=2, $R_1$=4-FPh, $R_2$=4-[Me(CO)NH]Ph, $R_3$=Me, $R_4$=H, $R_5$=H
67. m=1, n=2, $R_1$=4-FPh, $R_2$=4-[Me(CO)NH]Ph, $R_3$=Me, $R_4$=H, $R_5$=H
68. m=1, n=2, $R_1$=4-(pyrimidin-5-yl)Ph, $R_2$=4-FPh, $R_3$=$CH_2F$, $R_4$=H, $R_5$=H
69. m=1, n=2, $R_1$=4-(pyrimidin-5-yl)Ph, $R_2$=4-FPh, $R_3$=$CH_2F$, $R_4$=H, $R_5$=H
70. m=1, n=2, $R_1$=4-FPh, $R_2$=4-(NH—CHO)Ph, $R_3$=Me, $R_4$=H, $R_5$=H
71. m=1, n=2, $R_1$=4-FPh, $R_2$=4-(NH—CHO)Ph, $R_3$=Me, $R_4$=H, $R_5$=H
72. m=1, n=2, $R_1$=4-(NH—CHO)Ph, $R_2$=4-FPh, $R_3$=$CH_2F$, $R_4$=H, $R_5$=H
73. m=1, n=2, $R_1$=4-(NH—CHO)Ph, $R_2$=4-FPh, $R_3$=$CH_2F$, $R_4$=H, $R_5$=H
74. m=1, n=2, $R_1$=4-(NH—CHO)Ph, $R_2$=4-FPh, $R_3$=Me, $R_4$=CHO, $R_5$=H
75. m=1, n=2, $R_1$=4-(NH—CHO)Ph, $R_2$=Ph, $R_3$=Me, $R_4$=CHO, $R_5$=H
76. m=1, n=2, $R_1$=4-(NH—CHO)Ph, $R_2$=Ph, $R_3$=Me, $R_4$=CHO, $R_5$=H
77. m=1, n=2, $R_1$=4-(NH—CHO)Ph, $R_2$=Ph, $R_3$=Me, $R_4$=H, $R_5$=H
78. m=1, n=2, $R_1$=4-(NH—CHO)Ph, $R_2$=Ph, $R_3$=Me, $R_4$=H, $R_5$=H
79. m=1, n=2, $R_1$=4-$NH_2$Ph, $R_2$=4-FPh, $R_3$=$CH_2F$, $R_4$=H, $R_5$=H
80. m=1, n=2, $R_1$=4-$NH_2$Ph, $R_2$=4-FPh, $R_3$=$CH_2F$, $R_4$=H, $R_5$=H
81. m=1, n=2, $R_1$=4-FPh, $R_2$=4-FPh, $R_3$=$CF_2H$, $R_4$=H, $R_5$=H
82. m=1, n=2, $R_1$=4-FPh, $R_2$=4-FPh, $R_3$=$CF_2H$, $R_4$=H, $R_5$=H
83. m=1, n=2, $R_1$=4-(pyridin-3-yl)Ph, $R_2$=4-FPh, $R_3$=$CH_2F$, $R_4$=H, $R_5$=H
84. m=1, n=2, $R_1$=4-(pyridin-3-yl)Ph, $R_2$=4-FPh, $R_3$=$CH_2F$, $R_4$=H, $R_5$=H
85. m=1, n=2, $R_1$=4-BrPh, $R_2$=4-FPh, $R_3$=$CH_2F$, $R_4$=H, $R_5$=H
86. m=1, n=2, $R_1$=4-BrPh, $R_2$=4-FPh, $R_3$=$CH_2F$, $R_4$=H, $R_5$=H
87. m=1, n=2, $R_1$=4-(NH—CHO)Ph, $R_2$=4-FPh, $R_3$=Me, $R_4$=H, $R_5$=H
88. m=1, n=2, $R_1$=4-(NH—CHO)Ph, $R_2$=4-FPh, $R_3$=Me, $R_4$=H, $R_5$=H
89. m=1, n=2, $R_1$=4-(NH—CHO)Ph, $R_2$=4-FPh, $R_3$=Me, $R_4$=H, $R_5$=H
90. m=1, n=2, $R_1$=4-(NH—CHO)Ph, $R_2$=4-FPh, $R_3$=Me, $R_4$=H, $R_5$=H
91. m=1, n=2, $R_1$=4-FPh, $R_2$=1H-indole-3-yl, $R_3$=Me, $R_4$=H, $R_5$=H
92. m=1, n=2, $R_1$=4-FPh, $R_2$=1H-indole-3-yl, $R_3$=Me, $R_4$=H, $R_5$=H
93. m=1, n=2, $R_1$=4-FPh, $R_2$=4-[NH(cyclobutyl)]Ph, $R_3$=Me, $R_4$=H, $R_5$=H
94. m=1, n=2, $R_1$=4-FPh, $R_2$=4-$NH_2$Ph, $R_3$=Me, $R_4$=H, $R_5$=H
95. m=1, n=2, $R_1$=4-FPh, $R_2$=4-$NH_2$Ph, $R_3$=Me, $R_4$=H, $R_5$=H
96. m=1, n=2, $R_1$=3,4-diFPh, $R_2$=4-pyridyl, $R_3$=Me, $R_4$=H, $R_5$=H
97. m=1, n=2, $R_1$=3,4-diFPh, $R_2$=4-pyridyl, $R_3$=Me, $R_4$=H, $R_5$=H
98. m=1, n=2, $R_1$=Ph, $R_2$=Ph, $R_3$=$CH_2F$, $R_4$=H, $R_5$=H
99. m=1, n=2, $R_1$=Ph, $R_2$=Ph, $R_3$=$CH_2F$, $R_4$=H, $R_5$=H
100. m=1, n=2, $R_1$=4-FPh, $R_2$=Ph, $R_3$=$CH_2F$, $R_4$=H, $R_5$=H
101. m=1, n=2, $R_1$=Ph, $R_2$=4-FPh, $R_3$=$CH_2F$, $R_4$=H, $R_5$=H
102. m=1, n=2, $R_1$=Ph, $R_2$=4-FPh, $R_3$=$CH_2F$, $R_4$=H, $R_5$=H
103. m=1, n=2, $R_1$=4-$NH_2$Ph, $R_2$=4-pyridyl, $R_3$=Me, $R_4$=H, $R_5$=H
104. m=1, n=2, $R_1$=4-$NH_2$Ph, $R_2$=Ph, $R_3$=Me, $R_4$=H, $R_5$=H
105. m=1, n=2, $R_1$=4-$NH_2$Ph, $R_2$=Ph, $R_3$=Me, $R_4$=H, $R_5$=H
106. m=1, n=2, $R_1$=4-$NH_2$Ph, $R_2$=Ph, $R_3$=Me, $R_4$=H, $R_5$=H
107. m=1, n=2, $R_1$=4-FPh, $R_2$=4-$NH_2$Ph, $R_3$=$CH_2F$, $R_4$=H, $R_5$=H
108. m=1, n=2, $R_1$=4-FPh, $R_2$=4-$NH_2$Ph, $R_3$=$CH_2F$, $R_4$=H, $R_5$=H
109. m=1, n=2, $R_1$=4-$NH_2$Ph, $R_2$=4-FPh, $R_3$=Me, $R_4$=H, $R_5$=H
110. m=1, n=2, $R_1$=4-$NH_2$Ph, $R_2$=4-FPh, $R_3$=Me, $R_4$=H, $R_5$=H 111. m=1, n=2, $R_1$=4-$NH_2$Ph, $R_2$=4-FPh, $R_3$=Me, $R_4$=H, $R_5$=H
112. m=1, n=2, $R_1$=4-$NH_2$Ph, $R_2$=4-FPh, $R_3$=Me, $R_4$=H, $R_5$=H
113. m=1, n=2, $R_1$=4-$NO_2$Ph, $R_2$=4-pyridyl, $R_3$=Me, $R_4$=H, $R_5$=H
114. m=1, n=2, $R_1$=4-$NO_2$Ph, $R_2$=4-pyridyl, $R_3$=Me, $R_4$=H, $R_5$=H
115. m=1, n=2, $R_1$=4-$NO_2$Ph, $R_2$=Ph, $R_3$=Me, $R_4$=H, $R_5$=H
116. m=1, n=2, $R_1$=4-$NO_2$Ph, $R_2$=Ph, $R_3$=Me, $R_4$=H, $R_5$=H
117. m=1, n=2, $R_1$=4-$NO_2$Ph, $R_2$=4-FPh, $R_3$=Me, $R_4$=H, $R_5$=H
118. m=1, n=2, $R_1$=4-$NO_2$Ph, $R_2$=4-FPh, $R_3$=Me, $R_4$=H, $R_5$=H
119. m=1, n=2, $R_1$=4-$NO_2$Ph, $R_2$=4-FPh, $R_3$=Me, $R_4$=H, $R_5$=H
120. m=1, n=2, $R_1$=4-$NO_2$Ph, $R_2$=4-FPh, $R_3$=Me, $R_4$=H, $R_5$=H
121. m=1, n=2, $R_1$=4-$NO_2$Ph, $R_2$=4-BrPh, $R_3$=Me, $R_4$=H, $R_5$=H
122. m=1, n=2, $R_1$=4-$NO_2$Ph, $R_2$=4-BrPh, $R_3$=Me, $R_4$=H, $R_5$=H
123. m=1, n=2, $R_1$=4-FPh, $R_2$=4-$NO_2$Ph, $R_3$=$CH_2$F, $R_4$=H, $R_5$=H
124. m=1, n=2, $R_1$=4-FPh, $R_2$=4-$NO_2$Ph, $R_3$=$CH_2$F, $R_4$=H, $R_5$=H
125. m=1, n=2, $R_1$=4-$NO_2$Ph, $R_2$=4-ClPh, $R_3$=Me, $R_4$=H, $R_5$=H
126. m=1, n=2, $R_1$=4-FPh, $R_2$=Ph, $R_3$=Me, $R_4$=H, $R_5$=H
127. m=1, n=2, $R_1$=4-FPh, $R_2$=Ph, $R_3$=Me, $R_4$=H, $R_5$=H
128. m=1, n=2, $R_1$=4-FPh, $R_2$=4-pyridyl, $R_3$=$CH_2$OH, $R_4$=H, $R_5$=H
129. m=1, n=2, $R_1$=4-FPh, $R_2$=4-pyridyl, $R_3$=$CH_2$OH, $R_4$=H, $R_5$=H
130. m=1, n=2, $R_1$=4-FPh, $R_2$=1H-pyrazole-1-yl, $R_3$=$CH_2$OH, $R_4$=H, $R_5$=H
131. m=1, n=2, $R_1$=4-FPh, $R_2$=1H-pyrazole-1-yl, $R_3$=$CH_2$OH, $R_4$=H, $R_5$=H
132. m=1, n=2, $R_1$=4-FPh, $R_2$=1H-pyrazole-1-yl, $R_3$=Me, $R_4$=H, $R_5$=H
133. m=1, n=2, $R_1$=4-FPh, $R_2$=1H-pyrazole-1-yl, $R_3$=Me, $R_4$=H, $R_5$=H
134. m=1, n=2, $R_1$=4-FPh, $R_2$=1H-imidazole-1-yl, $R_3$=Me, $R_4$=H, $R_5$=H
135. m=1, n=2, $R_1$=4-FPh, $R_2$=1H-imidazole-1-yl, $R_3$=Me, $R_4$=H, $R_5$=H
136. m=1, n=2, $R_1$=4-FPh, $R_2$=Ph, $R_3$=isopropyl, $R_4$=H, $R_5$=H
137. m=1, n=2, $R_1$=4-FPh, $R_2$=4-$MeSO_2$Ph, $R_3$=$CH_2$F, $R_4$=H, $R_5$=H
138. m=1, n=2, $R_1$=4-FPh, $R_2$=4-$MeSO_2$Ph, $R_3$=Me, $R_4$=H, $R_5$=H
139. m=1, n=2, $R_1$=4-FPh, $R_2$=4-$MeSO_2$Ph, $R_3$=Me, $R_4$=H, $R_5$=H
140. m=1, n=2, $R_1$=4-FPh, $R_2$=4-BrPh, $R_3$=isopropyl, $R_4$=H, $R_5$=H
141. m=1, n=2, $R_1$=4-FPh, $R_2$=4-BrPh, $R_3$=isopropyl, $R_4$=H, $R_5$=H
142. m=1, n=2, $R_1$=4-FPh, $R_2$=4-pyridyl, $R_3$=$CH_2$F, $R_4$=H, $R_5$=H
143. m=1, n=2, $R_1$=4-FPh, $R_2$=4-pyridyl, $R_3$=$CH_2$F, $R_4$=H, $R_5$=H
144. m=1, n=2, $R_1$=4-FPh, $R_2$=4-MeSOPh, $R_3$=Me, $R_4$=H, $R_5$=H
145. m=1, n=2, $R_1$=4-FPh, $R_2$=4-BrPh, $R_3$=Me, $R_4$=H, $R_5$=H
146. m=1, n=2, $R_1$=4-FPh, $R_2$=4-BrPh, $R_3$=Me, $R_4$=H, $R_5$=H
147. m=1, n=2, $R_1$=4-FPh, $R_2$=4-FPh, $R_3$=$CH_2$OH, $R_4$=H, $R_5$=H
148. m=1, n=2, $R_1$=4-FPh, $R_2$=quinoline-4-yl, $R_3$=$CH_2$F, $R_4$=H, $R_5$=H
149. m=1, n=2, $R_1$=4-FPh, $R_2$=quinoline-4-yl, $R_3$=$CH_2$F, $R_4$=H, $R_5$=H
150. m=1, n=2, $R_1$=4-FPh, $R_2$=4-ClPh, $R_3$=$CH_2$F, $R_4$=H, $R_5$=H
151. m=1, n=2, $R_1$=4-FPh, $R_2$=4-ClPh, $R_3$=$CH_2$F, $R_4$=H, $R_5$=H
152. m=1, n=2, $R_1$=4-FPh, $R_2$=4-FPh, $R_3$=$CH_2$F, $R_4$=H, $R_5$=H
153. m=1, n=2, $R_1$=4-FPh, $R_2$=4-FPh, $R_3$=$CH_2$F, $R_4$=H, $R_5$=H
154. m=1, n=2, $R_1$=4-FPh, $R_2$=4-BrPh, $R_3$=$CH_2$OH, $R_4$=H, $R_5$=H
155. m=1, n=2, $R_1$=4-FPh, $R_2$=4-BrPh, $R_3$=$CH_2$OH, $R_4$=H, $R_5$=H
156. m=1, n=2, $R_1$=4-FPh, $R_2$=4-$NMe_2$Ph, $R_3$=Me, $R_4$=H, $R_5$=H
157. m=1, n=2, $R_1$=4-FPh, $R_2$=4-$NMe_2$Ph, $R_3$=Me, $R_4$=H, $R_5$=H
158. m=1, n=2, $R_1$=4-FPh, $R_2$=4-[EtO(CO)]Ph, $R_3$=Me, $R_4$=H, $R_5$=H
159. m=1, n=2, $R_1$=4-FPh, $R_2$=4-[EtO(CO)]Ph, $R_3$=Me, $R_4$=H, $R_5$=H
160. m=1, n=2, $R_1$=4-FPh, $R_2$=4-$NO_2$Ph, $R_3$=Me, $R_4$=H, $R_5$=H
161. m=1, n=2, $R_1$=4-FPh, $R_2$=4-$NO_2$Ph, $R_3$=Me, $R_4$=H, $R_5$=H
162. m=1, n=2, $R_1$=4-FPh, $R_2$=quinoline-4-yl, $R_3$=Me, $R_4$=H, $R_5$=H
163. m=1, n=2, $R_1$=4-FPh, $R_2$=quinoline-4-yl, $R_3$=Me, $R_4$=H, $R_5$=H
164. m=1, n=2, $R_1$=4-$CF_3$Ph, $R_2$=4-pyridyl, $R_3$=Me, $R_4$=H, $R_5$=H
165. m=1, n=2, $R_1$=4-$CF_3$Ph, $R_2$=4-pyridyl, $R_3$=Me, $R_4$=H, $R_5$=H
166. m=1, n=2, $R_1$=4-FPh, $R_2$=4-(1-methyl-1H-pyrazol-5-yl)Ph, $R_3$=Me, $R_4$=H, $R_5$=H
167. m=1, n=2, $R_1$=4-FPh, $R_2$=4-(1-methyl-1H-pyrazol-5-yl)Ph, $R_3$=Me, $R_4$=H, $R_5$=H
168. m=1, n=2, $R_1$=4-pyridyl, $R_2$=4-BrPh, $R_3$=Me, $R_4$=H, $R_5$=H
169. m=1, n=2, $R_1$=4-pyridyl, $R_2$=4-BrPh, $R_3$=Me, $R_4$=H, $R_5$=H
170. m=1, n=2, $R_1$=4-(pyrimidin-5-yl)Ph, $R_2$=4-ClPh, $R_3$=Me, $R_4$=H, $R_5$=H
171. m=1, n=2, $R_1$=4-(pyrimidin-5-yl)Ph, $R_2$=4-ClPh, $R_3$=Me, $R_4$=H, $R_5$=H
172. m=1, n=2, $R_1$=4-pyridyl, $R_2$=4-MeOPh, $R_3$=Me, $R_4$=H, $R_5$=H
173. m=1, n=2, $R_1$=4-pyridyl, $R_2$=4-MeOPh, $R_3$=Me, $R_4$=H, $R_5$=H
174. m=1, n=2, $R_1$=4-BrPh, $R_2$=4-pyridyl, $R_3$=Me, $R_4$=H, $R_5$=H
175. m=1, n=2, $R_1$=4-BrPh, $R_2$=4-pyridyl, $R_3$=Me, $R_4$=H, $R_5$=H
176. m=1, n=2, $R_1$=4-FPh, $R_2$=4-pyridyl, $R_3$=Me, $R_4$=H, $R_5$=H
177. m=1, n=2, $R_1$=4-FPh, $R_2$=4-pyridyl, $R_3$=Me, $R_4$=H, $R_5$=H 178. m=1, n=2, $R_1$=4-pyridyl, $R_2$=4-OHPh, $R_3$=Me, $R_4$=H, $R_5$=H
179. m=1, n=2, $R_1$=4-pyridyl, $R_2$=4-OHPh, $R_3$=Me, $R_4$=H, $R_5$=H
180. m=1, n=2, $R_1$=4-BrPh, $R_2$=4-IPh, $R_3$=Me, $R_4$=H, $R_5$=H
181. m=1, n=2, $R_1$=4-BrPh, $R_2$=4-IPh, $R_3$=Me, $R_4$=H, $R_5$=H
182. m=1, n=2, $R_1$=4-FPh, $R_2$=4-IPh, $R_3$=Me, $R_4$=H, $R_5$=H
183. m=1, n=2, $R_1$=4-FPh, $R_2$=4-IPh, $R_3$=Me, $R_4$=H, $R_5$=H
184. m=1, n=2, $R_1$=4-BrPh, $R_2$=4-ClPh, $R_3$=Me, $R_4$=H, $R_5$=H
185. m=1, n=2, $R_1$=4-BrPh, $R_2$=4-ClPh, $R_3$=Me, $R_4$=H, $R_5$=H
186. m=1, n=2, $R_1$=4-pyridyl, $R_2$=4-FPh, $R_3$=Me, $R_4$=H, $R_5$=H
187. m=1, n=2, $R_1$=4-pyridyl, $R_2$=4-FPh, $R_3$=Me, $R_4$=H, $R_5$=H
188. m=1, n=2, $R_1$=4-FPh, $R_2$=4-ClPh, $R_3$=Me, $R_4$=H, $R_5$=H
189. m=1, n=2, $R_1$=4-FPh, $R_2$=4-ClPh, $R_3$=Me, $R_4$=H, $R_5$=H
190. m=1, n=2, $R_1$=4-FPh, $R_2$=4-FPh, $R_3$=Me, $R_4$=H, $R_5$=H
191. m=1, n=2, $R_1$=4-FPh, $R_2$=4-FPh, $R_3$=Me, $R_4$=H, $R_5$=H
192. m=1, n=2, $R_1$=4-(pyridin-3-yl)Ph, $R_2$=4-FPh, $R_3$=Me, $R_4$=H, $R_5$=H
193. m=1, n=2, $R_1$=4-(pyridin-3-yl)Ph, $R_2$=4-FPh, $R_3$=Me, $R_4$=H, $R_5$=H
194. m=1, n=2, $R_1$=Ph, $R_2$=4-$CF_3$Ph, $R_3$=Me, $R_4$=H, $R_5$=H
195. m=1, n=2, $R_1$=Ph, $R_2$=4-$CF_3$Ph, $R_3$=Me, $R_4$=H, $R_5$=H
196. m=1, n=2, $R_1$=4-(pyrimidin-5-yl)Ph, $R_2$=4-FPh, $R_3$=Me, $R_4$=H, $R_5$=H
197. m=1, n=2, $R_1$=4-(pyrimidin-5-yl)Ph, $R_2$=4-FPh, $R_3$=Me, $R_4$=H, $R_5$=H
198. m=1, n=2, $R_1$=Ph, $R_2$=4-MeOPh, $R_3$=Me, $R_4$=H, $R_5$=Me
199. m=1, n=2, $R_1$=Ph, $R_2$=4-MeOPh, $R_3$=Me, $R_4$=H, $R_5$=Me
200. m=1, n=2, $R_1$=4-BrPh, $R_2$=4-FPh, $R_3$=Me, $R_4$=H, $R_5$=H
201. m=1, n=2, $R_1$=4-BrPh, $R_2$=4-FPh, $R_3$=Me, $R_4$=H, $R_5$=H
202. m=1, n=2, $R_1$=Ph, $R_2$=4-(pyrimidin-5-yl)Ph, $R_3$=Me, $R_4$=H, $R_5$=H
203. m=1, n=2, $R_1$=Ph, $R_2$=4-(pyrimidin-5-yl)Ph, $R_3$=Me, $R_4$=H, $R_5$=H
204. m=1, n=2, $R_1$=Ph, $R_2$=4-pyridyl, $R_3$=Me, $R_4$=H, $R_5$=H
205. m=1, n=2, $R_1$=Ph, $R_2$=4-pyridyl, $R_3$=Me, $R_4$=H, $R_5$=H
206. m=1, n=2, $R_1$=Ph, $R_2$=4-(thiophen-2-yl)Ph, $R_3$=Me, $R_4$=H, $R_5$=H
207. m=1, n=2, $R_1$=Ph, $R_2$=4-OHPh, $R_3$=Et, $R_4$=H, $R_5$=H
208. m=1, n=2, $R_1$=Ph, $R_2$=4-OHPh, $R_3$=Et, $R_4$=H, $R_5$=H
209. m=1, n=2, $R_1$=4-$CF_3$Ph, $R_2$=4-OHPh, $R_3$=Me, $R_4$=H, $R_5$=H
210. m=1, n=2, $R_1$=Ph, $R_2$=4-(pyridin-3-yl)Ph, $R_3$=Me, $R_4$=H, $R_5$=H
211. m=1, n=2, $R_1$=Ph, $R_2$=4-(pyridin-3-yl)Ph, $R_3$=Me, $R_4$=H, $R_5$=H
212. m=1, n=2, $R_1$=Ph, $R_2$=4-IPh, $R_3$=Me, $R_4$=H, $R_5$=H
213. m=1, n=2, $R_1$=Ph, $R_2$=4-IPh, $R_3$=Me, $R_4$=H, $R_5$=H
214. m=1, n=2, $R_1$=Ph, $R_2$=4-FPh, $R_3$=Me, $R_4$=H, $R_5$=H
215. m=1, n=2, $R_1$=Ph, $R_2$=4-FPh, $R_3$=Me, $R_4$=H, $R_5$=H
216. m=1, n=2, $R_1$=Ph, $R_2$=4-SHPh, $R_3$=Me, $R_4$=H, $R_5$=H
217. m=1, n=2, $R_1$=Ph, $R_2$=4-SHPh, $R_3$=Me, $R_4$=H, $R_5$=H
218. m=1, n=2, $R_1$=Ph, $R_2$=4-BrPh, $R_3$=Me, $R_4$=H, $R_5$=H
219. m=1, n=2, $R_1$=Ph, $R_2$=4-BrPh, $R_3$=Me, $R_4$=H, $R_5$=H
220. m=1, n=2, $R_1$=Ph, $R_2$=4-$NH_2$Ph, $R_3$=Me, $R_4$=H, $R_5$=H
221. m=1, n=2, $R_1$=Ph, $R_2$=4-$NH_2$Ph, $R_3$=Me, $R_4$=H, $R_5$=H
222. m=1, n=2, $R_1$=Ph, $R_2$=4-$NO_2$Ph, $R_3$=Me, $R_4$=H, $R_5$=H
223. m=1, n=2, $R_1$=Ph, $R_2$=4-OHPh, $R_3$=Me, $R_4$=H, $R_5$=H
224. m=1, n=2, $R_1$=Ph, $R_2$=4-OHPh, $R_3$=Me, $R_4$=H, $R_5$=H
225. m=1, n=2, $R_1$=Ph, $R_2$=4-OHPh, $R_3$=Me, $R_4$=3-(4-hydroxyphenyl)propyl, $R_5$=H
226. m=1, n=2, $R_1$=Ph, $R_2$=4-OHPh, $R_3$=Me, $R_4$=3-(4-hydroxyphenyl)propyl, $R_5$=H
227. m=1, n=2, $R_1$=3,4-diFPh, $R_2$=benzofurazan, $R_3$=Me, $R_4$=H, $R_5$=H
228. m=1, n=2, $R_1$=3,4-diFPh, $R_2$=benzimidazole, $R_3$=Me, $R_4$=H, $R_5$=H
229. m=1, n=2, $R_1$=3,4-diFPh, $R_2$=4-ureaphenyl, $R_3$=Me, $R_4$=H, $R_5$=H
230. m=1, n=2, $R_1$=3,4-diFPh, $R_2$=4-(sulfonamide)Ph, $R_3$=Me, $R_4$=H, $R_5$=H
231. m=1, n=2, $R_1$=3,4-diFPh, $R_2$=4-($CONH_2$)Ph, $R_3$=Me, $R_4$=H, $R_5$=H
232. m=1, n=2, $R_1$=3,4-diFPh, $R_2$=quinoxaline, $R_3$=Me, $R_4$=H, $R_5$=H
233. m=1, n=2, $R_1$=3,4-diFPh, $R_2$=1H-indazol-6-yl, $R_3$=Me, $R_4$=H, $R_5$=H
234. m=1, n=2, $R_1$=3,4-diFPh, $R_2$=1H-indazol-5-yl, $R_3$=Me, $R_4$=H, $R_5$=H
235. m=1, n=2, $R_1$=3,4-diFPh, $R_2$=3-ureaphenyl, $R_3$=Me, $R_4$=H, $R_5$=H
236. m=1, n=2, $R_1$=3,4-diFPh, $R_2$=3-(sulfonamide)Ph, $R_3$=Me, $R_4$=H, $R_5$=H
237. m=1, n=2, $R_1$=3,4-diFPh, $R_2$=3-($CONH_2$)Ph, $R_3$=Me, $R_4$=H, $R_5$=H
238. m=1, n=2, $R_1$=3,4-diFPh, $R_2$=2-$NH_2$Ph, $R_3$=Me, $R_4$=H, $R_5$=H
239. m=1, n=2, $R_1$=4-FPh, $R_2$=acetanilide, $R_3$=Me, $R_4$=H, $R_5$=H
240. m=1, n=2, $R_1$=4-BrPh, $R_2$=4-$NH_2$Ph, $R_3$=Me, $R_4$=H, $R_5$=H
241. m=1, n=2, $R_1$=4-FPh, $R_2$=3-$NH_2$Ph, $R_3$=Me, $R_4$=H, $R_5$=H
242. m=1, n=2, $R_1$=4-FPh, $R_2$=$NH_2$ClPh, $R_3$=Me, $R_4$=H, $R_5$=H
243. m=1, n=2, $R_1$=Ph, $R_2$=4-pyridinePh, $R_3$=Me, $R_4$=H, $R_5$=H
244. m=1, n=2, $R_1$=3,4-diFPh, $R_2$=4-(1-methyl-1H-pyrazol-5-yl)Ph, $R_3$=Me, $R_4$=H, $R_5$=H
245. m=1, n=2, $R_1$=3,4-diFPh, $R_2$=2-(1-methyl-1H-pyrazol-5-yl)Ph, $R_3$=Me, $R_4$=H, $R_5$=H
246. m=1, n=2, $R_1$=1H-indole-3-yl, $R_2$=4-FPh, $R_3$=Me, $R_4$=H, $R_5$=H
247. m=1, n=2, $R_1$=3,4-diFPh, $R_2$=trifluoromethylpyridine, $R_3$=Me, $R_4$=H, $R_5$=H
248. m=1, n=2, $R_1$=4-FPh, $R_2$=4-FPh, $R_3$=$CH_2OH$, $R_4$=H, $R_5$=H 249. m=1, n=2, $R_1$=Ph, $R_2$=4-FPh, $R_3$=Me, $R_4$=H, $R_5$=H
250. m=1, n=2, $R_1$=3,4-diFPh, $R_2$=3-$CF_3$Ph, $R_3$=Me, $R_4$=H, $R_5$=H
251. m=1, n=2, $R_1$=4-FPh, $R_2$=$CF_3NO_2$Ph, $R_3$=Me, $R_4$=H, $R_5$=H
252. m=1, n=2, $R_1$=3,4-diFPh, $R_2$=benzothiazole, $R_3$=Me, $R_4$=H, $R_5$=H
253. m=1, n=2, $R_1$=3,4-diFPh, $R_2$=phthalide, $R_3$=Me, $R_4$=H, $R_5$=H
254. m=1, n=2, $R_1$=3,4-diFPh, $R_2$=1-methyl-1,3-dihydro-2H-benzimidazol-2-one, $R_3$=Me, $R_4$=H, $R_5$=H
255. m=1, n=2, $R_1$=3,4-diFPh, $R_2$=benzoxaol-7-yl, $R_3$=Me, $R_4$=H, $R_5$=H
256. m=1, n=2, $R_1$=3,4-diFPh, $R_2$=benzoxaol-6-yl, $R_3$=Me, $R_4$=H, $R_5$=H
257. m=1, n=2, $R_1$=3,4-diFPh, $R_2$=COOHPh, $R_3$=Me, $R_4$=H, $R_5$=H
258. m=1, n=2, $R_1$=Ph, $R_2$=4-$F_3$COPh, $R_3$=Me, $R_4$=H, $R_5$=H
259. m=1, n=2, $R_1$=3,4-diFPh, $R_2$=isopropoxybenzene, $R_3$=Me, $R_4$=H, $R_5$=H
260. m=1, n=2, $R_1$=Ph, $R_2$=thiophenol, $R_3$=Me, $R_4$=H, $R_5$=H
261. m=1, n=2, $R_1$=3,4-diFPh, $R_2$=thioanisole, $R_3$=Me, $R_4$=H, $R_5$=H
262. m=1, n=2, $R_1$=4-FPh, $R_2$=methyl phenyl sulfoxide, $R_3$=Me, $R_4$=H, $R_5$=H
263. m=1, n=2, $R_1$=4-FPh, $R_2$=methyl phenyl sulfone, $R_3$=Me, $R_4$=H, $R_5$=H
264. m=1, n=2, $R_1$=3,4-diFPh, $R_2$=tert-butylbenzene, $R_3$=Me, $R_4$=H, $R_5$=H
265. m=1, n=2, $R_1$=3,4-diFPh, $R_2$=3-$NH_2$Ph, $R_3$=Me, $R_4$=H, $R_5$=H
266. m=1, n=2, $R_1$=3,4-diFPh, $R_2$=N,N-dimethylaniline, $R_3$=Me, $R_4$=H, $R_5$=H
267. m=1, n=2, $R_1$=3,4-diFPh, $R_2$=3-ClPh, $R_3$=Me, $R_4$=H, $R_5$=H
268. m=1, n=2, $R_1$=3,4-diFPh, $R_2$=2-ClPh, $R_3$=Me, $R_4$=H, $R_5$=H
269. m=1, n=2, $R_1$=3,4-diFPh, $R_2$=2,4-diClPh, $R_3$=Me, $R_4$=H, $R_5$=H
270. m=1, n=2, $R_1$=3,4-diFPh, $R_2$=3,3-diClPh, $R_3$=Me, $R_4$=H, $R_5$=H
271. m=1, n=2, $R_1$=3,4-diFPh, $R_2$=2,3-diClPh, $R_3$=Me, $R_4$=H, $R_5$=H
272. m=1, n=2, $R_1$=3,4-diFPh, $R_2$=3,4-diClPh, $R_3$=Me, $R_4$=H, $R_5$=H
273. m=1, n=2, $R_1$=3,4-diFPh, $R_2$=3,4-$CF_3$ClPh, $R_3$=Me, $R_4$=H, $R_5$=H
274. m=1, n=2, $R_1$=3,4-diFPh, $R_2$=4-[(methylsulfonyl)amino]Ph, $R_3$=Me, $R_4$=H, $R_5$=H
275. m=1, n=2, $R_1$=4-FPh, $R_2$=4-[(methylsulfonyl)amino]Ph, $R_3$=Me, $R_4$=H, $R_5$=H
276. m=1, n=2, $R_1$=4-BrPh, $R_2$=acetanilide, $R_3$=Me, $R_4$=H, $R_5$=H
277. m=1, n=2, $R_1$=4-FPh, $R_2$=1H-indole-3-yl, $R_3$=Me, $R_4$=H, $R_5$=H
278. m=1, n=2, $R_1$=4-FPh, $R_2$=2-pyridine, $R_3$=Me, $R_4$=H, $R_5$=H
279. m=1, n=2, $R_1$=4-FPh, $R_2$=3-pyridine, $R_3$=Me, $R_4$=H, $R_5$=H
280. m=1, n=2, $R_1$=3,4-diFPh, $R_2$=pyridine, $R_3$=Me, $R_4$=H, $R_5$=H
281. m=1, n=2, $R_1$=3,4-diFPh, $R_2$=3-(1-methyl-1H-pyrazol-5-yl)Ph, $R_3$=Me, $R_4$=H, $R_5$=H
282. m=1, n=2, $R_1$=3,4-diFPh, $R_2$=2-pyridinePh, $R_3$=Me, $R_4$=H, $R_5$=H
283. m=1, n=2, $R_1$=3,4-diFPh, $R_2$=3-pyridinePh, $R_3$=Me, $R_4$=H, $R_5$=H
285. m=1, n=2, $R_1$=4-FPh, $R_2$=benzylamine, $R_3$=Me, $R_4$=H, $R_5$=H
286. m=1, n=2, $R_1$=4-FPh, $R_2$=4-BrPh, $R_3$=COOH, $R_4$=H, $R_5$=H
287. m=1, n=2, $R_1$=4-FPh, $R_2$=4-BrPh, $R_3$=2-amino-3-(1-benzyl-1H-imidazol-4-yl)propanoate, $R_4$=H, $R_5$=H
288. m=1, n=2, $R_1$=Ph, $R_2$=4-OHPh, $R_3$=Me, $R_4$=tert-butyl acetate, $R_5$=H
289. m=1, n=2, $R_1$=Ph, $R_2$=4-$NO_2$Ph, $R_3$=Me, $R_4$=benzyl acetate, $R_5$=H
290. m=1, n=2, $R_1$=Ph, $R_2$=4-IPh, $R_3$=Me, $R_4$=benzyl acetate, $R_5$=H
291. m=1, n=2, $R_1$=Ph, $R_2$=4-$NH_2$Ph, $R_3$=Me, $R_4$=benzyl acetate, $R_5$=H
292. m=1, n=2, $R_1$=4-FPh, $R_2$=Ph, $R_3$=ethylbenzene, $R_4$=H, $R_5$=H
293. m=1, n=2, $R_1$=4-$NO_2$Ph, $R_2$=4-FPh, $R_3$=Me, $R_4$=H, $R_5$=carbonyl
294. m=1, n=2, $R_1$=4-CNPh, $R_2$=4-FPh, $R_3$=Me, $R_4$=H, $R_5$=carbonyl
297. m=1, n=2, $R_1$=3,4-diFPh, $R_2$=3-Cl-4-($CONH_2$)Ph, $R_3$=Me, $R_4$=H, $R_5$=H
298. m=1, n=2, $R_1$=4-FPh, $R_2$=4-($CONH_2$)Ph, $R_3$=Me, $R_4$=H, $R_5$=H
299. m=1, n=2, $R_1$=3,4-diFPh, $R_2$=3-F-4-($CONH_2$)Ph, $R_3$=Me, $R_4$=H, $R_5$=H
300. m=1, n=2, $R_1$=3,5-diFPh, $R_2$=4-($CONH_2$)Ph, $R_3$=Me, $R_4$=H, $R_5$=H
301. m=1, n=2, $R_1$=3-($CONH_2$)Ph, $R_2$=4-FPh, $R_3$=Me, $R_4$=H, $R_5$=H
302. m=1, n=2, $R_1$=4-($NHCONH_2$)Ph, $R_2$=4-FPh, $R_3$=Me, $R_4$=H, $R_5$=H
303. m=1, n=2, $R_1$=benzimidazole, $R_2$=4-FPh, $R_3$=Me, $R_4$=H, $R_5$=H
304. m=1, n=2, $R_1$=4-($CONH_2$)Ph, $R_2$=4-FPh, $R_3$=Me, $R_4$=H, $R_5$=H
305. m=1, n=2, $R_1$=quinoxaline, $R_2$=4-[($SO_2$)$NH_2$]Ph, $R_3$=Me, $R_4$=H, $R_5$=H
306. m=1, n=2, $R_1$=3-($NHCONH_2$)Ph, $R_2$=4-FPh, $R_3$=Me, $R_4$=H, $R_5$=H
307. m=1, n=2, $R_1$=quinoxaline, $R_2$=4-($CONH_2$)Ph, $R_3$=Me, $R_4$=H, $R_5$=H
308. m=1, n=2, $R_1$=quinoxaline, $R_2$=4-FPh, $R_3$=Me, $R_4$=H, $R_5$=H
309. m=1, n=2, $R_1$=3-FPh, $R_2$=4-($CONH_2$)Ph, $R_3$=Me, $R_4$=H, $R_5$=H
310. m=1, n=2, $R_1$=3-$NH_2$Ph, $R_2$=4-FPh, $R_3$=Me, $R_4$=H, $R_5$=H
311. m=1, n=2, $R_1$=3,4-diFPh, $R_2$=benzo[d]isoxazole, $R_3$=Me, $R_4$=H, $R_5$=H
312. m=1, n=2, $R_1$=3,4-diFPh, $R_2$=1H-benzo[d][1,2,3]triazole, $R_3$=Me, $R_4$=H, $R_5$=H
313. m=1, n=2, $R_1$=Ph, $R_2$=4-$OCH_3$Ph, $R_3$=Me, $R_4$=H, $R_5$=H Compounds of formula (II) include the following compounds:

295. m=1, n=2, $R_1$=Ph, $R_2$=Ph, $R_3$=Me, $R_4$=H, $R_5$=H (racemic)
296. m=1, n=2, $R_1$=Ph, $R_2$=Ph, $R_3$=Me, $R_4$=H, $R_5$=H (isolated enantiomer)

Definitions

The term "aryl" refers to aromatic groups having 6 to 24 carbon atoms, and "substituted aryl" refers to aryl groups further bearing one or more substituents. The aryl groups may have one ring or two or more fused rings.

The term "alkyl" refers to straight or branched chain alkyl radicals having 1 to 19 carbon atoms, and "substituted alkyl" refers to alkyl radicals further bearing one or more substituents.

The term "lower alkyl" refers to straight or branched chain alkyl radicals having in the range of 1 to 4 carbon atoms.

The term "cycloalkyl" refers to cyclic ring-containing moieties containing 3 to 8 carbon atoms, and "substituted cycloalkyl" refers to cycloalkyl moieties further bearing one or more substituents.

The term "carboxamide" refers to a moiety of the general formula R—(C═O)—N(R')(R"), wherein R, R', and R" independently represent organic groups or hydrogen atoms. As used herein, any of R, R' and R" may be $R_1$ or $R_2$ as defined above in formula (I).

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents.

The term "heteroaryl" refers to aromatic groups containing one or more heteroatoms as part of the ring structure and having 3 to 24 carbon atoms, and "substituted heteroaryl" refers to heteroaryl moieties further bearing one or more substituents. Heteroaryl groups may have one ring or two or more fused rings.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents.

Heterocycle groups may have one ring or two or more fused rings.

The term "linked" refers to a first moiety (e.g., an aryl group or a heteroaryl group) that is directly bound to a second moiety (e.g., a second aryl group or heteroaryl group) via a single bond.

Pharmaceutically acceptable salts include $Cl^-$, $Br^-$, $I^-$, $NO_2^-$, $HSO_4^-$, $SO_4^-$, $HPO_4^-$, $PO_4^{2-}$, ethanesulfonate, triflurομethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar acid addition salts. The above salt forms may be in some cases hydrates or solvates with alcohols and other solvents.

Pharmaceutical Compositions

Also disclosed herein are pharmaceutical compositions comprising a compound of formula (I) and one or more pharmaceutically acceptable excipients. For example, the pharmaceutical composition may include a pharmaceutically acceptable additive, such as a stabilizer, buffer, salt, preservative, filler, flavor enhancer and the like, as known to those skilled in the art. Representative buffers include phosphates, carbonates, and citrates. Exemplary preservatives include EDTA, EGTA, BHA, and BHT.

The pharmaceutical composition disclosed herein may be administered by inhalation (i.e., intranasally as an aerosol or inhalation solution or suspension); topically (i.e., in the form of an ointment, cream or lotion); orally (i.e., in solid or liquid form (tablet, capsule, gel cap, time release capsule, powder, solution, or suspension in aqueous or non-aqueous liquid); intravenously as an infusion or injection (i.e., as a solution, suspension or emulsion in a pharmaceutically acceptable carrier); subcutaneously as an infusion or injection (i.e., as a solution, suspension or emulsion in a pharmaceutically acceptable carrier) or as a depot formulation; transdermally (e.g., via a transdermal patch), rectally (e.g., as a suppository), or intraperitoneally.

There is no limitation in the route of administration or dosage form, and the composition may be administered in accordance with specific form of the preparation, age, sex and the other conditions of a patient, severity of disease, etc. For example, in the case of tablet, pill, solution, suspension, emulsion, granule and capsule, the composition is orally administered. In the case of injection, the composition is intravenously administered alone or in a mixture with conventional replacement fluid such as glucose and amino acids, and if necessary, and the preparation alone may be also administered intramuscularly, intracutaneously, subcutaneously or intraperitoneally.

The compounds disclosed herein can be administered alone, combined with a pharmaceutically acceptable excipient, or co-administered with a second drug. Co-administration may provide a similar or synergistic effect. A compound of formula (I) or a pharmaceutically acceptable salt thereof can be administered subcutaneously as an infusion, injection, or depot formulation; intramuscularly as an infusion or injection; intravenously as an infusion or injection; transdermally, orally, topically, intranasally, intrapulmonary, intraperitoneally, or rectally.

The dose of the pharmaceutical composition of the present invention is appropriately selected in accordance with dosage regimen, age, sex and the other conditions of a patient. The amount to be administered depends to some extent on the lipophilicity of the specific compound selected, since it is expected that this property of the compound will cause it to partition into fat deposits of the subject. The precise amount to be administered can be determined by the skilled practitioner in view of desired dosages, side effects and medical history of the patient and the like.

The pharmaceutical composition may comprise a compound of formula (I) or an enantiomer or racemate thereof, or pharmaceutically acceptable salt thereof, and a pharmaceutically acceptable additive or a pharmaceutically acceptable excipient.

Treatment of Substance Use Disorders, Drug Dependence, or Drug Abuse/Addiction

VMAT2 is considered as a valid target for the development of treatments for the abuse of drugs, including, for example, methamphetamine (METH), amphetamine, cocaine, methylphenidate, and opiate abuse and use disorders. For example, METH decreases vesicular DA sequestration by inhibiting vesicular uptake through VMAT2 ($IC_{50}$=14.9 μM) and by diffusing across the vesicular membranes to decrease the pH gradient, resulting in the loss of free energy needed for monoamine transport.

Lobelane competitively inhibits $[^3H]$DA uptake into rat brain vesicles via interaction with VMAT2 ($K_i$=45 nM), decreases METH-evoked DA overflow from rat striatal slices, and decreases METH self-administration, but does not act as a psychostimulant, suggesting that it has potential as a novel treatment for METH abuse. Nor-Lobelane ($K_i$=44 nM) is equipotent with lobelane at VMAT2 in inhibiting $[^3H]$DA uptake.

METH can be considered as a structural fragment of lobelane/nor-lobelane, and introducing bulky substituents onto the N-atom of METH afforded compounds with increased inhibitory potency at VMAT2, reduced the psychostimulant effects of METH, diminishing its abuse potential. Importantly, these new analogs did not increase locomotor activity in rats, indicating they do not act as psychostimulants. Lee, N.-R. et al., Drug and Alcohol Dependence, “Enantiomers of (±)GZ-888 potently and selectively inhibit vesicular monoamine transporter-2 function and methamphetamine-stimulated locomotor activity,” (2016).

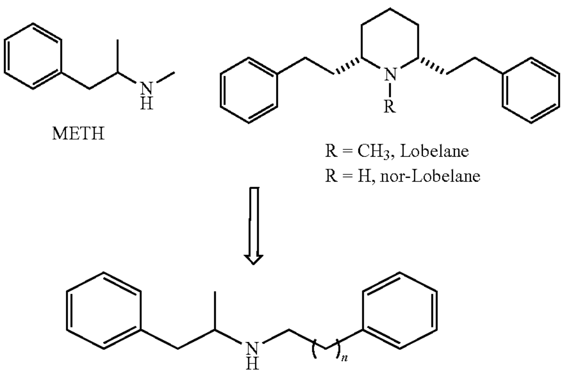

Treatment of a Disease or Pathology of the Central Nervous System or an Eating Disorder Modulation of VMAT2 has potential as a therapeutic for central nervous system diseases or pathologies. Thus, VMAT2 is a target for the development of treatments for a disease or pathology of the central nervous system, including, for example, cognitive disorders, brain trauma, memory loss, psychosis, sleep disorders, obsessive compulsive disorders, panic disorders, myasthenia gravis, Parkinson’s disease, Alzheimer’s disease, schizophrenia, Tourette’s syndrome, Huntington’s disease, attention deficit hyperactivity disorder, hyperkinetic syndrome, chronic nervous exhaustion, narcolepsy, pain, motion sickness, depression, and/or dyskinesias resulting from administration from another pharmaceutical compound.

VMAT2 is also a target for the development of treatments for eating disorders, including, for example, obesity. Compulsive eating is linked to addiction-like neuroadaptive responses in brain reward circuits. Johnson, P. M. et al., “Dopamine D2 receptors in addiction-like reward dysfunction and compulsive eating in obese rats,” Nature Neuroscience, 2010, 13, 635-641. Modulation of VMAT2 may lead to reduced reward responses, diminishing overeating.

A preferred compound is a compound of formula (I), wherein the compound is 3-(4-methoxyphenyl)-N-(1-phenylpropan-2-yl)propan-1-amine or an enantiomer; racemate; or pharmaceutically acceptable salt thereof.

Another preferred compound is a compound of formula (I), wherein the compound is 4-(3-((1-(3,4-difluorophenyl)propan-2-yl)amino)propyl)benzamide.

Another preferred compound is a compound of formula (I), wherein the compound is 4-(3-((1-(3,5-difluorophenyl)propan-2-yl)amino)propyl)benzamide.

Another preferred compound is (S)-3-(4-methoxyphenyl)-N-(1-phenylpropan-2-yl)propan-1-amine hydrochloride.

Another preferred embodiment is a pharmaceutical composition comprising 3-(4-methoxyphenyl)-N-(1-phenylpropan-2-yl)propan-1-amine or an enantiomer; racemate; or pharmaceutically acceptable salt thereof and a pharmaceutically acceptable additive or a pharmaceutically acceptable excipient. A further preferred embodiment is a pharmaceutical composition comprising (S)-3-(4-methoxyphenyl)-N-(1-phenylpropan-2-yl)propan-1-amine hydrochloride and a pharmaceutically acceptable additive or a pharmaceutically acceptable excipient.

Another preferred embodiment is a pharmaceutical composition comprising 4-(3-((1-(3,4-difluorophenyl)propan-2-yl)amino)propyl)benzamide or an enantiomer; racemate; or pharmaceutically acceptable salt thereof and a pharmaceutically acceptable additive or a pharmaceutically acceptable excipient.

Another preferred embodiment is a pharmaceutical composition comprising 4-(3-((1-(3,5-difluorophenyl)propan-2-yl)amino)propyl)benzamide or an enantiomer; racemate; or pharmaceutically acceptable salt thereof and a pharmaceutically acceptable additive or a pharmaceutically acceptable excipient.

Other preferred embodiments of the present invention include

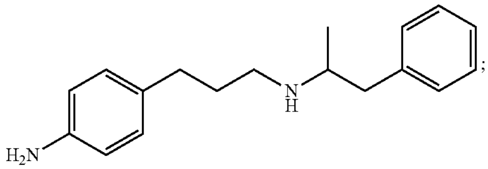
;

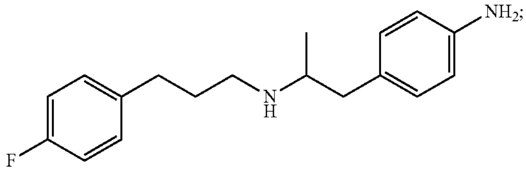
;

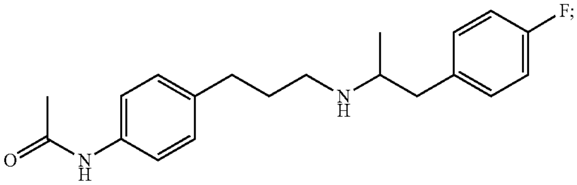
;

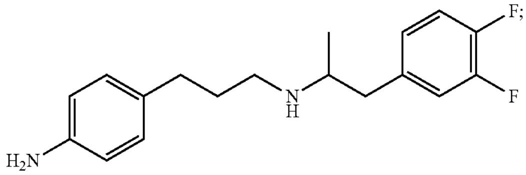
;

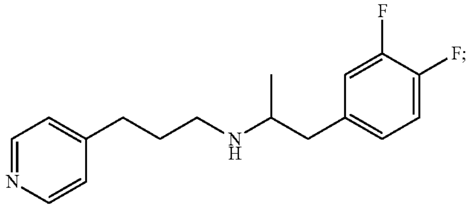
;

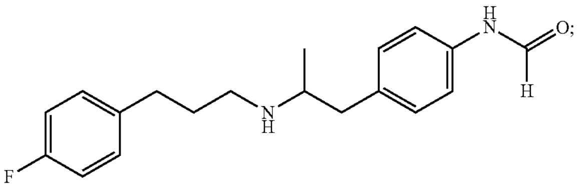
;

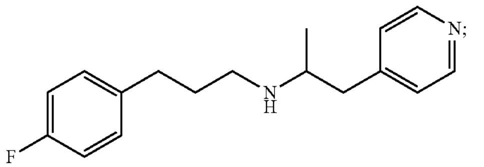
;

-continued
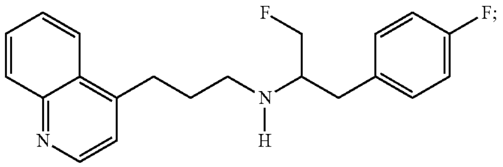
and
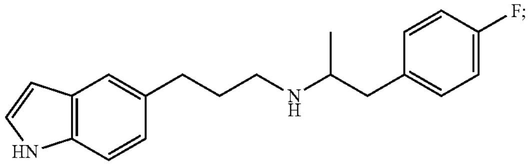
or an enantiomer; racemate; or pharmaceutically acceptable salt thereof.
Other preferred embodiments of the present invention include
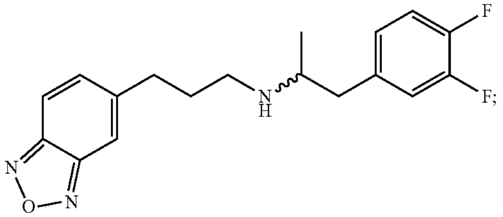
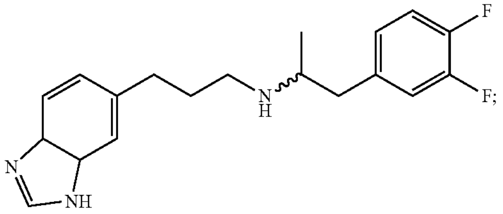
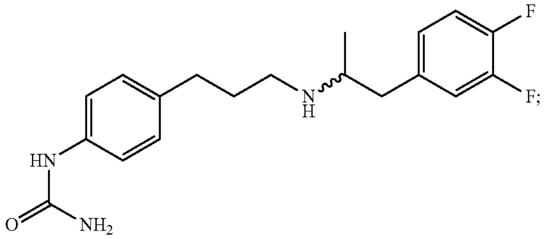
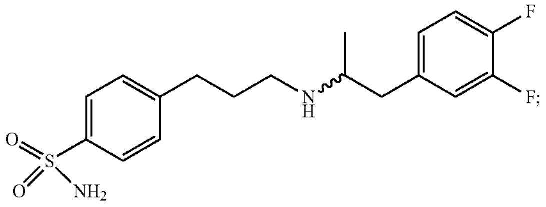
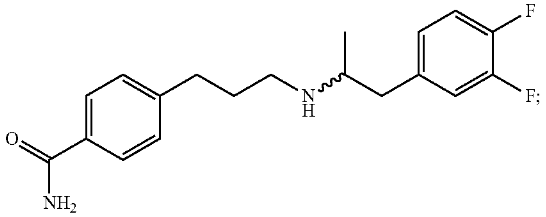
-continued
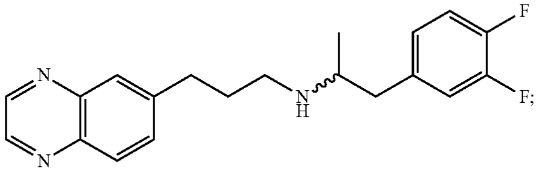
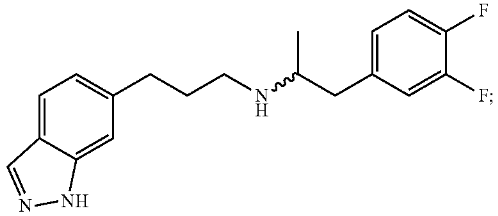
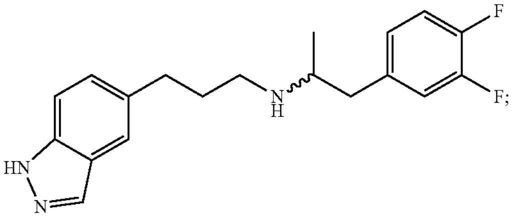
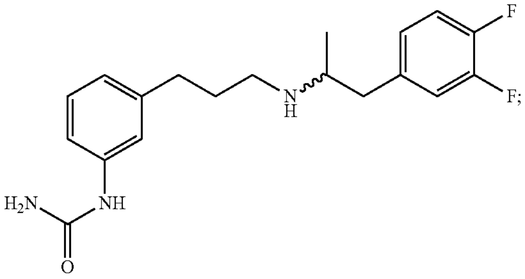
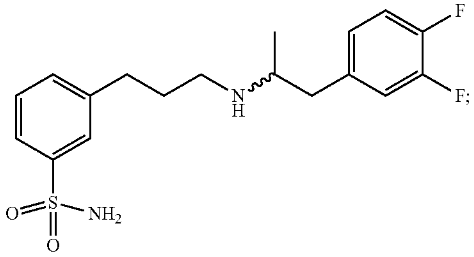
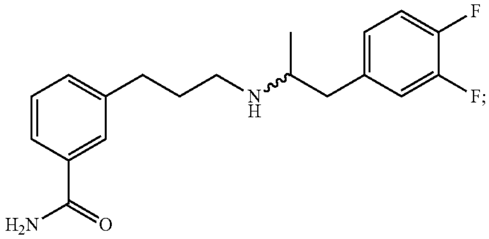
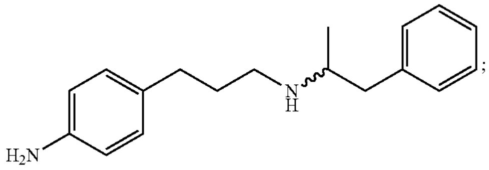
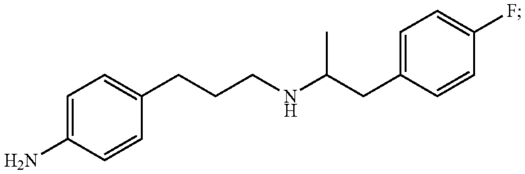

-continued
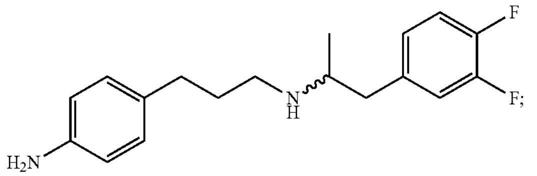
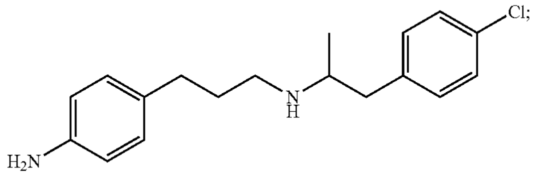
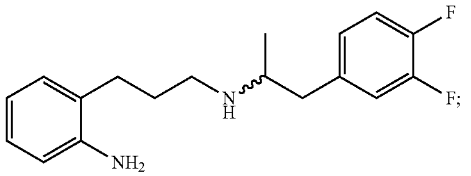
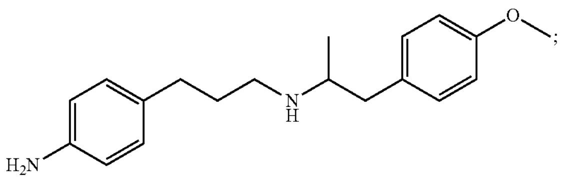
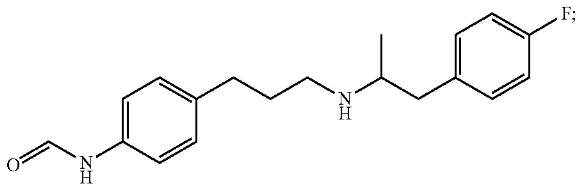
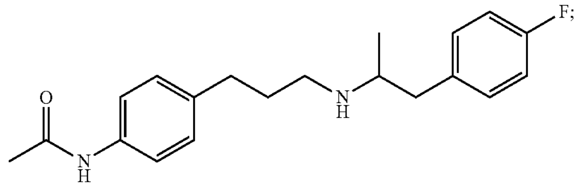
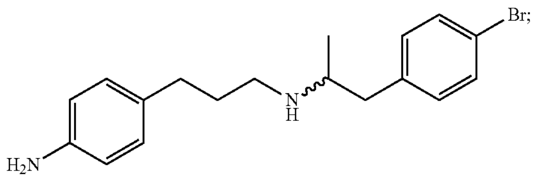
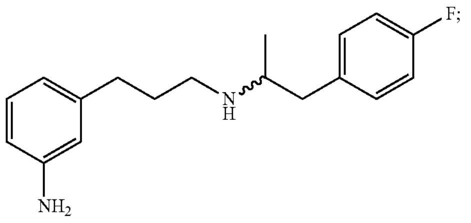
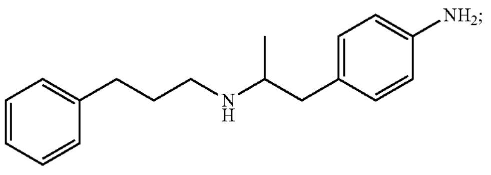
-continued
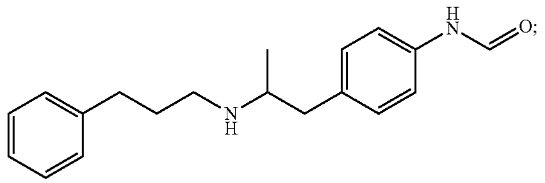
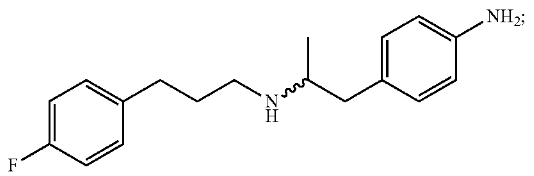
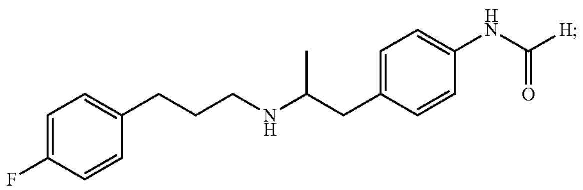
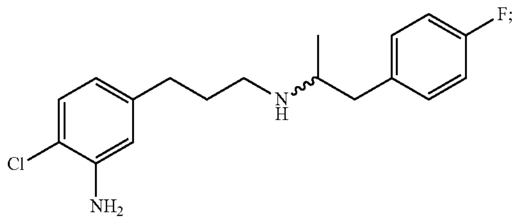
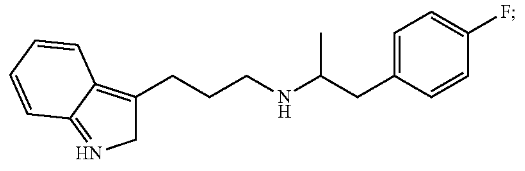
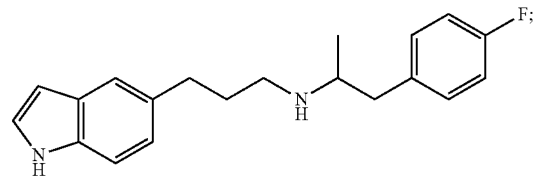
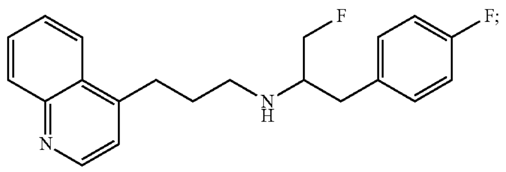
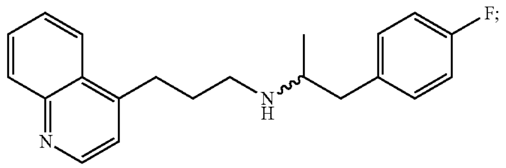
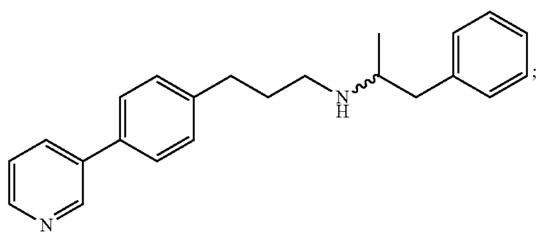

-continued
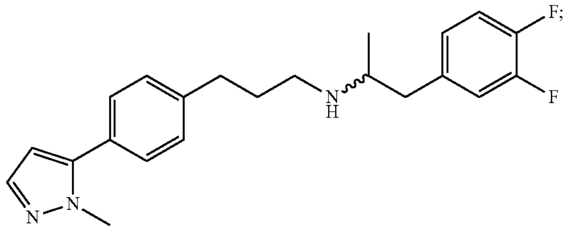
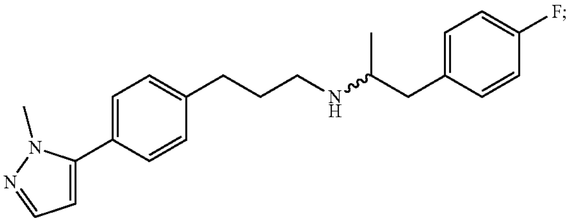
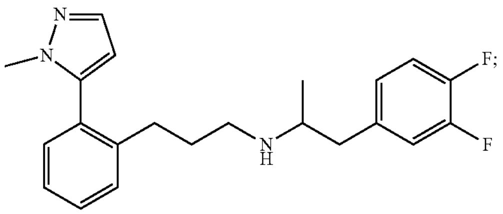
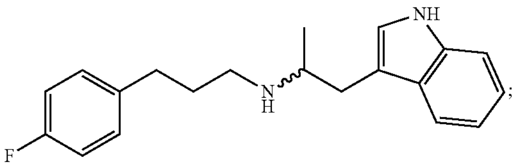
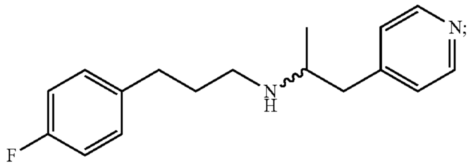
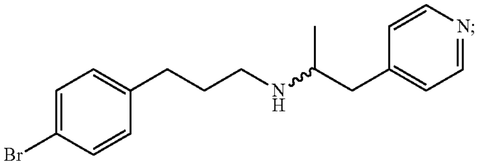
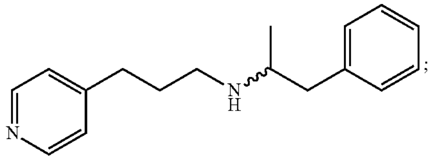
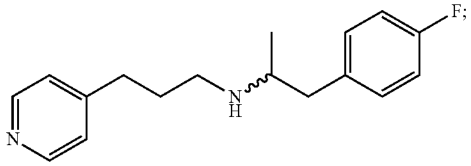
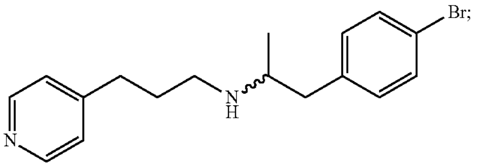
-continued
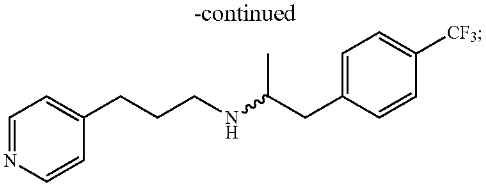
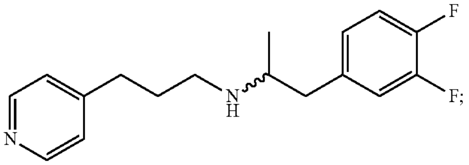
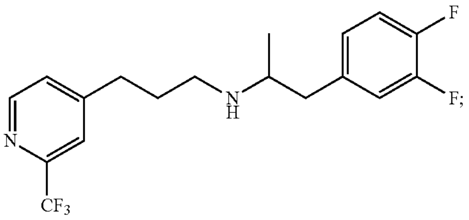
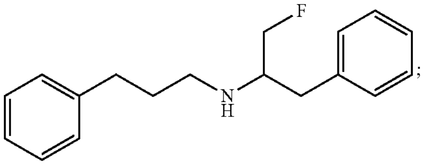
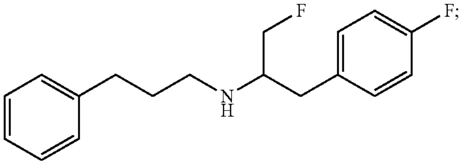
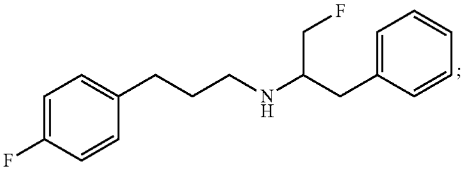
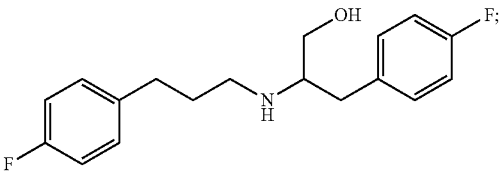
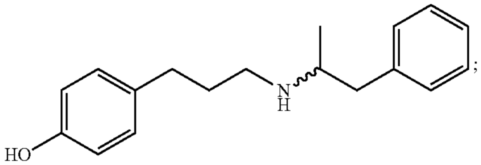
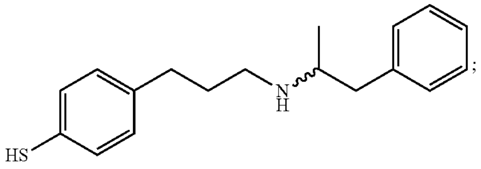
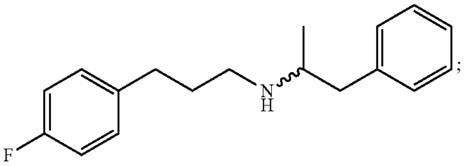

-continued
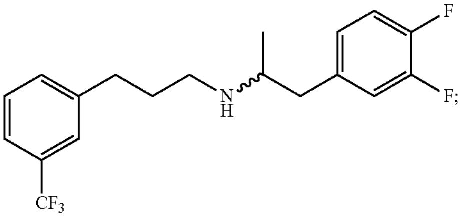
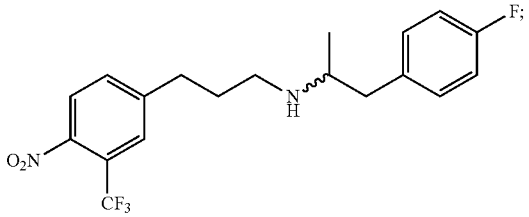
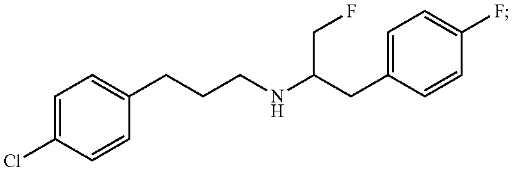
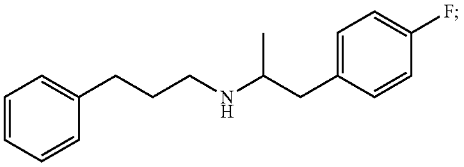
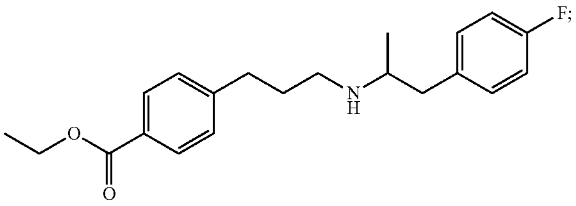
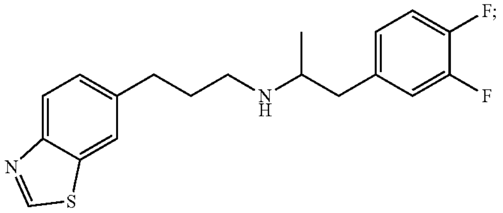
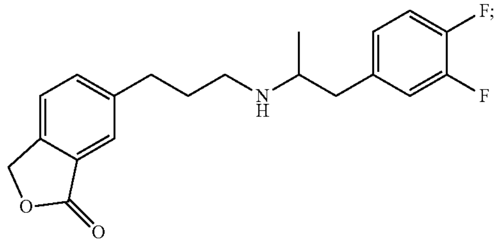
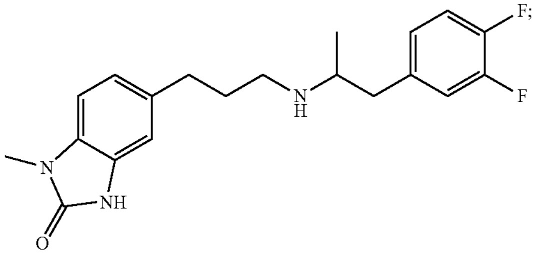
-continued
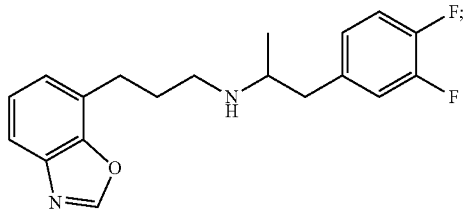
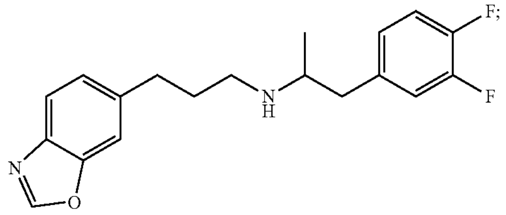
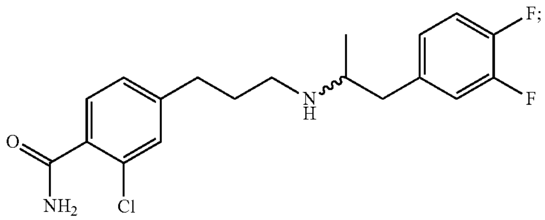
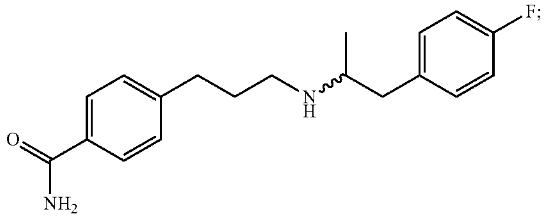
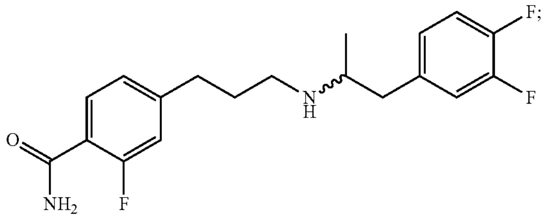
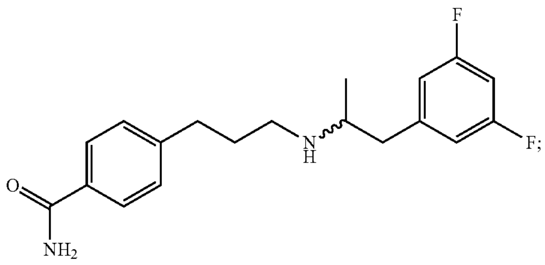
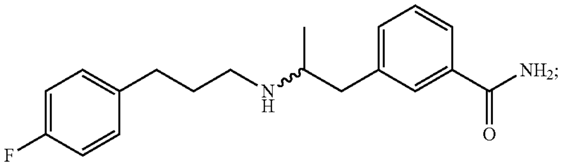
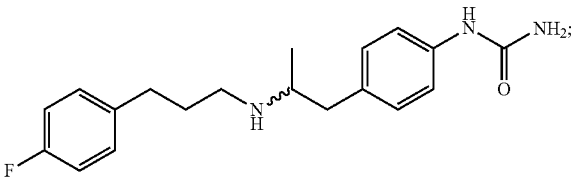

-continued

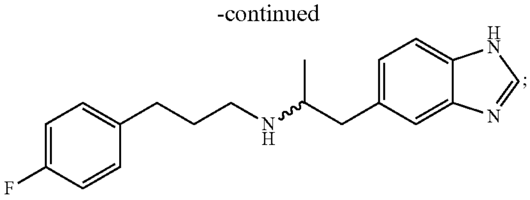
;

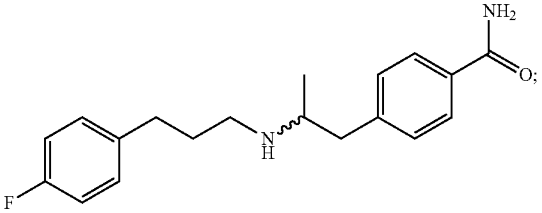
;

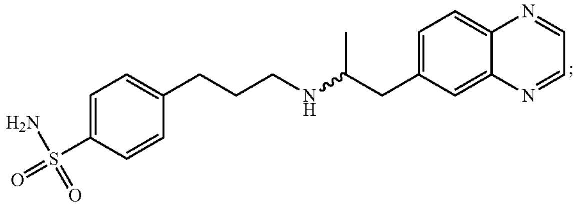
;

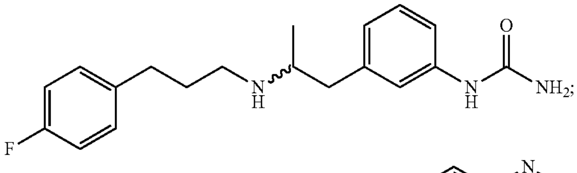
;

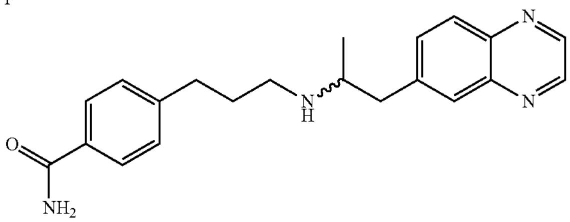
;

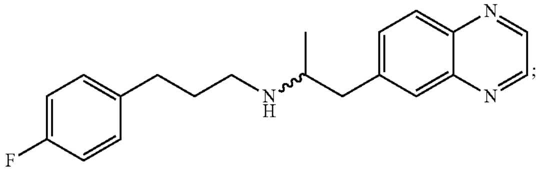
;

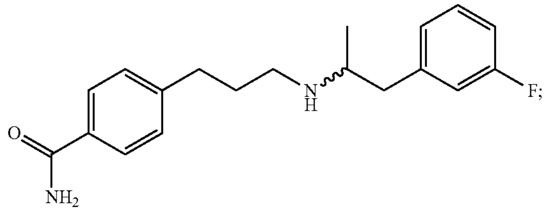
;

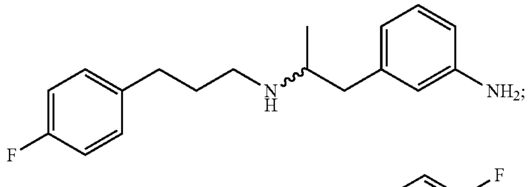
;

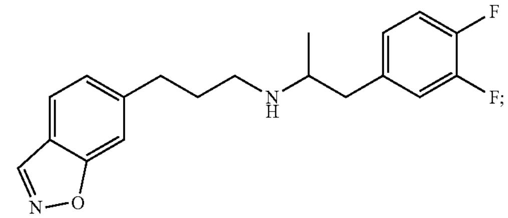
;

-continued

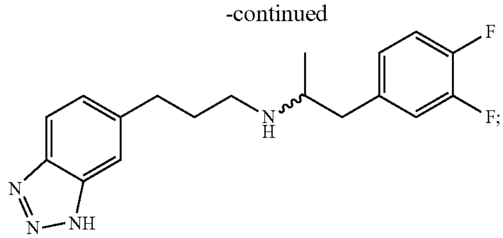
; and

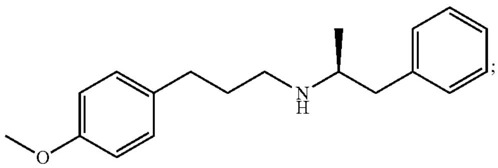
;

or an enantiomer; racemate; or pharmaceutically acceptable salt thereof.

Another preferred embodiment of the invention is a method of treating a disease or pathology of the central nervous system or an eating disorder in an individual in need thereof, wherein the method comprises the step of administering to the individual a compound of formula (I) or a pharmaceutically acceptable salt thereof.

The compounds of the present invention may be used in a method of treating a disease or pathology of the central nervous system, wherein the disease may be cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit hyperactivity disorder, hyperkinetic syndrome, chronic nervous exhaustion, narcolepsy, pain, motion sickness, depression, and/or dyskinesias resulting from administration from another pharmaceutical compound.

The compounds of the present invention may also be used in a method of treating an eating disorder. The eating disorder may be obesity.

The compounds of the present invention may be used in a method of treating one or more substance use disorders, drug dependence/abuse/addiction or withdrawal from drug dependence/abuse/addiction in an individual in need thereof. Substance use disorder and drug dependence/abuse/addiction includes dependence/abuse/addiction of psychostimulants or drugs that release dopamine. For example, the drug which the individual is using and/or dependent upon may be amphetamine, methamphetamine, and other drugs that release dopamine.

EXAMPLES

A series of VMAT2 inhibitors were synthesized and evaluated for their activity at VMAT2, dopamine transporters (DAT), and serotonin transporters (SERT) using rat striatum, hERG channels expressed by HEK-293 cells, and for their effect on METH-stimulated locomotor activity in rats. Compounds of the invention exhibited affinity at VMAT2 as well as selectivity at VMAT2 over hERG, DAT, and SERT. Further, a significant reduction of METH-stimulated locomotor activity was observed after administration of the compounds.

Example 1

Synthesis of Compound 10. (S)-3-(4-methoxyphenyl)-N-(1-phenylpropan-2-yl)propan-1-amine To a solution of phenyllithium (50 mL, 1.8 M in dibutyl ether) in THF (50 mL) was added (R)-propylene oxide (5 g) dropwise at −78° C. The resulting mixture was stirred at the same temperature for 1 hr before warmed to room temperature. After stirred at room temperature overnight, the reaction was quenched by adding saturated $NH_4Cl$ aqueous solution. The aqueous phase was extracted with ethyl acetate (3×50 mL) and the combined organic layers were washed with brine (100 mL), dried over anhydrous $Na_2SO_4$, filtered and concentrated under reduced pressure. The crude product was chromatographed on silica (hexanes/ethyl acetate 10:1 to 3:1) to afford (R)-1-phenylpropan-2-ol (10.4 g) as a colorless oil.

To a solution of (R)-1-phenylpropan-2-ol (4.16 g, 30.50 mmol) and triethylamine (7.72 g, 10.64 mL, 76.27 mmol) in dichloromethane (100 mL) was added methanesulfonyl chloride (4.54 gm, 3.07 mL, 39.65 mmol) dropwise at 0° C. The resulting mixture was stirred at 0° C. for 15 min. Dichloromethane (100 mL) was added to the mixture and then washed with water (2×150 mL). The organic layer was dried over anhydrous $Na_2SO_4$, filtered and concentrated under reduced pressure. The resulting light yellow oil was mixed with sodium azide (5.95 g, 91.5 mmol) in DMF (40 mL) and heated at 55° C. for 3 hrs. The reaction mixture was diluted with diethyl ether (150 mL) and washed with water (2×100 mL) and brine (100 mL). The organic layer was dried over anhydrous $Na_2SO_4$, filtered and concentrated under reduced pressure. The crude product was chromatographed on silica (hexanes/ethyl acetate 50:1 to 20:1) to afford (S)-(2-azidopropyl)benzene (4.38 g) as a colorless oil.

To a solution of (S)-(2-azidopropyl)benzene (4.0 g, 24.81 mmol) in THF (90 mL) and water (10 mL) was added triphenylphosphine (9.11 g, 34.74 mmol) at room temperature. The resulting mixture was stirred for 18 hrs and water (50 mL) was added. The resulting mixture was treated with HCl (1.0 M) to pH ~1 and the aqueous phase was extracted with diethyl ether (3×100 mL) and dichloromethane (2×100 mL). NaOH (15%) was added dropwise to the aqueous phase to adjust the pH to about 11 and extracted with dichloromethane (5×60 mL). The combined organic layers were dried over anhydrous $Na_2SO_4$, filtered and concentrated under reduced pressure to afford (S)-1-phenylpropan-2-amine as a colorless oil. The crude amino product (3.03 g, 22.41 mmol) was mixed with 3-(4-methoxyphenyl)propanoic acid (4.44 g, 24.65 mmol), and HOBt (3.63 g, 26.89 mmol) in dichloromethane (60 mL) at room temperature. Triethylamine (5.67 g, 56.03 mmol) was added followed by EDCI (5.15 g, 26.89 mmol). The resulting mixture was stirred overnight. The reaction mixture was diluted with dichloromethane (100 mL) and washed with water (3×50 mL), and brine (50 mL). The organic layer was dried over anhydrous $Na_2SO_4$, filtered and concentrated under reduced pressure. The crude product was chromatographed on silica (dichloromethane/ethyl acetate 10:1) to afford (S)-3-(4-methoxyphenyl)-N-(1-phenylpropan-2-yl)propanamide (6.18 g) as a white solid. (S)-3-(4-Methoxyphenyl)-N-(1-phenylpropan-2-yl)propanamide (5.0 g, 16.81 mmol) in THF was cooled to 0° C. LAH (60 mL, 1.0 M in THF) was added dropwise and the resulted reaction mixture was heated at reflux for 6 hrs. After cooled to 0° C., water (2.28 mL) was carefully added, followed by NaOH (15%, 2.28 mL) and water (6.84 mL). The resulted mixture was warmed to room temperature and stirred for 2 hrs. Filtered over celite and washed with ethyl acetate. The filtrate was concentrated under reduced pressure and the crude product was chromatographed on silica (dichloromethane/methanol 30:1 to 10:1) to afford compound 10 (4.3 g) as a white solid.

Example 2

[$^3$H]Dihydrotetrabenazine ([$^3$H]DTBZ) Binding Assay, Vesicular Preparation

Synaptic vesicles were prepared from rat brain using a modification of a previously described procedure (Teng et al., 1998). Briefly, fresh whole brain (excluding cerebellum) was homogenized using a Teflon pestle (clearance 0.003 inches) with 7 vertical strokes at 800 rpm in 20 vol of ice-cold 0.32 M sucrose and centrifuged at 1000 g for 12 min at 4° C. The resulting supernatant (Si) was then centrifuged at 22,000 g for 10 min at 4° C. The synaptosomal pellets ($P_2$) were homogenized in 18 mL of ice-cold Milli-Q water and exposed for 5 min for lysing synaptosomes. Osmolarity was restored by addition of 2 mL of 25 mM HEPES with 100 mM dipotassium tartrate (pH 7.5). Samples were centrifuged at 20,000 g for 20 min at 4° C. to remove lysed synaptosomal membranes. $MgSO_4$ (1 mM) was added to the supernatant ($S_3$), and was centrifuged at 100,000 g for 45 min at 4° C. The final vesicular pellets ($P_4$) were resuspended in ice-cold assay buffer (see below) providing ~15 μg protein/100 μL, determined by the method of Bradford (1976) using bovine serum albumin as the standard. Aliquot parts (100 μL) of suspension of vesicle membrane protein were incubated in assay buffer (25 mM HEPES, 100 mM dipotassium tartrate, 5 mM $MgSO_4$, 0.1 mM EDTA and 0.05 mM EGTA, pH 7.5, at 25° C.) in the presence of 3 nM [$^3$H]DTBZ and at least 7 concentrations (1 nM-1 mM) of compound for 1 hr at room temperature. Nonspecific binding was determined in the presence of 20 μM tetrabenazine, a standard compound. Assays were performed in duplicate using a 96-well plate format. Reactions were terminated by filtration of samples on a Unifilter-96 GF/B filter plates (presoaked in 0.5% polyethylenimine), using a FilterMate harvester (Packard BioScience Co., Meriden, Conn.). After washing 5 times with 350 μL of the ice-cold wash buffer (25 mM HEPES, 100 mM dipotassium tartrate, 5 mM $MgSO_4$ and 10 mM NaCl, pH 7.5), filter plates were dried, sealed and each well filled with 40 μL Packard's MicroScint 20 cocktail. Bound [$^3$H]DTBZ was measured using a Packard TopCount NXT scintillation counter with a Packard Windows NT based operating system.

Example 3

[$^3$H]Dopamine ([H]DA) Uptake Assay, Vesicular Preparation

Inhibition of [$^3$H]DA uptake was conducted using isolated synaptic vesicle preparations (Teng et al., 1997). Briefly, rat striata were homogenized with 10 up-and-down strokes of a Teflon pestle homogenizer (clearance ~0.003") in 14 ml of 0.32 M sucrose solution. Homogenates were centrifuged (2,000 g for 10 min at 4° C.), and then the supernatants were centrifuged (10,000 g for 30 min at 4° C.). Pellets were resuspended in 2 ml of 0.32 M sucrose solution and subjected to osmotic shock by adding 7 ml of ice-cold MilliQ water to the preparation. After 1 min, osmolarity was restored by adding 900 μl of 0.25 M HEPES buffer and 900

μl of 1.0 M potassium tartrate solution. Samples were centrifuged (20,000 g for 20 min at 4° C.), and the supernatants were centrifuged (55,000 g for 1 hr at 4° C.), followed by addition of 100 μl of 10 mM $MgSO_4$, 100 μl of 0.25 M HEPES and 100 μl of 1.0 M potassium tartrate solution prior to the final centrifugation (100,000 g for 45 min at 4° C.). Final pellets were resuspended in 2.4 ml of assay buffer (25 mM HEPES, 100 mM potassium tartrate, 50 μM EGTA, 100 μM EDTA, 1.7 mM ascorbic acid, 2 mM ATP-$Mg^{2+}$, pH 7.4). Aliquots of the vesicular suspension (100 μl) were added to tubes containing assay buffer, various concentrations of compound (0.1 nM-10 mM) and 0.1 μM [$^3$H]DA in a final volume of 500 μl, and incubated at 37° C. for 8 min. Nonspecific uptake was determined in the presence of the standard compound, Ro4-1284 (10 μM). Reactions were terminated by filtration, and radioactivity retained by the filters was determined by liquid scintillation spectrometry (Tri-Carb 2100TR liquid scintillation analyzer; PerkinElmer Life and Analytical Sciences, Boston, MA).

Example 4

[$^3$H]Dofetilide Binding Assay, HEK-293 Cell Membrane Preparation

[$^3$H]Dofetilide binding assays were conducted using commercially available HEK-293 cell membranes which stably express the hERG channel. Membranes were suspended in assay buffer (50 mM Tris, 10 mM KCl, 1 mM $MgCl_2$, pH 7.4) prior to the experiment. Assays were performed in duplicate in a total volume of 250 μL. Aliquots of the HEK-293 cell membrane suspension which contained 5 μg membrane protein were added to tubes containing assay buffer, 5 nM [3H]dofetilide and a range of concentrations of analog (10 nM-100 μM). Nonspecific binding was determined in the presence of amitriptyline (1 mM). Samples were incubated for 1 hr. at 24° C., followed by rapid filtration. Radioactivity retained by the filters was determined by liquid scintillation spectrometry as described above for the [$^3$H]DA uptake assay. The affinity for the [3H]dofetilide binding site on the hERG channel expressed in the HEK-293 cellular membrane was determined from the analog concentration response curves.

Example 5

[$^3$H]DA and [$^3$H]5-HT Uptake Assay, Synaptosomal Preparation

[$^3$H]DA and [3H]5-HT uptake into striatal synaptosomes was determined to evaluate compound inhibition of the dopamine transporter (DAT) and the serotonin transporter (SERT), respectively. Striata from individual rats were homogenized in ice-cold sucrose solution containing 5 mM $NaHCO_3$ (pH 7.4), with 16 up-and-down strokes of a Teflon pestle homogenizer (clearance ≈0.003"). Homogenates were centrifuged at 2000 g for 10 min at 4° C., and resulting supernatants were centrifuged at 20,000 g for 17 min at 4° C. Pellets were resuspended in 2.4 mL (for DAT assays) or 1.5 mL (for SERT assays) of assay buffer (125 mM NaCl, 5 mM KCl, 1.5 mM $MgSO_4$, 1.25 mM $CaCl_2$), 1.5 mM $KH_2PO_4$, 10 mM alpha-D-glucose, 25 mM HEPES, 0.1 mM EDTA, 0.1 mM pargyline, 0.1 mM ascorbic acid, saturated with 95% $O_2$/5% $CO_2$, pH 7.4). Assays were performed in duplicate in a total volume of 500 μL (for DAT assays) or 250 μL (for SERT assays). Aliquots of the synaptosomal suspension (25 μL for DAT, 50 μL for SERT) were added to tubes containing assay buffer and various concentrations of analog (1 nM-100 μM), and incubated at 34° C. for 5 min. Nonspecific uptake was determined in the presence of nomifensine (10 μM) for DAT assays or fluoxetine (10 μM) for SERT assays. GBR-12935 (100 nM) was included in the assay buffer for the SERT assay to maximally inhibit [$^3$H] 5-HT uptake through DAT and isolate uptake to SERT. Samples were placed on ice, and 50 μL of 0.1 μM [$^3$H]DA (for DAT assays) or 25 μL of 0.1 μM [$^3$H]5-HT (for SERT assays) was added to each tube, and incubated for 10 min at 34° C. Reactions were terminated by addition of 3 mL of ice-cold assay buffer and subsequent filtration and radioactivity retained by the filters was determined by liquid scintillation spectrometry (Tri-Carb 2100TR liquid scintillation analyzer; PerkinElmer Life and Analytical Sciences, Boston, MA).

Exemplary compounds 1-53 were tested in [3H]dihydrotetrabenazine ([$^3$H]DTBZ) binding assay according to Example 2 and the [3H]dopamine ([3H]DA) uptake assay according to Example 3. The results of these assays are set forth in Table 1.

TABLE 1

| Compound | Structure | [$^3$H]DTBZ binding (Ki) VMAT2 (μM) | [$^3$H]DA uptake (Ki) VMAT2 (μM) |
|---|---|---|---|
| 1 | 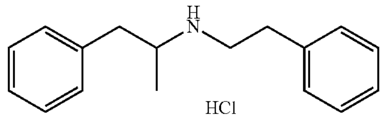 [SMILES: CC(Cc1ccccc1)NCCc1ccccc1 ; Cl] | 7.70 ± 1.25 | 0.063 ± 0.005 |
| 2 | 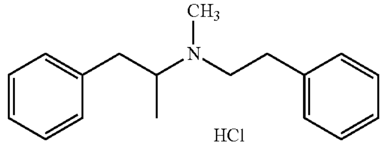 [SMILES: CC(Cc1ccccc1)N(C)CCc1ccccc1 ; Cl] | 7.53 ± 2.16 | 0.51 ± 0.10 |
| 3 | 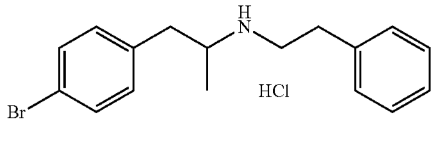 [SMILES: CC(Cc1ccc(Br)cc1)NCCc1ccccc1 ; Cl] | 1.23 ± 0.13 | 0.033 ± 0.007 |

TABLE 1-continued
| Compound | Structure | [$^3$H]DTBZ binding (Ki) VMAT2 (μM) | [$^3$H]DA uptake (Ki) VMAT2 (μM) |
|---|---|---|---|
| 4 | 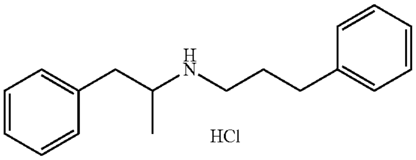 [SMILES: CC(Cc1ccccc1)NCCCc1ccccc1 ; Cl] | 1.13 ± 0.31 | 0.007 ± 0.002 |
| 5 | 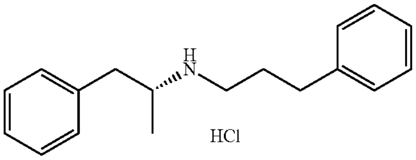 [SMILES: C[C@H](Cc1ccccc1)NCCCc1ccccc1 ; Cl] | 0.91 ± 0.59 | 0.006 ± 0.001 |
| 6 | 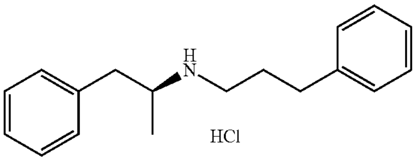 [SMILES: C[C@@H](Cc1ccccc1)NCCCc1ccccc1 ; Cl] | 0.75 ± 0.14 | 0.065 ± 0.004 |
| 7 | 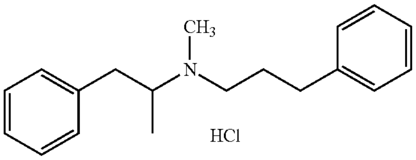 [SMILES: CC(Cc1ccccc1)N(C)CCCc1ccccc1 ; Cl] | 1.56 ± 0.47 | 0.096 ± 0.010 |
| 8 | 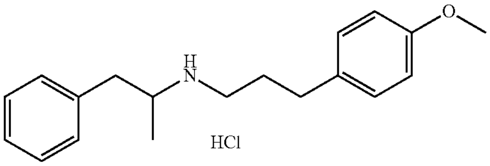 | 2.2 ± 0.11 | 0.014 ± 0.003 |
| 9 | 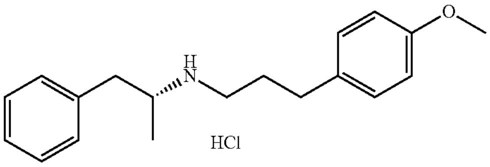 [SMILES: COc1ccc(CCCNC(C)Cc2ccccc2)cc1 ; Cl] | — | 0.0087 ± 0.0065 |
| 10 | 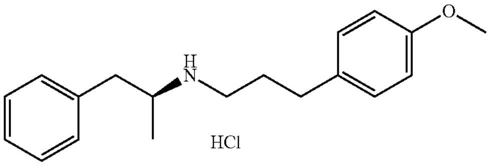 [SMILES: COc1ccc(CCCN[C@@H](C)Cc2ccccc2)cc1 ; Cl] | — | 0.026 ± 0.0036 |
| 11 | 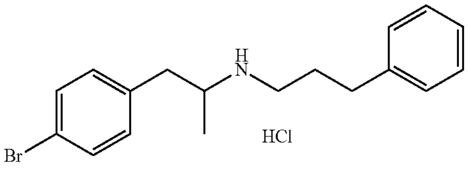 [SMILES: CC(Cc1ccc(Br)cc1)NCCCc1ccccc1 ; Cl] | 0.70 ± 0.063 | 0.008 ± 0.001 |
| 12 | 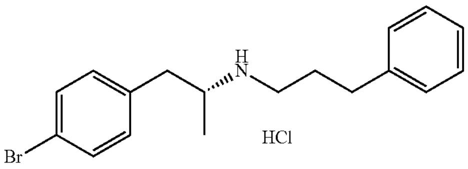 [SMILES: C[C@H](Cc1ccc(Br)cc1)NCCCc1ccccc1 ; Cl] | — | 0.006 ± 0.001 |

TABLE 1-continued
| Compound | Structure | [$^{3}$H]DTBZ binding (Ki) VMAT2 (μM) | [$^{3}$H]DA uptake (Ki) VMAT2 (μM) |
|---|---|---|---|
| 13 | 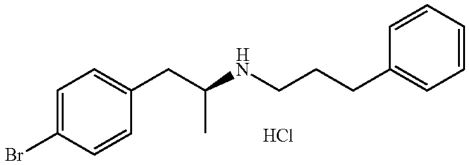 [SMILES: C[C@@H](Cc1ccc(Br)cc1)NCCCc1ccccc1 ; Cl] | — | 0.032 ± 0.004 |
| 14 | 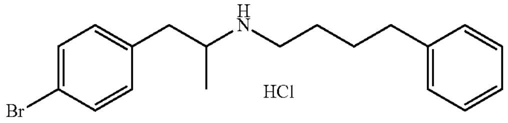 [SMILES: CC(Cc1ccc(Br)cc1)NCCCCc1ccccc1 ; Cl] | 0.081 ± 0.016 | 0.003 ± 0.0003 |
| 15 | 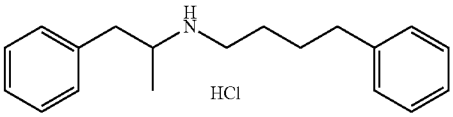 [SMILES: CC(Cc1ccccc1)NCCCCc1ccccc1 ; Cl] | 0.19 ± 0.020 | 0.003 ± 0.002 |
| 16 | 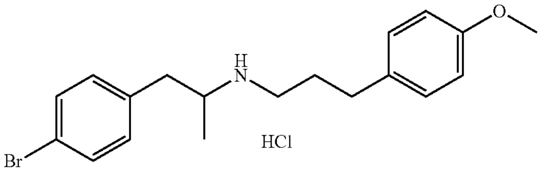 [SMILES: COc1ccc(CCCNC(C)Cc2ccc(Br)cc2)cc1 ; Cl] | 0.46 ± 0.08 | 0.012 ± 0.003 |
| 17 | 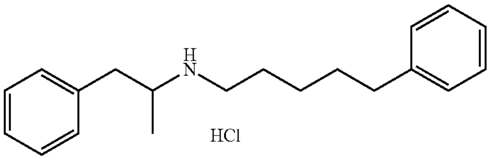 [SMILES: CC(Cc1ccccc1)NCCCCCc1ccccc1 ; Cl] | 0.63 | 0.014 ± 0.001 |
| 18 | 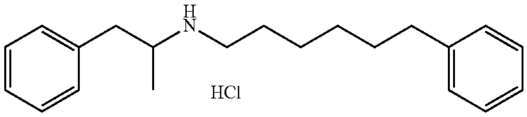 [SMILES: CC(Cc1ccccc1)NCCCCCCc1ccccc1 ; Cl] | 0.91 ± 0.59 | 0.009 ± 0.002 |
| 19 | 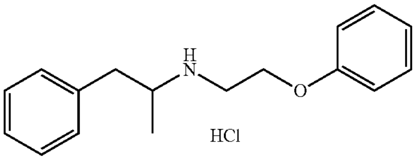 | 4.1 ± 0.3 | 0.059 ± 0.007 |
| 20 | 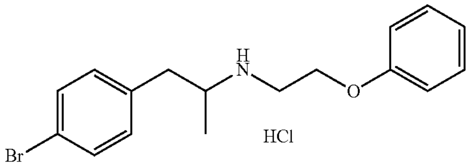 [SMILES: CC(Cc1ccc(Br)cc1)NCCOc1ccccc1 ; Cl] | 2.0 ± 0.1 | 0.013 ± 0.009 |
| 21 | 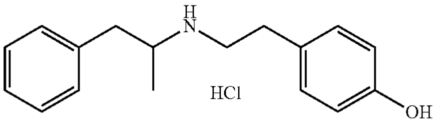 [SMILES: CC(Cc1ccccc1)NCCc1ccc(O)cc1 ; Cl] | 1.5 ± 0.2 | 0.12 ± 0.01 |
| 22 | 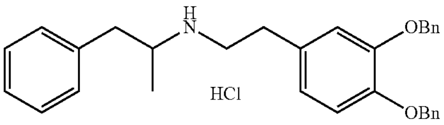 [SMILES: CC(Cc1ccccc1)NCCc1ccc(OCc2ccccc2)c(OCc2ccccc2)c1 ; Cl] | 2.0 ± 0.1 | 0.12 ± 0.001 |

TABLE 1-continued
| Compound | Structure | [3H]DTBZ binding (Ki) VMAT2 (μM) | [3H]DA uptake (Ki) VMAT2 (μM) |
|---|---|---|---|
| 23 | 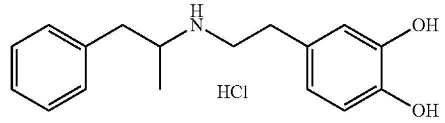 [SMILES: CC(Cc1ccccc1)NCCc1ccc(O)c(O)c1 ; Cl] | 3.4 ± 0.6 | 0.092 ± 0.017 |
| 24 | 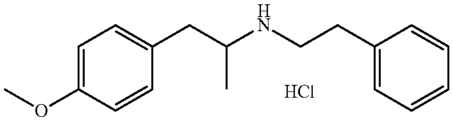 [SMILES: COc1ccc(CC(C)NCCc2ccccc2)cc1 ; Cl] | 3.77 ± 0.99 | 0.074 ± 0.002 |
| 25 | 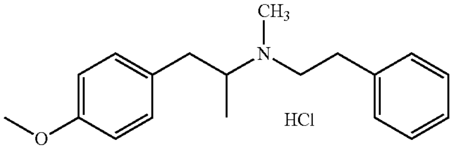 [SMILES: COc1ccc(CC(C)N(C)CCc2ccccc2)cc1 ; Cl] | 11.9 ± 1.84 | 0.46 ± 0.075 |
| 26 | 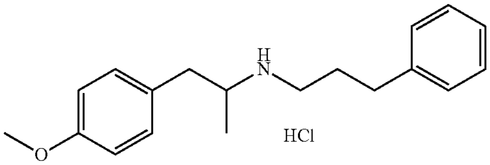 [SMILES: COc1ccc(CC(C)NCCCc2ccccc2)cc1 ; Cl] | 1.27 ± 0.09 | 0.022 ± 0.003 |
| 27 | 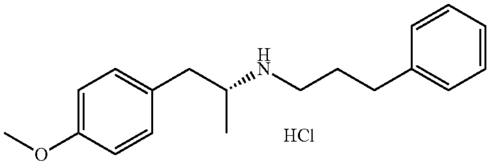 [SMILES: COc1ccc(C[C@@H](C)NCCCc2ccccc2)cc1 ; Cl] | — | 0.045 ± 0.004 |
| 28 | 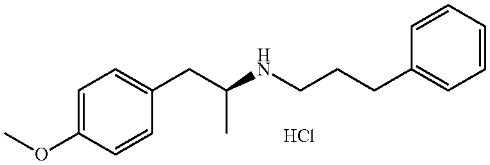 [SMILES: COc1ccc(C[C@H](C)NCCCc2ccccc2)cc1 ; Cl] | — | 0.020 ± 0.001 |
| 29 | 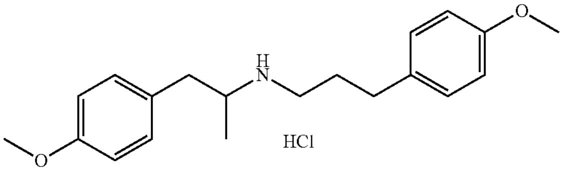 | 0.41 ± 0.14 | 0.011 ± 0.002 |
| 30 | 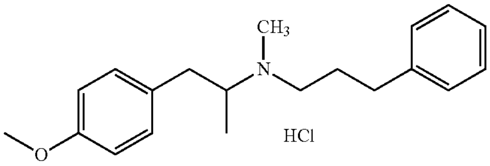 [SMILES: COc1ccc(CC(C)N(C)CCCc2ccccc2)cc1 ; Cl] | 7.11 ± 0.82 | 0.27 ± 0.038 |
| 31 | 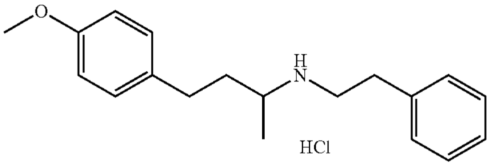 [SMILES: COc1ccc(CCC(C)NCCc2ccccc2)cc1 ; Cl] | 2.4 ± 0.1 | 0.062 ± 0.029 |

TABLE 1-continued
| Compound | Structure | [3H]DTBZ binding (Ki) VMAT2 (μM) | [3H]DA uptake (Ki) VMAT2 (μM) |
|---|---|---|---|
| 32 | 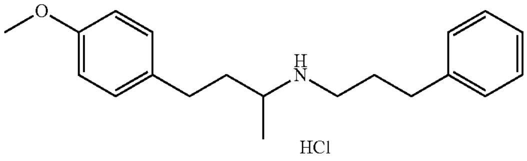 [SMILES: COc1ccc(CCC(C)NCCCc2ccccc2)cc1 ; Cl] | 4.7 ± 0.4 | 0.030 ± 0.002 |
| 33 | 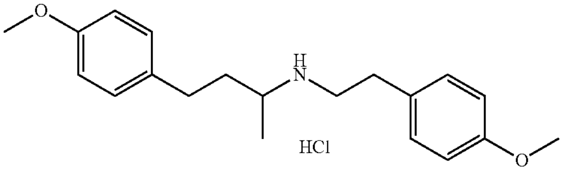 | 1.5 ± 0.2 | 0.060 ± 0.007 |
| 34 | 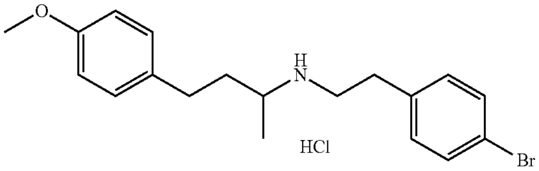 [SMILES: COc1ccc(CCC(C)NCCc2ccc(Br)cc2)cc1 ; Cl] | 0.87 ± 0.03 | 0.010 ± 0.004 |
| 35 | 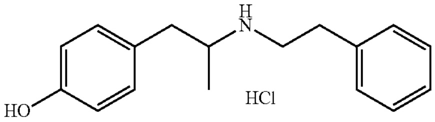 [SMILES: CC(Cc1ccc(O)cc1)NCCc1ccccc1 ; Cl] | 2.6 ± 0.4 | 0.047 ± 0.006 |
| 36 | 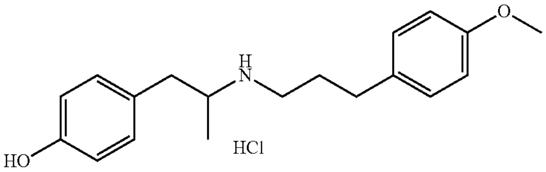 [SMILES: COc1ccc(CCCNC(C)Cc2ccc(O)cc2)cc1 ; Cl] | 0.23 ± 0.06 | 0.072 ± 0.030 |
| 37 | 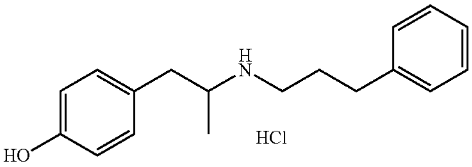 [SMILES: CC(Cc1ccc(O)cc1)NCCCc1ccccc1 ; Cl] | 0.82 ± 0.27 | 0.033 ± 0.008 |
| 38 | 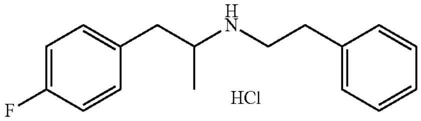 [SMILES: CC(Cc1ccc(F)cc1)NCCc1ccccc1 ; Cl] | 2.5 ± 1.6 | 0.069 ± 0.009 |
| 39 | 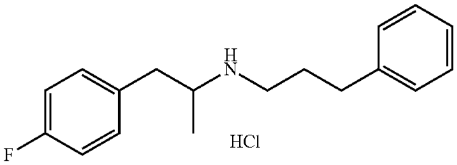 [SMILES: CC(Cc1ccc(F)cc1)NCCCc1ccccc1 ; Cl] | 1.3 ± 0.3 | 0.010 ± 0.0002 |
| 40 | 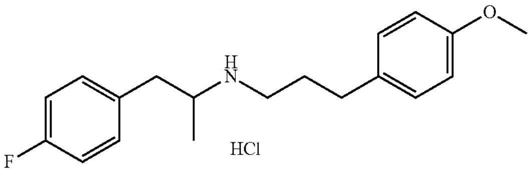 [SMILES: COc1ccc(CCCNC(C)Cc2ccc(F)cc2)cc1 ; Cl] | 1.7 ± 0.4 | 0.017 ± 0.003 |

TABLE 1-continued
| Compound | Structure | [3H]DTBZ binding (Ki) VMAT2 (μM) | [3H]DA uptake (Ki) VMAT2 (μM) |
|---|---|---|---|
| 41 | 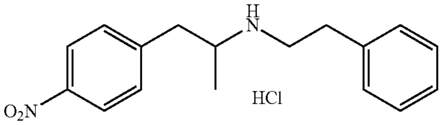 [SMILES: CC(Cc1ccc([N+](=O)[O-])cc1)NCCc1ccccc1 ; Cl] | 5.1 ± 1.2 | 0.060 ± 0.007 |
| 42 | 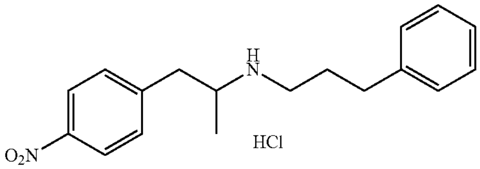 | 2.0 ± 0.3 | 0.013 ± 0.004 |
| 43 | 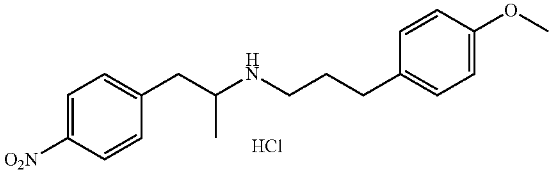 [SMILES: COc1ccc(CCCNC(C)Cc2ccc([N+](=O)[O-])cc2)cc1 ; Cl] | 1.4 ± 0.4 | 0.008 ± 0.002 |
| 44 | 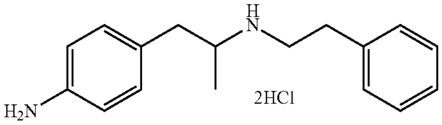 [SMILES: CC(Cc1ccc(N)cc1)NCCc1ccccc1 ; "2HCl"] | 17 ± 6.6 | 0.21 ± 0.08 |
| 45 | 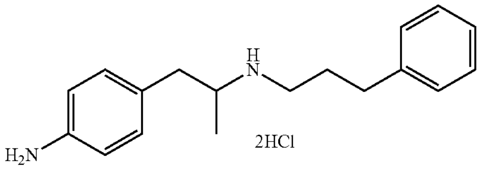 [SMILES: CC(Cc1ccc(N)cc1)NCCCc1ccccc1 ; "2HCl"] | 2.8 ± 0.7 | 0.036 ± 0.003 |
| 46 | 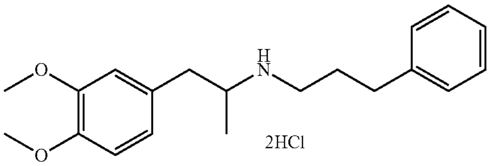 [SMILES: COc1ccc(CC(C)NCCCc2ccccc2)cc1OC ; "2HCl"] | 3.8 ± 0.1 | 0.14 ± 0.013 |
| 47 | 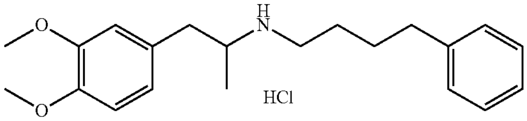 [SMILES: COc1ccc(CC(C)NCCCCc2ccccc2)cc1OC ; Cl] | 1.1 ± 0.1 | 0.029 ± 0.011 |
| 48 | 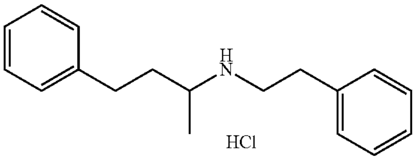 [SMILES: CC(CCc1ccccc1)NCCc1ccccc1 ; Cl] | 1.60 ± 0.33 | 0.050 ± 0.004 |
| 49 | 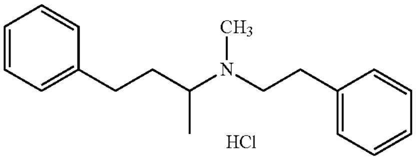 [SMILES: CC(CCc1ccccc1)N(C)CCc1ccccc1 ; Cl] | 29.8 ± 11.2 | 0.084 ± 0.004 |

TABLE 1-continued

| Compound | Structure | [$^3$H]DTBZ binding (Ki) VMAT2 (μM) | [$^3$H]DA uptake (Ki) VMAT2 (μM) |
|---|---|---|---|
| 50 | 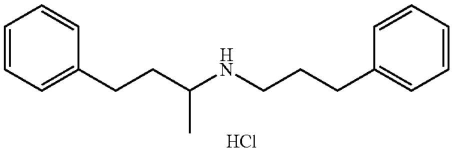 [SMILES: CC(CCc1ccccc1)NCCCc1ccccc1 ; Cl] | 4.81 ± 1.13 | 0.050 ± 0.012 |
| 51 | 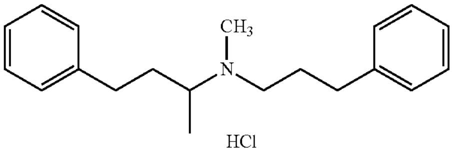 [SMILES: CC(CCc1ccccc1)N(C)CCCc1ccccc1 ; Cl] | 17.2 ± 6.33 | 0.36 ± 0.034 |
| 52 | 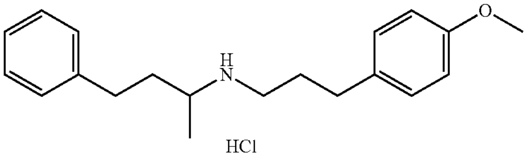 [SMILES: COc1ccc(CCCNC(C)CCc2ccccc2)cc1 ; Cl] | 3.2 ± 0.1 | 0.026 ± 0.002 |
| 53 | 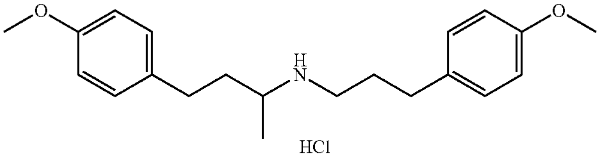 | 1.5 ± 0.7 | 0.024 ± 0.006 |

As illustrated by Table 1, compounds of the invention exhibited high affinity at VMAT2. Selectivity at VMAT2 over hERG, DAT, and SERT were also observed. For example, Compound 9 exhibited a $K_i$ value of 8.71±3.65 nM at VMAT2, and Compound 10 exhibited a $K_i$ value of 25.5±3.57 nM at VMAT2. Further, both Compound 9 and Compound 10 exhibited a >30-fold selectivity at VMAT2 over hERG, DAT, and SERT.

The compounds of the invention were also evaluated for their effect on METH-stimulated locomotor activity in rats. The compounds were observed to exhibit a significant reduction of METH-stimulated locomotor activity after administration. For example, a significant reduction of METH-stimulated locomotor activity was observed after administration of Compound 9 (3 mg/kg, s.c.) and Compound 10 (17 mg/kg, s.c.).

Further exemplary Compounds 54-226 were synthesized and are illustrated in Table 2 below. An additional exemplary synthetic procedure is set forth below in Example 6.

Exemplary compounds 54-226 were tested using the [$^3$H]dopamine ([$^3$H]DA) uptake assay according to Example 3, and the microsomal assays according to Example 7. The results of these assays are set forth in Table 2. In addition, various exemplary compounds from among 54-226 were tested using the pharmacokinetic assays according to Example 8.

TABLE 2

| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 54 | 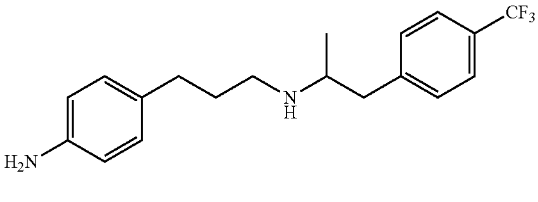 [SMILES: CC(Cc1ccc(C(F)(F)F)cc1)NCCCc1ccc(N)cc1] | 61.8 ± 1.69 | 908 ± 102 | | | |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 55 | 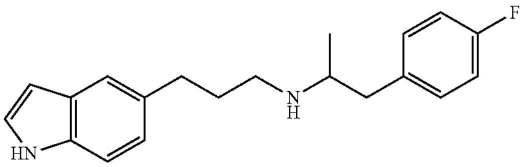 [SMILES: CC(Cc1ccc(F)cc1)NCCCc1ccc2[nH]ccc2c1] | 27.4 ± 8.93 | 1550 ± 630 | Rat | <0.1 | >400 |
| 56 | 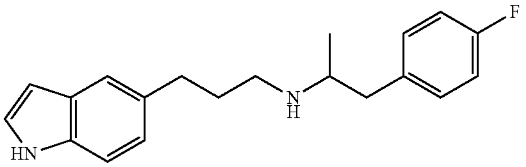 [SMILES: CC(Cc1ccc(F)cc1)NCCCc1ccc2[nH]ccc2c1] | 27.4 ± 8.93 | 1550 ± 630 | Human | 0.2 | 106 |
| 57 | 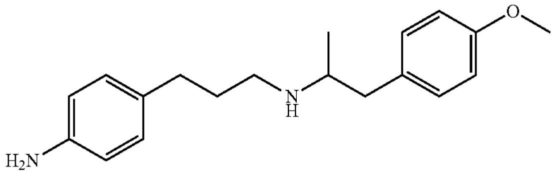 | 68.9 ± 13.3 | 4250 ± 0220 | | | |
| 58 | 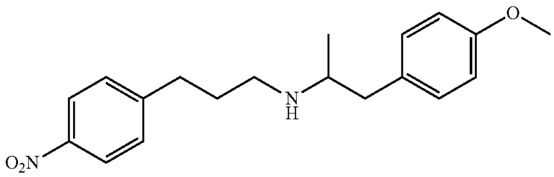 [SMILES: COc1ccc(CC(C)NCCCc2ccc([N+](=O)[O-])cc2)cc1] | 16.6 ± 3.99 | 42.3 ± 8.21 | | | |
| 59 | 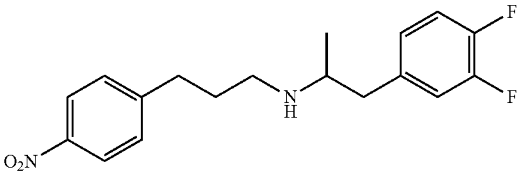 | 13.1 ± 2.87 | 55.6 ± 7.7 | | | |
| 60 | 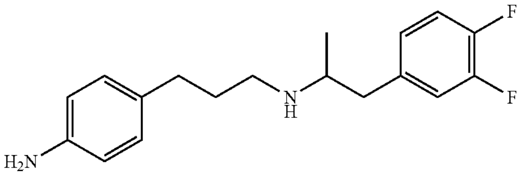 | 48.3 ± 16.4 | 3140 ± 1550 | Rat | 1 | 30.7 |
| 61 | 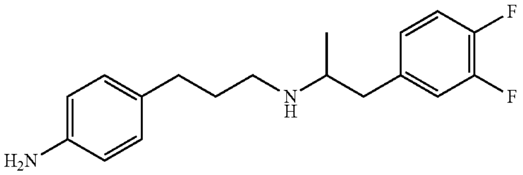 [SMILES: CC(Cc1ccc(F)c(F)c1)NCCCc1ccc([N+](=O)[O-])cc1] | 48.3 ± 16.4 | 3140 ± 1550 | Human | 2.2 | 9.6 |
| 62 | 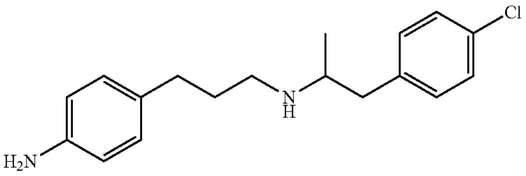 [SMILES: CC(Cc1ccc(Cl)cc1)NCCCc1ccc(N)cc1] | 31.6 ± 4.66 | 2380 ± 1120 | Rat | 0.6 | 83 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 63 | 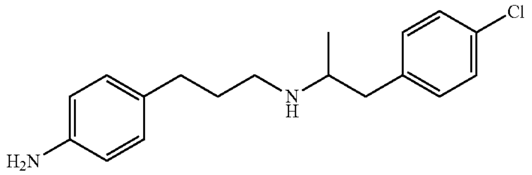 [SMILES: CC(Cc1ccc(Cl)cc1)NCCCc1ccc(N)cc1] | 31.6 ± 4.66 | 2380 ± 1120 | Human | 1.8 | 11.6 |
| 64 | 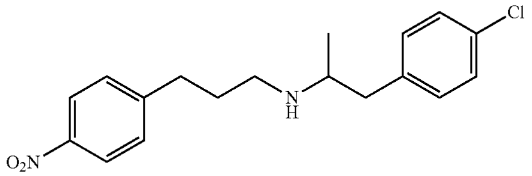 | 16.4 ± 1.47 | 28.8 ± 13.7 | | | |
| 65 | 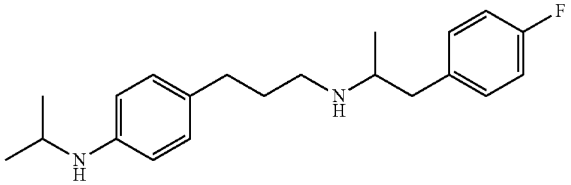 [SMILES: CC(C)Nc1ccc(CCCNC(C)Cc2ccc(F)cc2)cc1] | 112 ± 16.8 | Not determined | | | |
| 66 | 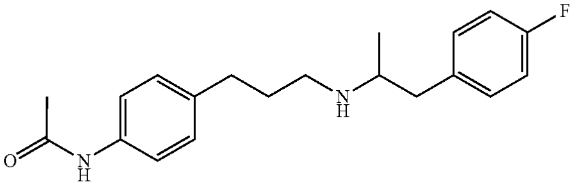 [SMILES: CC(=O)Nc1ccc(CCCNC(C)Cc2ccc(F)cc2)cc1] | 32.5 ± 3.52 | 10100 ± 3350 | rat | 1.5 | 30.7 |
| 67 | 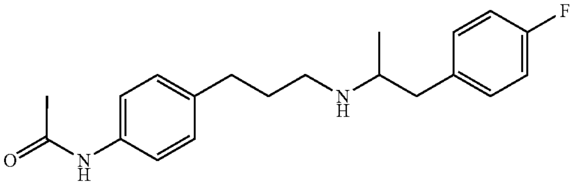 [SMILES: CC(=O)Nc1ccc(CCCNC(C)Cc2ccc(F)cc2)cc1] | 32.5 ± 3.52 | 10100 ± 3350 | Human | >4 | <10.0 |
| 68 | 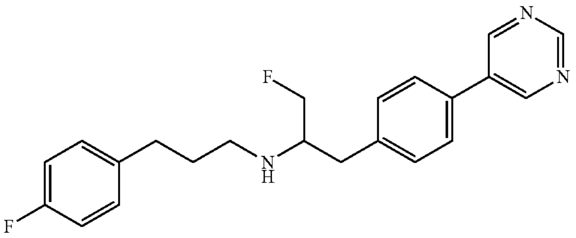 [SMILES: FCC(Cc1ccc(-c2cncnc2)cc1)NCCCc1ccc(F)cc1] | 5.53 ± 0.567 | 633 ± 46.3 | Human | <0.1 | >400 |
| 69 | 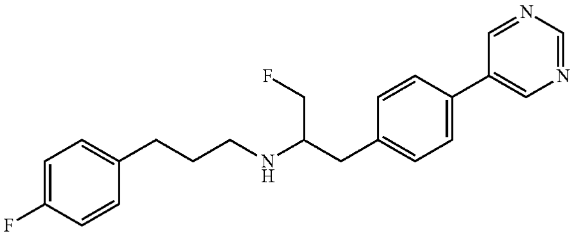 [SMILES: FCC(Cc1ccc(-c2cncnc2)cc1)NCCCc1ccc(F)cc1] | 5.53 ± 0.567 | 633 ± 46.3 | Rat | 0.6 | 76.8 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 70 | 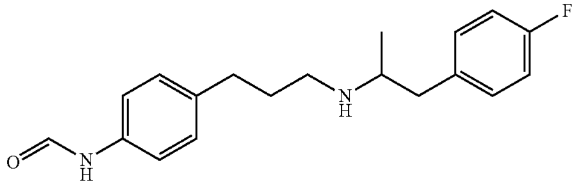 [SMILES: CC(Cc1ccc(F)cc1)NCCCc1ccc(NC=O)cc1] | 22.5 ± 4.48 | 2600 ± 711 | Human | 0.9 | 23 |
| 71 | 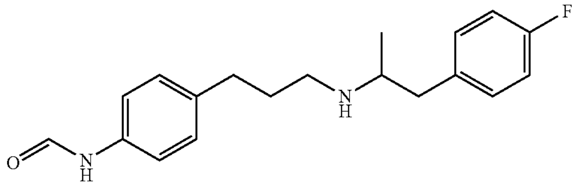 [SMILES: CC(Cc1ccc(F)cc1)NCCCc1ccc(NC=O)cc1] | 22.5 ± 4.48 | 2600 ± 711 | Rat | 0.5 | 97.2 |
| 72 | 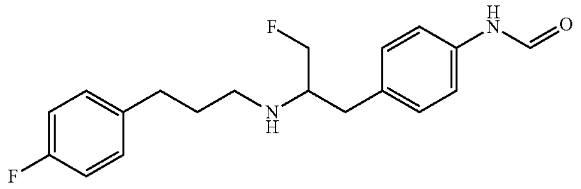 [SMILES: O=CNc1ccc(CC(CF)NCCCc2ccc(F)cc2)cc1] | 16.4 ± 2.89 | 516 ± 63.6 | Human | 0.8 | 26.5 |
| 73 | 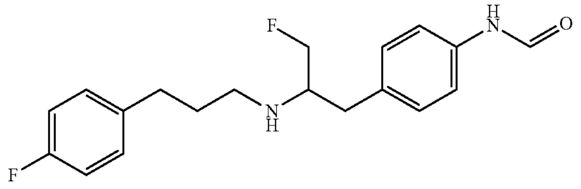 [SMILES: O=CNc1ccc(CC(CF)NCCCc2ccc(F)cc2)cc1] | 16.4 ± 2.89 | 516 ± 63.6 | Rat | 1.1 | 43.7 |
| 74 | 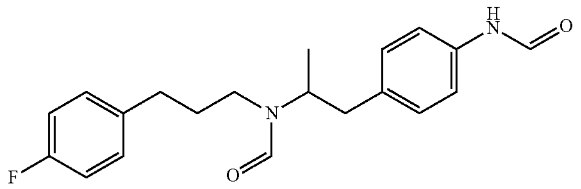 [SMILES: CC(Cc1ccc(NC=O)cc1)N(C=O)CCCc1ccc(F)cc1] | 8.82 ± 2.05 | 831 ± 187 | | | |
| 75 | 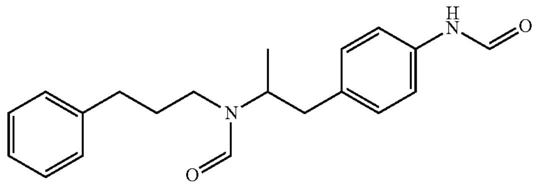 [SMILES: CC(Cc1ccc(NC=O)cc1)N(C=O)CCCc1ccccc1] | 22700 ± 432 | Not determined | Human | 0.2 | 121 |
| 76 | 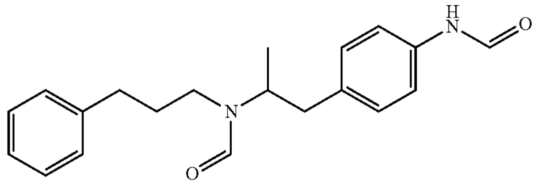 [SMILES: CC(Cc1ccc(NC=O)cc1)N(C=O)CCCc1ccccc1] | 22700 ± 432 | Not determined | Rat | 0.8 | 56 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 77 | 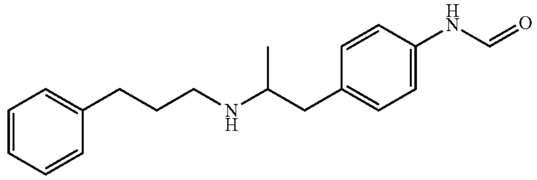 [SMILES: CC(Cc1ccc(NC=O)cc1)NCCCc1ccccc1] | 21 ± 1.1 | 1760 ± 630 | Human | 1.9 | 11.2 |
| 78 | 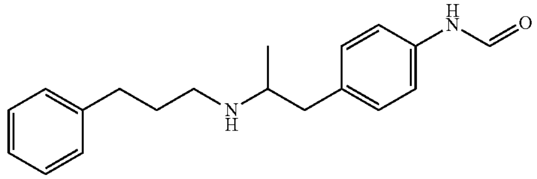 [SMILES: CC(Cc1ccc(NC=O)cc1)NCCCc1ccccc1] | 21 ± 1.1 | 1760 ± 630 | Rat | 0.3 | 167 |
| 79 | 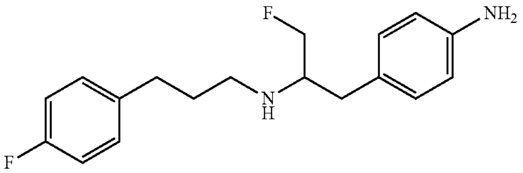 [SMILES: Nc1ccc(CC(CF)NCCCc2ccc(F)cc2)cc1] | 19.8 ± 9.29 | 3441 ± 983 | Rat | 2.2 | 21.1 |
| 80 | 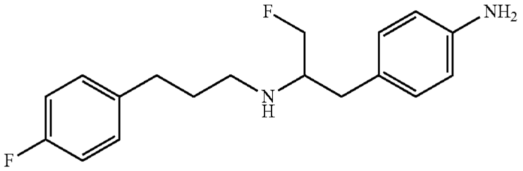 [SMILES: Nc1ccc(CC(CF)NCCCc2ccc(F)cc2)cc1] | 19.8 ± 9.29 | 3441 ± 983 | Human | 0.7 | 29.5 |
| 81 | 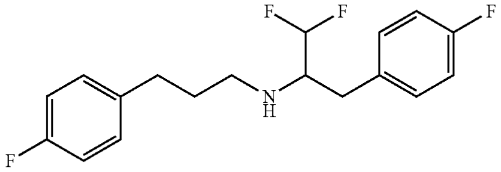 [SMILES: Fc1ccc(CCCNC(Cc2ccc(F)cc2)C(F)F)cc1] | 386 ± 194 | Not determined | Rat | 0.6 | 83.2 |
| 82 | 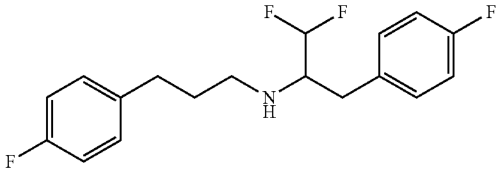 [SMILES: Fc1ccc(CCCNC(Cc2ccc(F)cc2)C(F)F)cc1] | 386 ± 194 | Not determined | Human | 0.8 | 26.3 |
| 83 | 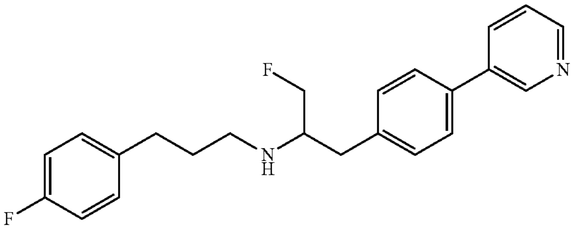 [SMILES: FCC(Cc1ccc(-c2cccnc2)cc1)NCCCc1ccc(F)cc1] | 27.7 ± 13.9 | 6751 ± 3617 | Rat | 0.4 | 113 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 84 | 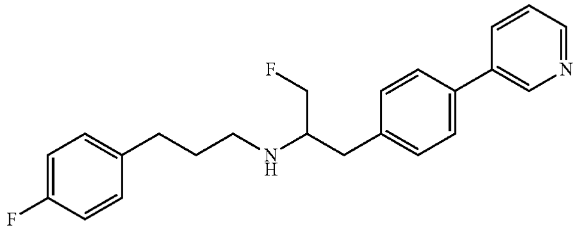 [SMILES: FCC(Cc1ccc(-c2cccnc2)cc1)NCCCc1ccc(F)cc1] | 27.7 ± 13.9 | 6751 ± 3617 | Human | 0.1 | 173 |
| 85 | 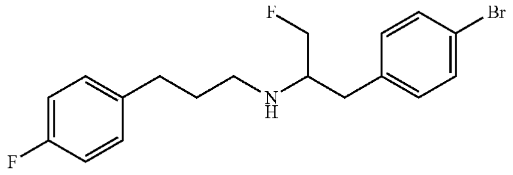 [SMILES: FCC(Cc1ccc(Br)cc1)NCCCc1ccc(F)cc1] | 35.7 ± 7.32 | 1134 ± 711 | Rat | 0.1 | 335 |
| 86 | 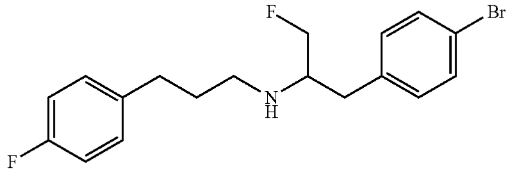 [SMILES: FCC(Cc1ccc(Br)cc1)NCCCc1ccc(F)cc1] | 35.7 ± 7.32 | 1134 ± 711 | Human | 1.1 | 18.1 |
| 87 | 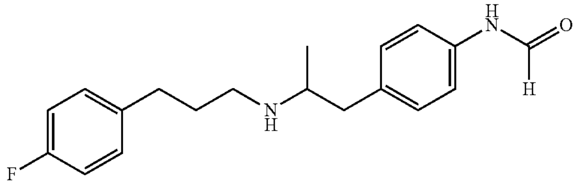 [SMILES: CC(Cc1ccc(NC=O)cc1)NCCCc1ccc(F)cc1] Batch A | 12.7 ± 2.85 | 738 ± 244 | Rat | 3.5 | 13.3 |
| 88 | 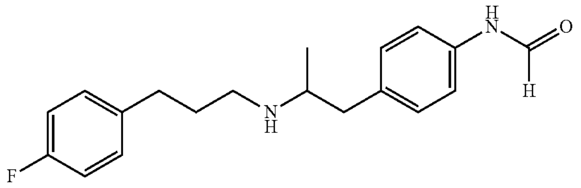 [SMILES: CC(Cc1ccc(NC=O)cc1)NCCCc1ccc(F)cc1] Batch A | 12.7 ± 2.85 | 738 ± 244 | Human | 1.6 | 13.4 |
| 89 | 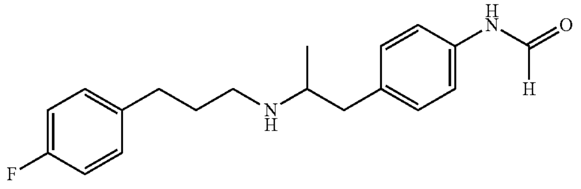 [SMILES: CC(Cc1ccc(NC=O)cc1)NCCCc1ccc(F)cc1] Batch B | 12.7 ± 2.85 | 738 ± 244 | Human | 1.5 | 14 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 90 | 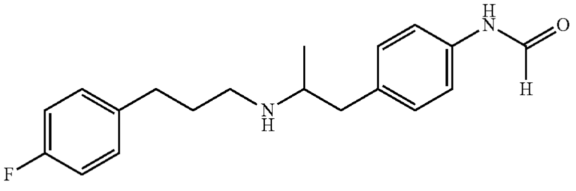 [SMILES: CC(Cc1ccc(NC=O)cc1)NCCCc1ccc(F)cc1]<br>Batch B | 12.7 ± 2.85 | 738 ± 244 | Rat | 1.9 | 24.9 |
| 91 | 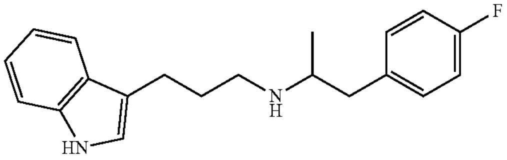 [SMILES: CC(Cc1ccc(F)cc1)NCCCc1c[nH]c2ccccc12] | 36.5 ± 5.56 | 2200 ± 124 | Rat | <0.1 | >400 |
| 92 | 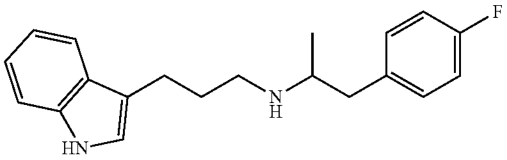 [SMILES: CC(Cc1ccc(F)cc1)NCCCc1c[nH]c2ccccc12] | 36.5 ± 5.56 | 2200 ± 124 | Human | 0.2 | 112 |
| 93 | 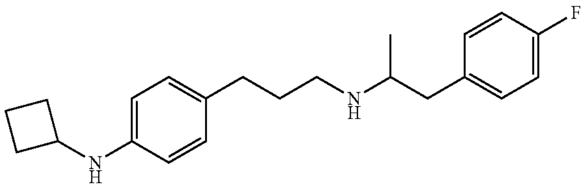 [SMILES: CC(Cc1ccc(F)cc1)NCCCc1ccc(NC2CCC2)cc1] | 129 ± 7.41 | Not determined | | | |
| 94 | 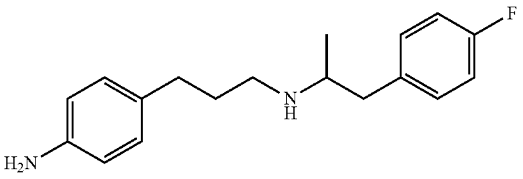 [SMILES: CC(Cc1ccc(F)cc1)NCCCc1ccc(N)cc1] | 84.6 ± 29.1 | 3980 ± 3410 | Rat | 0.4 | 119 |
| 95 | 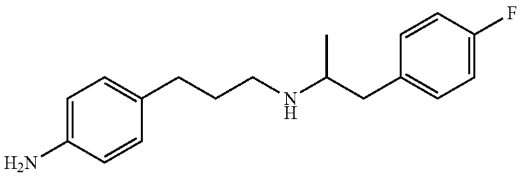 [SMILES: CC(Cc1ccc(F)cc1)NCCCc1ccc(N)cc1] | 84.6 ± 29.1 | 3980 ± 3410 | Human | 1.6 | 12.9 |
| 96 | 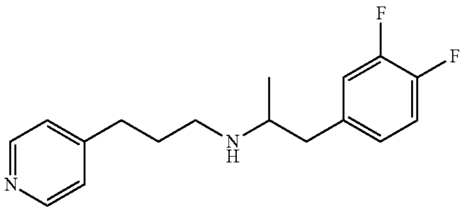 [SMILES: CC(Cc1ccc(F)c(F)c1)NCCCc1ccncc1] | 78.5 ± 15.8 | 4070 ± 734 | Rat | 0.5 | 96.8 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 97 | 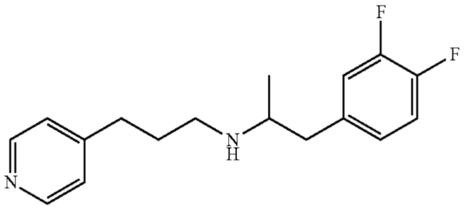 [SMILES: CC(Cc1ccc(F)c(F)c1)NCCCc1ccncc1] | 78.5 ± 15.8 | 4070 ± 734 | Human | 1.7 | 11.9 |
| 98 | 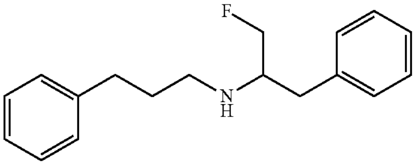 [SMILES: FCC(Cc1ccccc1)NCCCc1ccccc1] | 27.8 ± 5.29 | 17100 ± 12100 | Rat | <0.1 | >400 |
| 99 | 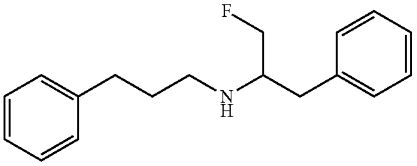 [SMILES: FCC(Cc1ccccc1)NCCCc1ccccc1] | 27.8 ± 5.29 | 17100 ± 12100 | Human | 0.2 | 119 |
| 100 | 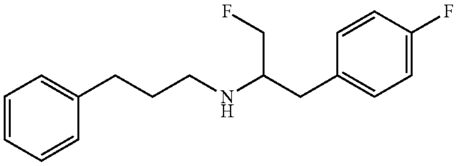 [SMILES: FCC(Cc1ccc(F)cc1)NCCCc1ccccc1] | 51.2 ± 12 | 7390 ± 1360 | | | |
| 101 | 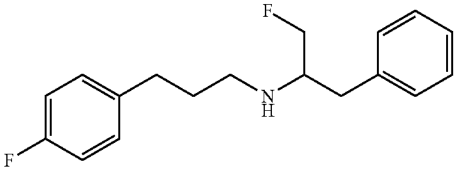 [SMILES: FCC(Cc1ccccc1)NCCCc1ccc(F)cc1] | 14.7 ± 9.28 | 4800 ± 940 | Rat | 0.2 | 253 |
| 102 | 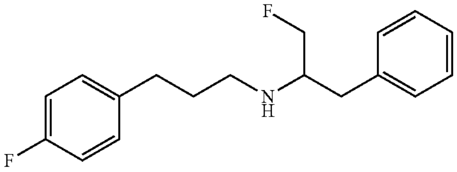 [SMILES: FCC(Cc1ccccc1)NCCCc1ccc(F)cc1] | 14.7 ± 9.28 | 4800 ± 940 | Human | 0.6 | 33.9 |
| 103 | 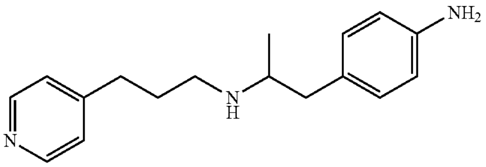 [SMILES: CC(Cc1ccc(N)cc1)NCCCc1ccncc1] | 378 ± 30 | Not determined | | | |
| 104 | See Compound 105 and Compound 106 | | | | | |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 105 | 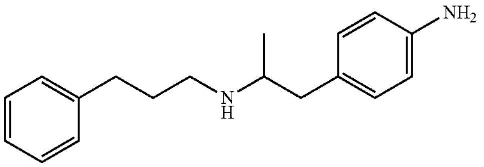 [SMILES: CC(Cc1ccc(N)cc1)NCCCc1ccccc1] | 26.8 ± 6.49 | 4610 ± 1010 | Human | 0.7 | 29.6 |
| 106 | 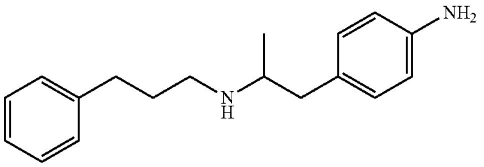 [SMILES: CC(Cc1ccc(N)cc1)NCCCc1ccccc1] | 26.8 ± 6.49 | 4610 ± 1010 | Rat | 2.6 | 17.9 |
| 107 | 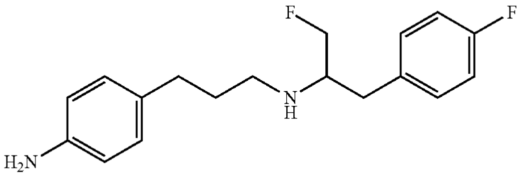 [SMILES: Nc1ccc(CCCNC(CF)Cc2ccc(F)cc2)cc1] | 105 ± 0.189 | Not determined | Rat | 0.6 | 82.2 |
| 108 | 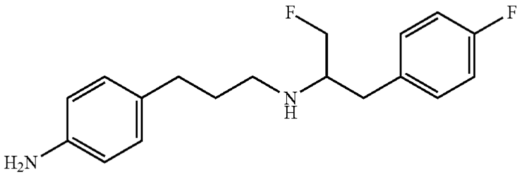 [SMILES: Nc1ccc(CCCNC(CF)Cc2ccc(F)cc2)cc1] | 105 ± 0.189 | Not determined | Human | 2.2 | 9.6 |
| 109 | 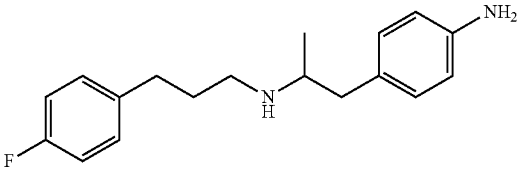 [SMILES: CC(Cc1ccc(N)cc1)NCCCc1ccc(F)cc1] Batch A | 19.2 ± 4.43 | 2594 ± 792 | Human | 0.8 | 25.2 |
| 110 | 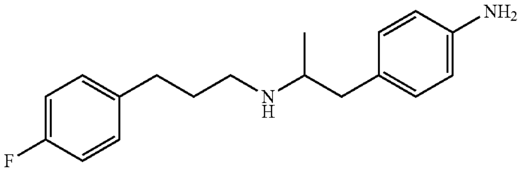 [SMILES: CC(Cc1ccc(N)cc1)NCCCc1ccc(F)cc1] Batch A | 19.2 ± 4.43 | 2594 ± 792 | Rat | >4 | <10.0 |
| 111 | 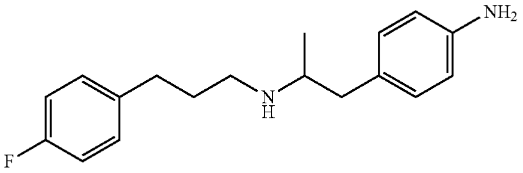 [SMILES: CC(Cc1ccc(N)cc1)NCCCc1ccc(F)cc1] Batch B | 16.7 ± 3.34 | 2501 ± 435 | Rat | 2.4 | 19.5 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 112 | 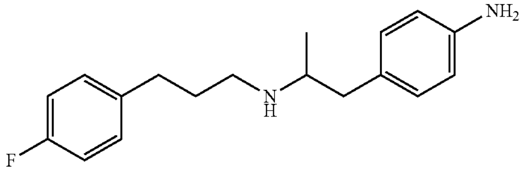 [SMILES: CC(Cc1ccc(N)cc1)NCCCc1ccc(F)cc1] Batch B | 16.7 ± 3.34 | 2501 ± 435 | Human | 0.9 | 23.5 |
| 113 | 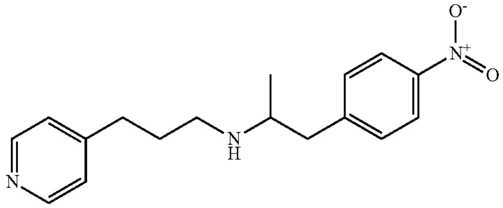 [SMILES: CC(Cc1ccc([N+](=O)[O-])cc1)NCCCc1ccncc1] | 157 ± 72.5 | Not determined | Human | 3.3 | 6.3 |
| 114 | 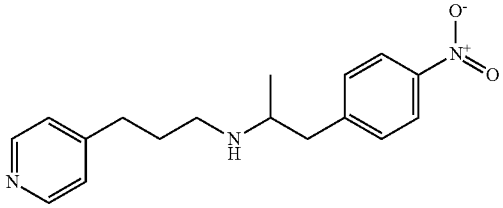 [SMILES: CC(Cc1ccc([N+](=O)[O-])cc1)NCCCc1ccncc1] | 157 ± 72.5 | Not determined | Rat | 0.5 | 95.9 |
| 115 | 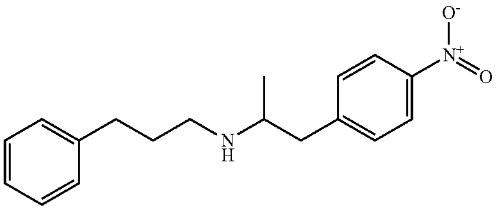 [SMILES: CC(Cc1ccc([N+](=O)[O-])cc1)NCCCc1ccccc1] | 19 ± 3.81 | 285 ± 78.8 | Human | >4 | <5.20 |
| 116 | 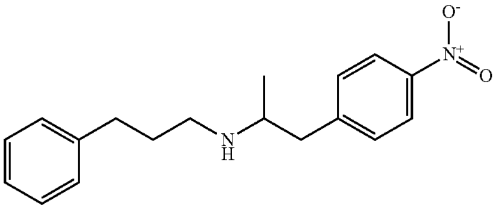 [SMILES: CC(Cc1ccc([N+](=O)[O-])cc1)NCCCc1ccccc1] | 19 ± 3.81 | 285 ± 78.8 | Rat | <0.1 | >400 |
| 117 | 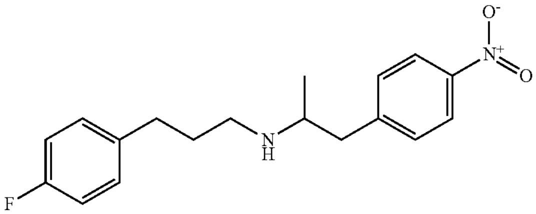 [SMILES: CC(Cc1ccc([N+](=O)[O-])cc1)NCCCc1ccc(F)cc1] Batch A | 7.08 ± 1.29 | 206 ± 137 | Rat | 0.3 | 148 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 118 | 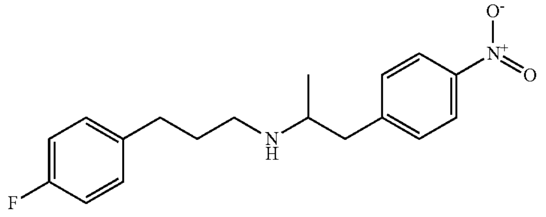 [SMILES: CC(Cc1ccc([N+](=O)[O-])cc1)NCCCc1ccc(F)cc1] Batch A | 7.08 ± 1.29 | 206 ± 137 | Human | >4 | <5.20 |
| 119 | 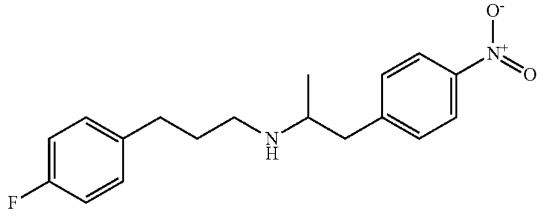 [SMILES: CC(Cc1ccc([N+](=O)[O-])cc1)NCCCc1ccc(F)cc1] Batch B | 9.85 ± 1.62 | 130 ± 25.6 | Rat | 0.4 | 112 |
| 120 | 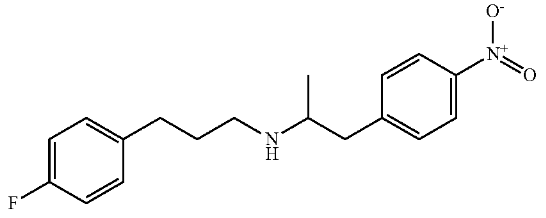 [SMILES: CC(Cc1ccc([N+](=O)[O-])cc1)NCCCc1ccc(F)cc1] | 9.85 ± 1.62 | 130 ± 25.6 | Human | >4 | <5.20 |
| 121 | 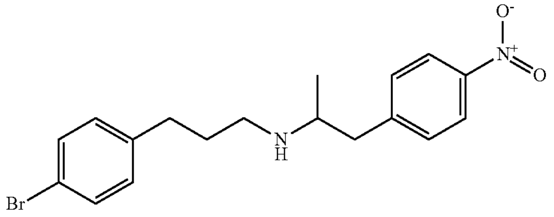 | 13.4 ± 4.8 | 80 ± 67.7 | Human | > 4 | <5.20 |
| 122 | 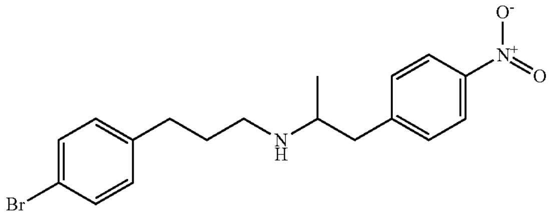 | 13.4 ± 4.8 | 80 ± 67.7 | Rat | <0.1 | >400 |
| 123 | 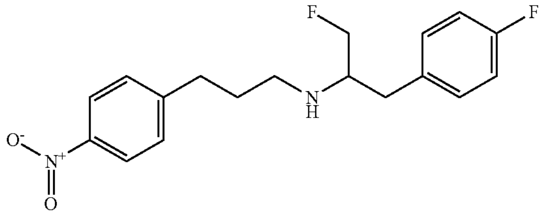 [SMILES: O=[N+]([O-])c1ccc(CCCNC(CF)Cc2ccc(F)cc2)cc1] | 43.7 ± 8.77 | 223 ± 199 | Human | 1.2 | 18.1 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 124 | 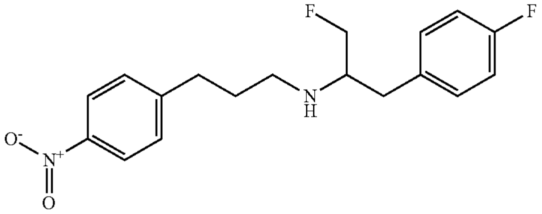 [SMILES: O=[N+]([O-])c1ccc(CCCNC(CF)Cc2ccc(F)cc2)cc1] | 43.7 ± 8.77 | 223 ± 199 | Rat | 0.4 | 116 |
| 125 | 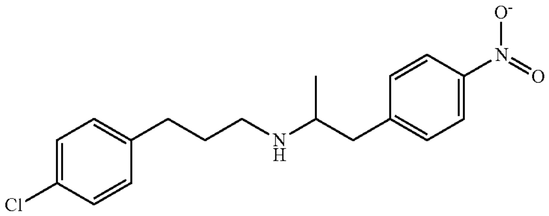 | 8.58 ± 3.71 | 82 ± 12.7 | | | |
| 126 | 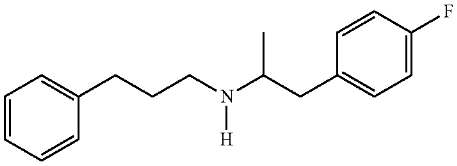 [SMILES: CC(Cc1ccc(F)cc1)NCCCc1ccccc1] | 19.3 ± 5.14 | 2050 ± 773 | Human | 1.8 | 11.5 |
| 127 | 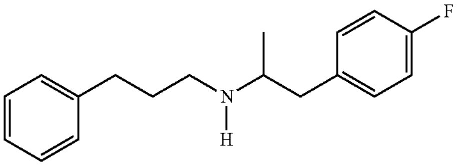 [SMILES: CC(Cc1ccc(F)cc1)NCCCc1ccccc1] | 19.3 ± 5.14 | 2050 ± 773 | Rat | <0.1 | >400 |
| 128 | 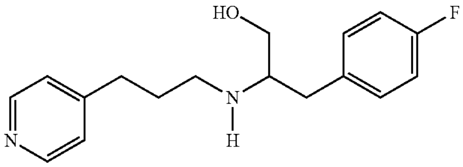 [SMILES: OCC(Cc1ccc(F)cc1)NCCCc1ccncc1] | 963 ± 50.5 | Not determined | Rat | >4 | <10.0 |
| 129 | 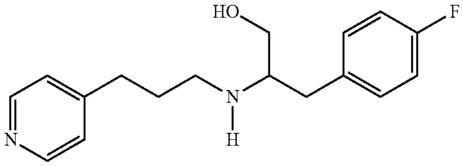 [SMILES: OCC(Cc1ccc(F)cc1)NCCCc1ccncc1] | 963 ± 50.5 | Not determined | Human | >4 | <5.20 |
| 130 | 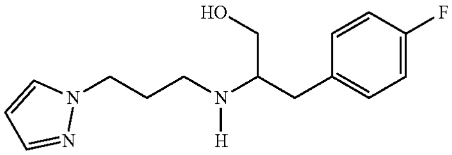 [SMILES: OCC(Cc1ccc(F)cc1)NCCCn1cccn1] | 634 ± 195 | Not determined | Human | 0.6 | 37.3 |
| 131 | 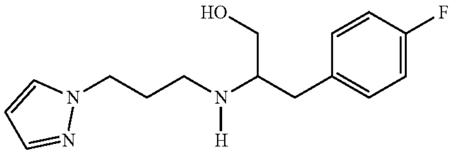 [SMILES: OCC(Cc1ccc(F)cc1)NCCCn1cccn1] | 634 ± 195 | Not determined | Rat | 0.3 | 139 |

TABLE 2-continued

| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 132 | 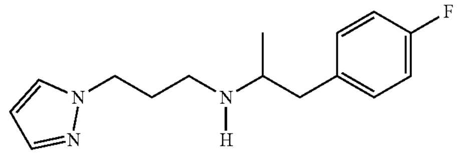 [SMILES: CC(Cc1ccc(F)cc1)NCCCn1cccn1] | 709 ± 172 | Not determined | Rat | 0.3 | 180 |
| 133 | 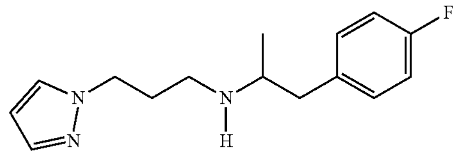 [SMILES: CC(Cc1ccc(F)cc1)NCCCn1cccn1] | 709 ± 172 | Not determined | Human | >4 | <5.20 |
| 134 | 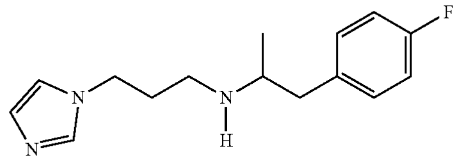 [SMILES: CC(Cc1ccc(F)cc1)NCCCn1ccnc1] | 517 ± 112 | Not determined | Human | >4 | <5.20 |
| 135 | 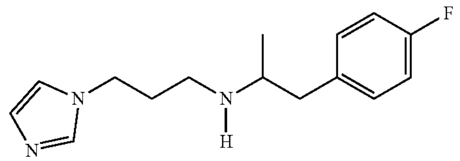 [SMILES: CC(Cc1ccc(F)cc1)NCCCn1ccnc1] | 517 ± 112 | Not determined | Rat | >4 | <7.00 |
| 136 | 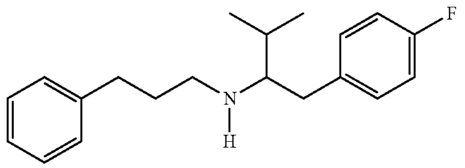 [SMILES: CC(C)C(Cc1ccc(F)cc1)NCCCc1ccccc1] | 386 ± 66.4 | Not determined | | | |
| 137 | 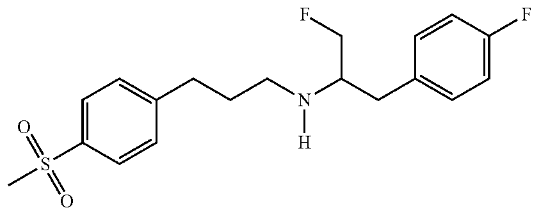 [SMILES: CS(=O)(=O)c1ccc(CCCNC(CF)Cc2ccc(F)cc2)cc1] | 182 ± 56.7 | Not determined | | | |
| 138 | 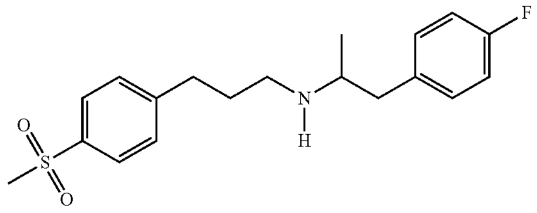 [SMILES: CC(Cc1ccc(F)cc1)NCCCc1ccc(S(C)(=O)=O)cc1] | 146 ± 41.9 | Not determined | Human | >4 | <5.20 |

TABLE 2-continued

| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 139 | 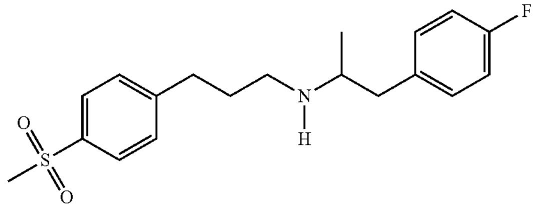 [SMILES: CC(Cc1ccc(F)cc1)NCCCc1ccc(S(C)(=O)=O)cc1] | 146 ± 41.9 | Not determined | Rat | >4 | <7.00 |
| 140 | 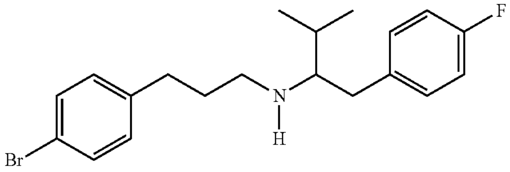 [SMILES: CC(C)C(Cc1ccc(F)cc1)NCCCc1ccc(Br)cc1] | 132 ± 29.5 | Not determined | Human | 1.4 | 14.4 |
| 141 | 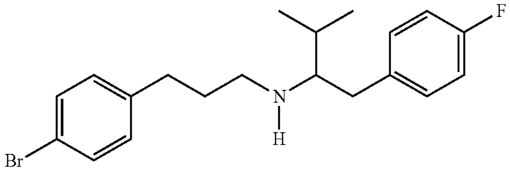 [SMILES: CC(C)C(Cc1ccc(F)cc1)NCCCc1ccc(Br)cc1] | 132 ± 29.5 | Not determined | Rat | <0.1 | >450 |
| 142 | 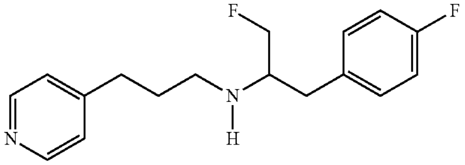 [SMILES: FCC(Cc1ccc(F)cc1)NCCCc1ccncc1] | 117 ± 18.7 | Not determined | Rat | 0.5 | 38.3 |
| 143 | 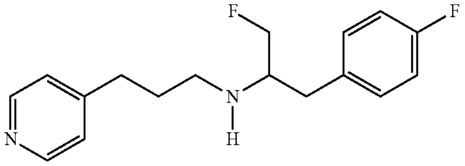 [SMILES: FCC(Cc1ccc(F)cc1)NCCCc1ccncc1] | 117 ± 18.7 | Not determined | Human | 0.5 | 98.1 |
| 144 | 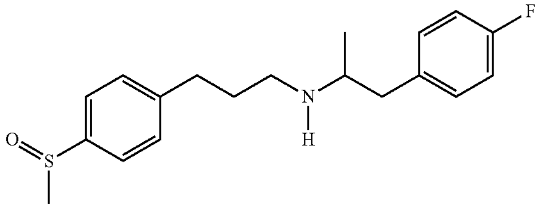 [SMILES: CC(Cc1ccc(F)cc1)NCCCc1ccc(S(C)=O)cc1] | 178 ± 78.9 | Not determined | | | |
| 145 | 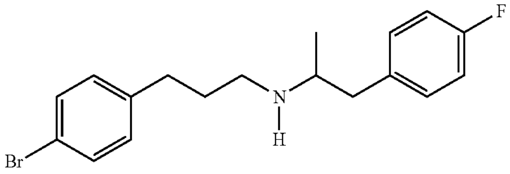 | 22.1 ± 6.5 | 506 ± 199 | Rat | 0.1 | 402 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 146 | 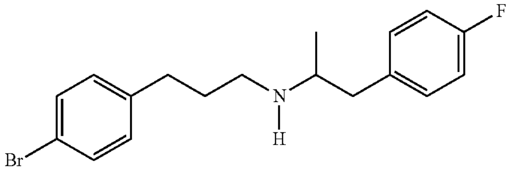 [SMILES: CC(Cc1ccc(F)cc1)NCCCc1ccc(Br)cc1] | 22.1 ± 6.5 | 506 ± 199 | Human | >4 | <5.20 |
| 147 | 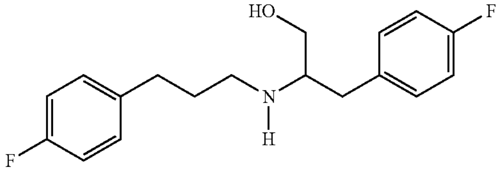 [SMILES: OCC(Cc1ccc(F)cc1)NCCCc1ccc(F)cc1] | 30.1 ± 14.2 | 1150 ± 417 | | | |
| 148 | 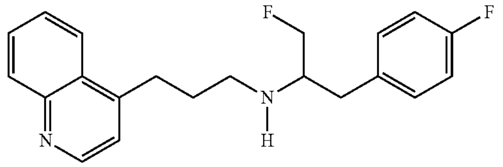 [SMILES: FCC(Cc1ccc(F)cc1)NCCCc1ccnc2ccccc12] | 70.3 ± 13 | 4700 ± 373 | Rat | <0.1 | >400 |
| 149 | 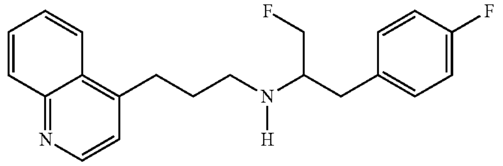 [SMILES: FCC(Cc1ccc(F)cc1)NCCCc1ccnc2ccccc12] | 70.3 ± 13 | 4700 ± 373 | Human | 0.1 | 162 |
| 150 | 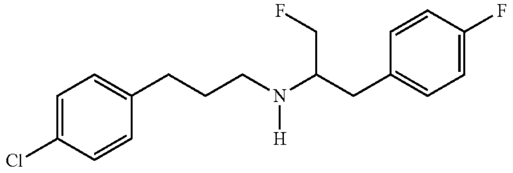 [SMILES: FCC(Cc1ccc(F)cc1)NCCCc1ccc(Cl)cc1] | 39.1 ± 7.97 | 2340 ± 1070 | Rat | 0.1 | 540 |
| 151 | 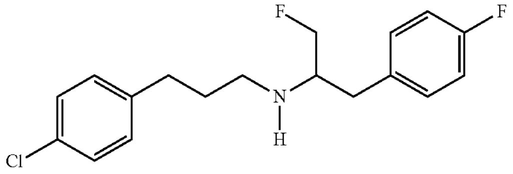 [SMILES: FCC(Cc1ccc(F)cc1)NCCCc1ccc(Cl)cc1] | 39.1 ± 7.97 | 2340 ± 1070 | Human | 0.9 | 22.6 |
| 152 | 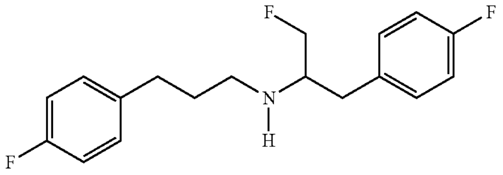 [SMILES: FCC(Cc1ccc(F)cc1)NCCCc1ccc(F)cc1] | 27.3 ± 12.8 | 5697 ± 2972 | Rat | 0.2 | 298 |
| 153 | 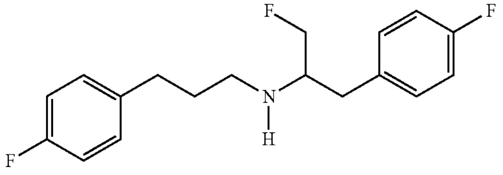 [SMILES: FCC(Cc1ccc(F)cc1)NCCCc1ccc(F)cc1] | 27.3 ± 12.8 | 5697 ± 2972 | Human | 1 | 20.5 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 154 | 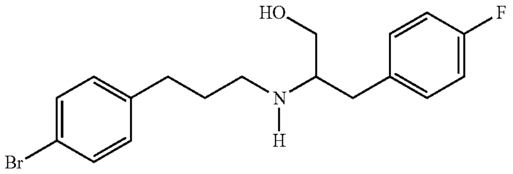 | 69.1 ± 13.6 | 1910 ± 62.7 | Human | >4 | <5.20 |
| 155 | 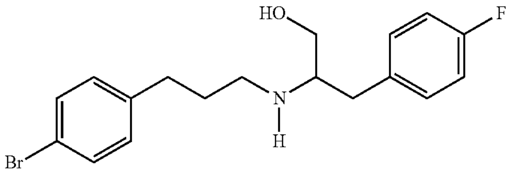 | 69.1 ± 13.6 | 1910 ± 62.7 | Rat | <0.1 | >450 |
| 156 | 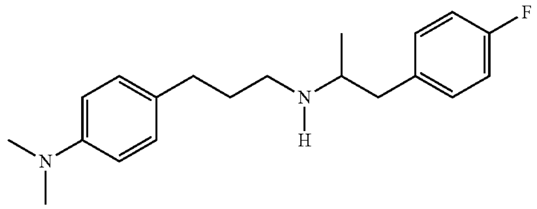 [SMILES: CC(Cc1ccc(F)cc1)NCCCc1ccc(N(C)C)cc1] | 118 ± 25.8 | Not determined | Human | 0.1 | 182 |
| 157 | 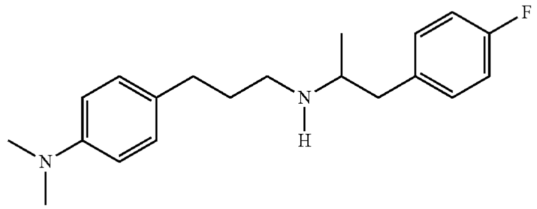 [SMILES: CC(Cc1ccc(F)cc1)NCCCc1ccc(N(C)C)cc1] | 118 ± 25.8 | Not determined | Rat | <0.1 | >400 |
| 158 | 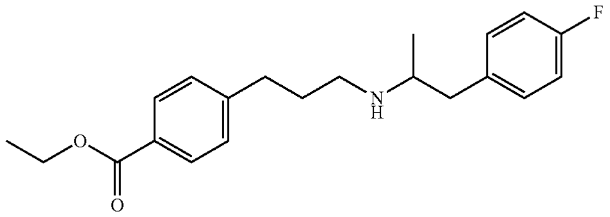 [SMILES: CCOC(=O)c1ccc(CCCNC(C)Cc2ccc(F)cc2)cc1] | 42.8 ± 8.89 | 1410 ± 275 | Rat | 0.4 | 120 |
| 159 | 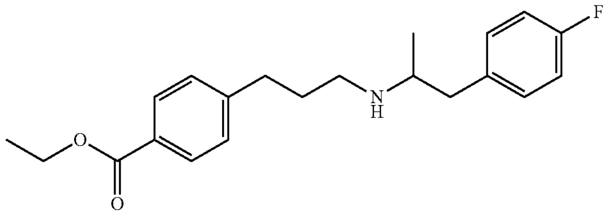 [SMILES: CCOC(=O)c1ccc(CCCNC(C)Cc2ccc(F)cc2)cc1] | 42.8 ± 8.89 | 1410 ± 275 | Human | 0.1 | 216 |
| 160 | 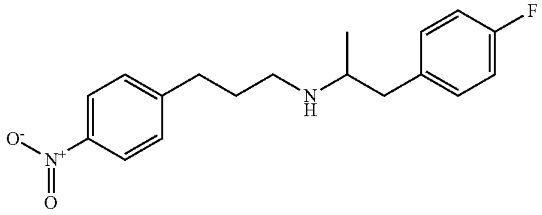 [SMILES: CC(Cc1ccc(F)cc1)NCCCc1ccc([N+](=O)[O-])cc1] | 14.3 ± 2.2 | 67.1 ± 14.7 | Rat | 0.4 | 119 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 161 | 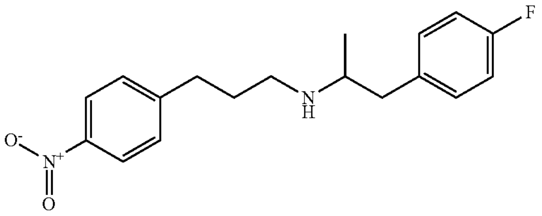 [SMILES: CC(Cc1ccc(F)cc1)NCCCc1ccc([N+](=O)[O-])cc1] | 14.3 ± 2.2 | 67.1 ± 14.7 | Human | >4 | <5.20 |
| 162 | 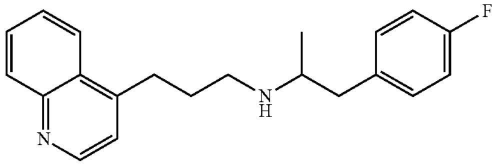 [SMILES: CC(Cc1ccc(F)cc1)NCCCc1ccnc2ccccc12] | 30.5 ± 8.59 | 2951 ± 1360 | Human | 0.2 | 102 |
| 163 | 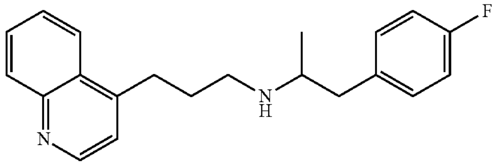 [SMILES: CC(Cc1ccc(F)cc1)NCCCc1ccnc2ccccc12] | 30.5 ± 8.59 | 2951 ± 1360 | Rat | <0.1 | >400 |
| 164 | 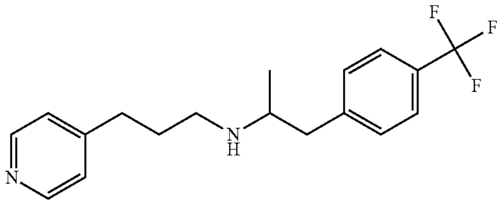 [SMILES: CC(Cc1ccc(C(F)(F)F)cc1)NCCCc1ccncc1] | 53.2 ± 6.5 | 1889 ± 639 | Rat | 0.6 | 83.3 |
| 165 | 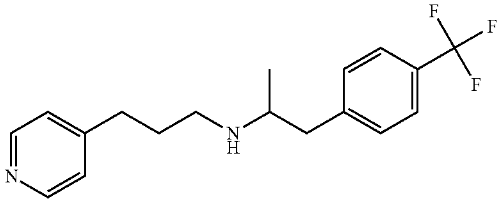 [SMILES: CC(Cc1ccc(C(F)(F)F)cc1)NCCCc1ccncc1] | 53.2 ± 6.5 | 1889 ± 639 | Human | >4 | <5.20 |
| 166 | 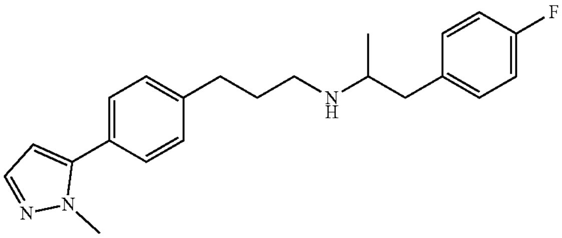 [SMILES: CC(Cc1ccc(F)cc1)NCCCc1ccc(-c2ccnn2C)cc1] | 46.5 ± 8.97 | 2200 ± 251 | Human | 0.6 | 34.3 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 167 | 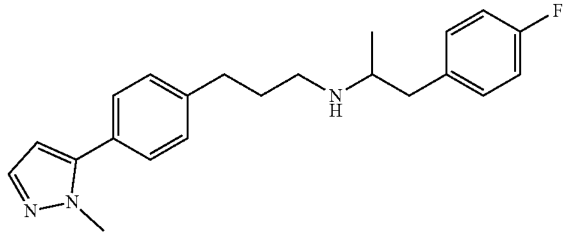 [SMILES: CC(Cc1ccc(F)cc1)NCCCc1ccc(-c2ccnn2C)cc1] | 46.5 ± 8.97 | 2200 ± 251 | Rat | 0.4 | 111 |
| 168 | 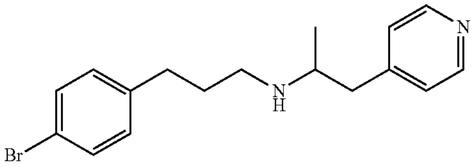 [SMILES: CC(Cc1ccncc1)NCCCc1ccc(Br)cc1] | 41 ± 11.1 | 1780 ± 468 | Human | 3.5 | 6 |
| 169 | 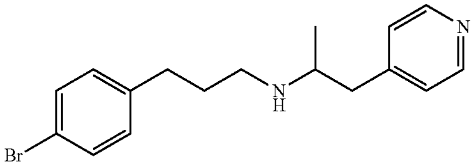 [SMILES: CC(Cc1ccncc1)NCCCc1ccc(Br)cc1] | 41 ± 11.1 | 1780 ± 468 | Rat | 0.2 | 200 |
| 170 | 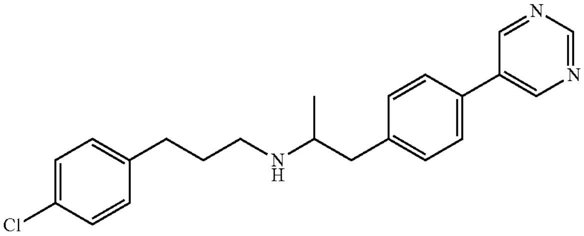 [SMILES: CC(Cc1ccc(-c2cncnc2)cc1)NCCCc1ccc(Cl)cc1] | 6.74 ± 2.59 | 199 ± 64.9 | Rat | 1.4 | 34.2 |
| 171 | 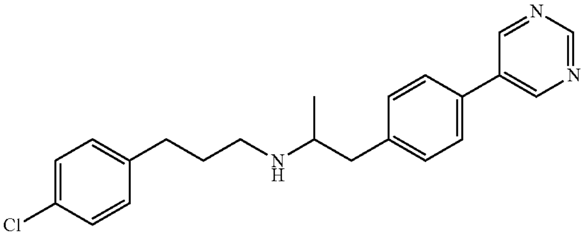 [SMILES: CC(Cc1ccc(-c2cncnc2)cc1)NCCCc1ccc(Cl)cc1] | 6.74 ± 2.59 | 199 ± 64.9 | Human | 0.3 | 75.2 |
| 172 | 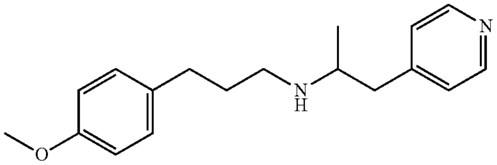 [SMILES: COc1ccc(CCCNC(C)Cc2ccncc2)cc1] | 186 ± 127 | Not determined | Human | 0.5 | 42.9 |
| 173 | 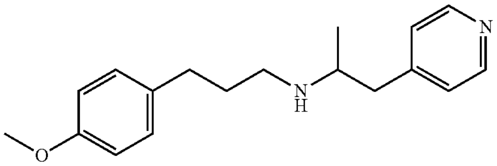 [SMILES: COc1ccc(CCCNC(C)Cc2ccncc2)cc1] | 186 ± 127 | Not determined | Rat | 0.4 | 126 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 174 | 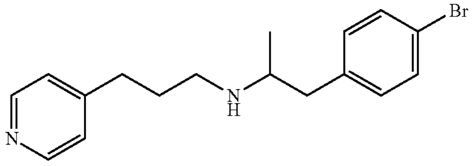 [SMILES: CC(Cc1ccc(Br)cc1)NCCCc1ccncc1] | 52.1 ± 35.9 | 880 ± 251 | Rat | 0.4 | 126 |
| 175 | 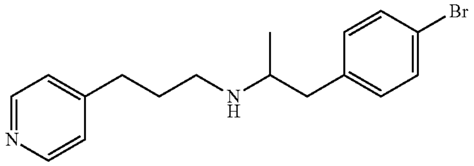 [SMILES: CC(Cc1ccc(Br)cc1)NCCCc1ccncc1] | 52.1 ± 35.9 | 880 ± 251 | Human | >4 | <5.20 |
| 176 | 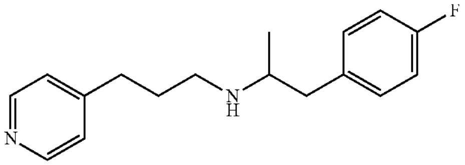 [SMILES: CC(Cc1ccc(F)cc1)NCCCc1ccncc1] | 80.7 ± 21 | 3770 ± 2.04 | Rat | 0.7 | 71.8 |
| 177 | 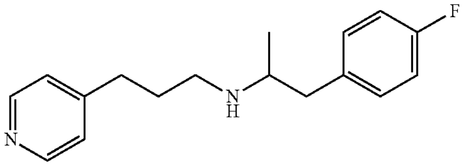 [SMILES: CC(Cc1ccc(F)cc1)NCCCc1ccncc1] | 80.7 ± 21 | 3770 ± 2.04 | Human | >4 | <5.20 |
| 178 | 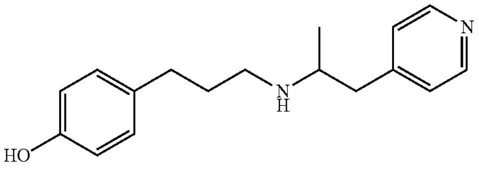 [SMILES: CC(Cc1ccncc1)NCCCc1ccc(O)cc1] | 124 ± 29.4 | 5070 ± 71.4 | Rat | 0.5 | 89.3 |
| 179 | 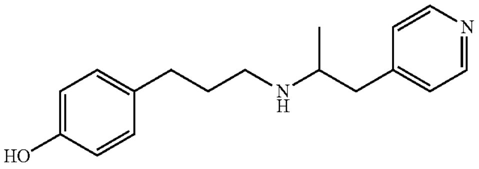 [SMILES: CC(Cc1ccncc1)NCCCc1ccc(O)cc1] | 124 ± 29.4 | 5070 ± 71.4 | Human | >4 | <5.20 |
| 180 | 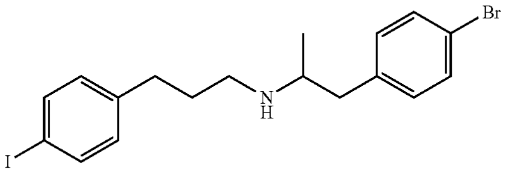 [SMILES: CC(Cc1ccc(Br)cc1)NCCCc1ccc(I)cc1] | 48.4 ± 19.4 | 601 ± 195 | Rat | 0.2 | 290 |
| 181 | 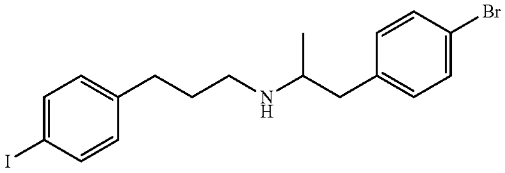 [SMILES: CC(Cc1ccc(Br)cc1)NCCCc1ccc(I)cc1] | 48.4 ± 19.4 | 601 ± 195 | Human | >4 | <5.20 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 182 | 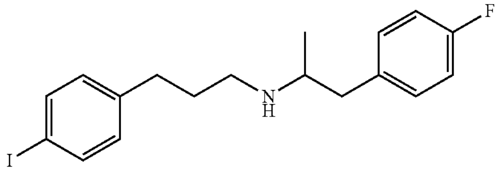 [SMILES: CC(Cc1ccc(F)cc1)NCCCc1ccc(I)cc1] | 52.7 ± 6.35 | 512 ± 126 | Rat | 0.1 | 375 |
| 183 | 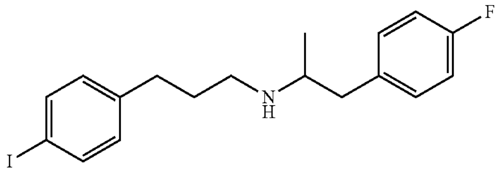 [SMILES: CC(Cc1ccc(F)cc1)NCCCc1ccc(I)cc1] | 52.7 ± 6.35 | 512 ± 126 | Human | >4 | <5.20 |
| 184 | 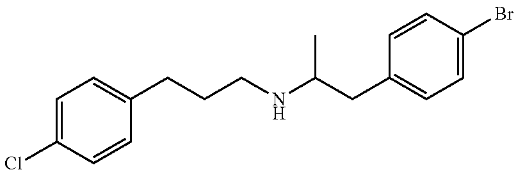 [SMILES: CC(Cc1ccc(Br)cc1)NCCCc1ccc(Cl)cc1] | 9.06 ± 1.61 | 196 ± 30.5 | Rat | 0.1 | 452 |
| 185 | 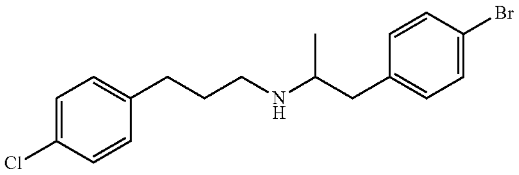 [SMILES: CC(Cc1ccc(Br)cc1)NCCCc1ccc(Cl)cc1] | 9.06 ± 1.61 | 196 ± 30.5 | Human | >4 | <5.20 |
| 186 | 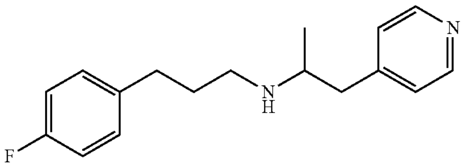 [SMILES: CC(Cc1ccncc1)NCCCc1ccc(F)cc1] | 72.4 ± 29.8 | 3320 ± 1930 | Human | 4.8 | 4.3 |
| 187 | 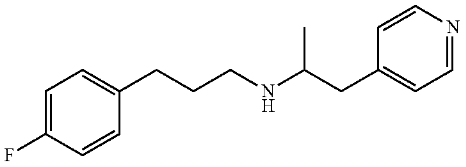 [SMILES: CC(Cc1ccncc1)NCCCc1ccc(F)cc1] | 72.4 ± 29.8 | 3320 ± 1930 | Rat | 0.3 | 150 |
| 188 | 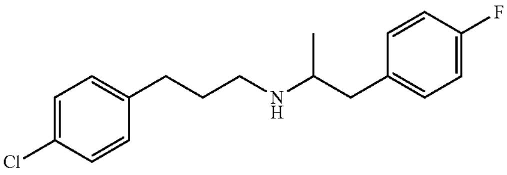 [SMILES: CC(Cc1ccc(F)cc1)NCCCc1ccc(Cl)cc1] | 22 ± 7.72 | 467 ± 280 | Human | 4.4 | 4.7 |
| 189 | 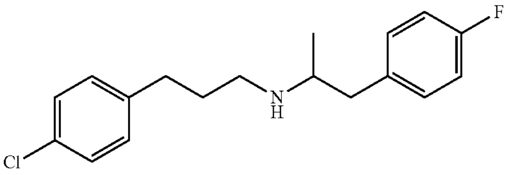 [SMILES: CC(Cc1ccc(F)cc1)NCCCc1ccc(Cl)cc1] | 22 ± 7.72 | 467 ± 280 | Rat | <0.1 | >400 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 190 | 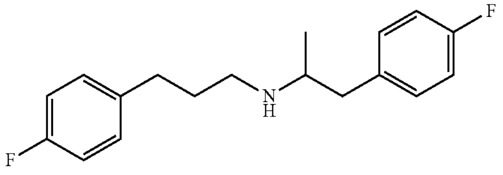 [SMILES: CC(Cc1ccc(F)cc1)NCCCc1ccc(F)cc1] | 8.28 ± 0.736 | 789 ± 221 | Human | 3.9 | 5.4 |
| 191 | 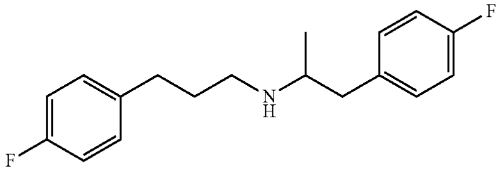 [SMILES: CC(Cc1ccc(F)cc1)NCCCc1ccc(F)cc1] | 8.28 ± 0.736 | 789 ± 221 | Rat | 0.2 | 195 |
| 192 | 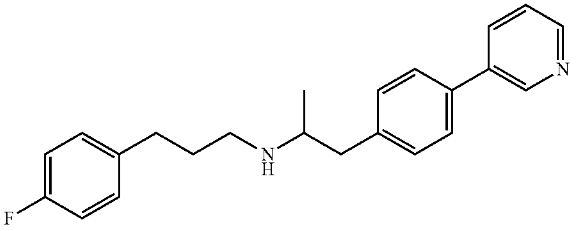 [SMILES: CC(Cc1ccc(-c2cccnc2)cc1)NCCCc1ccc(F)cc1] | 11.9 ± 9.94 | 675 ± 127 | Rat | 0.6 | 77.2 |
| 193 | 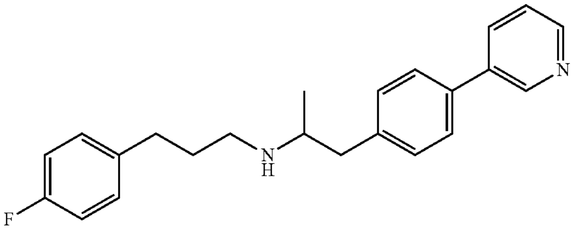 [SMILES: CC(Cc1ccc(-c2cccnc2)cc1)NCCCc1ccc(F)cc1] | 11.9 ± 9.94 | 675 ± 127 | Human | 0.1 | 144 |
| 194 | 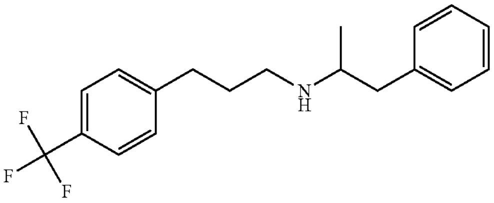 [SMILES: CC(Cc1ccccc1)NCCCc1ccc(C(F)(F)F)cc1] | 27.7 ± 7.81 | 791 ± 270 | Rat | 0.3 | 138 |
| 195 | 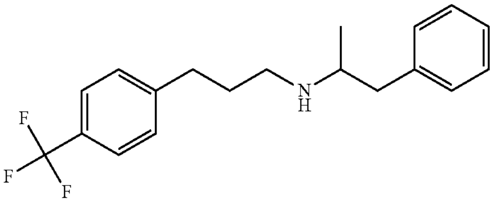 [SMILES: CC(Cc1ccccc1)NCCCc1ccc(C(F)(F)F)cc1] | 27.7 ± 7.81 | 791 ± 270 | Human | >4 | <5.20 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 196 | 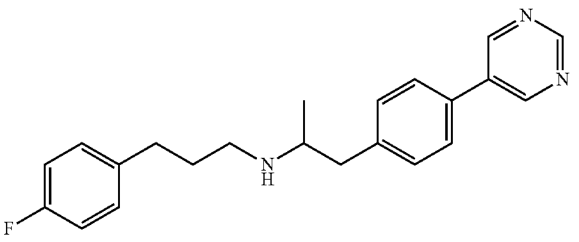 [SMILES: CC(Cc1ccc(-c2cncnc2)cc1)NCCCc1ccc(F)cc1] | 7.12 ± 1.59 | 402 ± 72.2 | Rat | 3.2 | 14.7 |
| 197 | 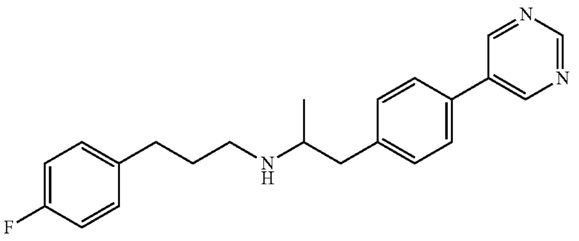 [SMILES: CC(Cc1ccc(-c2cncnc2)cc1)NCCCc1ccc(F)cc1] | 7.12 ± 1.59 | 402 ± 72.2 | Human | 0.5 | 40.4 |
| 198 | 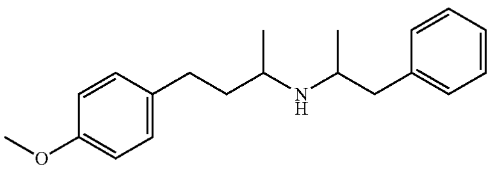 [SMILES: COc1ccc(CCC(C)NC(C)Cc2ccccc2)cc1] | 152 + 25.6 | Not determined | Rat | 0.1 | 414 |
| 199 | 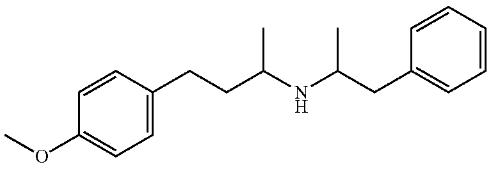 [SMILES: COc1ccc(CCC(C)NC(C)Cc2ccccc2)cc1] | 152 + 25.6 | Not determined | Human | <0.1 | >400 |
| 200 | 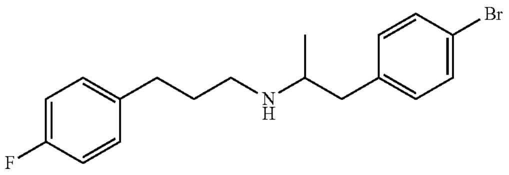 | 15.2 ± 8.86 | 242 ± 76 | Rat | 0.3 | 186 |
| 201 | 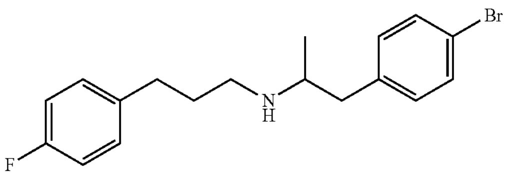 | 15.2 ± 8.86 | 242 ± 76 | Human | >4 | <5.20 |
| 202 | 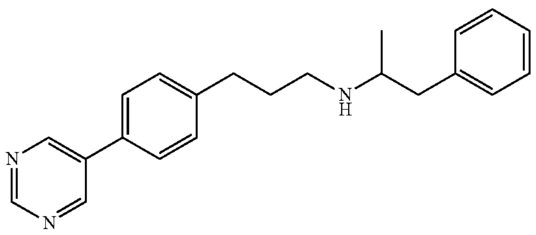 [SMILES: CC(Cc1ccccc1)NCCCc1ccc(-c2cncnc2)cc1] | 119 ± 31.8 | Not determined | Human | 0.1 | 155 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 203 | 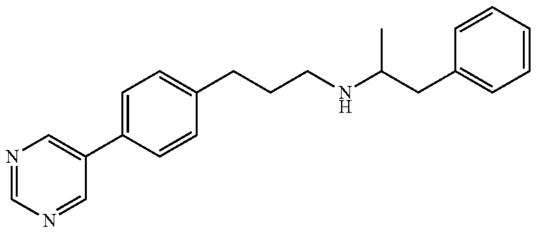 [SMILES: CC(Cc1ccccc1)NCCCc1ccc(-c2cncnc2)cc1] | 119 ± 31.8 | Not determined | Rat | 0.2 | 248 |
| 204 | 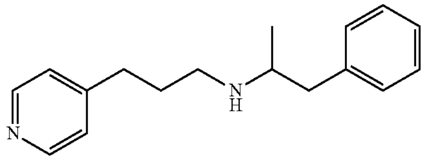 [SMILES: CC(Cc1ccccc1)NCCCc1ccncc1] | 49.1 ± 3.51 | 8460 ± 4580 | Human | 3.6 | 5.8 |
| 205 | 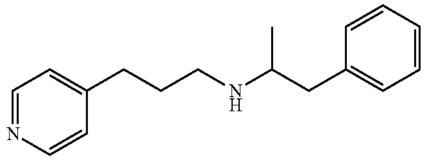 [SMILES: CC(Cc1ccccc1)NCCCc1ccncc1] | 49.1 ± 3.51 | 8460 ± 4580 | Rat | 0.5 | 90.6 |
| 206 | 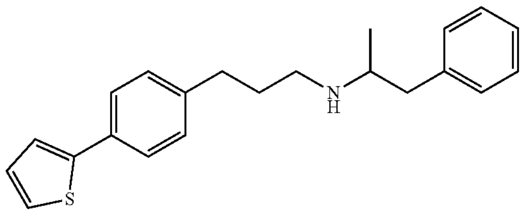 [SMILES: CC(Cc1ccccc1)NCCCc1ccc(-c2cccs2)cc1] | 125 ± 25.4 | Not determined | | | |
| 207 | 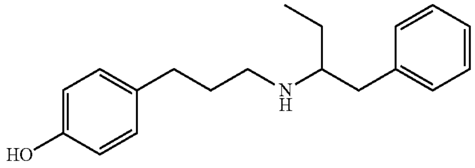 [SMILES: CCC(Cc1ccccc1)NCCCc1ccc(O)cc1] | 37.8 ± 6.59 | 2380 ± 517 | Rat | <0.1 | >400 |
| 208 | 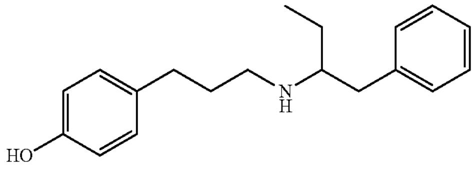 [SMILES: CCC(Cc1ccccc1)NCCCc1ccc(O)cc1] | 37.8 ± 6.59 | 2380 ± 517 | Human | <0.1 | >400 |
| 209 | 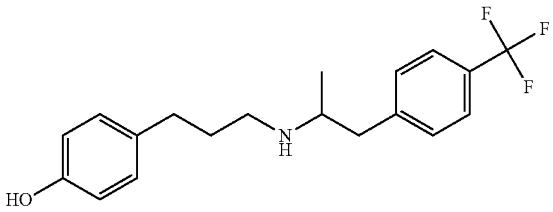 [SMILES: CC(Cc1ccc(C(F)(F)F)cc1)NCCCc1ccc(O)cc1] | 17.1 ± 6.86 | 252 ± 109 | | | |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 210 | 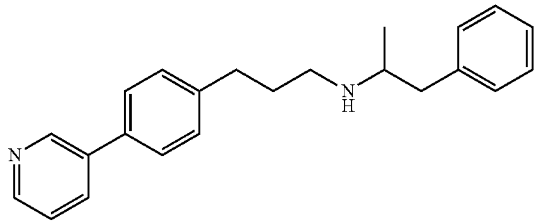 [SMILES: CC(Cc1ccccc1)NCCCc1ccc(-c2cccnc2)cc1] | 55.4 ± 7.94 | 3120 ± 251 | Rat | 0.1 | 392 |
| 211 | 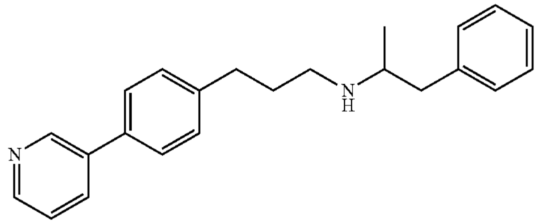 [SMILES: CC(Cc1ccccc1)NCCCc1ccc(-c2cccnc2)cc1] | 55.4 ± 7.94 | 3120 ± 251 | Human | <0.1 | >400 |
| 212 | 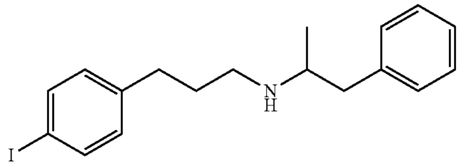 [SMILES: CC(Cc1ccccc1)NCCCc1ccc(I)cc1] | 22.2 ± 2.21 | 642 ± 168 | Rat | 0.1 | 439 |
| 213 | 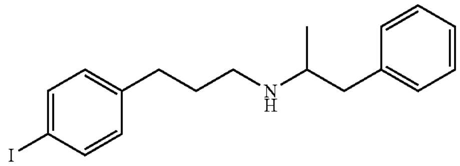 [SMILES: CC(Cc1ccccc1)NCCCc1ccc(I)cc1] | 22.2 ± 2.21 | 642 ± 168 | Human | >4 | <5.20 |
| 214 | 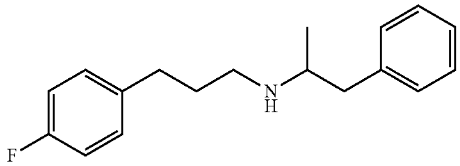 | 6.86 ± 1.81 | 3043 ± 1373 | Human | 1.2 | 17.6 |
| 215 | 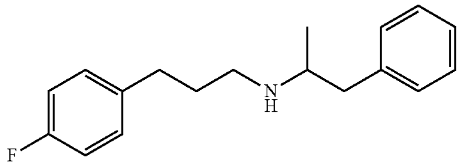 | 6.86 ± 1.81 | 3043 ± 1373 | Rat | 0.3 | 148 |
| 216 | 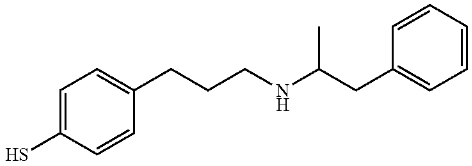 [SMILES: CC(Cc1ccccc1)NCCCc1ccc(Br)cc1] | 65.4 ± 23.4 | 4190 ± 1080 | Rat | 0.3 | 170 |

TABLE 2-continued
| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 217 | 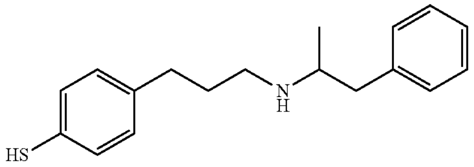 | 65.4 ± 23.4 | 4190 ± 1080 | Rat | 0.3 | 170 |
| 218 | 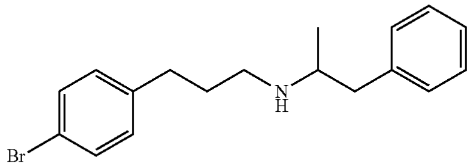 [SMILES: CC(Cc1ccccc1)NCCCc1ccc(Br)cc1] | 14.2 ± 2.17 | 421 ± 38.1 | Human | 2.2 | 9.5 |
| 219 | 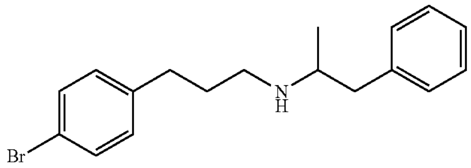 | 14.2 ± 2.17 | 421 ± 38.1 | Rat | <0.1 | >400 |
| 220 | 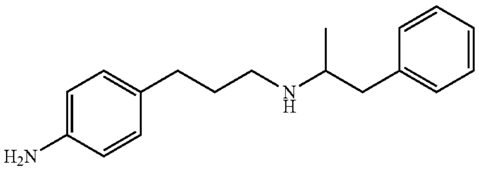 | 40.4 ± 4.72 | 5340 ± 5630 | Rat | 0.7 | 65.3 |
| 221 | See Compound 220 | | | | | |
| 222 | 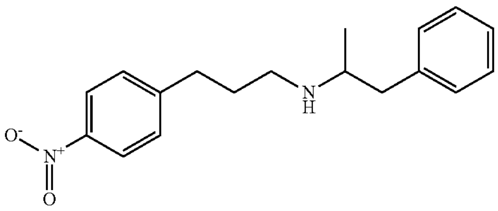 [SMILES: CC(Cc1ccccc1)NCCCc1ccc([N+](=O)[O-])cc1] | 4.97 ± 3.08 | 96.1 ± 28.3 | Rat | <0.1 | >400 |
| 223 | 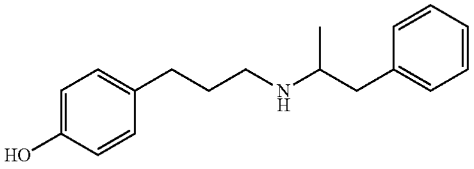 Batch A | 5.01 ± 1.72 | 2750 ± 1080 | | | |
| 224 | 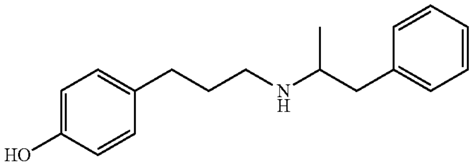 Batch B | | | Rat | <0.1 | >400 |

TABLE 2-continued

| | Structure | VMAT2 (rat) Inhibition: Mean Ki (nM) ± Standard Deviation | hERG Binding: Mean Ki (nM) ± Standard Deviation | Micro-somal stability assays: Species | Micro-somal assays: Half-life (hr) | Micro-somal stability assays: Clearance (ml/min /kg) |
|---|---|---|---|---|---|---|
| 225 | 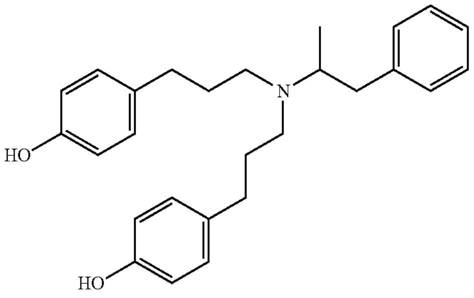 [SMILES: CC(Cc1ccccc1)N(CCCc1ccc(O)cc1)CCCc1ccc(O)cc1] | 4.99 ± 1.19 | | | | |
| 226 | See Compound 225 | | | | | |

Example 6

Synthesis of [N-3-(4-fluorophenyl)-propan-1-yl]-3-(4-aminophenyl)-1-fluoro-2-propylamine 2-(4-Nirophenylmethylene)oxirane (3.58 g, 20.0 mmol, 1 eq), triethylaminetrihydro-fluoride (3.22 g, 20.0 mmole, 1 eq) and diisopropylethylamine (5.17 g, 40.0 mmol, 2 eq) were placed in a thick-walled glass pressure vial (50 ml) and heated overnight in an oil bath of 150° C. Subsequently, the reaction was cooled to ambient temperature and diluted with 100 ml of ethyl ether. The solution was extracted with 2×20 ml of 10% hydrochloric acid, 20 ml of a concentrated solution of sodium bicarbonate, and 25 ml of brine. The organic layer was separated and concentrated at 25° C. under vacuum of 40 Torr to yield 3.36 g of a mixture (9:1) of 1-fluoro-3-(4-nitrophenyl)-propan-2-ol with 2-fluoro-3-(4-nitrophenyl)-propan-1-ol, which was submitted to flash chromatography on silica gel using a solvent mixture of ethyl acetate and hexane (1:8) as an eluent. The desired product, 1-fluoro-3-(4-nitrophenyl)-propan-2-ol, was collected as the first fraction and the eluents containing it were concentrated at 35° C. and 20 Torr to yield 2.94 g (74% yield) of a light yellow, viscous, transparent oil.

A solution of 1-fluoro-3-(4-nitrophenyl)-propan-2-ol (2.76 g, 13.85 mmol, 1 eq) in 10 ml anhydrous DCM was added drop by drop by a syringe into a suspension of pyridinium chlorochromate (4.48 g, 20.8 mmol, 1.5 eq) and 4.0 g of Celite in 200 ml of anhydrous DCM while agitated well at ambient temperature. The reaction was energetically agitated at ambient temperature for 17 hours. Subsequently the mixture was diluted with 150 ml of ethyl ether, stirred for an additional 30 minutes, and filtered through a 10 cm-thick layer of 100 ml silica gel. The gel was washed with 3×25 ml of ethyl ether. The filtrates were concentrated at 35° C. and under vacuum of 40 Torr to yield 2.76 g of yellow-brown viscous oil which was purified by flash chromatography on silica-gel using a solvent mixture of ethyl acetate and hexane (1:9). The eluents colored light yellow were evaporated under vacuum at 40° C. and under 15 Torr to yield 2.56 g (93.8% yield) of the desired product, 2-fluoro-3-(4-nitrophenyl)-propan-1-ol, as light yellow viscous oil.

Into a stirred suspension of 5 g of A4 dry molecular sieves in 30 ml of anhydrous 1,2-dichloroethane were added 1-fluoro-3-(4-nitrophenyl)-propan-2-one (2.4 g, 12.1 mmol, 1.0 eq) and 1-(4-fluorophenyl)-3-propylamine (1.86 g, 12.1 mmol, 1.0 eq), and the mixture was stirred for 5 hours at ambient temperature. Subsequently, sodium borohydridetri-acetate (4.53 g, 21 mmole, 1.75 eq) was added at ambient temperature, in a single portion, with intense agitation that was maintained overnight. Subsequently, the reaction mixture was diluted with 50 ml of DCM, the liquids were decanted, and the residue A4 molecular sieves were washed 5× with 10 ml of DCM each. All of the solutions were combined and placed in a separatory funnel, washed with a standard solution of sodium bicarbonate 3×20 ml, and then washed with brine 2×25 ml. The lower, organic phase was collected and dried with anhydrous sodium sulfate, filtered, and concentrated under vacuum at 45° C. and 15 Torr to yield 3.5 g of a yellow-orange colored viscous oil, which was submitted to flash chromatography on silicagel using a solvent mixture of methanol and dichloromethane (1:10). The desired product, [N-3-(4-fluorophenyl)-propan-1-yl]-3-(4-nitrophenyl)-1-fluoro-2-propylamine ($R_f$ 0.45), was collected after removal of solvents under vacuum at 35° C. and at 15 Torr as a viscous yellow oil in amount of 2.91 g (71.9% yield).

[N-3-(4-fluorophenyl)-propan-1-yl]-3-(4-nitrophenyl)-1-fluoro-2-propylamine (334 mg, 1.0 mmol, 1. eq) was suspended/dissolved in 4.0 ml of methanol placed in a 25 ml flask under septum. The flask was flushed with nitrogen, then 60 mg of 5% palladium on carbon was added under nitrogen, which was subsequently replaced with hydrogen from a balloon. The reduction was run overnight under the pressure of the hydrogen from the balloon at ambient temperature. The reaction mixture was filtered through a layer of Celite, concentrated under vacuum at 25° C. and 15 Torr to yield 272 mg (89.4% yield) of viscous, oily product of the desired [N-3-(4-fluorophenyl)-propan-1-yl]-3-(4-aminophenyl)-1-fluoro-2-propylamine.

A scheme for the synthesis of [N-3-(4-fluorophenyl)-propan-1-yl]-3-(4-aminophenyl)-1-fluoro-2-propylamine is provided below:

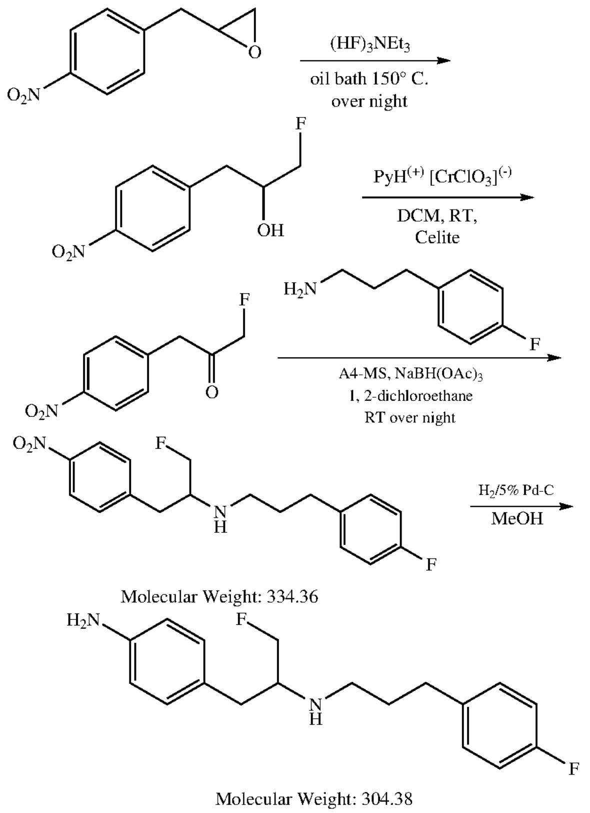

Example 7

Microsomal Assays

Liver microsomes (20 mg/ml protein) were purchased from Fisher scientific (female Sprague-Dawley rat microsomes, #50-722-704; pooled mix gender human liver microsomes, #50-722-516). Liver microsomes (0.73 ml) were mixed with EDTA solution (0.06 ml, 0.5 M in water) and potassium phosphate buffer (22.31 ml, 0.1M, pH 7.4, 37° C.) to make 23.1 mL of liver microsome solution (20 mg/mL liver microsome protein). 10 mM stocks of compound in DMSO were diluted with DMSO and acetonitrile (1:4, v:v) to a final concentration of 0.08 mM. 10 mM stocks of controls in DMSO (diphenhydramine HCl, verapamil HCl) were diluted to a final concentration of 0.4 mM. Each diluted compound stock (37.8 μL) was added to an aliquot of the liver microsomal solution (3 ml) and vortexed. The resulting solution was added to each of 3 wells of a master assay plate (pION Inc., MA, #110323). Each plate holds triplicate samples of two controls (0.4 mM) and up to 14 compounds (0.08 mM) in rat and human liver microsomes. Aliquots of each well of the plate (175 μl of each well) were transferred from the master plate into 5 assay plates. For 0-hr time point, pre-cooled (4° C.) internal standard (437.5 μM, 2 μM caffeine in methanol) was added to the first plate before the reaction starts. NADPH regenerating system solution A (6.05 ml, Fisher Scientific, #NC9255727) was combined with NADPH regenerating system solution B (1.21 ml, Fisher Scientific, #NC9016235) in potassium phosphate buffer (15.8 ml, 0.1 M, pH 7.4, 37° C.). The resulting NADPH solution (43.8 μl) was added to each well of all the 96-well assay plates and mixed with pipette briefly making the final protein and compound concentrations respectively: 0.5 mg/ml, 0.08 μM (0.4 μM for controls). Plates were sealed, and all plates except the 0-hr plate were incubated at 37° C., shaken at a speed of 60 rpm. A single assay plate was tested at each time point: 0.5 hr, 1 hr, 2 hr, and 4 hr. At each time point, 437.5 μL of pre-cooled internal standard was added each well of the plate to quench the reaction. The quenched plate was then centrifuged (model 5810R, Eppendorf, Westbury, NY) at 3300 rpm for 15 minutes at 4° C. 120 μl supernatant was transferred to a 96-well plate, centrifuged again and analyzed by UPLC-MS (Waters Inc., Milford, MA). The compounds and internal standard were detected by selected ion recording (SIR).

The amount of material was measured as a ratio of peak area to the internal standard and graphed. Using the slope from the initial linear portion of this curve, the degradation rate constant is calculated using equation [1]. The rate constant was then used to calculate the compounds half-life in plasma using equation [2]. Intrinsic clearance was calculated as CLint'=(0.693/(t½))*(1/microsomal concentration in the reaction solution)*(45 mg microsome/gram liver)*(gram liver/kg b.w.), where microsomal concentration in the reaction solution is 0.5 mg/ml, and gram liver/kg b.w. of rat and human are 45, 32 and 20, respectively. Intrinsic clearance was also calculated as CLint' (μL/min/mg protein)=(1000)*(0.693/(t½*60))/0.5.

$$k = -\text{slope} \times 2.303 \quad [1]$$

$$t_{1/2} = \frac{\ln 2}{k} \quad [2]$$

Example 8

Pharmacokinetic Assays

Animals: Oral and intravenous dose pharmacokinetic studies were conducted in tandem in age matched female Swiss Webster mice and/or age matched male Sprague-Dawley rats purchased from Envigo-Harlan. Animals were housed in IVC cages with wood chip bedding and given food and water ad libitum. All experiments were conducted in accordance with recommendations in the *Guide for the Care and Use of Laboratory Animals*, 8$^{th}$ Ed., and were approved by the University of Kentucky's Institutional Animal Care and Use Committee.

Dose Formulation and Administration Volumes: Hydrochloric acid salts or free base forms were used for formulation. Dose solutions of these compounds were prepared gravimetrically in 15% Kolliphor EL: 85% Saline (w:w) at concentrations allowing for administration volumes of 2.5×-10× animal body weight (kg animal body weight to mL dose volume conversion factor) depending upon compound solubility in the excipients. Drug solutions were typically warmed to 60° C. while mixing at 650 rpm for 0.25-1 h on an incubating shaker, then sterilized by filtration through 0.2μ nylon syringe filter.

Pharmacokinetic Studies: Groups of 6 animals were dosed with formulated test compound by bolus lateral tail vein injection (iv), by oral gavage (po), or by subcutaneous injection (sc) into left hind flank. At predefined timepoints (typically 5-15 min, 20-30 min, 1 h, 3 h, 6 h, and 8-9 h), whole blood samples were collected from the saphenous vein using pre-heparinized pipet tips (n=3/timepoint from the 6 animals/group/compound having been divided into 2 groups of 3 with sampling alternated between the 2 groups). Whole blood samples were collected into microtubes and centrifuged at 4000×g for 2 min. Plasma supernatants were collected and immediately frozen on dry ice, then transferred to a −80° C. freezer to await processing for LC-MS/MS analysis. Typical dose rates were 2 mg/kg iv, 10 mg/kg po, and <30 mg/kg sc.

Calibrator and Quality Control (OC) Preparation: Analyte spiking solutions (21× concentrated solutions in 50:50 MeOH:$H_2O$) were created by independent dilutions from 1 or 100 μg/mL compound solutions in 50:50 MeOH:$H_2O$). Plasma calibrators (usually 0.25, 0.5, 1, 5, 15, 30, 100, 400, 700, and 1000 ng/mL) were generated by the addition of 5 μL of appropriate spiking solution into 100 μL blank plasma followed by vortex mixing. Plasma QC samples (usually 0.75, 25, 500, and 850 ng/mL) were prepared in a similar manner using an independent $2^{nd}$ analyte stock solution. Calibrators and QCs were stored alongside experimental samples at −80° C. until analysis.

Calibrator and Quality Control (OC) Preparation: Analyte spiking solutions (21× concentrated solutions in 50:50 MeOH:$H_2O$) were created by independent dilutions from 1 or 100 μg/mL compound solutions in 50:50 MeOH:$H_2O$). Plasma calibrators (usually 0.25, 0.5, 1, 5, 15, 30, 100, 400, 700, and 1000 ng/mL) were generated by the addition of 5 μL of appropriate spiking solution into 100 μL blank plasma followed by vortex mixing. Plasma QC samples (usually 0.75, 25, 500, and 850 ng/mL) were prepared in a similar manner using an independent $2^{nd}$ analyte stock solution. Calibrators and QCs were stored alongside experimental samples at −80° C. until analysis.

LC-MS/MS Analysis: Methanolic supernatants were analyzed for compound-specific m z molecular ion/fragment transitions and m z 294.2→105.2 (for GZ-361b ISTD) by LC-MS/MS using multiple reaction monitoring (MRM). Analyte and internal standard contained in 5 μL sample injections (15° C. temp.; 1.5 mL 0.1% formic acid in MeOH or 1:1 MeOH: isopropanol injector rinse; 10 sec rinse dip time) were eluted from a guard-protected (2.7 μL, 3×5 mm) Agilent Poroshell 120 EC-C18 (2.7 μL, 3×50 mm; oven temp. 40° C.) analytical column with a 0.1% formic acid in water (mobile Phase-A): 0.1% formic acid in acetonitrile (mobile Phase-B) gradient. Flow rate was constant at 0.4 mL/min and the gradient usually progressed from an initial 0.5 min hold at 10% mobile Phase-B increased linearly to 90% over 3.8 min. The 90% mobile Phase-B was typically maintained for 1.2 min before returning to the initial 10% over a 1 min ramp, with re-equilibration at 10% organic for 1.5 min (7.5 min total run time). Positive-mode ESI Turbo V® source and MS gas, temperature, and probe settings were optimized for 0.4 mL flow rate at CUR=35/ISV=4500/TEM=550/GS1=65/GS2=65/CAD=10 with the probe position=7/0.5 horizontal/vertical. Whereas compound-dependent voltage potential settings were optimized prior to analysis using infusions of ~100 ng/mL drug standards in 50:50 mobile phase mixture (e.g., Analyte SK-4-292; DP=30, EP=10, CE=47, CXP=15). ISTD voltage potentials were set at DP=70, EP=10, CE=35 and CXP=6. Sample sequences consisted of single randomized experimental sample injections flanked by sets of blanks, calibrators and QCs with QCs interspersed, as needed, to maintain >5% total QC to experimental sample occurrence. High QCs (5,000 and 10,000 ng/mL) were inserted at end of sequence prior to second calibrator injections. Calibration curves were typically constructed by weighted ($1/x^2$) non-linear regression analysis of analyte/ISTD concentration ratios to analyte/ISTD peak area ratios using AB SciexMultiQuant software (Ver 3.0.31721.0).

Various exemplary compounds were tested using the [3H]dopamine ([3H]DA) uptake assay according to Example 3, the [$^3$H]Dofetilide binding assay according to Example 4, the microsomal assays according to Example 7, and the pharmacokinetic assays according to Example 8. The results of these assays are set forth in Table 3.

TABLE 3

| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 220 | 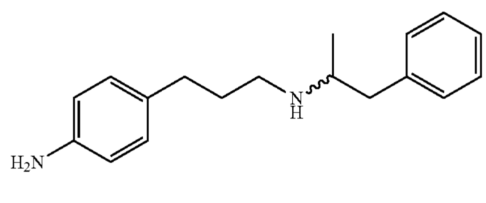 | 40 | 5,340 | 3.87 | 3.97 | Fmice: quant; Frat: quant | Rat: 0.7 hr |
| 94 | 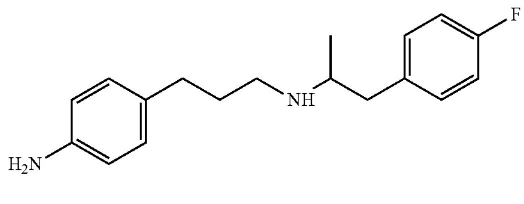 [SMILES: CC(Cc1ccc(F)cc1)NCCCc1ccc(N)cc1] | 85 | 3,980 N = 2 | 4.01 | 3.90 | | Rat: 0.4 hr Human: 1.6 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 60 | 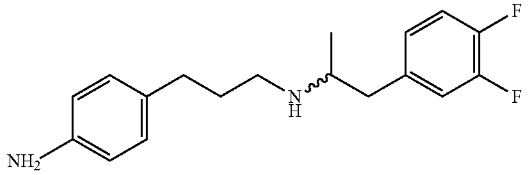 [SMILES: CC(Cc1ccc(F)c(F)c1)NCCCc1ccc(N)cc1] | 48 | 3,140 N = 2 | 4.15 | 3.83 | | Rat: 1 hr Human: 2.2 hr |
| 62 | 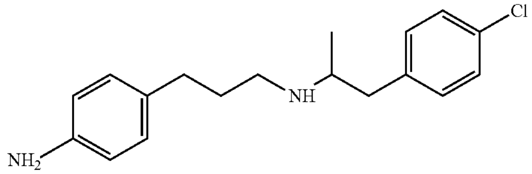 [SMILES: CC(Cc1ccc(Cl)cc1)NCCCc1ccc(N)cc1] | 32 | 2,380 | 4.47 | 3.67 | | Rat: 0.6 hr Human: 1.8 hr |
| 57 | 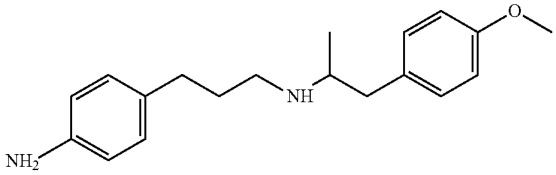 [SMILES: COc1ccc(CC(C)NCCCc2ccc(N)cc2)cc1] | 69 | 4,250 N = 2 | 3.71 | 4.15 | | Not Deter-mined |
| 70 | 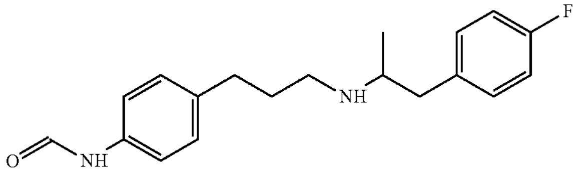 [SMILES: CC(Cc1ccc(F)cc1)NCCCc1ccc(NC=O)cc1] | 23 | 2,600 | 4.03 | 3.99 | | |
| 105 | 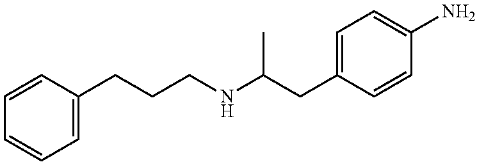 [SMILES: CC(Cc1ccc(N)cc1)NCCCc1ccccc1] | 27 | 4,610 | 3.87 | 3.97 | | |
| 77 | 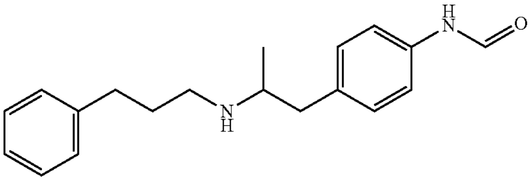 [SMILES: CC(Cc1ccc(NC=O)cc1)NCCCc1ccccc1] | 21 | 1,760 N = 2 | 3.88 | 4.06 | | Rat: 0.3 hr Human: 1.9 hr |
| 109 | 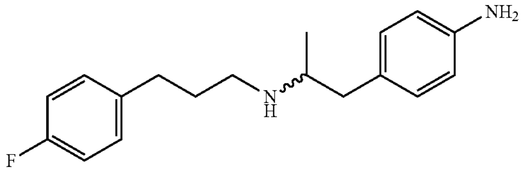 [SMILES: CC(Cc1ccc(N)cc1)NCCCc1ccc(F)cc1] | 19 | 2,500 | 4.01 | 3.90 | | Rat: >4 hr Human: 0.8 hr |
| 88 | 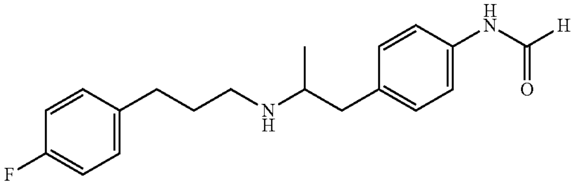 [SMILES: CC(Cc1ccc(NC=O)cc1)NCCCc1ccc(F)cc1] | 12 N = 4 | 738 N = 2 | 4.03 | 3.99 | | Rat: 3.5 hr Human: 1.6 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Microsomal stability assays: Species/Half-life (hr) |
|---|---|---|---|---|---|---|---|
| 91 | 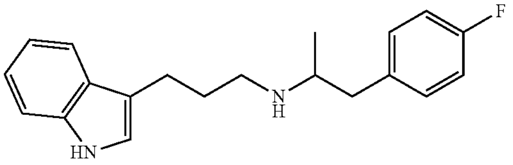 [SMILES: CC(Cc1ccc(F)cc1)NCCCc1c[nH]c2ccccc12] | 37 | 2,200 N = 2 | 4.94 | 2.85 | | Rat: 0.1 hr Human: 0.2 hr |
| 56 | 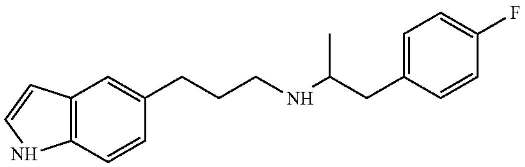 [SMILES: CC(Cc1ccc(F)cc1)NCCCc1ccc2[nH]ccc2c1] | 27 | 1,260 N = 2 | 4.94 | 2.86 | | Rat: 0.1 hr Human: 0.2 hr |
| 148 | 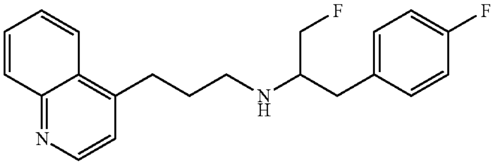 [SMILES: FCC(Cc1ccc(F)cc1)NCCCc1ccnc2ccccc12] | 70 | 4,700 | 4.84 | 3.05 | | Rat: 0.1 hr Human: 0.1 hr |
| 162 | 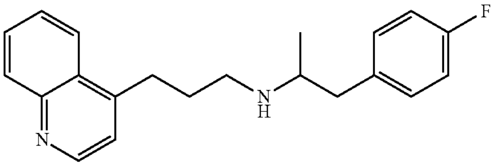 [SMILES: CC(Cc1ccc(F)cc1)NCCCc1ccnc2ccccc12] | 30 | 3,000 | 4.99 | 2.98 | | Rat: <0.1 hr Human: 0.2 hr |
| 166 | 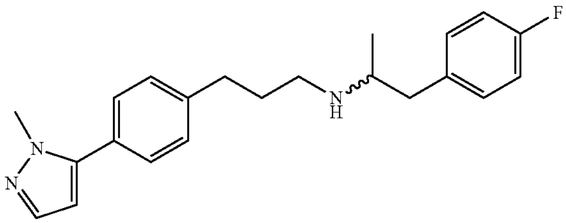 [SMILES: CC(Cc1ccc(F)cc1)NCCCc1ccc(-c2ccnn2C)cc1] | 47 | 2,200 | 4.83 | 3.40 | | Rat: 0.4 hr Human: 0.6 hr |
| 187 | 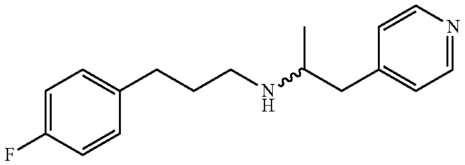 [SMILES: CC(Cc1ccncc1)NCCCc1ccc(F)cc1] | 72 | 3,320 | 3.62 | 3.77 | Fmice: 9.4% | Rat: 0.3 hr Human: >4 hr |
| 168 | 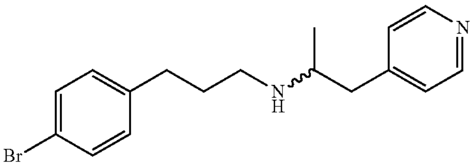 [SMILES: CC(Cc1ccncc1)NCCCc1ccc(Br)cc1] | 41 | 1,780 | 4.25 | 3.46 | | Rat: 0.2 hr Human: 3.5 hr |
| 204 | 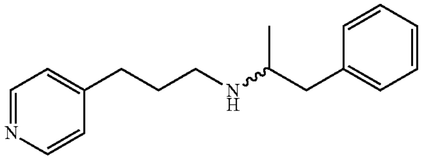 [SMILES: CC(Cc1ccccc1)NCCCc1ccncc1] | 49 | 8,460 | 3.48 | 3.84 | Fmice: 10% (prelim rat done) | Rat: 0.5 hr Human: 3.6 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 176 | 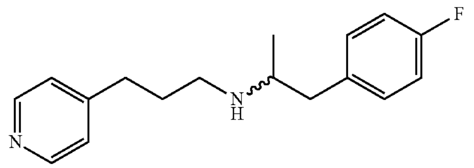 [SMILES: CC(Cc1ccc(F)cc1)NCCCc1ccncc1] | 81 | 5,100 | 3.62 | 3.77 | Fmice: ~22% (prelim rat done) | Rat: 0.7 hr Human: >4 hr |
| 174 | 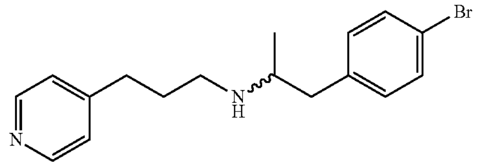 [SMILES: CC(Cc1ccc(Br)cc1)NCCCc1ccncc1] | 52 | 880 | 4.25 | 3.46 | | Rat: 0.4 hr Human: >4 hr |
| 164 | 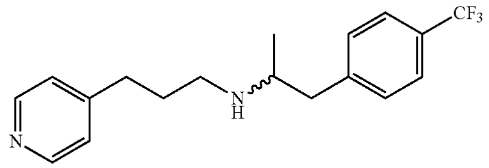 [SMILES: CC(Cc1ccc(C(F)(F)F)cc1)NCCCc1ccncc1] | 53 | 1,900 | 4.35 | 3.40 | | Rat: 0.6 hr Human: >4 hr |
| 96 | 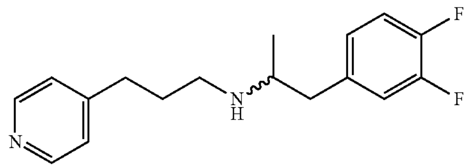 [SMILES: CC(Cc1ccc(F)c(F)c1)NCCCc1ccncc1] | 79 | 4,070 N = 2 | 3.76 | 3.70 | | Rat: 0.5 hr Human: 1.7 hr |
| 98 | 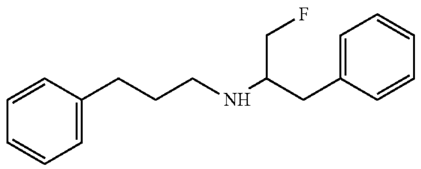 [SMILES: FCC(Cc1ccccc1)NCCCc1ccccc1] | 29 | 17,100 N = 2 | 4.54 | 3.10 | | Rat: 0.1 hr Human: 0.2 hr |
| 100 | 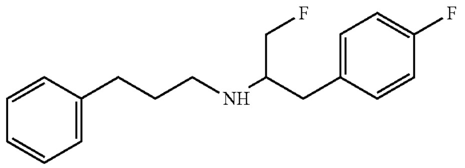 [SMILES: FCC(Cc1ccc(F)cc1)NCCCc1ccccc1] | 49 | 7,390 N = 2 | 4.68 | 2.95 | | Not Deter-mined |
| 101 | 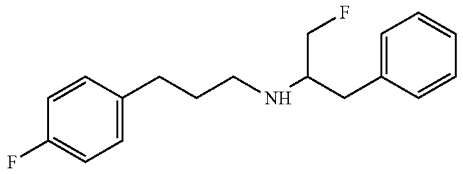 [SMILES: FCC(Cc1ccccc1)NCCCc1ccc(F)cc1] | 17 | 4,800 N = 2 | 4.68 | 2.95 | | Rat: 0.2 hr Human: 0.6 hr |
| 223 | 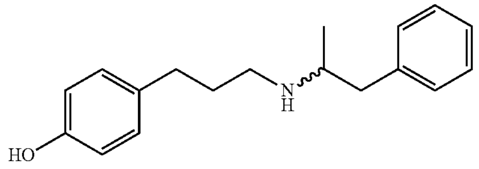 | 5 | 2,750 | 3.65 | 3.79 | Fmice: 8.9% | Not Deter-mined |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 216 | 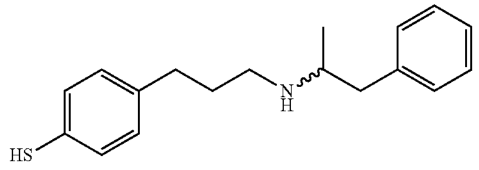 [SMILES: CC(Cc1ccccc1)NCCCc1ccc(S)cc1] | 65 | 4,190 | 4.31 | 1.85 | Fmice: 0.9% | Rat: 0.3% |
| 150 | 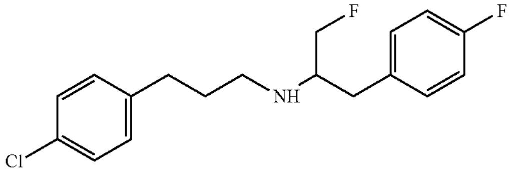 [SMILES: FCC(Cc1ccc(F)cc1)NCCCc1ccc(Cl)cc1] | 39 | 2,340 | 5.29 | 2.49 | | Rat: 0.1 hr Human: 0.9 hr |
| 126 | 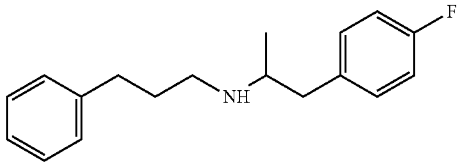 [SMILES: CC(Cc1ccc(F)cc1)NCCCc1ccccc1] | 19 | 2,050 | 4.84 | 2.90 | | Rat: 0.1 hr Human: 1.8 hr |
| 158 | 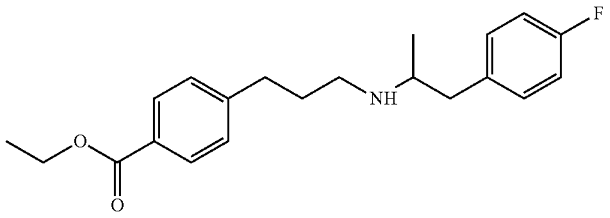 [SMILES: CCOC(=O)c1ccc(CCCNC(C)Cc2ccc(F)cc2)cc1] | 43 | 1,410 | 5.2 | 3.54 | | Rat: 0.4 hr Human: 0.1 hr |
| 222 | 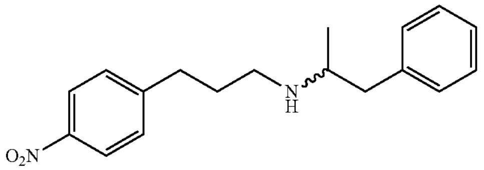 [SMILES: CC(Cc1ccccc1)NCCCc1ccc([N+](=O)[O-])cc1] | 5 | 100 | 4.63 | 4.02 | | Not Deter-mined |
| 194 | 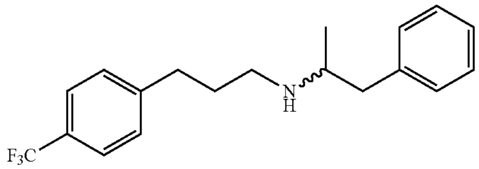 [SMILES: CC(Cc1ccccc1)NCCCc1ccc(C(F)(F)F)cc1] | 28 | 800 | 5.57 | 2.47 | Fmice: 11.9% | Rat: 0.3 hr Human: >4 hr |
| 94 | 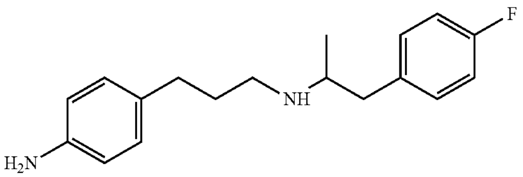 [SMILES: CC(Cc1ccc(F)cc1)NCCCc1ccc(N)cc1] | 85 | 3,980 N = 2 | 4.01 | 3.57 | | Rat: 0.4 hr Human: 1.6 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 188 | 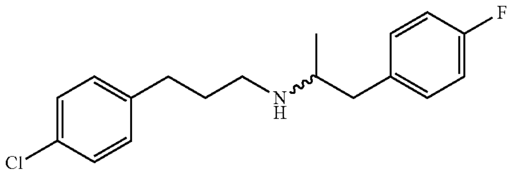 [SMILES: CC(Cc1ccc(F)cc1)NCCCc1ccc(Cl)cc1] | 22 | 500 | 5.44 | 2.52 | | Rat: <0.1 hr Human: 4.4 hr |
| 190 | 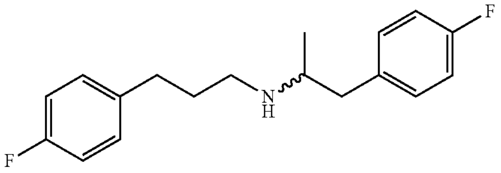 [SMILES: CC(Cc1ccc(F)cc1)NCCCc1ccc(F)cc1] | 9 | 790 | 4.98 | 2.76 | Fmice: 5% | Rat: 0.2 hr Human: 3.9 hr |
| 156 | 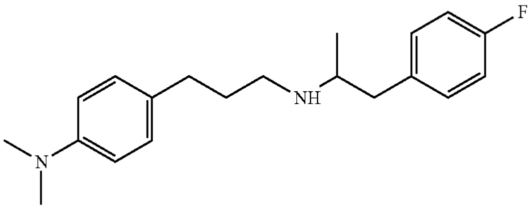 [SMILES: CC(Cc1ccc(F)cc1)NCCCc1ccc(N(C)C)cc1] | 118 | 49,000 N = 1 | 4.95 | 2.81 | | Rat: 0.1 hr Human: 0.1 hr |
| 178 | 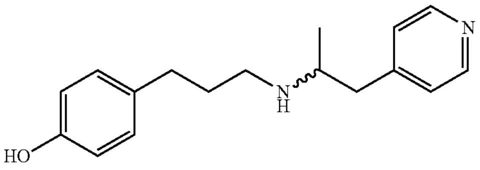 [SMILES: CC(Cc1ccncc1)NCCCc1ccc(O)cc1] | 124 | 5,070 N = 2 | 2.52 | 4.5 | | Rat: 0.5 hr Human: >4 hr |
| 172 | 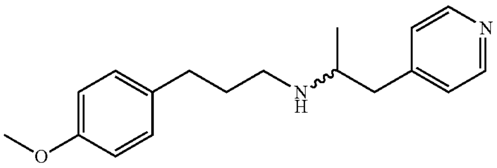 [SMILES: COc1ccc(CCCNC(C)Cc2ccncc2)cc1] | 186 | Not Deter-mined | 3.32 | 4.38 | | Rat: 0.1 hr Human: 0.5 hr |
| 103 | 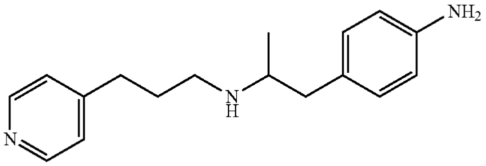 [SMILES: CC(Cc1ccc(N)cc1)NCCCc1ccncc1] | 386 | Not Deter-mined | 2.65 | 4.17 | | Not Deter-mined |
| 134 | 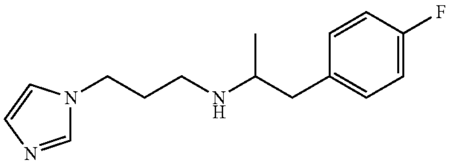 [SMILES: CC(Cc1ccc(F)cc1)NCCCn1ccnc1] | 515 | Not Deter-mined | 2.35 | 4.33 | | Rat: >4 hr Human: >4 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 192 | 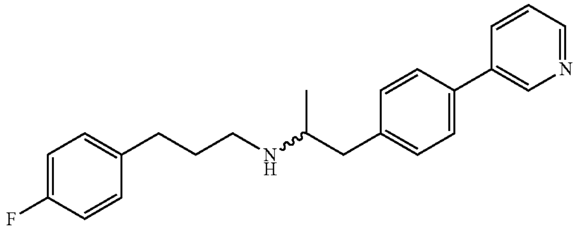 [SMILES: CC(Cc1ccc(-c2cccnc2)cc1)NCCCc1ccc(F)cc1] | 12 | 680 | 5.27 | 2.86 | Fmice: 6.7% | Rat: 0.6 hr Human: 0.1 hr |
| 196 | 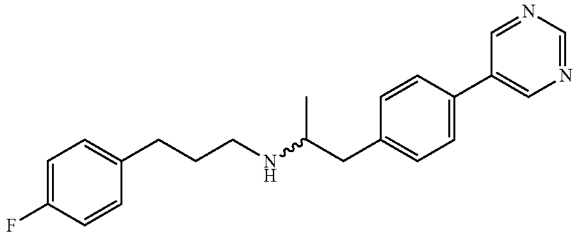 [SMILES: CC(Cc1ccc(-c2cncnc2)cc1)NCCCc1ccc(F)cc1] | 8 | 400 | 4.56 | 3.94 | Fmice: 3.4% (prelim rat done) | Rat: 3.2 hr Human: 0.5 hr |
| 154 | 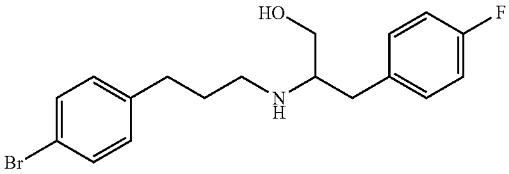 [SMILES: OCC(Cc1ccc(F)cc1)NCCCc1ccc(Br)cc1] | 69 | 1900 | 4.56 | 3.28 | | Rat: 0.1 hr Human: >4 hr |
| 136 | 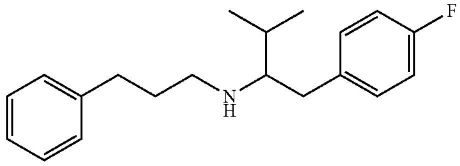 [SMILES: CC(C)C(Cc1ccc(F)cc1)NCCCc1ccccc1] | 460 | Not Deter-mined | 5.72 | 2.46 | | Not Deter-mined |
| 140 | 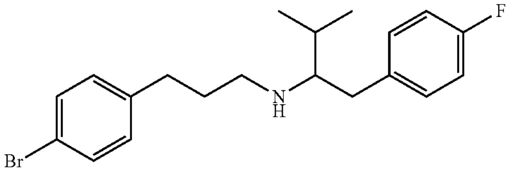 [SMILES: CC(C)C(Cc1ccc(F)cc1)NCCCc1ccc(Br)cc1] | 132 | Not Deter-mined | 6.49 | 1.94 | | Rat: 0.1 hr Human: 1.4 hr |
| 207 | 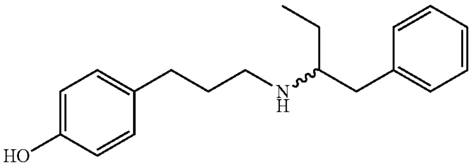 [SMILES: CCC(Cc1ccccc1)NCCCc1ccc(O)cc1] | 38 | 2,380 | 4.07 | 3.57 | | Rat: 0.1 hr Human: 0.1 hr |
| 198 | 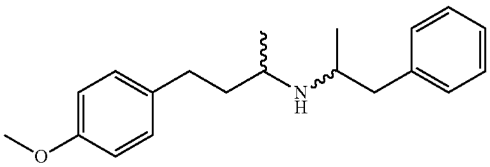 [SMILES: COc1ccc(CCC(C)NC(C)Cc2ccccc2)cc1] | 152 | Not Deter-mined | 4.95 | 2.89 | | Rat: 0.1 hr Human: <0.1 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 218 | 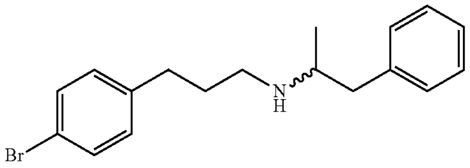 [SMILES: CC(Cc1ccccc1)NCCCc1ccc(Br)cc1] | 14 | 420 | 5.46 | 2.52 | | Rat: <0.1 hr Human: 2.2 hr |
| 212 | 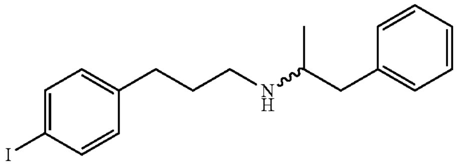 [SMILES: CC(Cc1ccccc1)NCCCc1ccc(I)cc1] | 22 | 640 | 5.62 | 2.3 | | Rat: 0.1 hr Human: >4 hr |
| 184 | 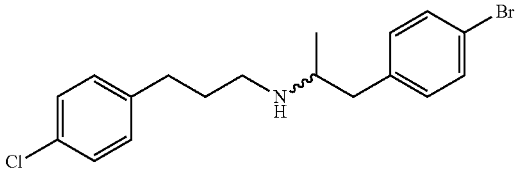 [SMILES: CC(Cc1ccc(Br)cc1)NCCCc1ccc(Cl)cc1] | 9 | 202 | 6.07 | 2.16 | | Rat: 0.1 hr Human: >4 hr |
| 200 | 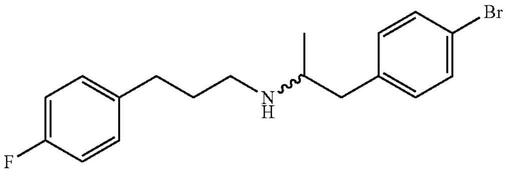 [SMILES: CC(Cc1ccc(Br)cc1)NCCCc1ccc(F)cc1] | 15 | 242 | 5.61 | 2.44 | | Rat: 0.3 hr Human: >4 hr |
| 85 | 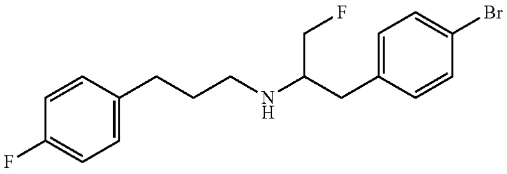 [SMILES: FCC(Cc1ccc(Br)cc1)NCCCc1ccc(F)cc1] | 37 | 1134 | 5.45 | 2.35 | | Rat: 0.1 hr Human: 1.1 hr |
| 182 | 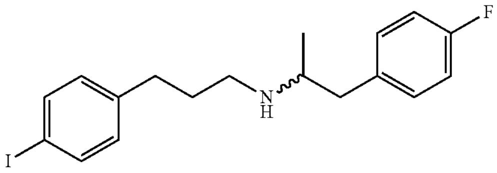 [SMILES: CC(Cc1ccc(F)cc1)NCCCc1ccc(I)cc1] | 53 | 512 | 5.77 | 2.09 | | Rat: 0.1 hr Human: >4 hr |
| 180 | 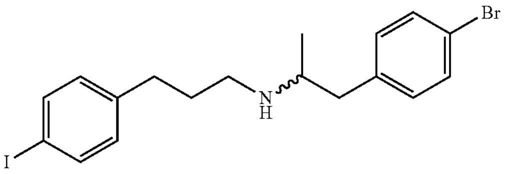 [SMILES: CC(Cc1ccc(Br)cc1)NCCCc1ccc(I)cc1] | 48 | 600 | 6.39 | 1.35 | | Rat: 0.2 hr Human: >4 hr |
| 145 | 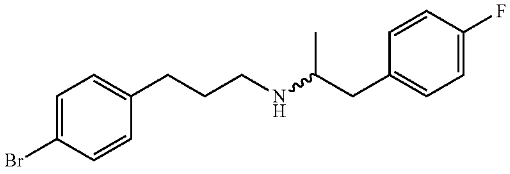 | 23 | 500 | 5.61 | 2.43 | | Rat: 0.1 hr Human: >4 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 209 | 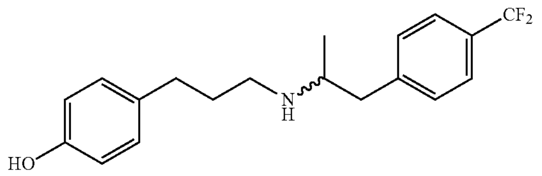 | 17 | 252 | 4.55 | 3.11 | | Rat: 0.2 hr Human: 0.1 hr |
| 121 | 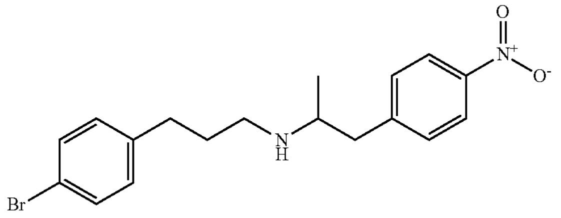 [SMILES: CC(Cc1ccc([N+](=O)[O-])cc1)NCCCc1ccc(Cl)cc1] | 13 | 80 | 5.4 | 3.37 | | Rat: 0.1 hr Human: >4 hr |
| 125 | 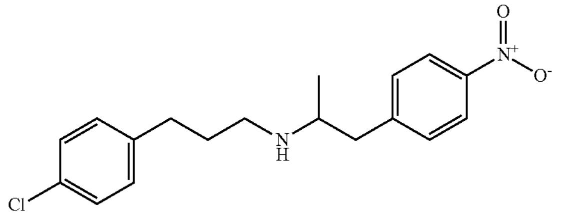 | 9 | 82 N = 2 | 5.24 | 3.57 | | |
| 79 | 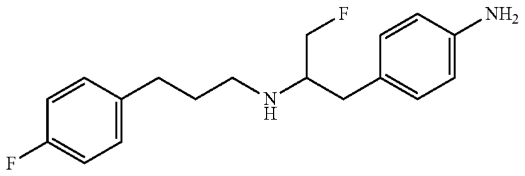 [SMILES: Nc1ccc(CC(CF)NCCCc2ccc(F)cc2)cc1] | 20 | 3441 | 3.85 | 4.02 | | Rat: 2.2 hr Human: 0.7 hr |
| 58 | 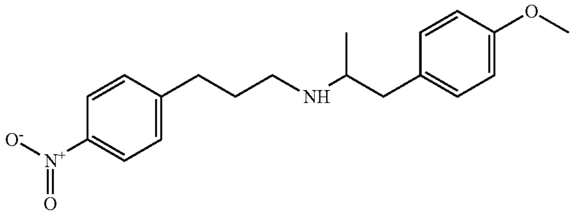 [SMILES: COc1ccc(CC(C)NCCCc2ccc([N+](=O)[O-])cc2)cc1] | 17 | 42 | 4.48 | 4.09 | | Not Deter-mined |
| 160 | 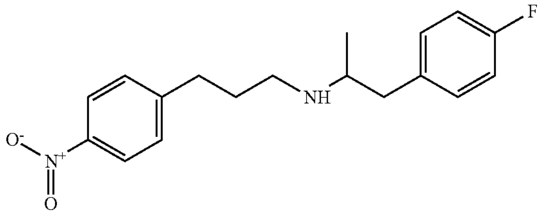 [SMILES: CC(Cc1ccc(F)cc1)NCCCc1ccc([N+](=O)[O-])cc1] | 14 | 67 | 4.78 | 3.94 | | Rat: 0.4 hr Human: >4 hr |
| 64 | 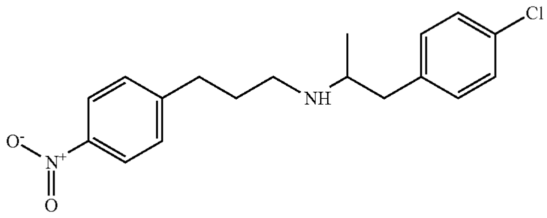 [SMILES: CC(Cc1ccc(Cl)cc1)NCCCc1ccc([N+](=O)[O-])cc1] | 16 | 29 | 5.24 | 3.6NP H-NB1-226 | | Not Deter-mined |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 59 | 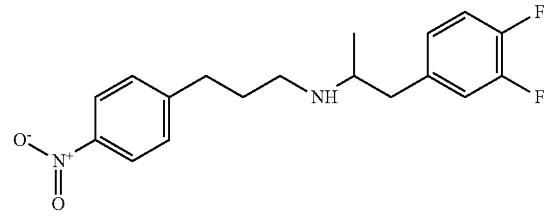 [SMILES: CC(Cc1ccc(F)c(F)c1)NCCCc1ccc([N+](=O)[O-])cc1] | 13 | 56 | 4.92 | 3.77 | | Not Deter-mined |
| 123 | 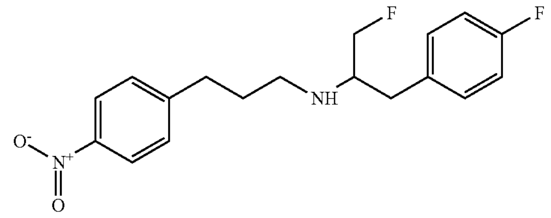 [SMILES: O=[N+]([O-])c1ccc(CCCNC(CF)Cc2ccc(F)cc2)cc1] | 44 | 223 | 4.62 | 4.02 | | Rat: 0.4 hr Human: 1.2 hr |
| 54 | 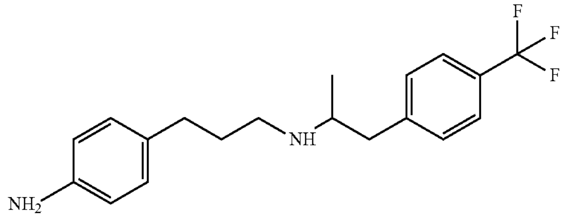 [SMILES: CC(Cc1ccc(C(F)(F)F)cc1)NCCCc1ccc(N)cc1] | 62 | 908 | 4.74 | 3.2 | | Not Deter-mined |
| 170 | 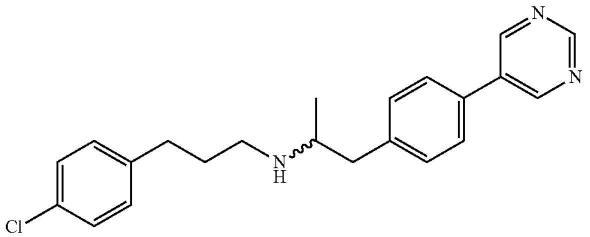 [SMILES: CC(Cc1ccc(-c2cncnc2)cc1)NCCCc1ccc(Cl)cc1] | 7 | 200 | 5.02 | 3.58 | | Rat: 1.4 hr Human: 0.3 hr |
| 68 | 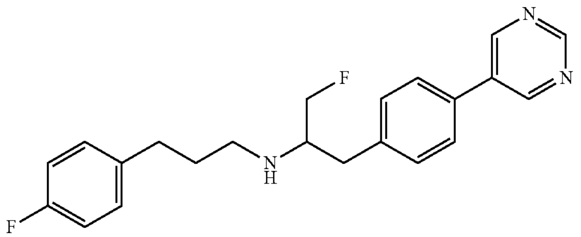 [SMILES: FCC(Cc1ccc(-c2cncnc2)cc1)NCCCc1ccc(F)cc1] | 5 | 633 | 4.41 | 4.07 | | Rat: 0.6 hr Human: 0.1 hr |
| 133 | 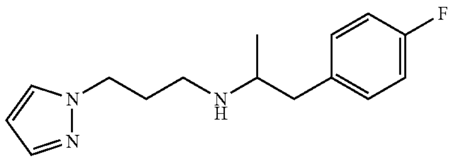 [SMILES: CC(Cc1ccc(F)cc1)NCCCn1cccn1] | 709 | Not Deter-mined | 2.67 | 4.33 | | Rat: 0.3 hr Human: >4 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 202 | 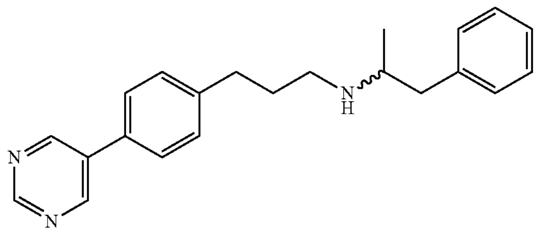 [SMILES: CC(Cc1ccccc1)NCCCc1ccc(-c2cncnc2)cc1] | 119 | Not Deter-mined | 4.42 | 4.01 | | Rat: 0.2 hr Human: 0.1 hr |
| 128 | 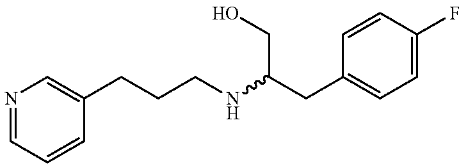 [SMILES: OCC(Cc1ccc(F)cc1)NCCCc1cccnc1] | 634 | Not Deter-mined | 1.62 | 4.67 | | Rat: 0.3 hr Human: 0.6 hr |
| 227 | 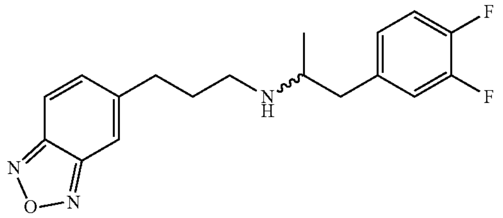 [SMILES: CC(Cc1ccc(F)c(F)c1)NCCCc1ccc2nonc2c1] | 49 | 650 | 4.33 | 4.14 | No detection | |
| 228 | 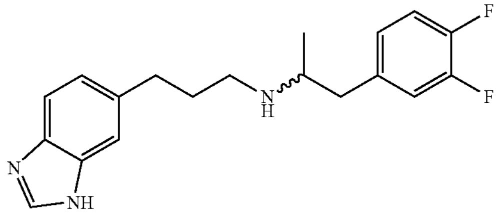 [SMILES: CC(Cc1ccc(F)c(F)c1)NCCCc1ccc2nc[nH]c2c1] | 41 | 6,770 | 4.27 | 3.87 | Frat: 5% | |
| 229 | 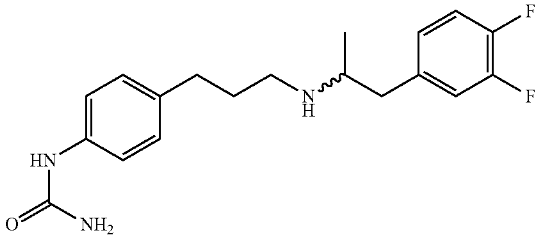 [SMILES: CC(Cc1ccc(F)c(F)c1)NCCCc1ccc(NC(N)=O)cc1] | 36 | 4,290 | 3.88 | 3.72 | Frat: 22% | |
| 230 | 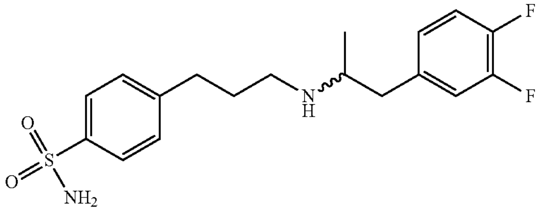 [SMILES: CC(Cc1ccc(F)c(F)c1)NCCCc1ccc(S(N)(=O)=O)cc1] | 42 | 1,030 | 3.03 | 4.43 | Frat: >100% | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 231 | 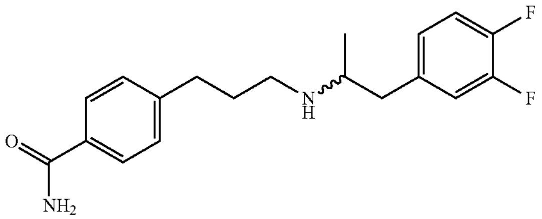 [SMILES: CC(Cc1ccc(F)c(F)c1)NCCCc1ccc(C(N)=O)cc1] | 29 | 3,500 | 3.83 | 4.08 | Frat: 80% | |
| 232 | 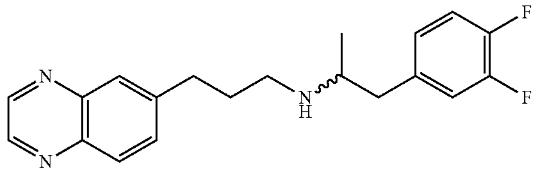 [SMILES: CC(Cc1ccc(F)c(F)c1)NCCCc1ccc2nccnc2c1] | 52 | 3,300 | 4.31 | 4.07 | | |
| 233 | 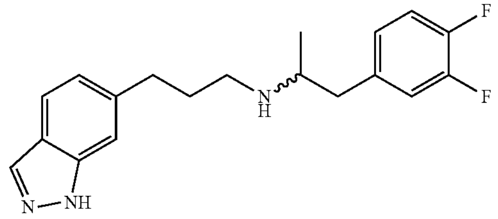 [SMILES: CC(Cc1ccc(F)c(F)c1)NCCCc1ccc2cn[nH]c2c1] | 33 | 483 | 4.66 | 3.67 | | |
| 234 | 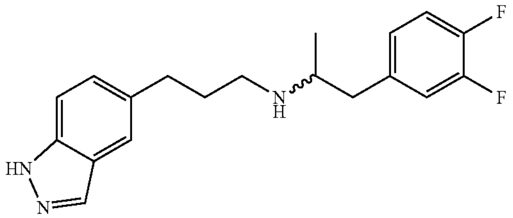 [SMILES: CC(Cc1ccc(F)c(F)c1)NCCCc1ccc2[nH]ncc2c1] | 54 | 1,020 | 4.66 | 3.67 | | |
| 235 | 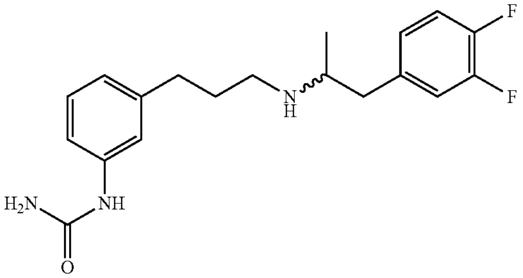 [SMILES: CC(Cc1ccc(F)c(F)c1)NCCCc1cccc(NC(N)=O)c1] | 4 N = 4 | 4,380 | 3.88 | 3.72 | | |
| 236 | 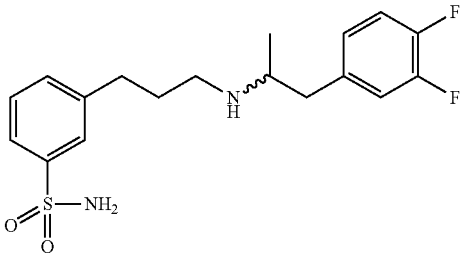 [SMILES: CC(Cc1ccc(F)c(F)c1)NCCCc1cccc(S(N)(=O)=O)c1] | 99 | 2,010 N = 4 | 2.99 | 4.44 | | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 237 | 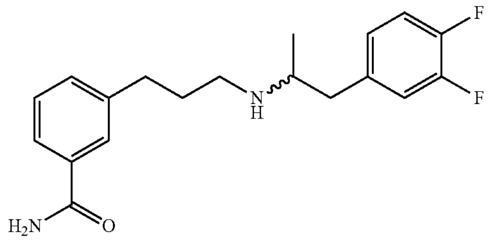 [SMILES: CC(Cc1ccc(F)c(F)c1)NCCCc1cccc(C(N)=O)c1] | 32 | 4,780 | 3.83 | 4.08 | | |
| 238 | 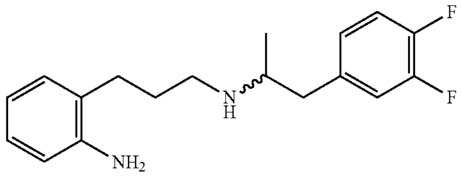 [SMILES: CC(Cc1ccc(F)c(F)c1)NCCCc1ccccc1N] | 220 | 3,250 | 4.15 | 3.83 | | |
| 239 | 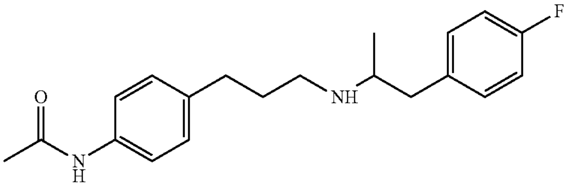 [SMILES: CC(=O)Nc1ccc(CCCNC(C)Cc2ccc(F)cc2)cc1] | 33 | 10,100 N = 2 | 4.15 | 3.83 | | Rat: 1.5 hr Human: >4 hr |
| 240 | 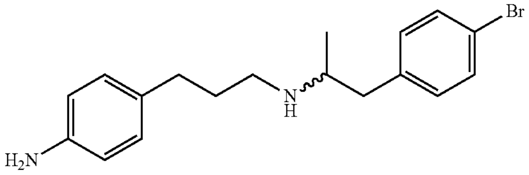 [SMILES: CC(Cc1ccc(Br)cc1)NCCCc1ccc(N)cc1] | 48 | 1,130 N = 2 | 4.63 | 3.59 | | |
| 241 | 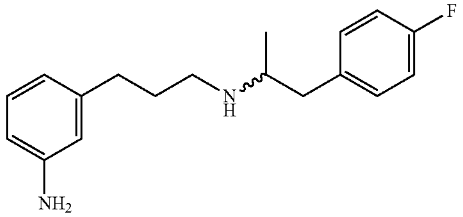 [SMILES: CC(Cc1ccc(F)cc1)NCCCc1cccc(N)c1] | 106 | 6,390 | 4.01 | 3.90 | | |
| 242 | 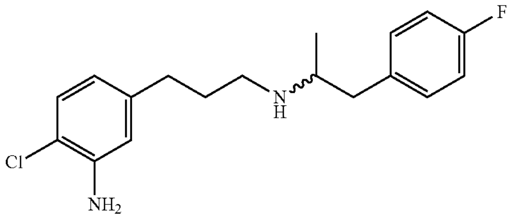 [SMILES: CC(Cc1ccc(F)cc1)NCCCc1ccc(Cl)c(N)c1] | 38 | 1,440 | 4.61 | 3.60 | | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 243 | 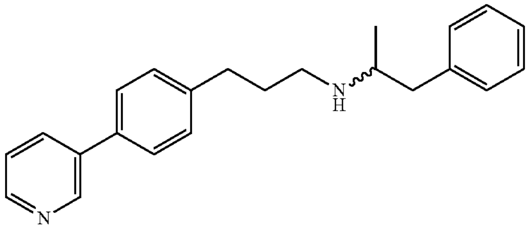 [SMILES: CC(Cc1ccccc1)NCCCc1ccc(-c2cccnc2)cc1] | 55 | 3,180 | 5.12 | 2.93 | | Rat: 0.1 hr Human: <0.1 hr |
| 244 | 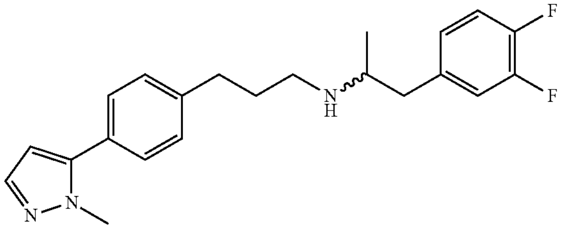 [SMILES: CC(Cc1ccc(F)c(F)c1)NCCCc1ccc(-c2ccnn2C)cc1] | 118 | 1,030 N = 2 | 4.98 | 3.16 | | |
| 245 | 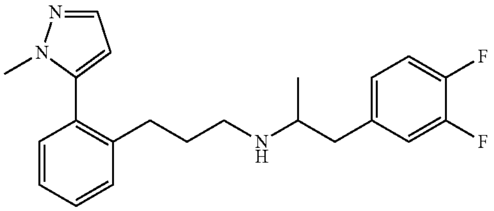 [SMILES: CC(Cc1ccc(F)c(F)c1)NCCCc1ccccc1-c1ccnn1C] | 136 | 2,240 N = 1 | 4.98 | 3.15 | | |
| 246 | 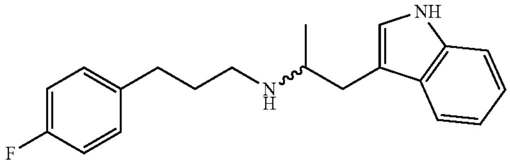 [SMILES: CC(Cc1c[nH]c2ccccc12)NCCCc1ccc(F)cc1] | 66 | 731 | 4.94 | 2.92 | | |
| 247 | 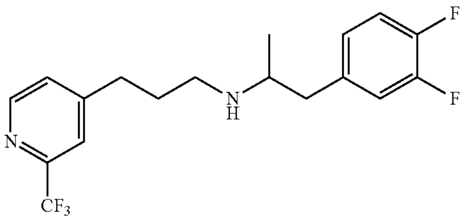 [SMILES: CC(Cc1ccc(F)c(F)c1)NCCCc1ccnc(C(F)(F)F)c1] | 349 | Not Deter-mined | 5.04 | 2.93 | | |
| 248 | 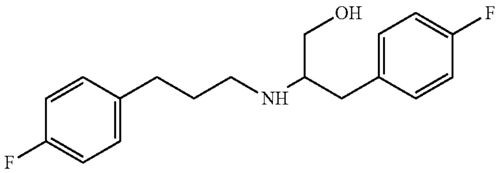 [SMILES: OCC(Cc1ccc(F)cc1)NCCCc1ccc(F)cc1] | 30 | 1,150 | 3.93 | 3.73 | | |
| 249 | 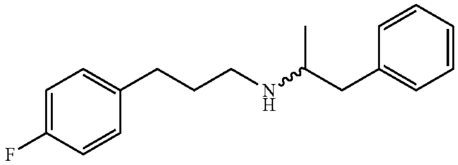 | 6 | 3,000 N = 4 | 4.84 | 2.91 | Fmice: 2.0% | Rat: 0.3 hr Human: 1.2 hr |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 250 | 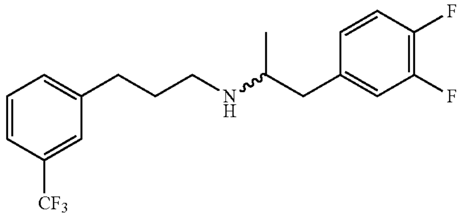 [SMILES: CC(Cc1ccc(F)c(F)c1)NCCCc1cccc(C(F)(F)F)c1] | 39 | 4,100 | 5.86 | 2.27 | | |
| 251 | 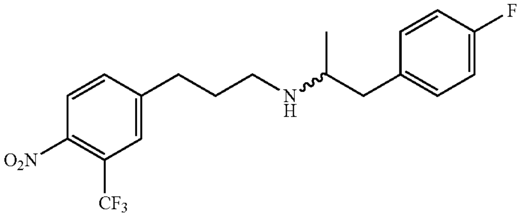 [SMILES: CC(Cc1ccc(F)cc1)NCCCc1ccc([N+](=O)[O-])c(C(F)(F)F)c1] | 55 | 535 | 5.66 | 3.22 | | |
| 252 | 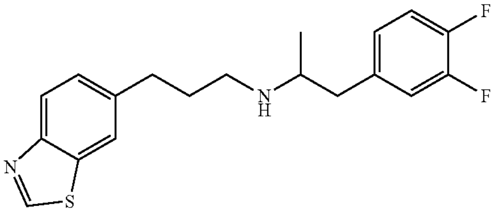 | 67 | 1,580 | 5.12 | 2.89 | | |
| 253 | 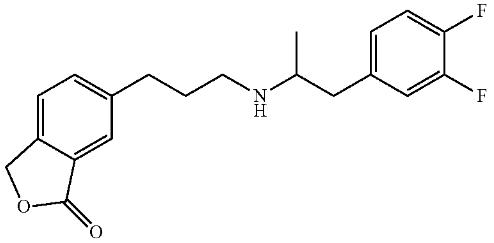 [SMILES: CC(Cc1ccc(F)c(F)c1)NCCCc1ccc2c(c1)C(=O)OC2] | 268 | Not Deter-mined | 4.53 | 3.98 | | |
| 254 | 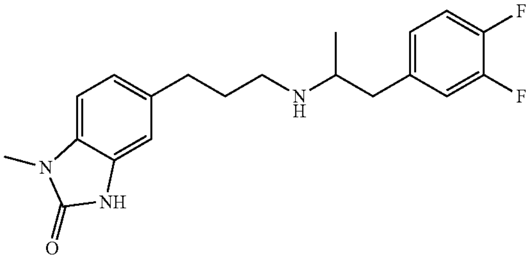 [SMILES: CC(Cc1ccc(F)c(F)c1)NCCCc1ccc2c(c1)[nH]c(=O)n2C] | 187 | Not Deter-mined | 4.20 | 3.90 | | |
| 255 | 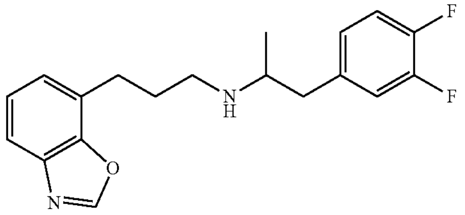 [SMILES: CC(Cc1ccc(F)c(F)c1)NCCCc1cccc2ncoc12] | 54 | 3,370 | 4.33 | 4.07 | | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 256 | 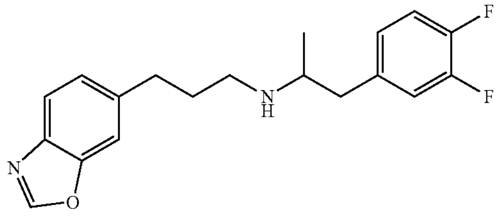 [SMILES: CC(Cc1ccc(F)c(F)c1)NCCCc1ccc2ncoc2c1] | 50 | 4,880 N = 2 | 4.33 | 4.07 | | |
| 257 | 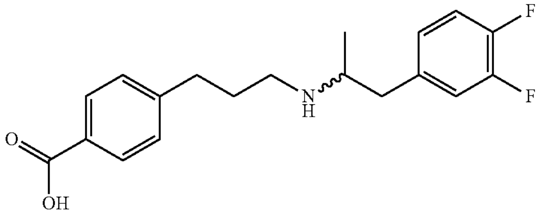 [SMILES: CC(Cc1ccc(F)c(F)c1)NCCCc1ccc(C(=O)O)cc1] | 6480 | >34,700 | 2.17 | 4.42 | | |
| 258 | 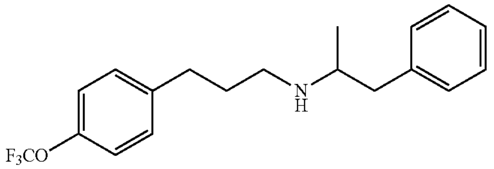 [SMILES: CC(Cc1ccccc1)NCCCc1ccc(OC(F)(F)F)cc1] | 16 | 90 | 6.13 | 2.25 | | Rat: Not Deter-mined Human: >4 hr |
| 259 | 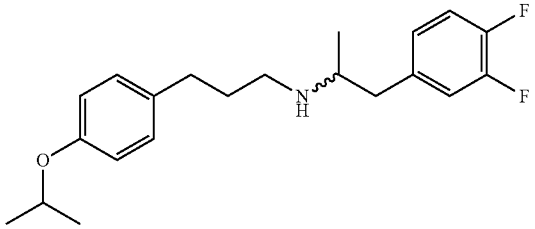 [SMILES: CC(Cc1ccc(F)c(F)c1)NCCCc1ccc(OC(C)C)cc1] | 104 | 818 | 5.6 | 2.48 | | |
| 260 | 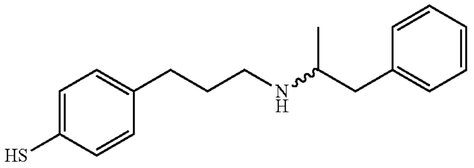 [SMILES: CC(Cc1ccccc1)NCCCc1ccc(S)cc1] | 65 | 4,190 | 4.31 | 1.85 | Fmice: 0.9% | Rat: 0.3 hr |
| 261 | 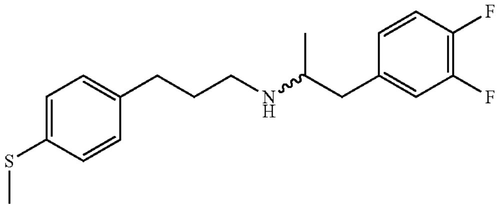 [SMILES: CSc1ccc(CCCNC(C)Cc2ccc(F)c(F)c2)cc1] | 32 | 316 | 5.61 | 2.4 | | |
| 262 | 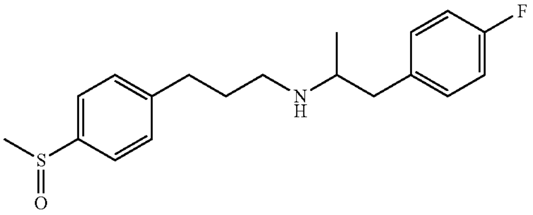 [SMILES: CC(Cc1ccc(F)cc1)NCCCc1ccc(S(C)=O)cc1] | 178 | Not Deter-mined | 3.57 | 4.0 | | Not Deter-mined |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 263 | 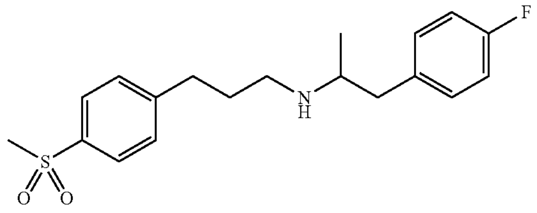 [SMILES: CC(Cc1ccc(F)cc1)NCCCc1ccc(S(C)(=O)=O)cc1] | 146 | Not Deter-mined | 3.68 | 4.49 | | Rat: >4 hr Human: >4 hr |
| 264 | 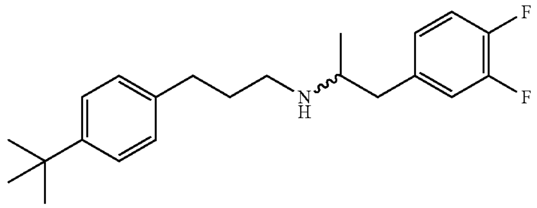 [SMILES: CC(Cc1ccc(F)c(F)c1)NCCCc1ccc(C(C)(C)C)cc1] | 209 | 2,190 | 6.52 | 1.95 | | |
| 265 | 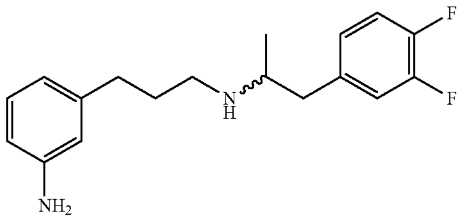 | 202 | 5,560 | 4.15 | 3.83 | | |
| 266 | 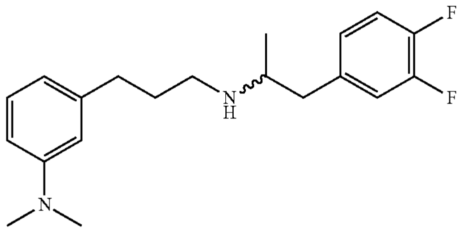 [SMILES: CC(Cc1ccc(F)c(F)c1)NCCCc1cccc(N(C)C)c1] | 171 | 2,460 | 5.09 | 2.67 | | |
| 267 | 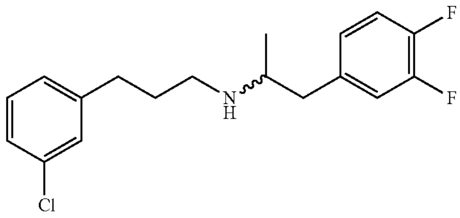 [SMILES: CC(Cc1ccc(F)c(F)c1)NCCCc1cccc(Cl)c1] | 19 | 1,000 | 5.58 | 2.41 | | |
| 268 | 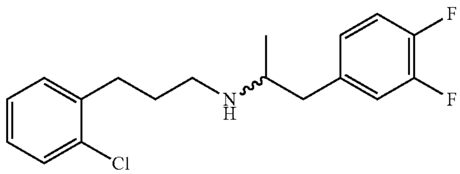 [SMILES: CC(Cc1ccc(F)c(F)c1)NCCCc1ccccc1Cl] | 28 | 233 | 5.58 | 2.40 | | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 269 | 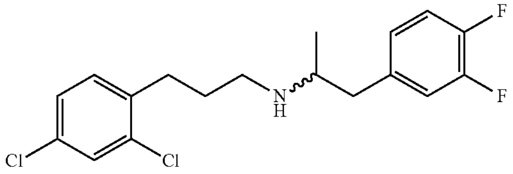 [SMILES: CC(Cc1ccc(F)c(F)c1)NCCCc1ccc(Cl)cc1Cl] | 61 | 279 | 6.19 | 2.1 | | |
| 270 | 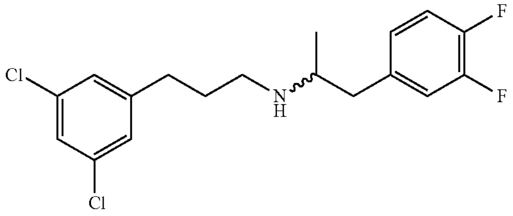 [SMILES: CC(Cc1ccc(F)c(F)c1)NCCCc1cc(Cl)cc(Cl)c1] | 38 | 1,500 | 6.19 | 2.09 | | |
| 271 | 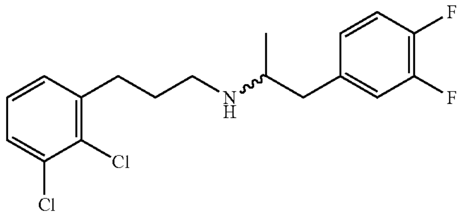 [SMILES: CC(Cc1ccc(F)c(F)c1)NCCCc1cccc(Cl)c1Cl] | 42 | 462 | 6.19 | 2.09 | | |
| 272 | 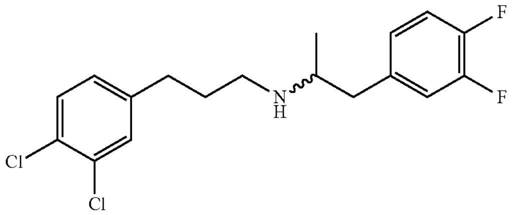 [SMILES: CC(Cc1ccc(F)c(F)c1)NCCCc1ccc(Cl)c(Cl)c1] | 57 | 462 | 6.19 | 2.11 | | |
| 273 | 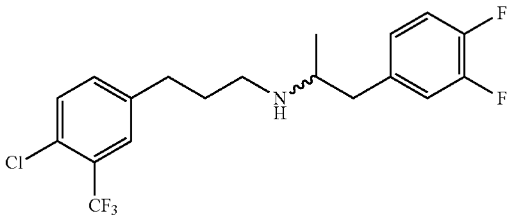 [SMILES: CC(Cc1ccc(F)c(F)c1)NCCCc1ccc(Cl)c(C(F)(F)F)c1] | 538 | 1,220 | 6.46 | 1.74 | | |
| 274 | 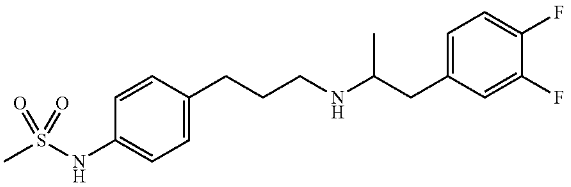 [SMILES: CC(Cc1ccc(F)c(F)c1)NCCCc1ccc(NS(C)(=O)=O)cc1] | 45 | 220 | 2.75 | 4.34 | | |
| 275 | 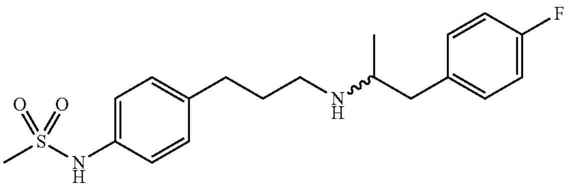 [SMILES: CC(Cc1ccc(F)cc1)NCCCc1ccc(NS(C)(=O)=O)cc1] | 53 | 308 | 2.55 | 4.47 | | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 276 | 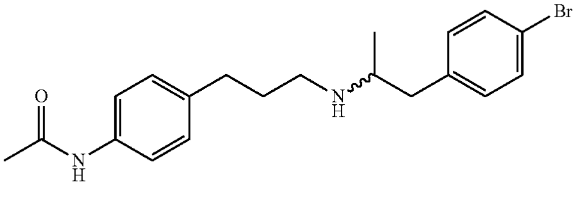 [SMILES: CC(=O)Nc1ccc(CCCNC(C)Cc2ccc(Br)cc2)cc1] | 24 | 3430 N = 2 | 4.70 | 3.44 | | |
| 277 | 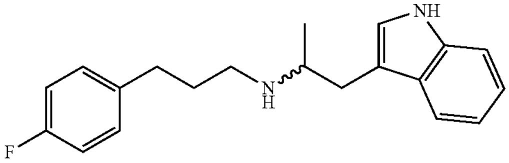 [SMILES: CC(Cc1c[nH]c2ccccc12)NCCCc1ccc(F)cc1] | 66 | 732 | 4.94 | 2.92 | | |
| 278 | 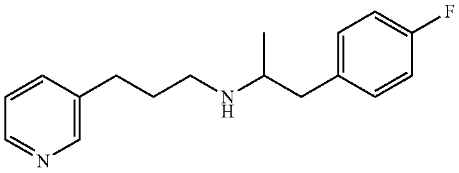 [SMILES: CC(Cc1ccc(F)cc1)NCCCc1cccnc1] | 98 | 3,980 | 3.62 | 3.77 | | |
| 279 | 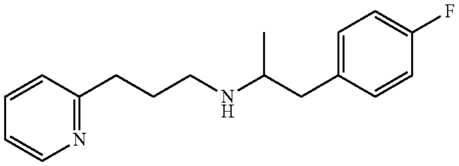 [SMILES: CC(Cc1ccc(F)cc1)NCCCc1ccccn1] | 200 | 2,400 N = 2 | 3.49 | 3.83 | | |
| 280 | 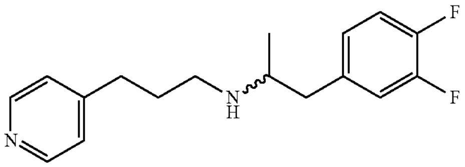 [SMILES: CC(Cc1ccc(F)c(F)c1)NCCCc1ccncc1] | 79 | 4,070 N = 2 | 3.76 | 3.7 | | Rat: 0.5 hr human: 1.7 hr |
| 281 | 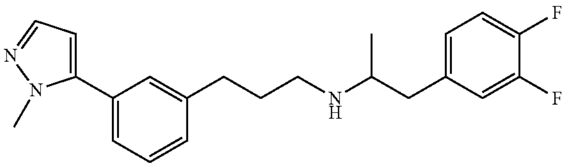 [SMILES: CC(Cc1ccc(F)c(F)c1)NCCCc1cccc(-c2ccnn2C)c1] | 51 | 592 | 4.98 | 3.15 | | |
| 282 | 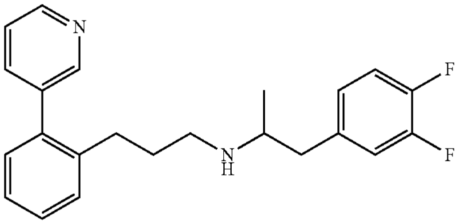 [SMILES: CC(Cc1ccc(F)c(F)c1)NCCCc1ccccc1-c1cccnc1] | 88 | 364 N = 2 | 5.41 | 2.70 | | |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 283 | 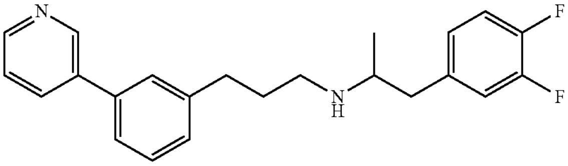 [SMILES: CC(Cc1ccc(F)c(F)c1)NCCCc1cccc(-c2cccnc2)c1] | 41 N = 4 | 182 | 5.41 | 2.7 | | |
| 285 | 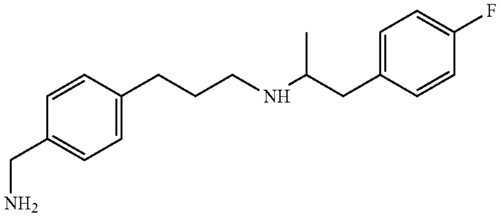 [SMILES: CC(Cc1ccc(F)cc1)NCCCc1ccc(CN)cc1] | 461 | Not Deter-mined | 3.96 | 3.59 | | Rat: >4 hr Human: >4 hr |
| 286 | 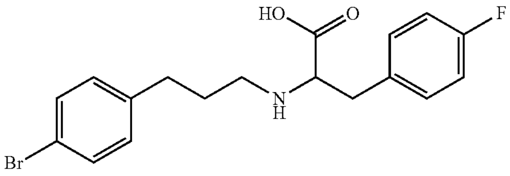 [SMILES: O=C(O)C(Cc1ccc(F)cc1)NCCCc1ccc(Br)cc1] | 3126 | Not Deter-mined | 2.41 | 4.15 | | |
| 287 | 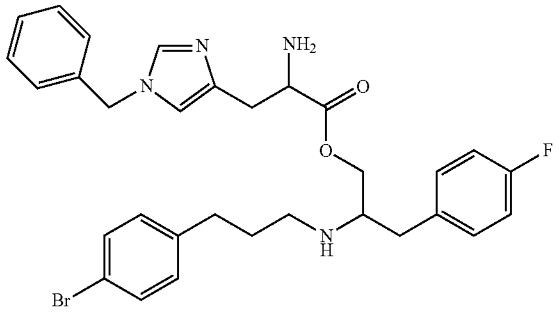 [SMILES: NC(Cc1cn(Cc2ccccc2)cn1)C(=O)OCC(Cc1ccc(F)cc1)NCCCc1ccc(Br)cc1] | 533 | Not Deter-mined | 6.16 | 1.49 | | |
| 288 | 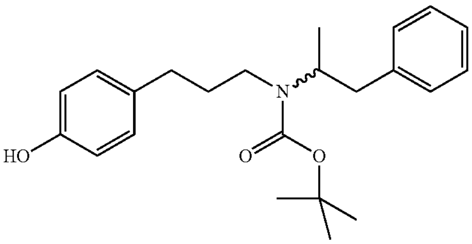 [SMILES: CC(Cc1ccccc1)N(CCCc1ccc(O)cc1)C(=O)OC(C)(C)C] | >100,000 | Not Deter-mined | 5.67 | 3.77 | | Not Deter-mined |
| 289 | 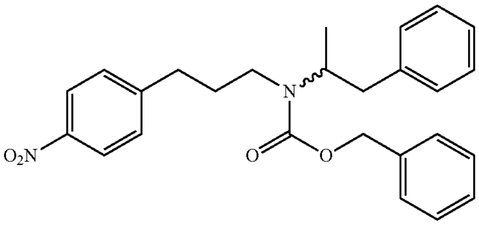 [SMILES: CC(Cc1ccccc1)N(CCCc1ccc([N+](=O)[O-])cc1)C(=O)OCc1ccccc1] | 2970 | Not Deter-mined | 6.59 | 3.48 | | Not Deter-mined |

TABLE 3-continued
| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 290 | 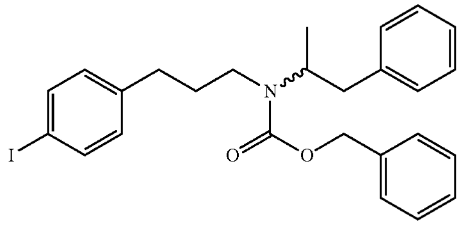 [SMILES: CC(Cc1ccccc1)N(CCCc1ccc(I)cc1)C(=O)OCc1ccccc1] | 4,800 | Not Deter-mined | 7.58 | 2.48 | | Not Deter-mined |
| 291 | 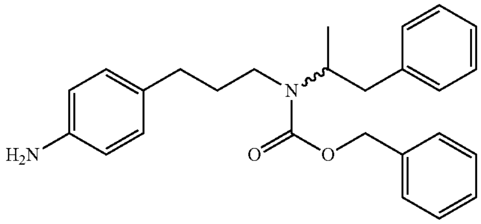 | 3,100 | Not Deter-mined | 5.82 | 3.2 | | Not Deter-mined |
| 292 | 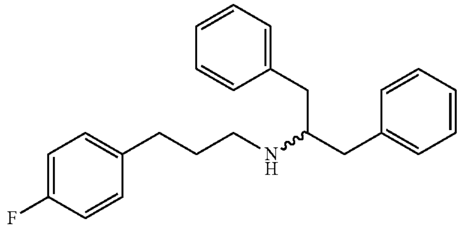 [SMILES: Fc1ccc(CCCNC(Cc2ccccc2)Cc2ccccc2)cc1] | 346 | Not Deter-mined | 6.49 | 2.04 | | Rat: <0.1 hr Human: 0.6 hr |
| 293 | 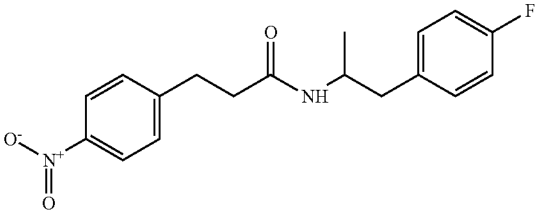 [SMILES: CC(Cc1ccc(F)cc1)NC(=O)CCc1ccc([N+](=O)[O-])cc1] | 10,800 | Not Deter-mined | 3.98 | 4.35 | | Rat: 0.5 hr Human: 0.4 hr |
| 294 | 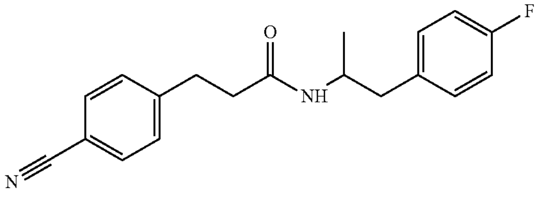 [SMILES: CC(Cc1ccc(F)cc1)NC(=O)CCc1ccc(C#N)cc1] | 40,600 | Not Deter-mined | 3.9 | 4.43 | | Rat: 0.8 hr Human: 0.8 hr |
| 295 | 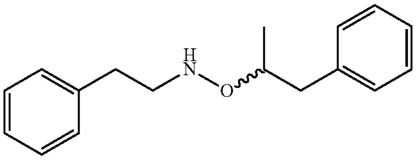 [SMILES: CC(Cc1ccccc1)ONCCc1ccccc1] | 41,300 | Not Deter-mined | 4.3 | 3.24 | | Not Deter-mined |

TABLE 3-continued

| | Structure | VMAT2 (rat) Inhibition: Mean Ki (nM)[a] | hERG Binding: Mean Ki (nM)[b] | clog P[c] | CNS MPO[d] | Bio-avail. (F %) | Micro-somal stability assays: Species/ Half-life (hr) |
|---|---|---|---|---|---|---|---|
| 296 | 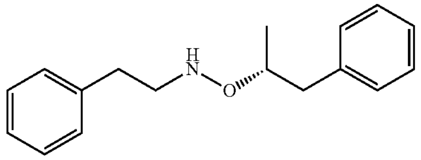 [SMILES: C[C@H](Cc1ccccc1)ONCCc1ccccc1] | 20,000 | Not Deter-mined | 4.3 | 3.24 | | Not Deter-mined |

[a]Unless otherwise indicated on Table 3, the VMAT2 values are mean values obtained minimally from n = 3 experiments.
[b]Unless otherwise indicated on Table 3, the hERG values are mean values obtained minimally from n = 3 experiments.
[c]cLogP, the calculated log of the partition coefficient between octanol and water with assumed neutral molecule, is calculated using methods embedded within Collaborative Drug Discovery software that implement Hansch's method, which sums the contributions of functional groups in previously parameterized non-overlapping fragments and includes Hammett corrections. Hansch C, Leo A(1979). "Chapter 5: Calculation of Octanol-Water Partition Coefficients from Fragments, etc.". Substituent Constants for Correlation Analysis in Chemistry and Biology. NewYork: John Wiley & Sons Ltd. ISBN 978-0-471-05062-9.
[d]CNS MPO score is calculated using methods embedded within Collaborative Drug Discovery software that implement Hager's method that integrates calculated cLogP, calculated log of the distribution constant of the ionized compounds at pH 7.4 (cLogD), molecular weight, total polar surface area, number of hydrogen bonds, and the most basic center on the molecule into a single score predicting central nervous system penetration. Wager T T, Hou X, Verhoest P R, Villalobos A. Moving beyond rules: the development of a central nervous system multiparameter optimization (CNS MPO) approach to enable alignment of druglike properties. ACS Chem Neurosci. 2010 Jun 16;1(6):435-49. doi: 10.1021/cn100008c. Epub 2010 Mar 25. PMID: 22778837; PMCID: PMC3368654.

Various exemplary compounds were tested using the [$^3$H]dopamine ([$^3$H]DA) uptake assay according to Example 3, the [$^3$H]Dofetilide binding assay according to Example 4, the [$^3$H]DA and [$^3$H]5-HT uptake assay according to Example 5, the microsomal assays according to Example 7, and the pharmacokinetic assays according to Example 8. The results of these assays are set forth in Table 3.

TABLE 4

| | Structure | VMAT2 (rat) Inhibition: Mean Ki (nM)[a] | hERG Binding: Mean Ki (nM)[b] | clog P[c] | CNS MPO[d] | DAT: Ki (nM)[e] | RLM $CL_{int}$ (mL/ min/ kg)[f] | Bioavail. (F %) |
|---|---|---|---|---|---|---|---|---|
| 231 | 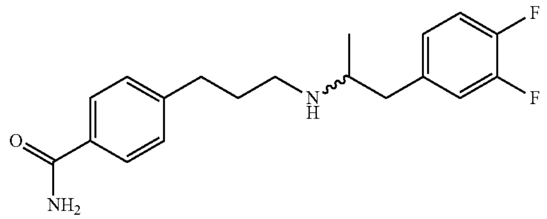 [SMILES: CC(Cc1ccc(F)c(F)c1)NCCCc1ccc(C(N)=O)cc1] | 29 | 3,500 | 3.83 | 4.08 | 2,750 | 23 | Rat oral: 62%; Rat SC: 84% |
| 230 | 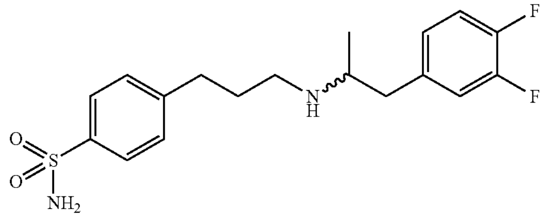 [SMILES: CC(Cc1ccc(F)c(F)c1)NCCCc1ccc(S(N)(=O)=O)cc1] | 42 | 1,030 | 3.03 | 4.43 | 8,240 | <17 | Rat oral: 94%; Rat SC: 44% |
| 229 | 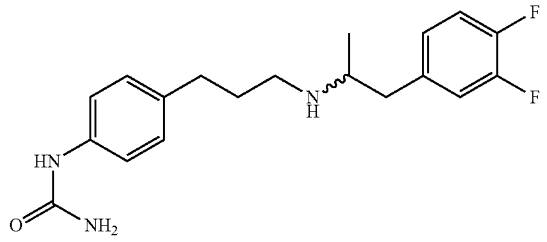 [SMILES: CC(Cc1ccc(F)c(F)c1)NCCCc1ccc(NC(N)=O)cc1] | 36 | 4,290 | 3.88 | 3.72 | 1,530 | 41 | Rat oral: 94% |

TABLE 4-continued
| | Structure | VMAT2 (rat) Inhibition: Mean Ki (nM)[a] | hERG Binding: Mean Ki (nM)[b] | clog P[c] | CNS MPO[d] | DAT: Ki (nM)[e] | RLM $CL_{int}$ (mL/min/kg)[f] | Bioavail. (F %) |
|---|---|---|---|---|---|---|---|---|
| 237 | 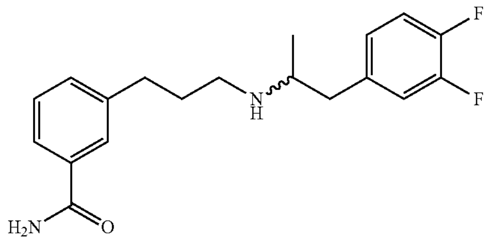 | 32 | 4,780 | 3.83 | 4.08 | 3,120 | 30 | Rat oral: 2% |
| 228 | 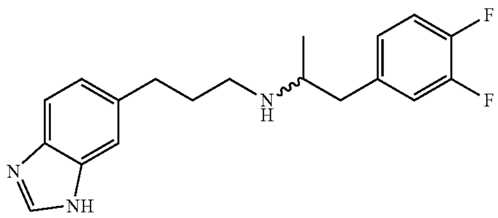 [SMILES: CC(Cc1ccc(F)c(F)c1)NCCCc1ccc2nc[nH]c2c1] | 41 | 6,770 | 4.27 | 3.87 | 3,040 | 48 | Rat oral: 6% |
| 235 | 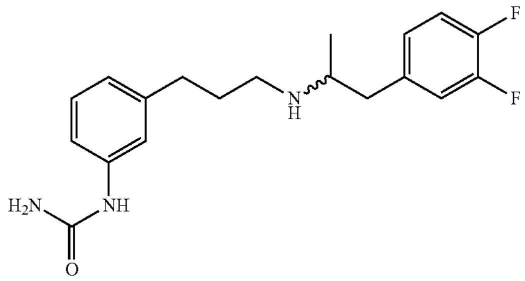 [SMILES: CC(Cc1ccc(F)c(F)c1)NCCCc1cccc(NC(N)=O)c1] | 4 N = 4 | 4,380 | 3.88 | 3.72 | 1,290 | 71 | Rat oral: 8% |
| 234 | 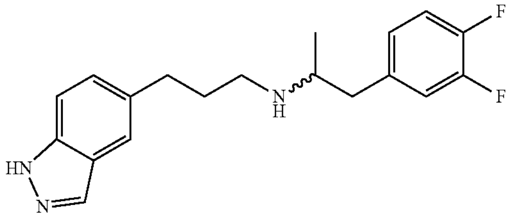 [SMILES: CC(Cc1ccc(F)c(F)c1)NCCCc1ccc2[nH]ncc2c1] | 54 | 1020 | 4.30 | 3.85 | 703 | 114 | |
| 232 | 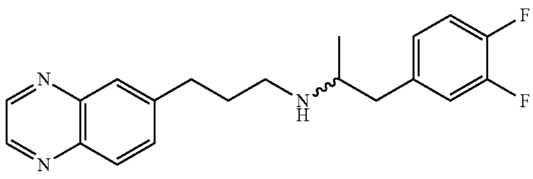 [SMILES: CC(Cc1ccc(F)c(F)c1)NCCCc1ccc2nccnc2c1] | 52 | 2,590 | 4.31 | 4.07 | 3,580 | 159 | |
| 297 | 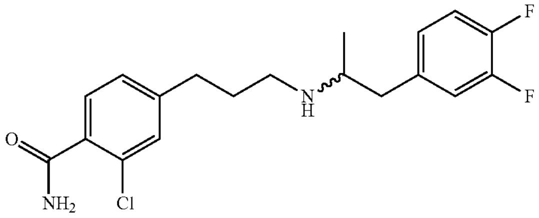 [SMILES: CC(Cc1ccc(F)c(F)c1)NCCCc1ccc(C(N)=O)c(Cl)c1] | 21 | 5,020 | 4.43 | 3.73 | 5,820 | <17 | |

TABLE 4-continued
| | Structure | VMAT2 (rat) Inhibition: Mean Ki (nM)[a] | hERG Binding: Mean Ki (nM)[b] | clog P[c] | CNS MPO[d] | DAT: Ki (nM)[e] | RLM $CL_{int}$ (mL/min/kg)[f] | Bioavail. (F %) |
|---|---|---|---|---|---|---|---|---|
| 298 | 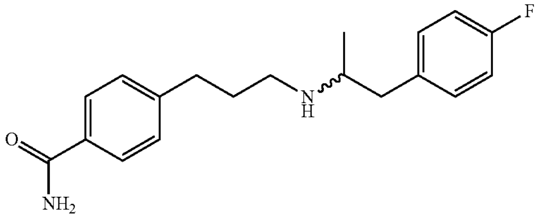 [SMILES: CC(Cc1ccc(F)cc1)NCCCc1ccc(C(N)=O)cc1] | 16 | 12,400 | 3.69 | 4.16 | 3,980 | 18 | |
| 299 | 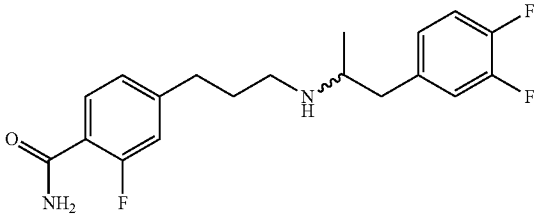 | 29 | 12,100 | 3.97 | 4.01 | 4,210 | 19 | |
| 300 | 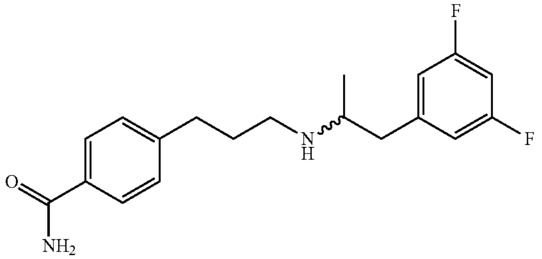 [SMILES: CC(Cc1cc(F)cc(F)c1)NCCCc1ccc(C(N)=O)cc1] | 6 | 8,100 | 3.83 | 4.08 | 1,570 | 21 | |
| 301 | 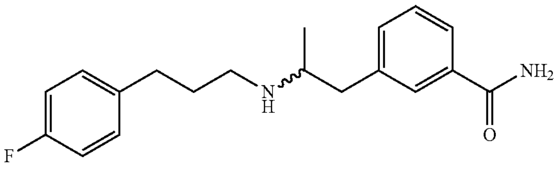 [SMILES: CC(Cc1cccc(C(N)=O)c1)NCCCc1ccc(F)cc1] | 43 | 1,310 | 3.69 | 4.16 | 6,070 | 22 | |
| 302 | 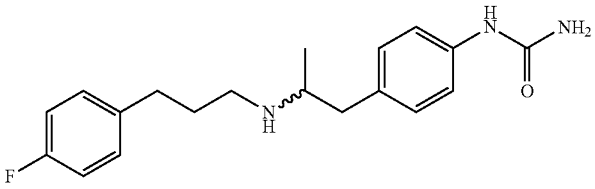 [SMILES: CC(Cc1ccc(NC(N)=O)cc1)NCCCc1ccc(F)cc1] | 34 | 7,110 | 3.74 | 3.80 | 3,130 | 30 | |
| 303 | 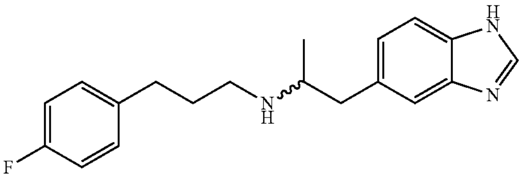 [SMILES: CC(Cc1ccc2[nH]cnc2c1)NCCCc1ccc(F)cc1] | 22 | 2,900 | 4.12 | 3.94 | 4,770 | 40 | |
| 304 | 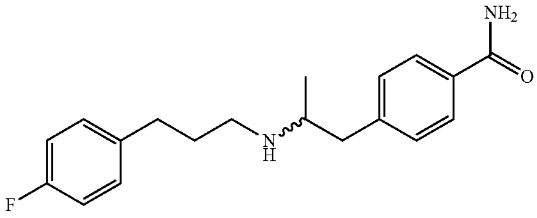 [SMILES: CC(Cc1ccc(C(N)=O)cc1)NCCCc1ccc(F)cc1] | 31 | 1,610 | 3.69 | 4.16 | 5,570 | 41 | |

TABLE 4-continued
| | Structure | VMAT2 (rat) Inhibition: Mean Ki (nM)[a] | hERG Binding: Mean Ki (nM)[b] | clog P[c] | CNS MPO[d] | DAT: Ki (nM)[e] | RLM $CL_{int}$ (mL/min/kg)[f] | Bioavail. (F %) |
|---|---|---|---|---|---|---|---|---|
| 305 | 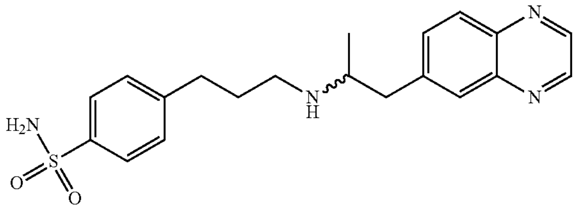 [SMILES: CC(Cc1ccc2nccnc2c1)NCCCc1ccc(S(N)(=O)=O)cc1] | 46 | 4,390 | 2.06 | 4.1 | 20,500 | 43 | |
| 306 | 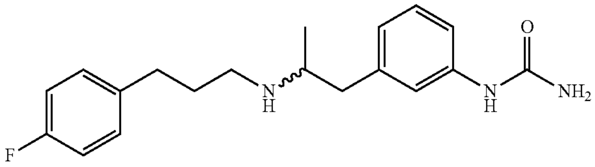 [SMILES: CC(Cc1cccc(NC(N)=O)c1)NCCCc1ccc(F)cc1] | 9 | 2,750 | 3.74 | 3.80 | 2,970 | 47 | |
| 307 | 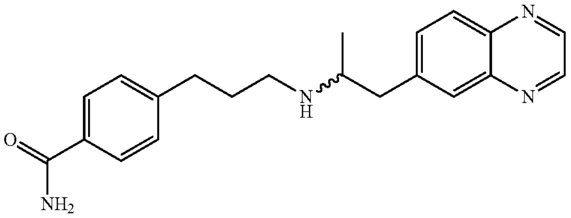 [SMILES: CC(Cc1ccc2nccnc2c1)NCCCc1ccc(C(N)=O)cc1] | 17 | 21,000 | 2.87 | 4.5 | 8,890 | 51 | Rat oral: 8%; Rat SC: >100% |
| 308 | 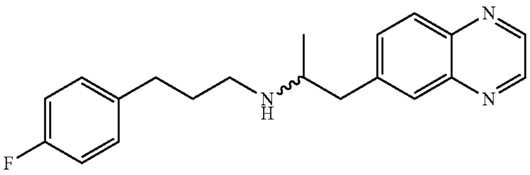 [SMILES: CC(Cc1ccc2nccnc2c1)NCCCc1ccc(F)cc1] | 13 | 1,900 | 4.16 | 4.5 | 2,930 | 56 | |
| 309 | 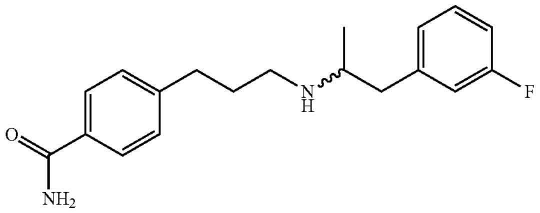 [SMILES: CC(Cc1cccc(F)c1)NCCCc1ccc(C(N)=O)cc1] | 6 | 12,000 | 3.69 | 4.16 | 1,630 | 57 | Rat oral: 5%; Rat SC: 76% |
| 310 | 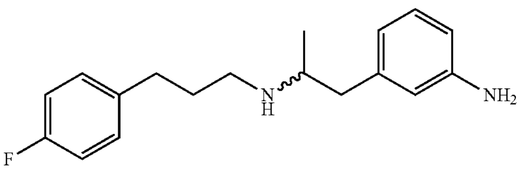 [SMILES: CC(Cc1cccc(N)c1)NCCCc1ccc(F)cc1] | 5 | 2,730 | 4.01 | 3.90 | 2,230 | 74 | |
| 311 | 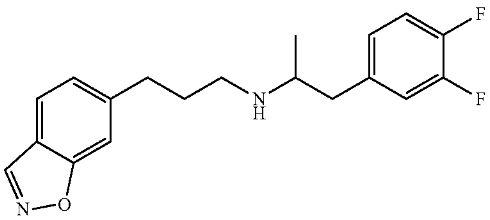 [SMILES: CC(Cc1ccc(F)c(F)c1)NCCCc1ccc2cnoc2c1] | 51 | 4,200 | 4.36 | 4.05 | 2,720 | 117 | |

TABLE 4-continued

| | Structure | VMAT2 (rat) Inhibition: Mean Ki (nM)[a] | hERG Binding: Mean Ki (nM)[b] | clog P[c] | CNS MPO[d] | DAT: Ki (nM)[e] | RLM $CL_{int}$ (mL/min/kg)[f] | Bioavail. (F %) |
|---|---|---|---|---|---|---|---|---|
| 312 | 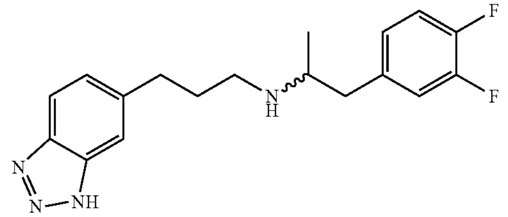 [SMILES: CC(Cc1ccc(F)c(F)c1)NCCCc1ccc2nn[nH]c2c1] | 8 | 3,000 | 3.02 | 4.5 | 1,900 (n = 1) | 115 | Rat oral: 7%; Rat SC: 42% |
| 313[g] | 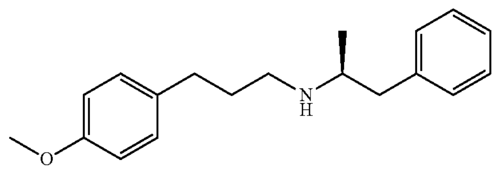 [SMILES: COc1ccc(CCCN[C@@H](C)Cc2ccccc2)cc1] | 72 N = 4 | 4,160 | | | | 978 | Frat: 3.4% |

[a]Unless otherwise indicated on Table 4, the VMAT2 values are mean values obtained minimally from n = 3 experiments.

[b]Unless otherwise indicated on Table 4, the hERG values are mean values obtained minimally from n = 3 experiments.

[c]cLogP, the calculated log of the partition coefficient between octanol and water with assumed neutral molecule, is calculated using methods embedded within Collaborative Drug Discovery software that implement Hansch's method, which sums the contributions of functional groups in previously parameterized non-overlapping fragments and includes Hammett corrections. Hansch C, Leo A(1979). "Chapter 5: Calculation of Octanol-Water Partition Coefficients from Fragments, etc.". Substituent Constants for Correlation Analysis in Chemistry and Biology. New York: John Wiley & Sons Ltd. ISBN 978-0-471-05062-9.

[d]CNS MPO score is calculated using methods embedded within Collaborative Drug Discovery software that implement Hager's method that integrates calculated cLogP, calculated log of the distribution constant of the ionized compounds at pH 7.4 (cLogD), molecular weight, total polar surface area, number of hydrogen bonds, and the most basic center on the molecule into a single score predicting central nervous system penetration. Wager T T, Hou X, Verhoest P R, Villalobos A. Moving beyond rules: the development of a central nervous system multiparameter optimization (CNS MPO) approach to enable alignment of druglike properties. ACS Chem Neurosci. 2010 Jun 16;1(6):435-49. doi: 10.1021/cn100008c. Epub 2010 Mar 25. PMID: 22778837; PMCID: PMC3368654.

[e]DAT $K_i$ values represent inhibition constants for the the dopamine transporter located on the Synaptosomal membrane. DAT $K_i$ values were calculated by subtracting nonspecific uptake determined in the presence of nomifensine (10 uM) from total uptake. $IC_{50}$ values were obtained from individual concentration-response curves via an iterative curve-fitting program (Prism 7.03; GraphPad Software, Inc., La Jolla, CA). Inhibition constants ($K_i$ values) were determined using the Cheng-Prusoff equation. Cheng Y and Prusoff W H (1973) Relationship between the inhibition constant (K1) and the concentration of inhibitor which causes 50 per cent inhibition (I50) of an enzymatic reaction. Biochem Pharmacol 22:3099-3108.

[f]Rat Liver Microsome Intrinsic Clearance.

[g]A microsomal stability assay using rat liver microsomes determined this compound to have a <0.1 hour Species/Half-life. This value was determined using the microsomal assays according to Example 7.

The foregoing description and examples have been set forth merely to illustrate the invention and are not meant to be limiting. Since modifications of the described embodiments incorporating the spirit and the substance of the invention may occur to persons skilled in the art, the invention should be construed broadly to include all variations within the scope of the claims and equivalents thereof.

The invention claimed is:

1. A compound of formula (I):

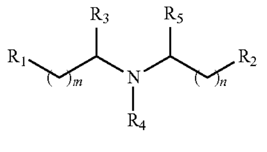

(I)

wherein m is an integer in the range from 1 to 3;

n is zero or an integer in the range from 1 to 5;

$R_1$ and $R_2$ are independently an aryl group or a heteroaryl group and which are independently unsubstituted or substituted by one or more substituents;

$R_3$ is =O, methyl; ethyl; propyl; isopropyl; hydroxymethyl; 2-hydroxyethyl; 1-hydroxyethyl; methoxymethyl; 2-methoxyethyl; 1-methoxyethyl; aminomethyl; 2-aminoethyl; 1-aminoethyl; N-methylaminomethyl; 2-N-methylaminoethyl; 1-N-methylaminoethyl; N,N-dimethylaminomethyl; 2-N,N-dimethylaminoethyl; 1-N,N-dimethylaminoethyl; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); amide ($-CONH_2$); methyl amide ($-CONHCH_3$), ethyl amide ($-CONHCH_2CH_3$); propyl amide ($-CONHCH_2CH_2CH_3$); isopropyl amide ($-CONHCH(CH_3)_2$); butylamide ($-CONHCH_2CH_2CH_2CH_3$); sec-butylamide ($-CONHCH(CH_3)(CH_2CH_3)$); tert-butylamide ($-CONHC(CH_3)_3$); dimethyl amide ($-CON(CH_3)_2$), diethyl amide ($-CON(CH_2CH_3)_2$); dipropyl amide ($-CON(CH_2CH_2CH_3)_2$); isopropyl amide ($-CON[CH(CH_3)_2]_2$); dibutylamide ($-CON(CH_2CH_2CH_2CH_3)_2$); di-sec-butylamide ($-CON[CH(CH_3)(CH_2CH_3)]_2$); di-tert-butylamide ($-CON[C(CH_3)_3]_2$); methyl, ethyl, propyl, or isopropyl substituted with one or more fluoro, chloro, bromo, or iodo; benzyl; or $-(CH_2)_a-O-(C{=}O)-CHR_6-NH_2$;

$R_4$ is a hydrogen atom; a methyl, ethyl, propyl, isopropyl, or carbonyl group; or a methyl, ethyl, propyl or isopropyl group substituted with a hydroxyaryl group; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); or benzyl ester ($-COOCH_2(C_6H_6)$); and $R_5$ is hydrogen, methyl, or =O;

$R_6$ is selected from the group consisting of methyl, ethyl, propyl, isopropyl, and $C_4$-$C_7$ straight chain or branched alkyl, wherein the methyl, ethyl, propyl, isopropyl, or $C_4$-$C_7$ straight chain or branched alkyl are unsubstituted or substituted with one or more substituents selected from the group consisting of substituted or unsubstituted aryl groups and substituted or unsubstituted heteroaryl groups;

a is an integer in the range from 1 to 5; or an enantiomer; racemate; or pharmaceutically acceptable salt thereof.

2. The compound of claim 1, wherein $R_1$ and $R_2$ are independently an unsubstituted or substituted aryl group selected from the group consisting of phenyl, naphthalenyl, cyclobutadienyl, cyclopentadienyl, indenyl, anthracenyl, phenanthrenyl, tirphenylenyl, fluorenyl, and pyrenyl; or an unsubstituted or substituted heteroaryl group selected from the group consisting of pyrrolyl, imidazolyl, pyrazolyl, thiazolyl, oxazolyl, isoxazolyl, thiazolyl, isothiazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, 1H-benzo[d]imidazole-2(3H)-thione, furanyl, carbazolyl, benzofuranyl, isobenzofuranyl, dibenzofuranyl, 2H-chromenyl, 1H-isochromenyl, 3H-isochromenyl, xanthenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, and benzo[c]thiophen-1(3H)-one.

3. The compound of claim 2, wherein substituents on $R_1$ and $R_2$ are independently selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); alkylsulfonyl; alkylsulfinyl; a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; ortho-, meta-, or para-substituted phenyl; ortho-, meta-, or para-substituted benzyl; ortho-, meta-, or para-substituted benzenephenyl; phenylethyl; amino; cycloalkylamino, isopropylamino; N-methylamino; N,N-dimethylamino; N-cyclopropylamino; N,N-dicyclopropylamino; N-cyclobutylamino; N,N-dicyclobutylamino; N-cyclopentylamino; N,N-dicyclopentylamino; N-cyclohexylamino; N,N-dicyclohexylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; phenyl; methylsulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl ($-S(=O)-CH_3$); ethylsulfinyl ($-S(=O)-CH_2CH_3$); propiosulfinyl ($-S(=O)-CH_2CH_2CH_3$); isopropiosulfinyl ($-S(=O)-CH(CH_3)_2$); methylsulfonyl ($-S(=O)_2-CH_3$); ethylsulfonyl ($-S(=O)_2-CH_2CH_3$); propiosulfonyl ($-S(=O)_2-CH_2CH_2CH_3$); isopropiosulfonyl ($-S(=O)_2-CH(CH_3)_2$); fluoro; chloro; bromo; iodo; trifluoromethyl; trichloromethyl; tribromomethyl; triiodomethyl; aminomethyl ($-CH_2NH_2$); vinyl; allyl; propargyl; nitro; carbamoyl; ureido ($-NH(C=O)-NH_2$); azido; isocyanate; thioisocyanate; hydroxylamino; nitrile; sulfonamide ($-S(=O)_2-NH_2$); methylsulfonamide ($-NH-S(=O)_2-CH_3$); ethylsulfonamide ($-NH_2-S(=O)_2-CH_2CH_3$); propiosulfonamide ($-NH_2-S(=O)_2-CH_2CH_2CH_3$); isopropiosulfonamide ($-NH_2-S(=O)_2-CH(CH_3)_2$); a saturated or unsaturated hydrocarbon ring; a nitrogen-containing heterocyclic or heteroaryl moiety; an oxygen-containing heterocyclic or heteroaryl moiety; a sulfur-containing heterocyclic or heteroaryl moiety; a selenium-containing heterocyclic or heteroaryl moiety; a mixed heterocyclic or heteroaryl moiety containing at least two atoms selected from the group consisting of nitrogen, oxygen, sulfur, and selenium; and ortho-, meta-, or para-substituted benzene, wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be substituted with one or more substituents selected from the group consisting of methyl; mono-, di-, or tri-deuterium methyl, mono-, di-, or tri-tritium; methyl; ethyl; propyl; isopropyl; $C_4$-$C_7$ straight chain or branched alkyl; $C_3$-$C_6$ cycloalkyl; $C_4$-$C_7$ alkenyl (including cis and trans geometrical forms); amino; cycloalkylamino, isopropylamino; N-methylamino; N,N-dimethylamino; hydroxyl; methoxy; mono-, di-, or tri-fluoromethoxy; ethoxy; propoxy; isopropoxy; thiol; methylthio; ethylthio; propiothiol; isopropiothiol; fluoro; chloro; bromo; iodo; trifluoromethyl; trichloromethyl; tribromomethyl; triiodomethyl; nitro; azido; isocyanate; thioisocyanate; hydroxylamino; and nitrile; and wherein one or more of the benzyl; phenyl; saturated or unsaturated hydrocarbon ring; nitrogen-containing heterocyclic or heteroaryl moiety; oxygen-containing heterocyclic or heteroaryl moiety; sulfur-containing heterocyclic or heteroaryl moiety; selenium-containing heterocyclic or heteroaryl moiety; mixed heterocyclic or heteroaryl moiety containing at least two atoms selected from the group consisting of nitrogen, oxygen, sulfur, and selenium; or ortho-, meta-, or para-substituted benzene substituent on $R_1$ or $R_2$ may be independently fused to $R_1$ or $R_2$ or linked to $R_1$ or $R_2$.

4. The compound of claim 1, wherein:

m is 1;

n is 2;

$R_1$ and $R_2$ are each independently selected from the group consisting of phenyl, pyrrolyl, imidazolyl, pyrazolyl, thiazolyl, isothiazolyl, oxazolyl, isoxazolyl, pyridinyl, pyridazinyl, pyrmidinyl, pyrazinyl, 1H-indolyl, 3H-indolyl, 2H-isoindolyl, indolizinyl, quinolinyl, isoquinolinyl, quinoxalinyl, cinnolinyl, quinazolinyl, phthalazinyl, purinyl, indazolyl, benzimidazolyl, benzo[d]

oxazole, benzo[d]thiazole, benzo[c]isoxazole, benzo[d]isoxazole, benzo[c]isothiazole, benzo[d]isothiazole, benzo[c][1,2,5]oxadiazole, benzo[c][1,2,5]thiadiazole, quinoline-2(1H)-one, isoquinoline-1(2H)-one, indolin-2-one, isoindolin-1-one, 1H-benzo[d]imidazole-2(3H)-one, furanyl, benzofuranyl, isobenzofuranyl, 2H-chromenyl, 1H-isochromenyl, 3H-isochromenyl, benzofuran-2(3H)-one, isobenzofuran-1(3H)-one, thiophenyl, benzo[b]thiophenyl, benzo[c]thiophenyl, benzo[b]thiophen-2(3H)-one, 1H-benzo[d][1,2,3]triazolyl, and benzo[c]thiophen-1(3H)-one;

wherein $R_1$ and $R_2$ are each independently unsubstituted or substituted with one or more substitutents selected from the group consisting of methyl; ethyl; propyl; isopropyl; $C_4$-$C_7$ straight chain or branched alkyl; amino; isopropylamino; N-methylamino; N,N-dimethylamino; N-cyclopropylamino; N,N-dicyclopropylamino; N-cyclobutylamino; N,N-dicyclobutylamino; carboxylate; methylcarboxylate; ethylcarboxylate; propylcarboxylate; isopropylcarboxylate; carboxaldehyde; acetoxy; propionyloxy; isopropionyloxy; cyano; aminomethyl; N-methylaminomethyl; N,N-dimethylaminomethyl; carboxamide; N-methylcarboxamide; N,N-dimethylcarboxamide; acetyl; propionyl; formyl; benzoyl; sulfate; hydroxyl; methoxy; mono-, di-, or tri-fluoromethoxy; ethoxy; propoxy; isopropoxy; thiol; methylthio; ethylthio; propiothiol; isopropiothiol; methylsulfinyl ($-S(=O)-CH_3$); ethylsulfinyl ($-S(=O)-CH_2CH_3$); propiosulfinyl ($-S(=O)-CH_2CH_2CH_3$); isopropiosulfinyl ($-S(=O)-CH(CH_3)_2$); methylsulfonyl ($-S(=O)_2-CH_3$); ethylsulfonyl ($-S(=O)_2-CH_2CH_3$); propiosulfonyl ($-S(=O)_2-CH_2CH_2CH_3$); isopropiosulfonyl ($-S(=O)_2-CH(CH_3)_2$); fluoro; chloro; bromo; iodo; trifluoromethyl; trichloromethyl; tribromomethyl; triiodomethyl; aminomethyl ($-CH_2NH_2$); nitro; carbamoyl; ureido ($-NH(C=O)-NH_2$); azido; isocyanate; thioisocyanate; hydroxylamino; nitrile; sulfonamide ($-S(=O)_2-NH_2$); methylsulfonamide ($-NH-S(=O)_2-CH_3$); ethylsulfonamide ($-NH_2-S(=O)_2-CH_2CH_3$); propiosulfonamide ($-NH_2-S(=O)_2-CH_2CH_2CH_3$); and isopropiosulfonamide ($-NH_2-S(=O)_2-CH(CH_3)_2$); phenyl; pyrrolyl; imidazolyl; pyrazolyl; thiazolyl; isothiazolyl; oxazolyl; isoxazolyl; pyridinyl; pyridazinyl; pyrmidinyl; pyrazinyl; 1H-indolyl; 3H-indolyl; 2H-isoindolyl; indolizinyl; quinolinyl; isoquinolinyl; quinoxalinyl; cinnolinyl; quinazolinyl; phthalazinyl; purinyl; indazolyl; benzimidazolyl; benzo[d]oxazole; benzo[d]thiazole; benzo[c]isoxazole; benzo[d]isoxazole; benzo[c]isothiazole; benzo[d]isothiazole; benzo[c][1,2,5]oxadiazole; benzo[c][1,2,5]thiadiazole; quinoline-2(1H)-one; isoquinoline-1(2H)-one; indolin-2-one; isoindolin-1-one; 1H-benzo[d]imidazole-2(3H)-one; furanyl; benzofuranyl; isobenzofuranyl; benzofuran-2(3H)-one; isobenzofuran-1(3H)-one; thiophenyl; benzo[b]thiophenyl; benzo[c]thiophenyl; benzo[b]thiophen-2(3H)-one; benzo[c]thiophen-1(3H)-one; and 1H-benzo[d][1,2,3]triazolyl;

$R_3$ is $=O$, methyl; ethyl; propyl; isopropyl; hydroxymethyl; 2-hydroxyethyl; 1-hydroxyethyl; methoxymethyl; carboxylate; methyl, ethyl, propyl, or isopropyl substituted with one or more fluoro, chloro, bromo, or iodo; benzyl; or $-(CH_2)_a-O-(C=O)-CHR_6-NH_2$;

$R_4$ is hydrogen; a methyl, ethyl, propyl, or isopropyl group substituted with a hydroxyaryl group; carboxylate; methyl ester ($-COOCH_3$), ethyl ester ($-COOCH_2CH_3$); propyl ester ($-COOCH_2CH_2CH_3$); isopropyl ester ($-COOCH(CH_3)_2$); butylester ($-COOCH_2CH_2CH_2CH_3$); sec-butylester ($-COOCH(CH_3)(CH_2CH_3)$); tert-butylester ($-COOC(CH_3)_3$); or benzyl ester ($-COOCH_2(C_6H_6)$);

$R_5$ is hydrogen, methyl, or $=O$; and $R_6$ is methyl substituted with one or more substituents selected from the group consisting of substituted aryl groups and substituted heteroaryl groups; or an enantiomer; racemate; or pharmaceutically acceptable salt thereof.

5. The compound of claim 4, wherein $R_6$ is an imidazole substituted with a substituent selected from the group consisting of methyl, ethyl, propyl, and isopropyl substituted with one or more fluoro, chloro, amino, phenyl, or pyridinyl.

6. The compound of claim 1, wherein:

m is 1;

n is 2;

$R_1$ is selected from the group consisting of phenyl, quinoxalinyl, and benzimidazolyl;

wherein $R_1$ is unsubstituted or substituted with one or more substitutents selected from the group consisting of fluoro; chloro; bromo; iodo; amino; carboxamide; ureido ($-NH(C=O)-NH_2$); and sulfonamide ($-S(=O)_2-NH_2$);

$R_2$ is selected from the group consisting of phenyl, quinoxalinyl, indazolyl, benzimidazolyl, benzo[d]oxazole, benzo[c]isoxazole, benzo[d]isoxazole, and 1H-benzo[d][1,2,3]triazolyl;

wherein $R_2$ is unsubstituted or substituted with one or more substitutents selected from the group consisting of fluoro; chloro; bromo; iodo; amino; carboxamide; ureido ($-NH(C=O)-NH_2$); and sulfonamide ($-S(=O)_2-NH_2$);

$R_3$ is methyl;

$R_4$ is hydrogen; and $R_5$ is hydrogen; or an enantiomer; racemate; or pharmaceutically acceptable salt thereof.

7. The compound of claim 1, wherein:

m is 1;

n is 2;

$R_1$ is selected from the group consisting of unsubstituted quinoxalinyl, unsubstituted benzimidazolyl, or phenyl substituted with 3-fluoro, 4-fluoro, 3-chloro, 4-chloro, 3-amine, 4-amine, 3-ureido, 4-ureido, 3-carboxamide, 4-carboxamide, 3,4-difluoro, 3,4-dichloro, 3,5-difluoro, or 3,5-dichloro;

$R_2$ is selected from the group consisting of unsubstituted quinoxalinyl, unsubstituted indazolyl, unsubstituted benzimidazolyl, unsubstituted benzo[d]oxazole, unsubstituted benzo[c]isoxazole, unsubstituted benzo[d]isoxazole, unsubstituted 1H-benzo[d][1,2,3]triazolyl, and phenyl substituted with 3-fluoro, 4-fluoro, 3-chloro, 4-chloro, 3-amine, 4-amine, 3-ureido, 4-ureido, 3-carboxamide, 4-carboxamide, 3-sulfonamide, 4-sulfonamide, 3,4-difluoro, 3,4-dichloro, 3,5-difluoro, 3,5-dichloro, 3-fluoro-4-carboxamide, 3-chloro-4-carboxamide, 3-fluoro-4-sulfonamide, 3-chloro-4-sulfonamide, 3-fluoro-4-ureido, or 3-chloro-4-ureido;

$R_3$ is methyl;
$R_4$ is hydrogen; and
$R_5$ is hydrogen; or
an enantiomer; racemate; or pharmaceutically acceptable salt thereof.
8. The compound of claim 1, wherein the compound is selected from the group consisting of:
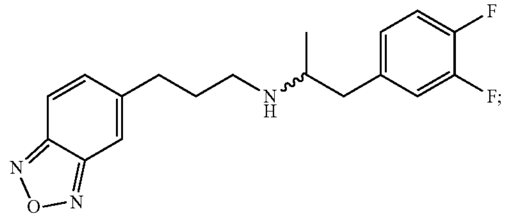
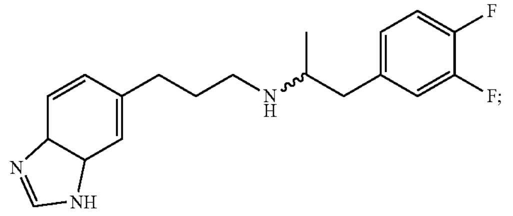
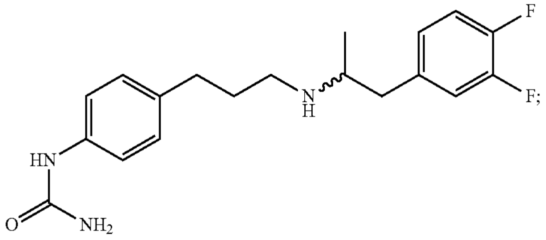
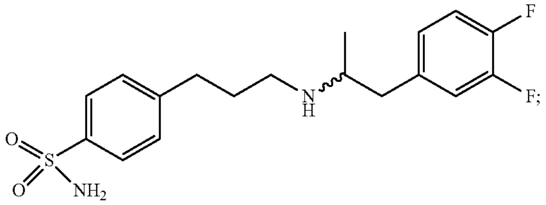
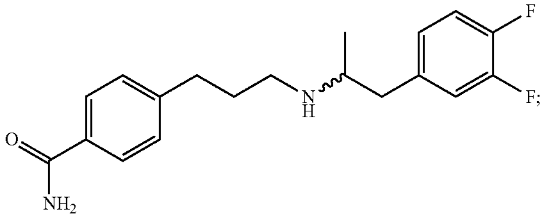
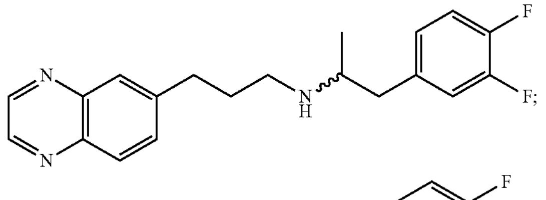
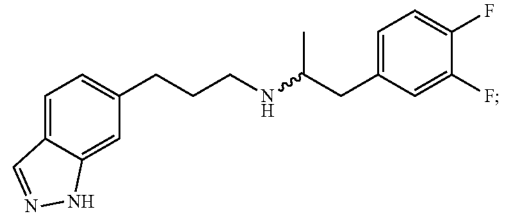
-continued
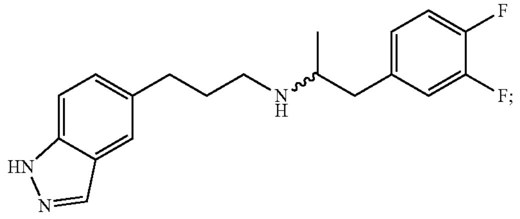
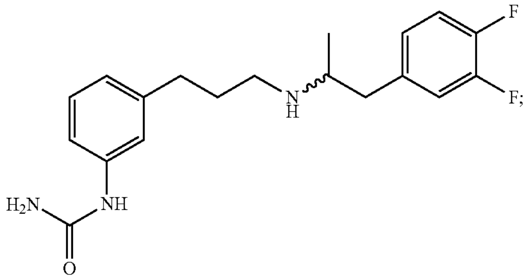
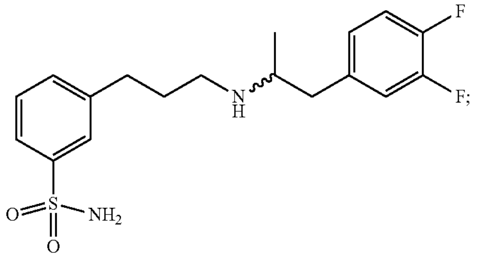
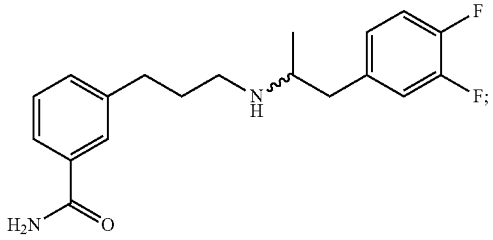
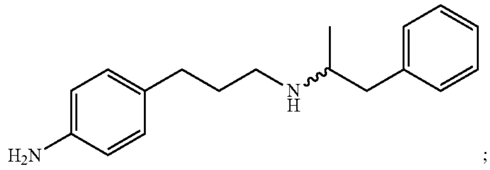
;
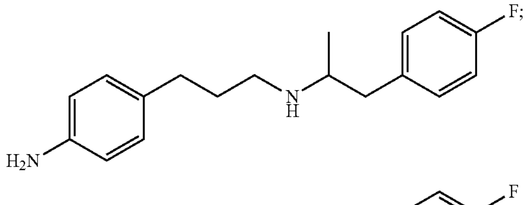
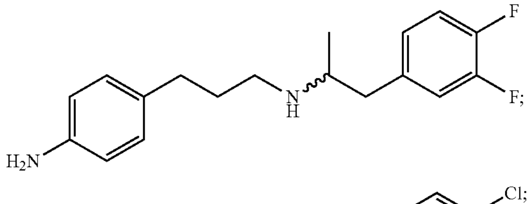
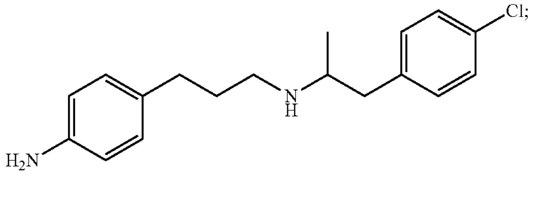

-continued
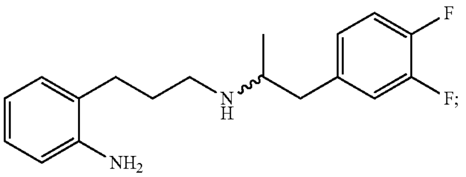
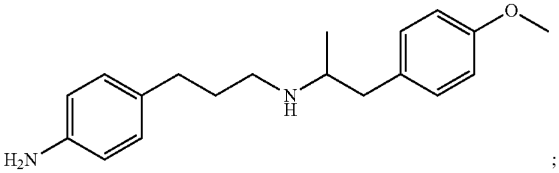
;
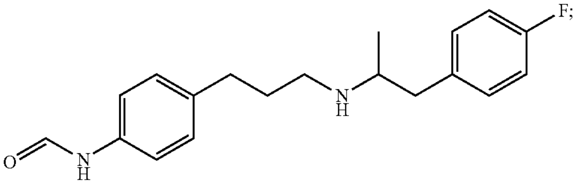
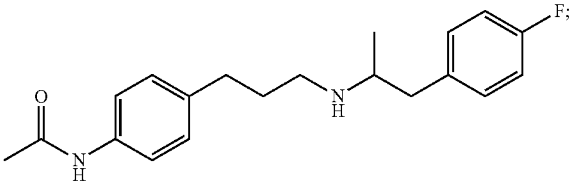
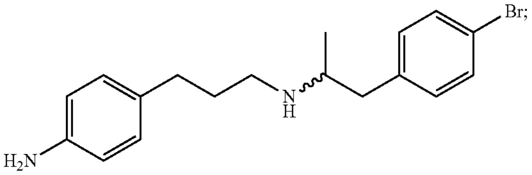
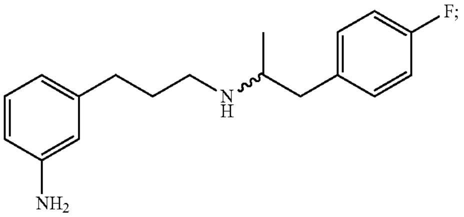
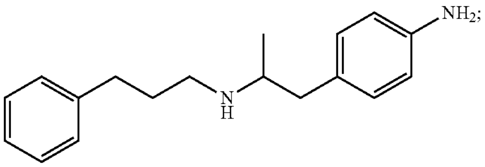
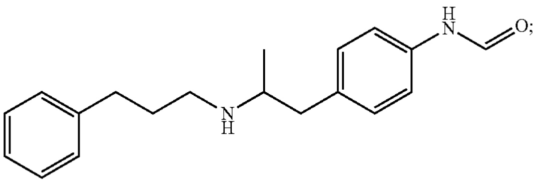
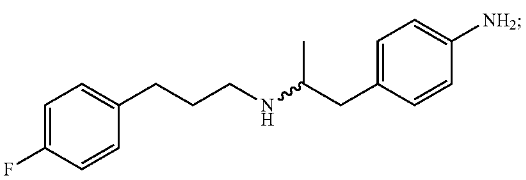
-continued
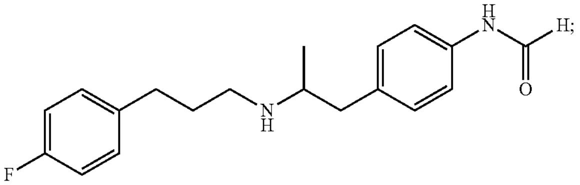
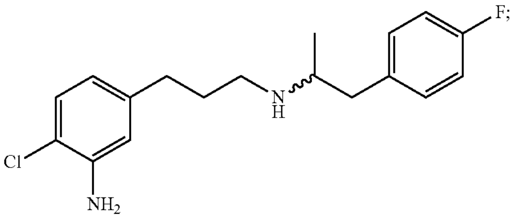
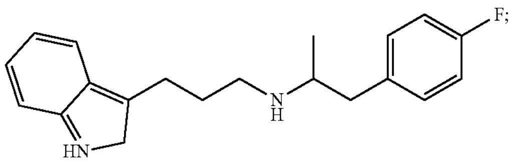
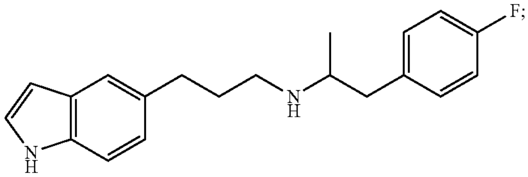
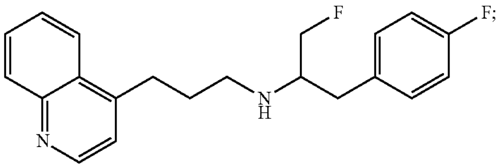
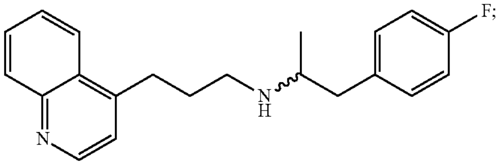
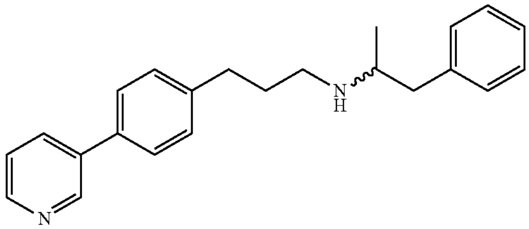
;
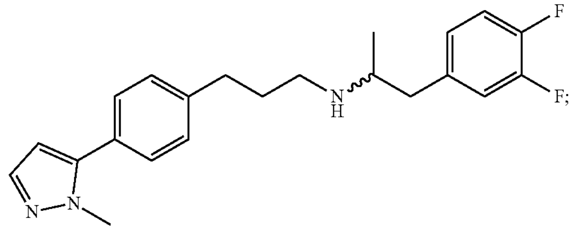

-continued
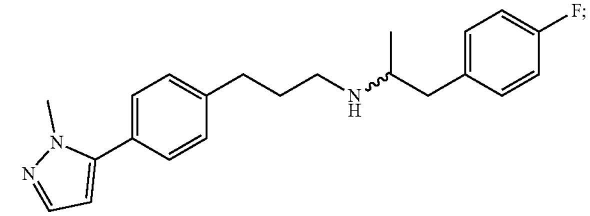
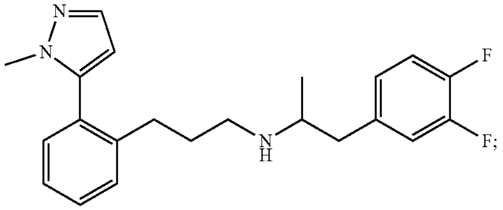
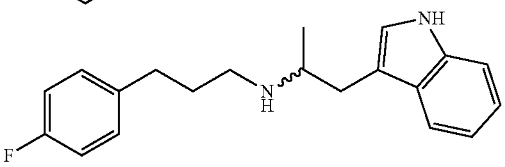
;
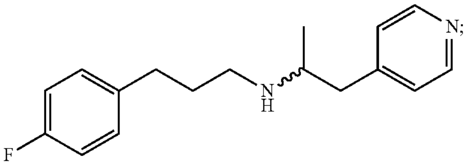
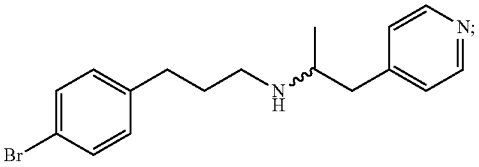
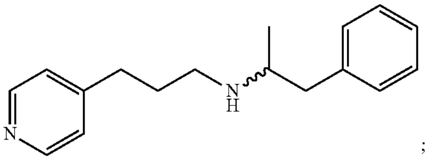
;
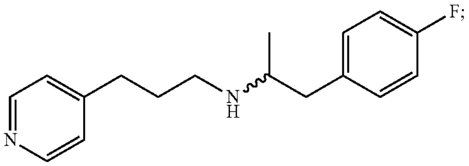
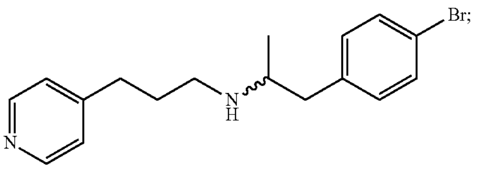
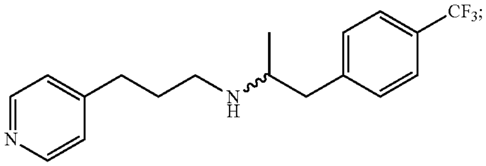
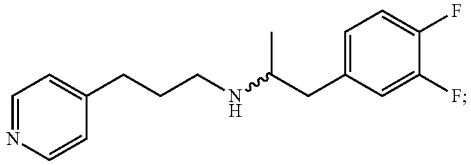
-continued
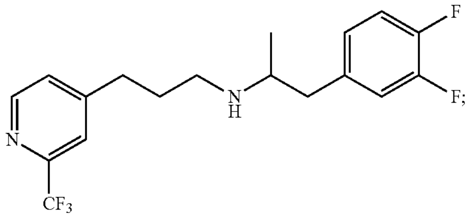
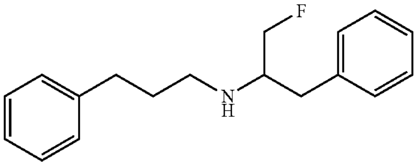
;
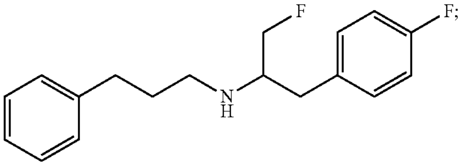
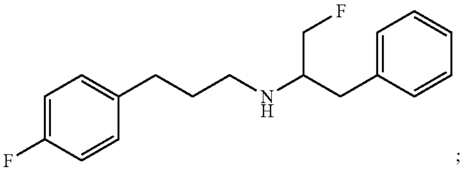
;
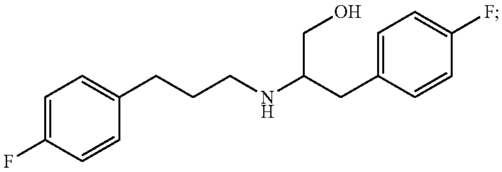
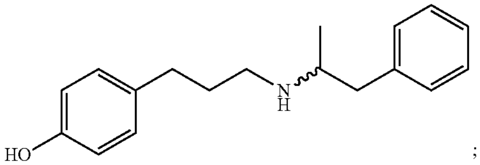
;
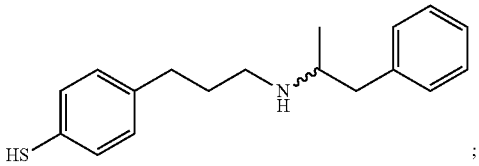
;
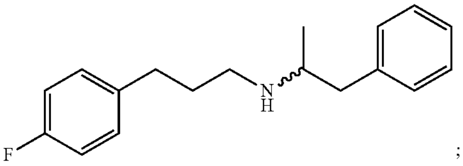
;
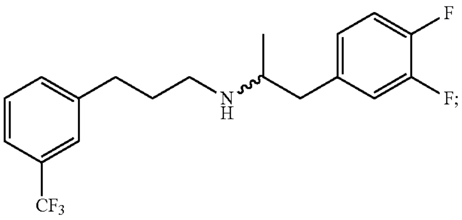

-continued
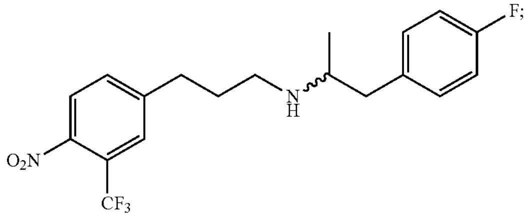
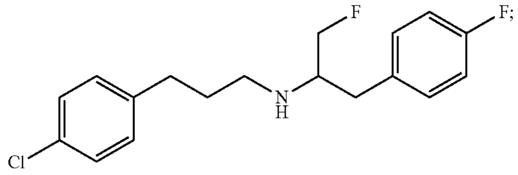
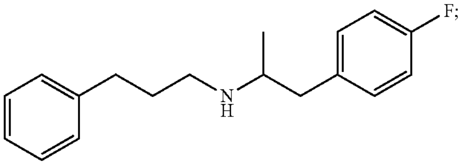
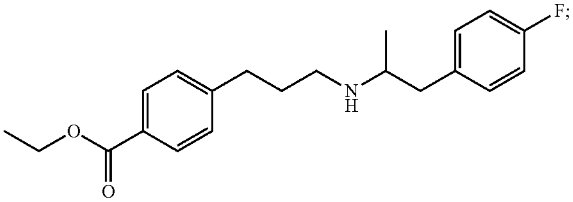
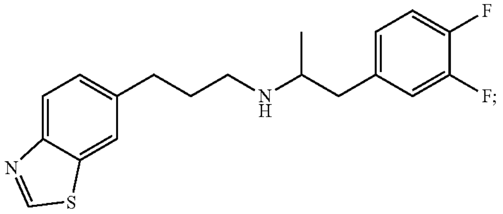
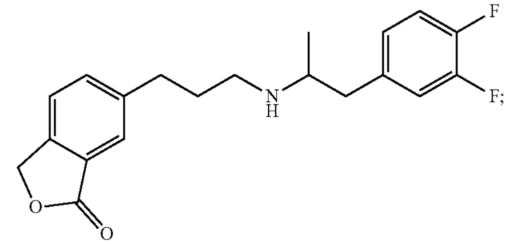
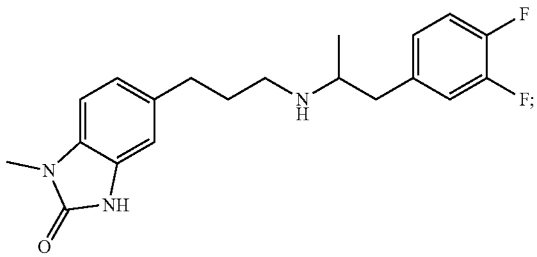
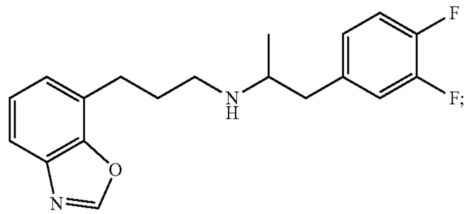
-continued
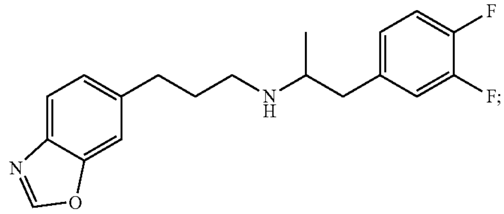
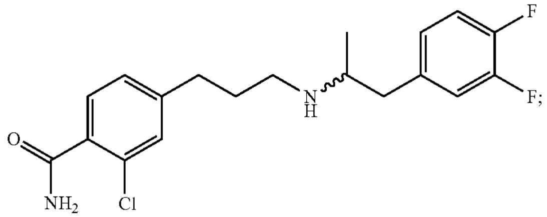
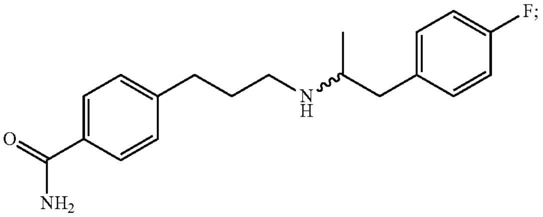
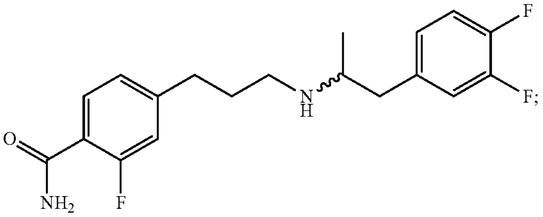
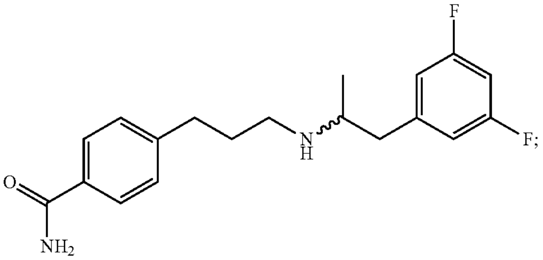
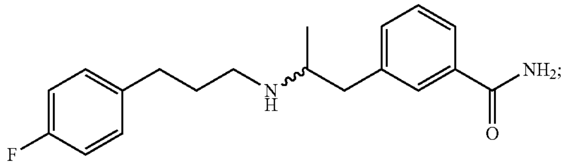
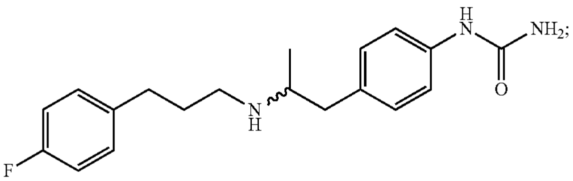
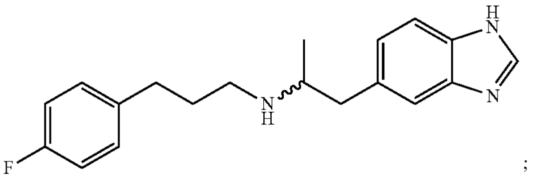
;

-continued

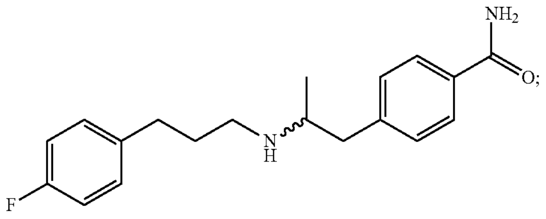

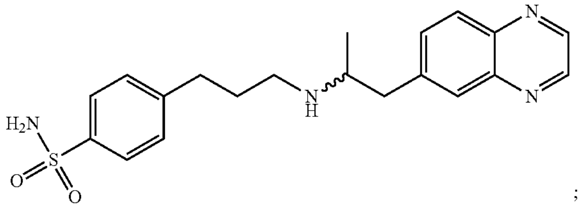

;

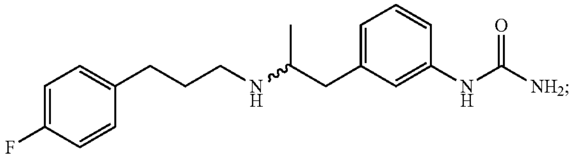

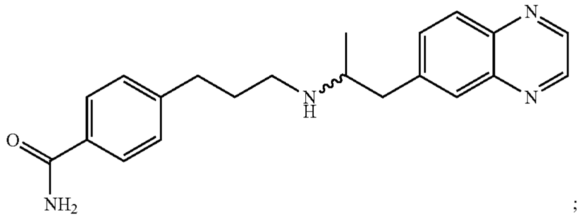

;

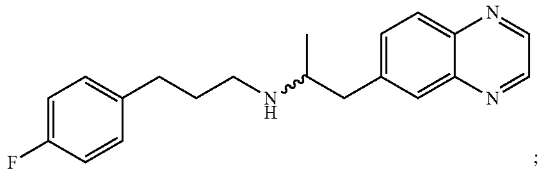

;

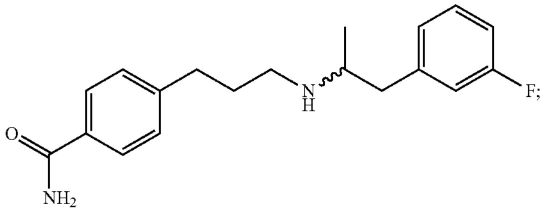

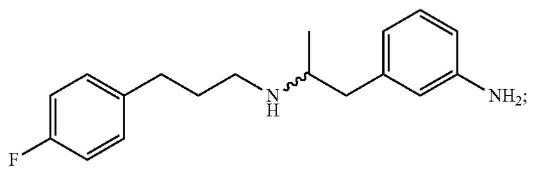

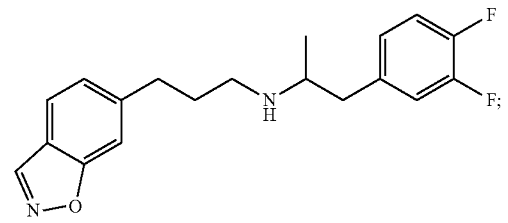

-continued

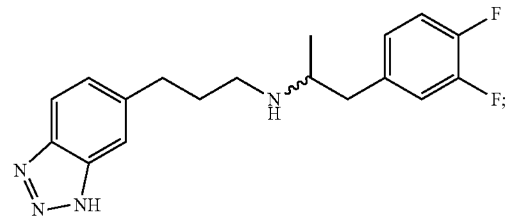

and

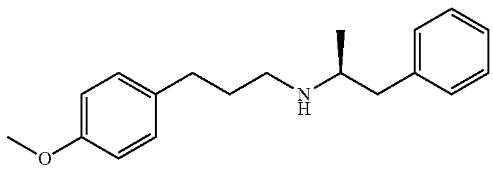

;

or an enantiomer; racemate; or pharmaceutically acceptable salt thereof.

9. The compound of claim 8, wherein the compound is selected from the group consisting of:

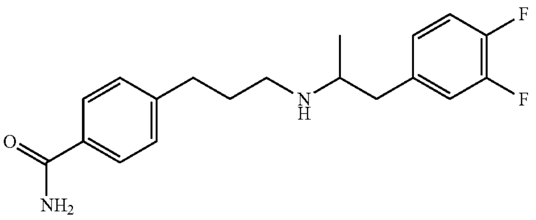

and

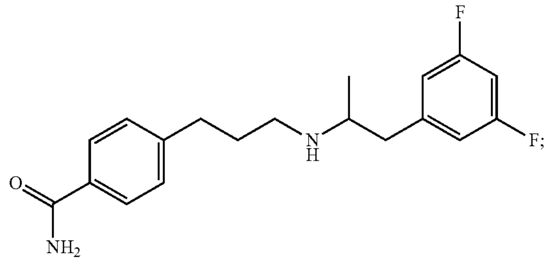

an enantiomer; racemate; or pharmaceutically acceptable salt thereof.

10. A pharmaceutical composition comprising a compound of claim 1 and a pharmaceutically acceptable additive.

11. The pharmaceutical composition of claim 10, wherein the compound is selected from the group consisting of:

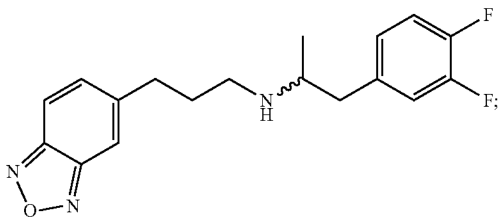

-continued
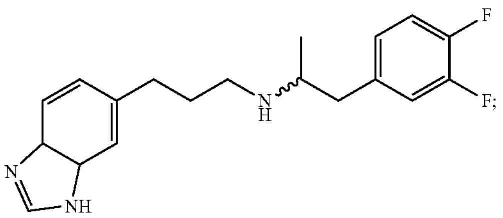
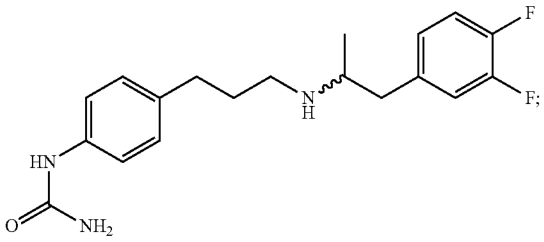
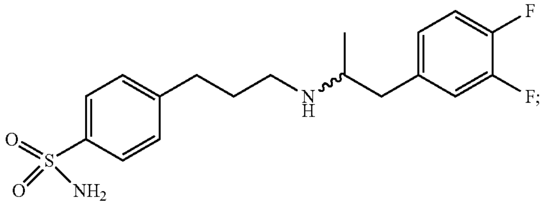
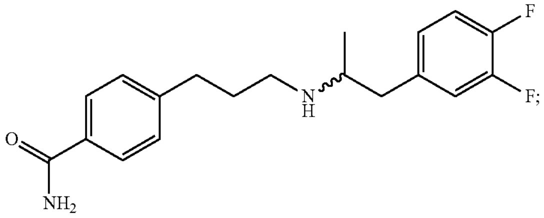
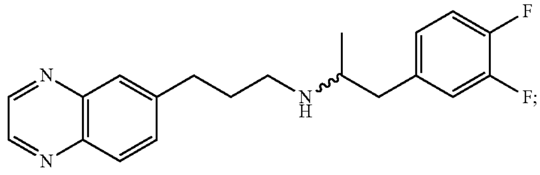
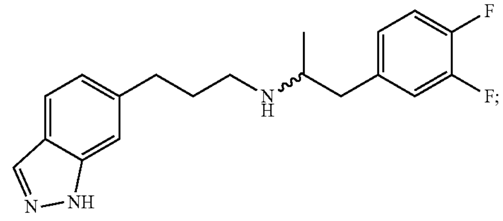
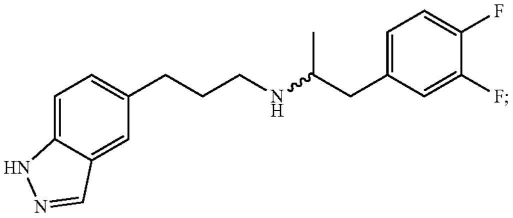
-continued
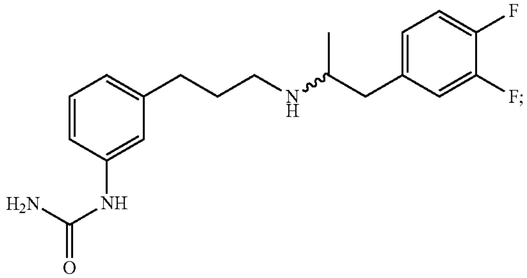
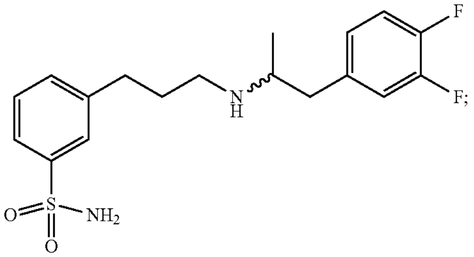
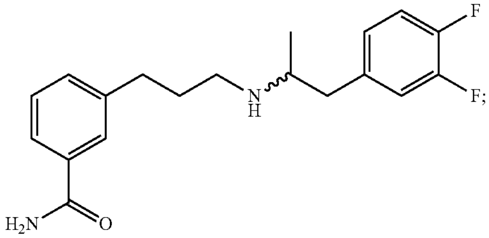
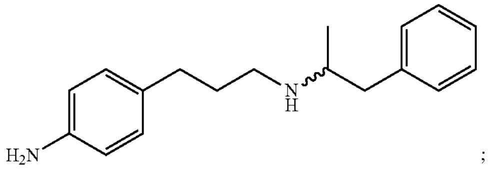
;
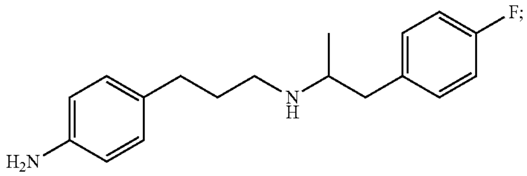
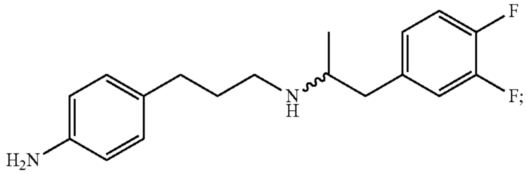
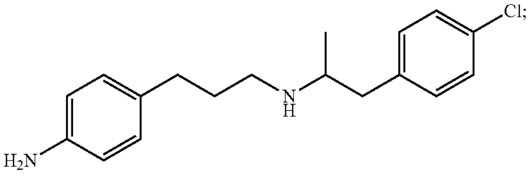
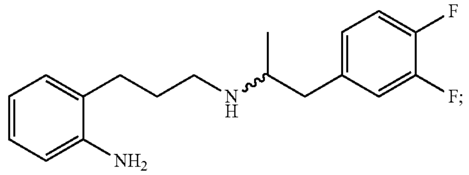

-continued
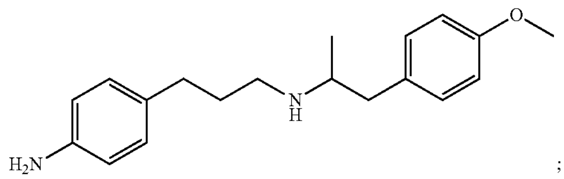
;
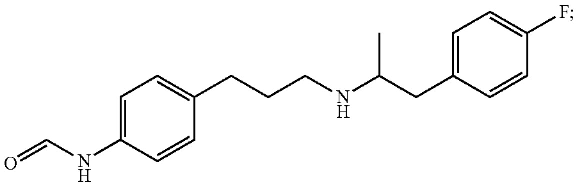
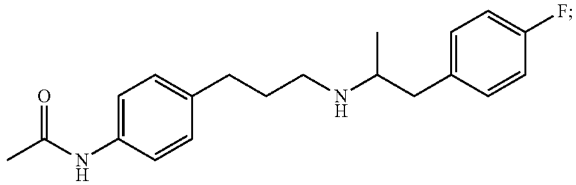
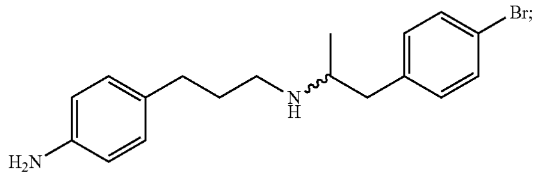
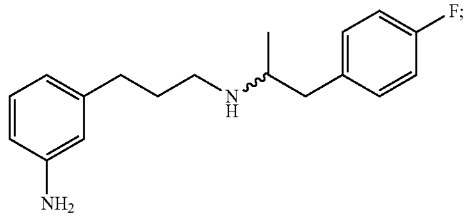
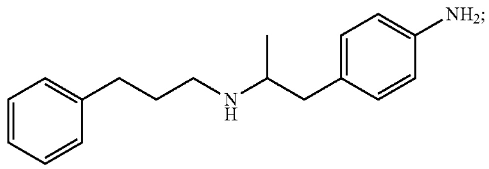
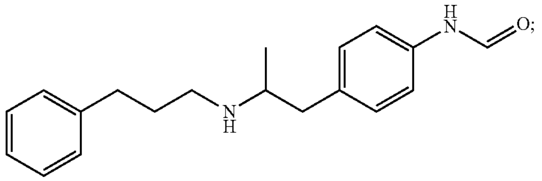
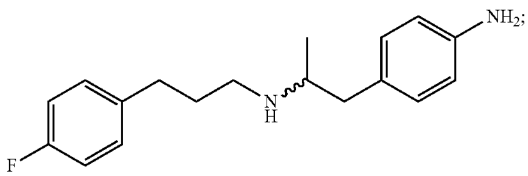
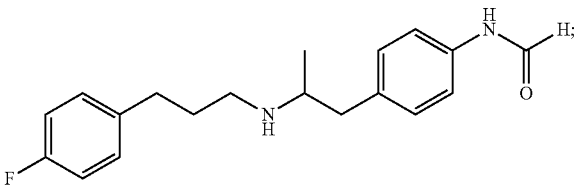
-continued
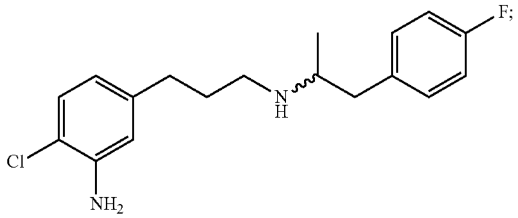
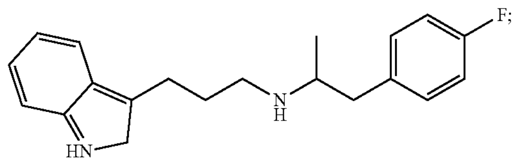
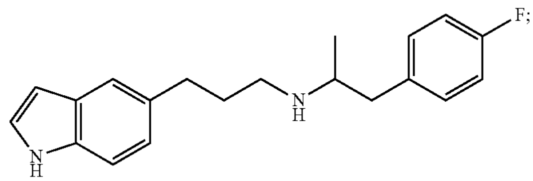
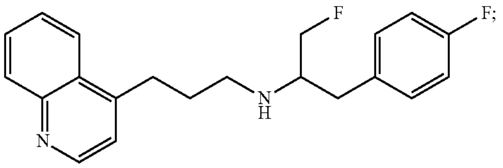
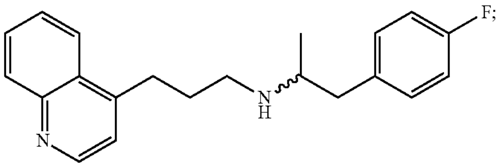
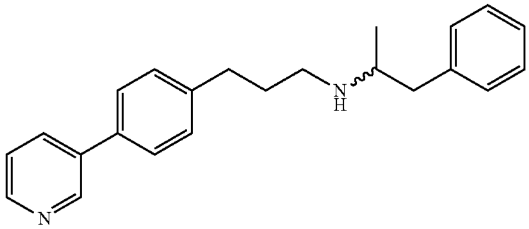
;
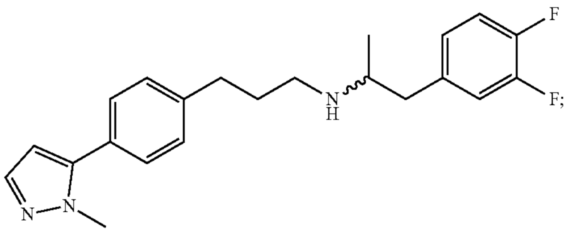
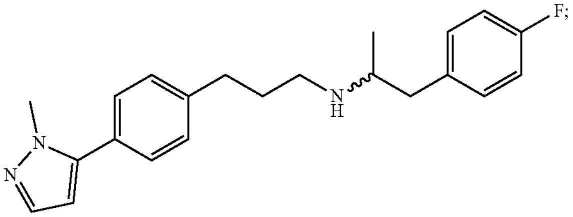

-continued
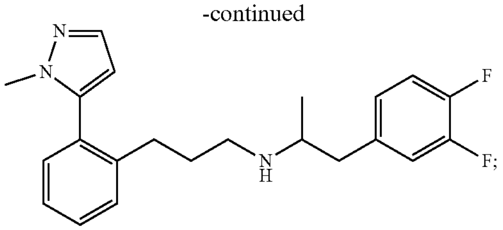
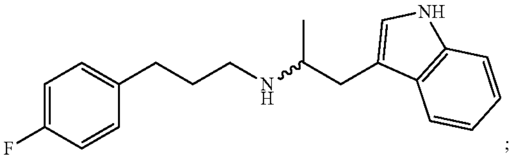
;
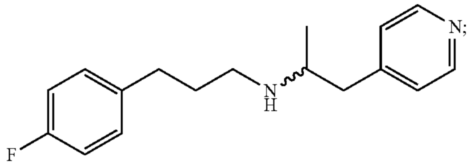
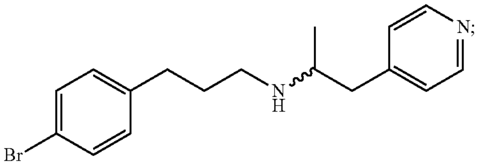
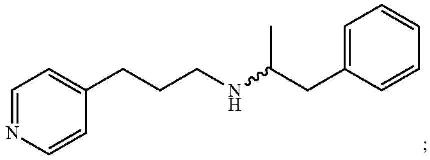
;
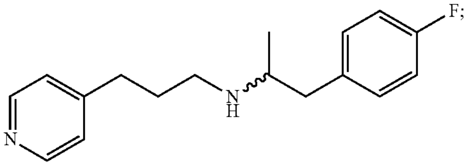
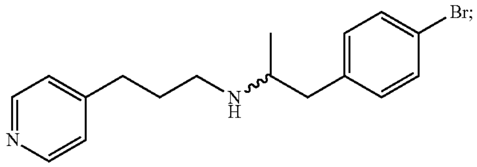
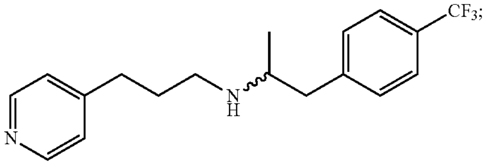
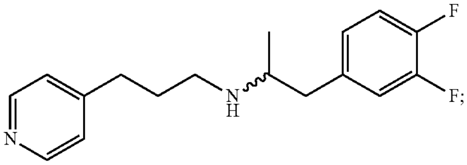
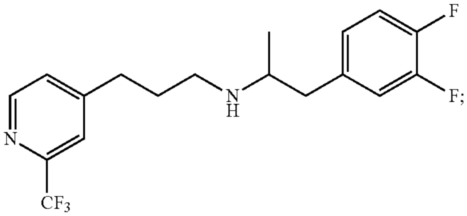
-continued
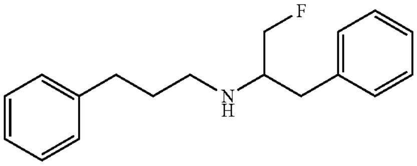
;
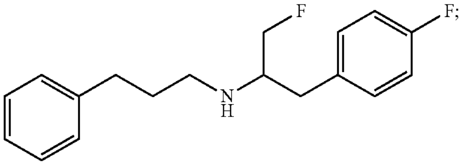
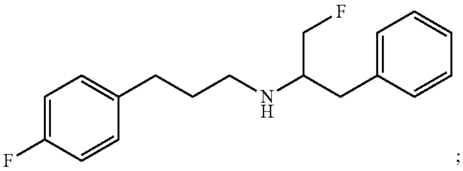
;
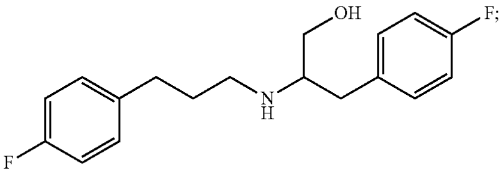
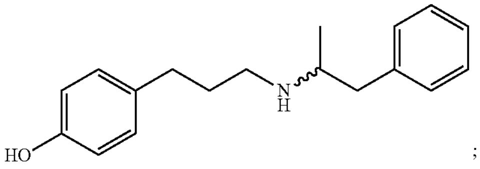
;
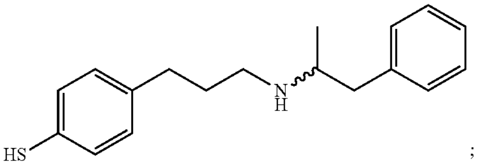
;
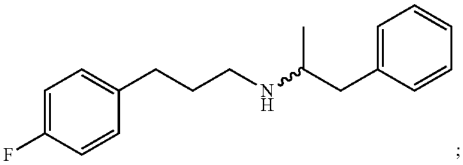
;
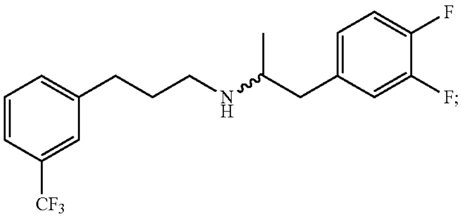
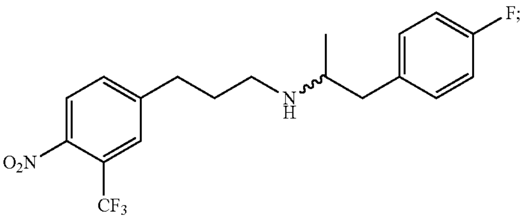

-continued
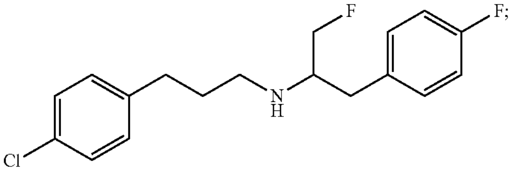
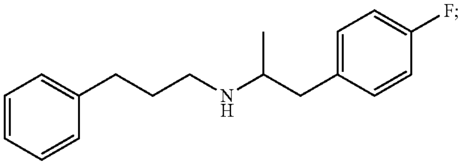
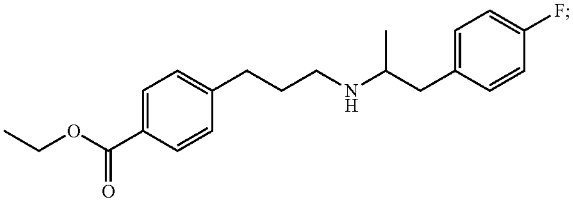
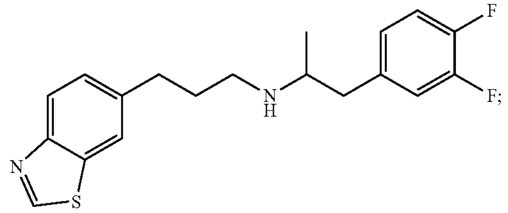
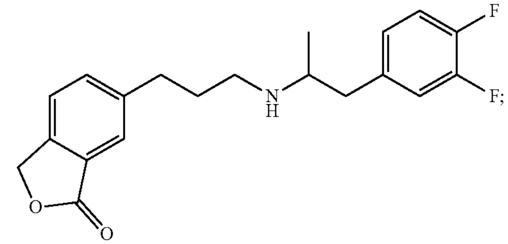
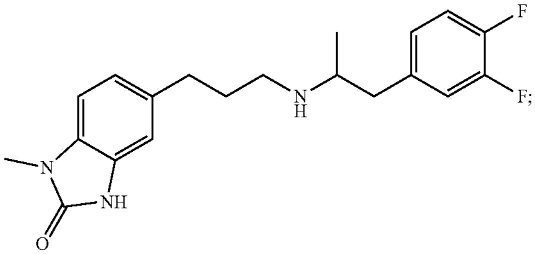
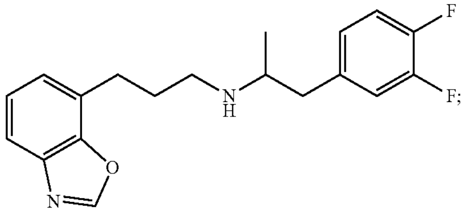
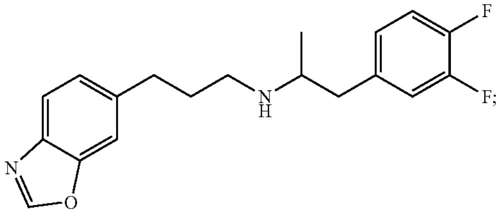
-continued
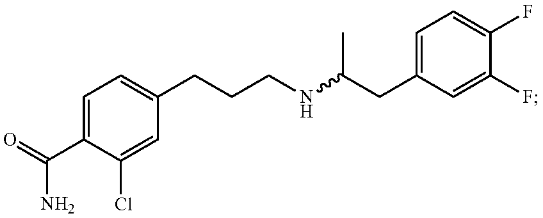
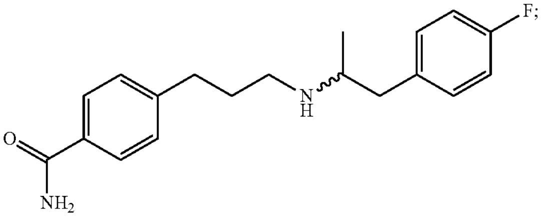
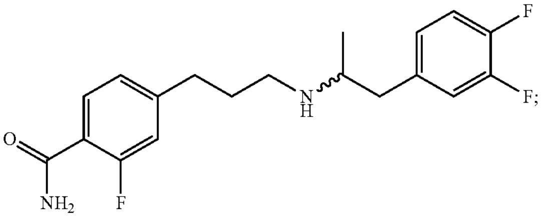
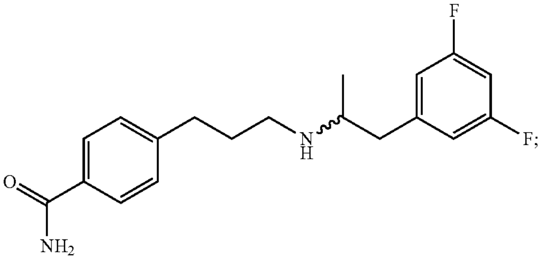
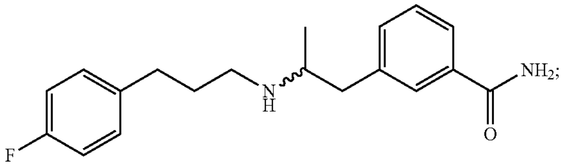
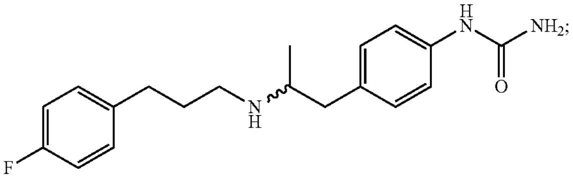
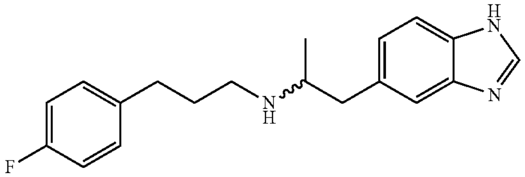
;
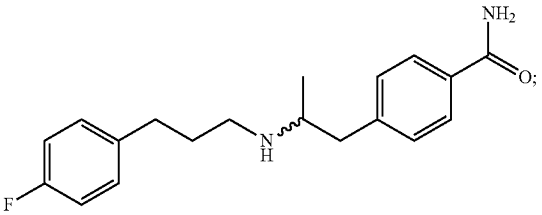

-continued

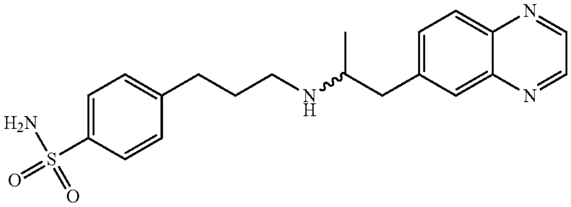

;

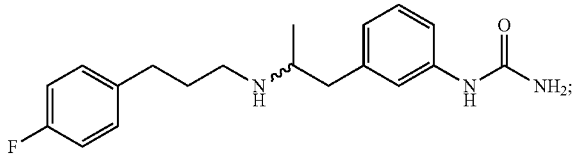

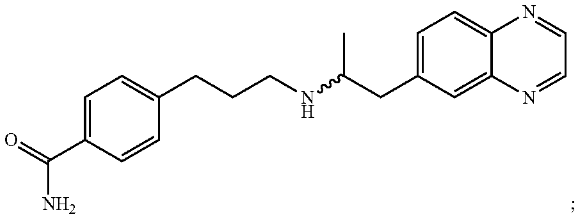

;

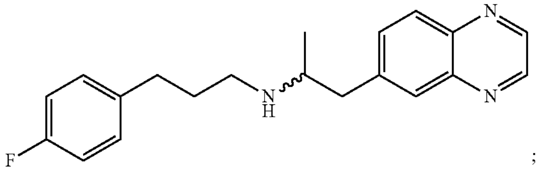

;

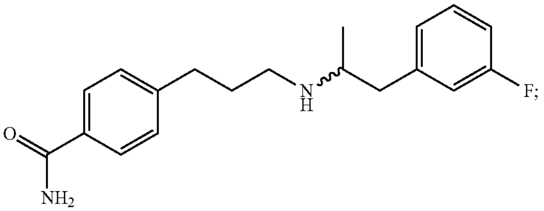

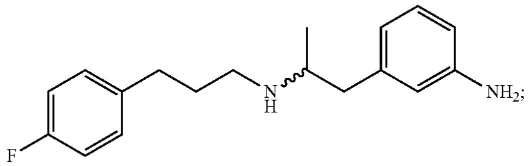

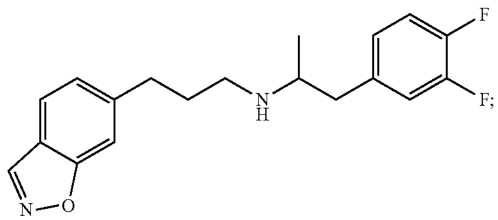

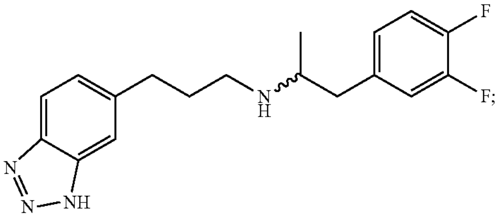

and

-continued

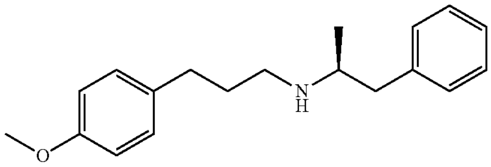

;

or an enantiomer; racemate; or pharmaceutically acceptable salt thereof.

12. The pharmaceutical composition of claim 11, wherein the compound is selected from the group consisting of:

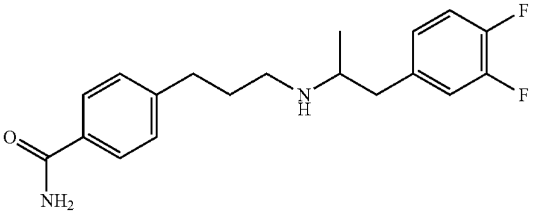

and

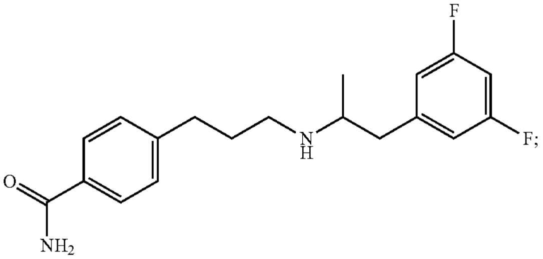

an enantiomer; racemate; or pharmaceutically acceptable salt thereof.

13. A method of treating a substance use disorder, drug dependence/abuse/addiction or withdrawal from drug dependence/abuse/addiction in an individual in need thereof, wherein the method comprises the step of administering to the individual a compound of claim 1.

14. The method of claim 13, wherein the compound is selected from the group consisting of:

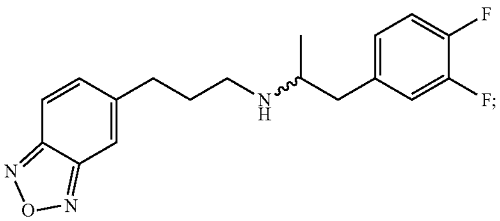

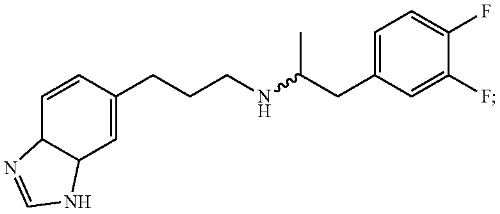

-continued
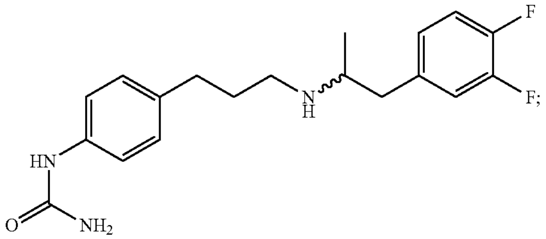
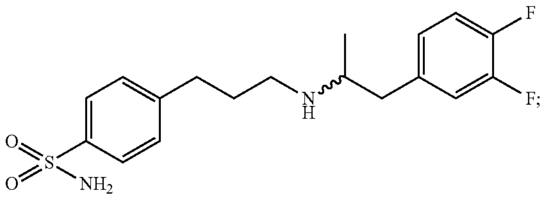
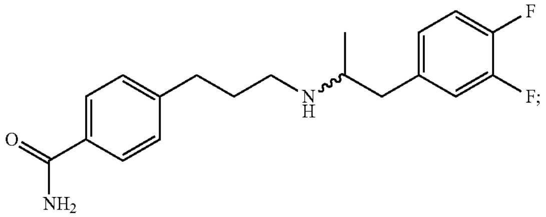
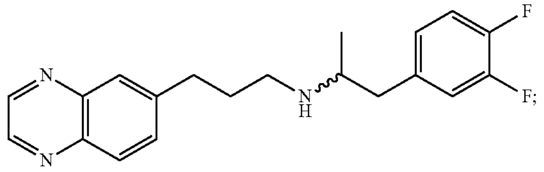
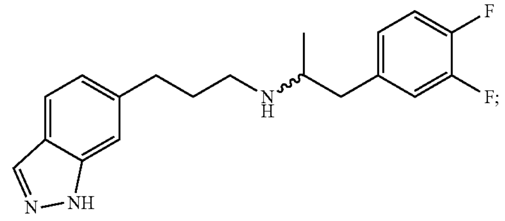
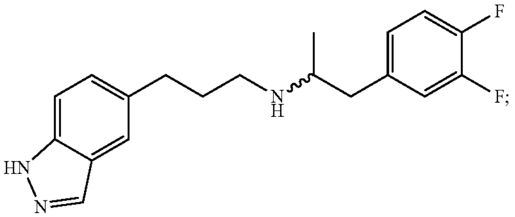
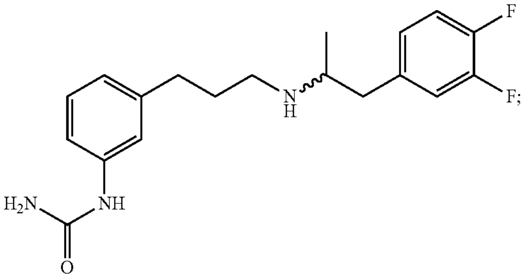
-continued
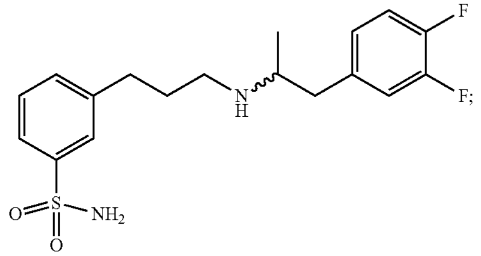
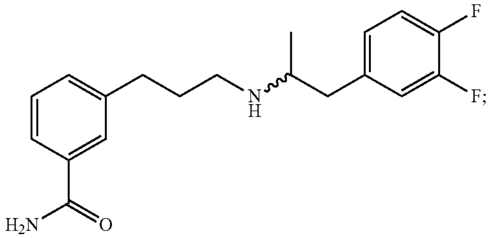
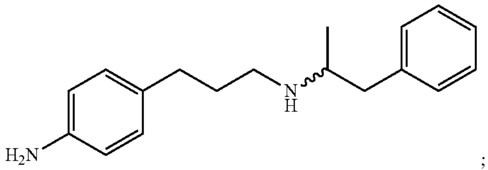
;
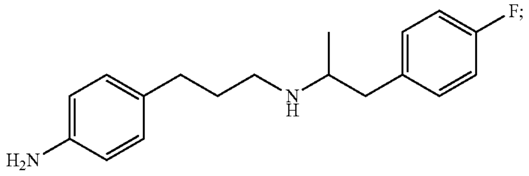
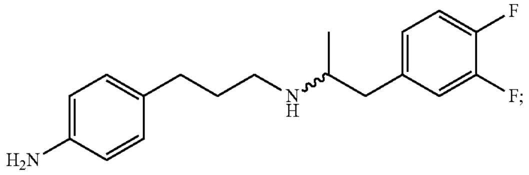
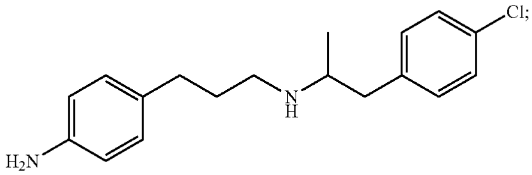
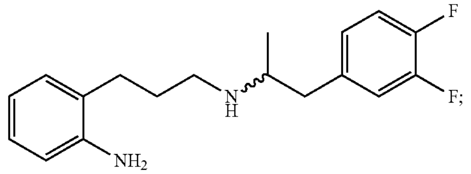
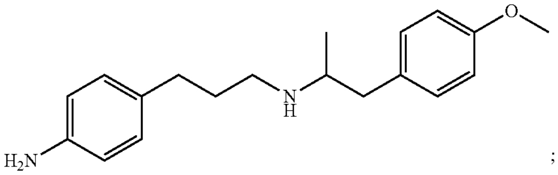
;
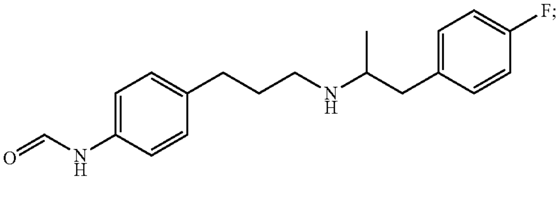

-continued
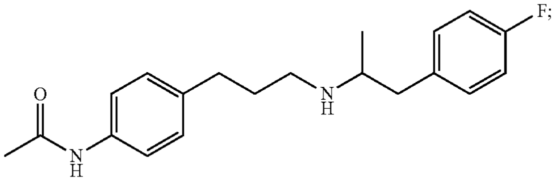
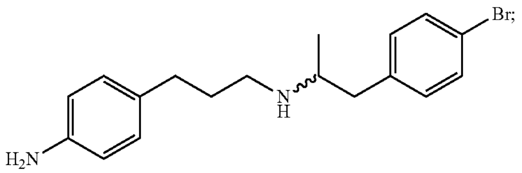
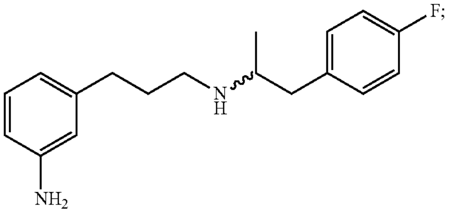
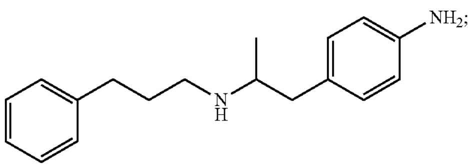
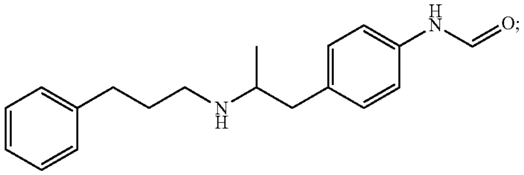
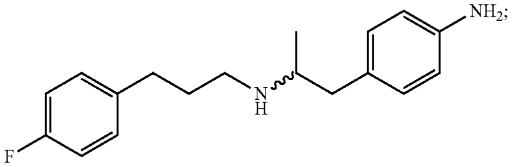
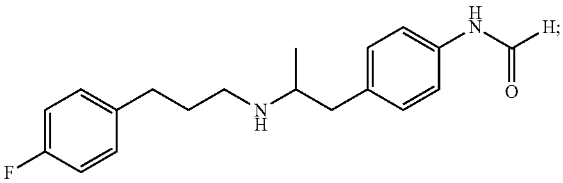
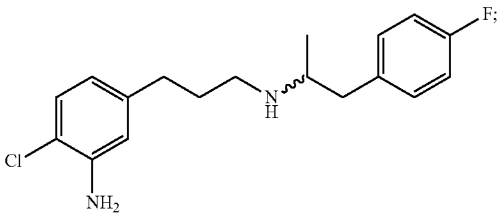
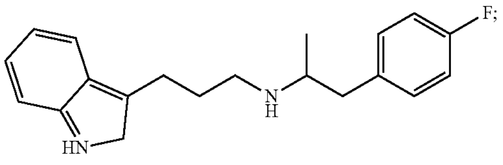
-continued
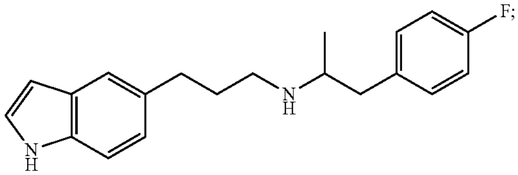
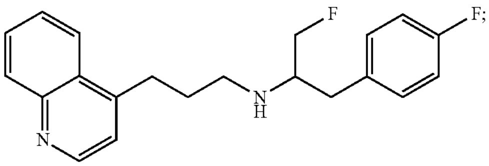
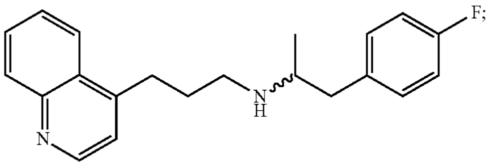
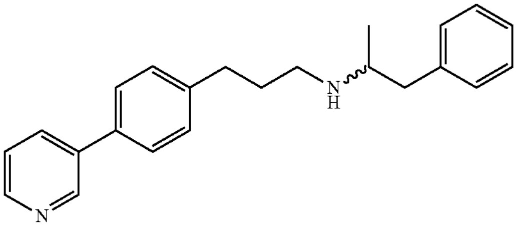
;
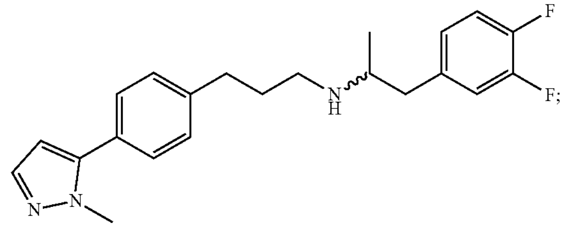
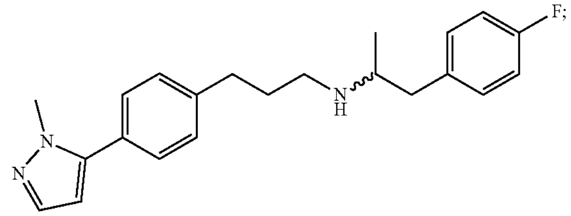
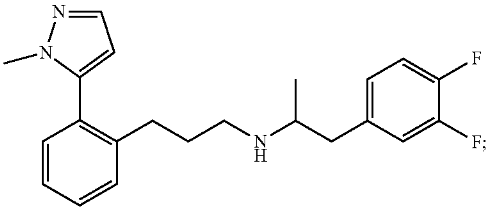
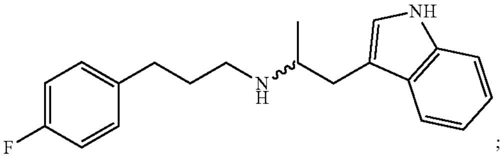
;
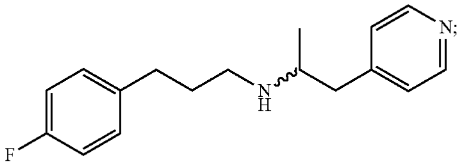

-continued
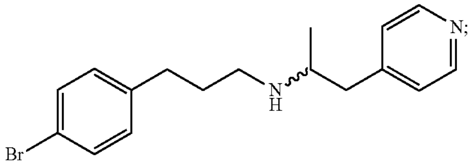
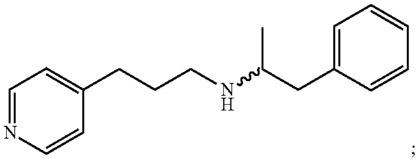
;
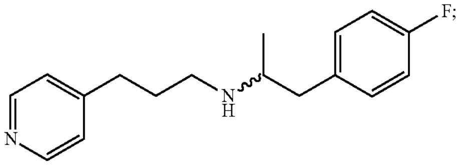
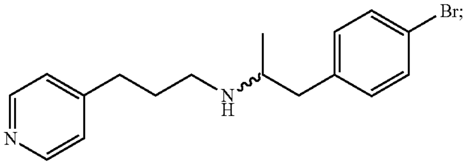
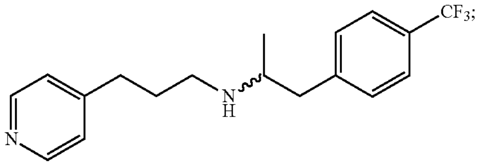
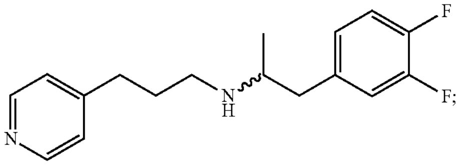
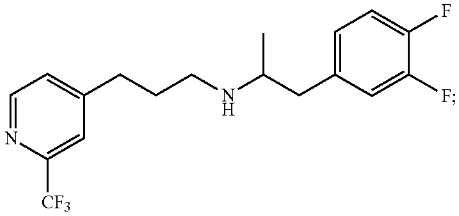
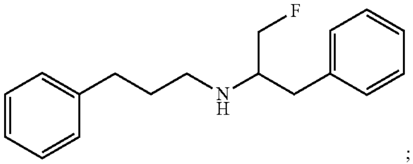
;
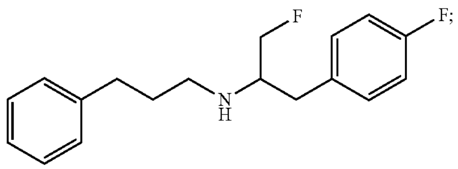
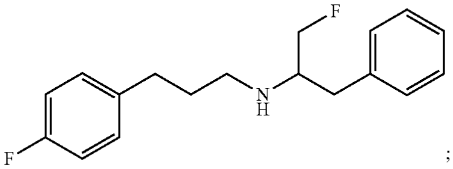
;
-continued
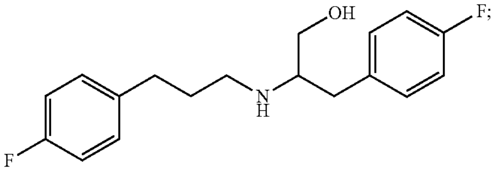
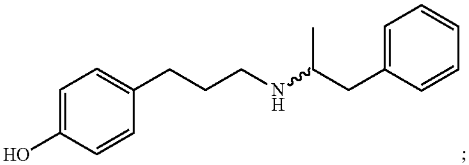
;
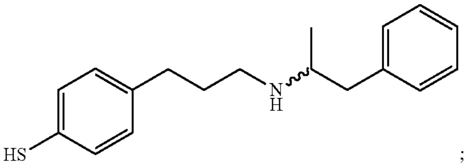
;
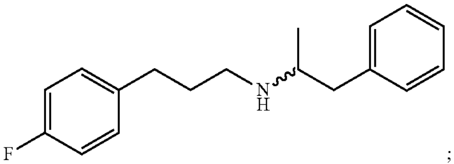
;
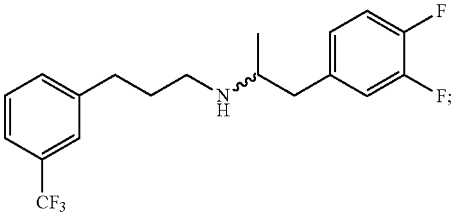
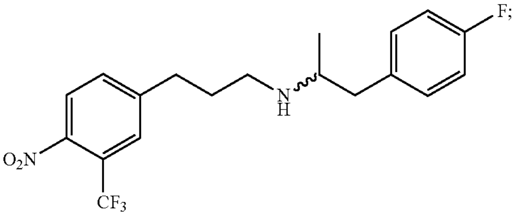
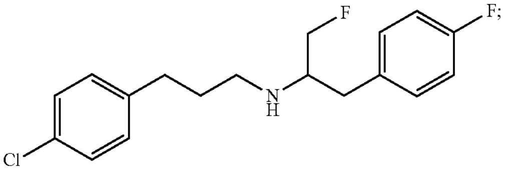
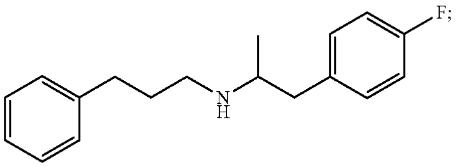
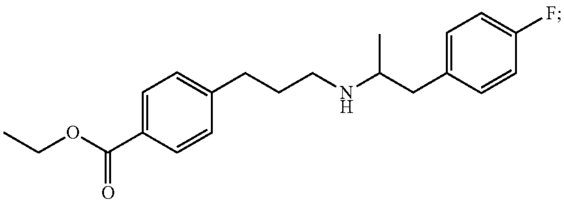

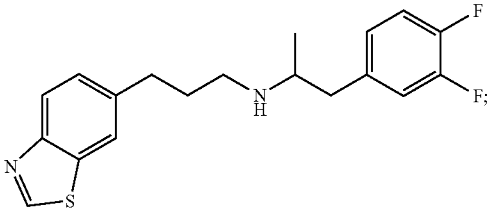
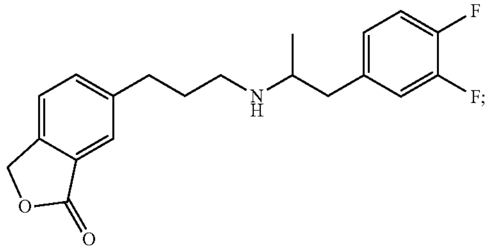
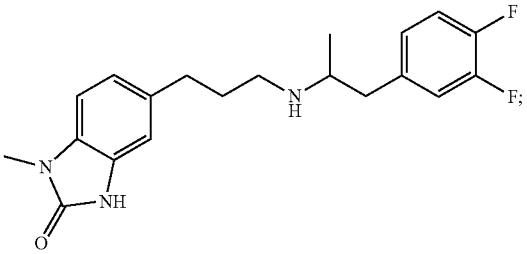
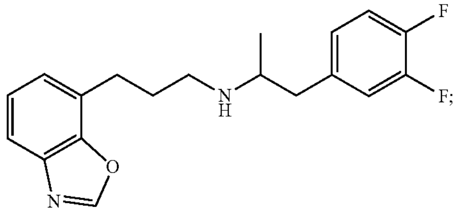
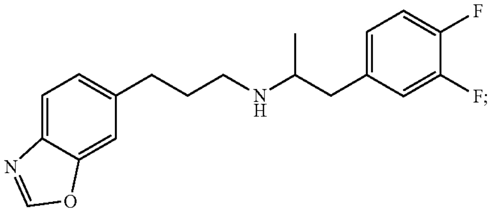
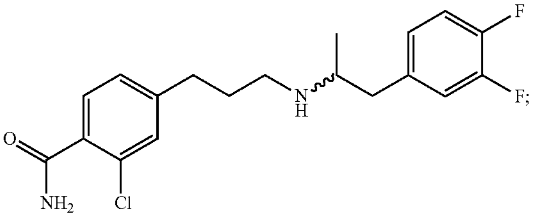
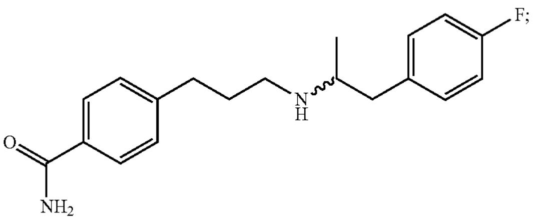
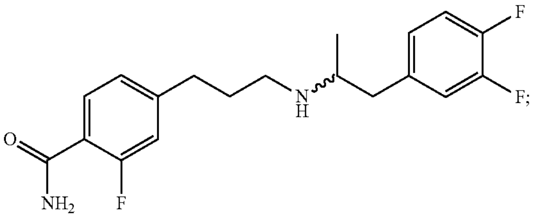
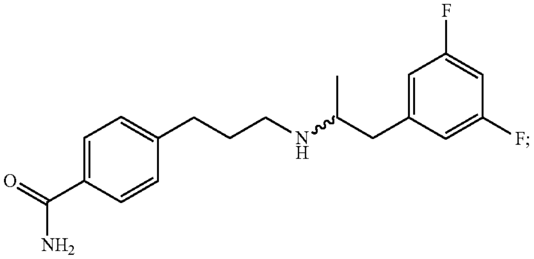
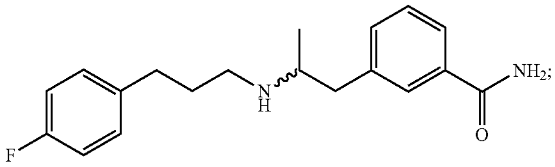
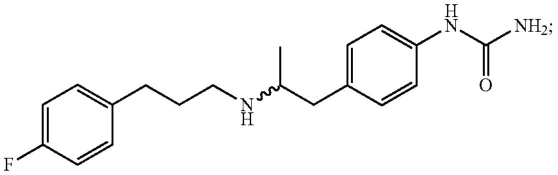
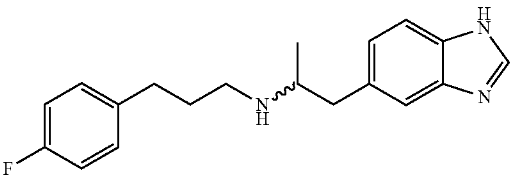
;
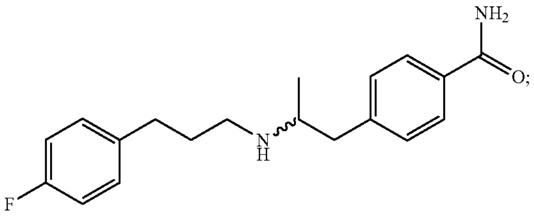
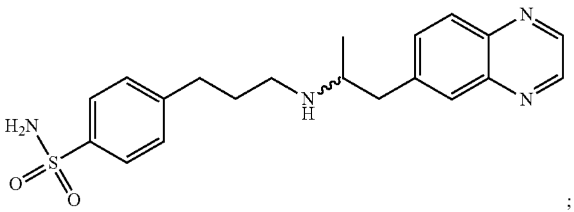
;
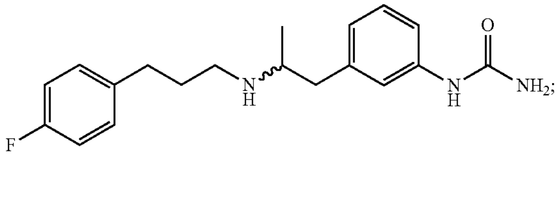

-continued

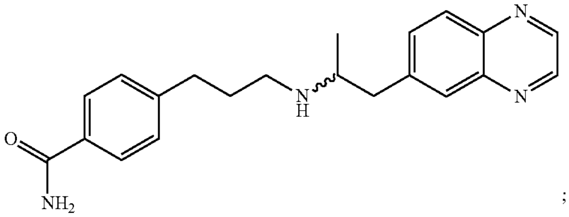

;

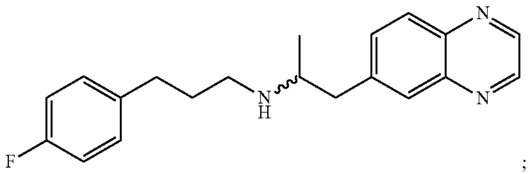

;

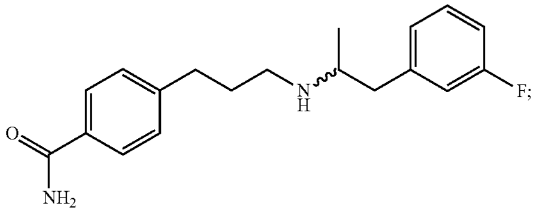

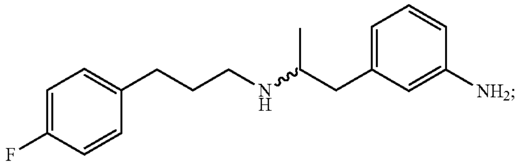

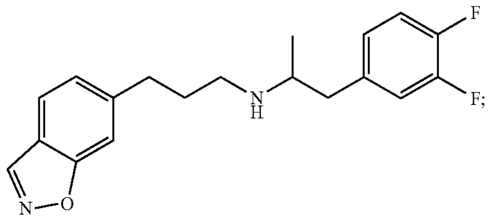

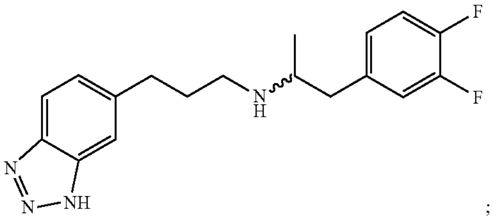

; and

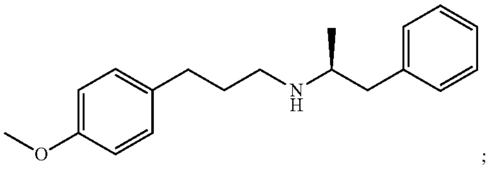

;

or an enantiomer; racemate; or pharmaceutically acceptable salt thereof.

15. The method of claim 14, wherein the compound is selected from the group consisting of:

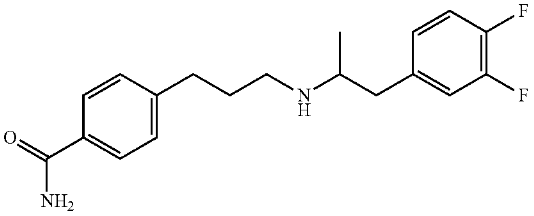

and

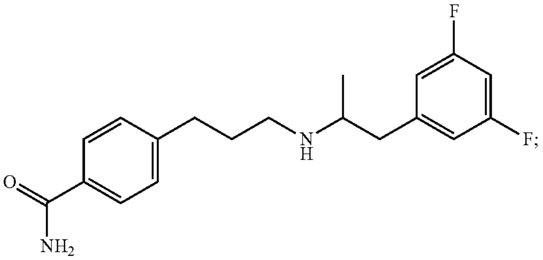

an enantiomer; racemate; or pharmaceutically acceptable salt thereof.

16. The method of claim 13, wherein the compound is administered to the individual intranasally; intrapulmonarily; topically; orally; intravenously as an infusion or injection; intramuscularly as an infusion or injection; subcutaneously as an infusion, injection, or depot formulation; transdermally; intraperitoneally; or rectally.

17. A method of treating a disease or pathology of the central nervous system, wherein the disease may be cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit hyperactivity disorder, hyperkinetic syndrome, chronic nervous exhaustion, narcolepsy, pain, motion sickness, depression, and/or dyskinesias resulting from administration from another pharmaceutical compound in an individual in need thereof, wherein the method comprises the step of administering to the individual a compound of claim 1.

18. The method of claim 17, wherein the compound is selected from the group consisting of:

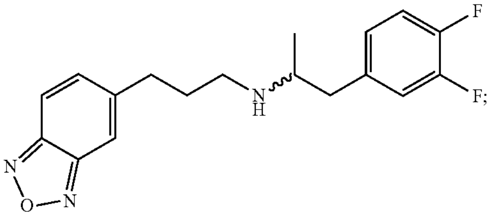

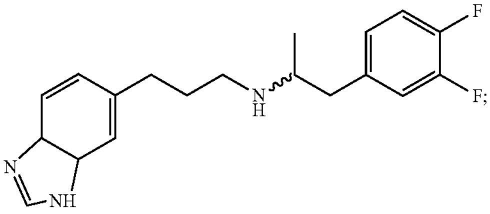

-continued
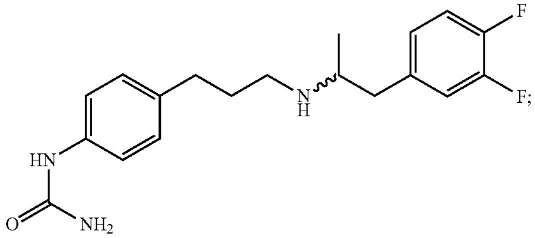
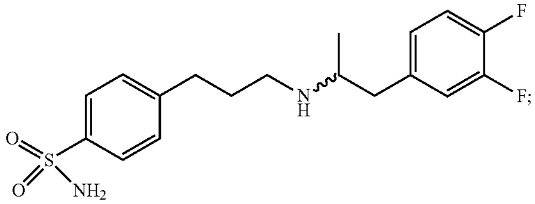
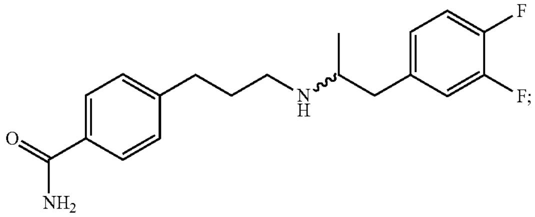
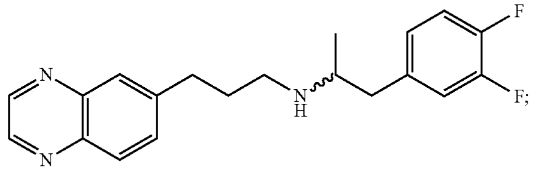
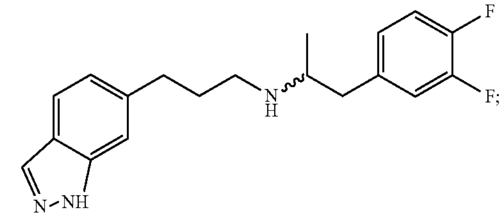
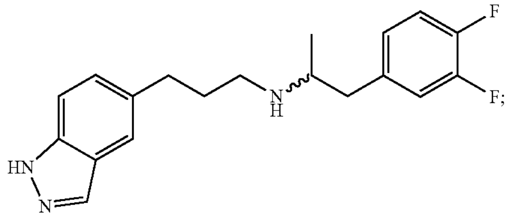
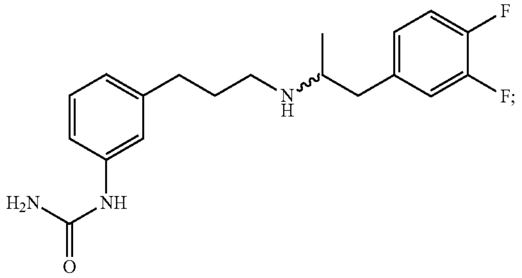
-continued
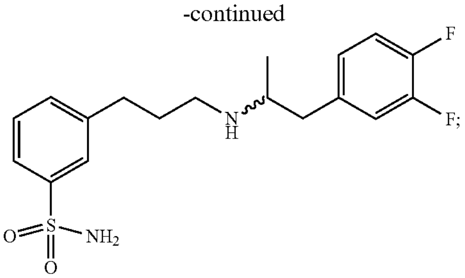
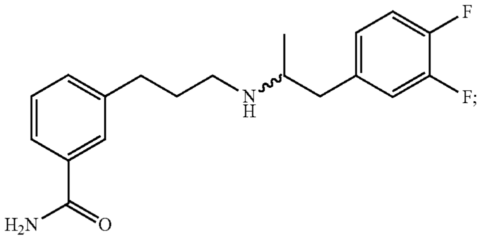
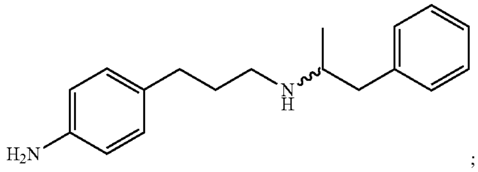
;
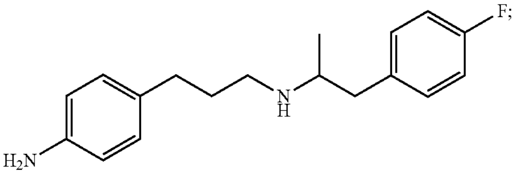
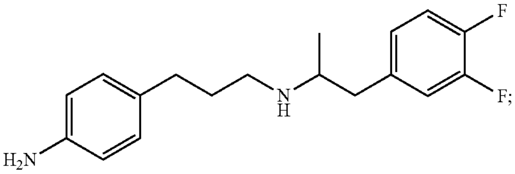
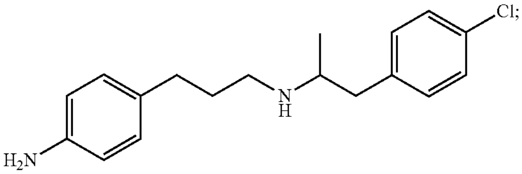
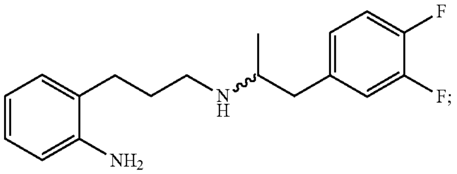
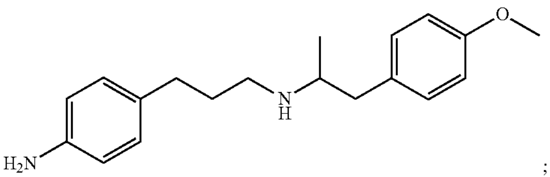
;
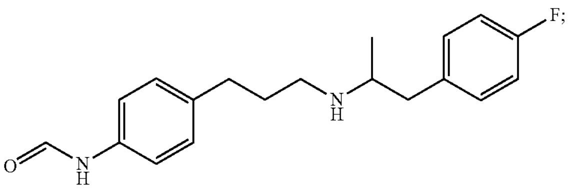

-continued
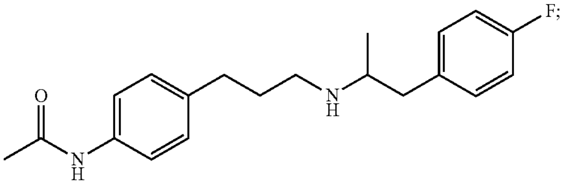
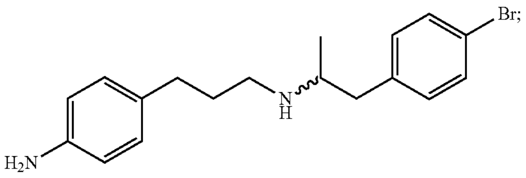
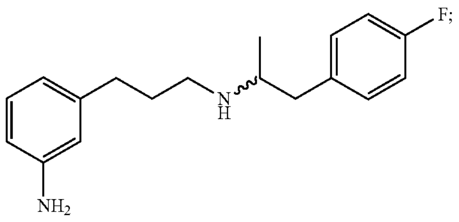
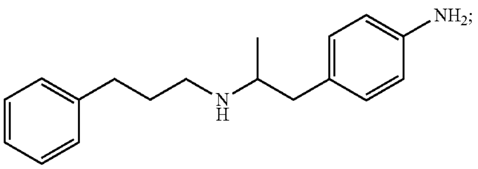
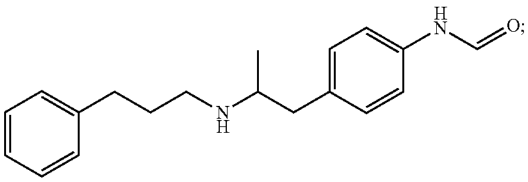
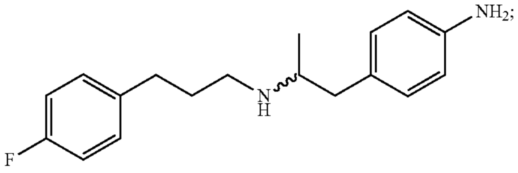
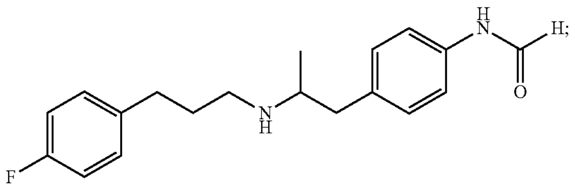
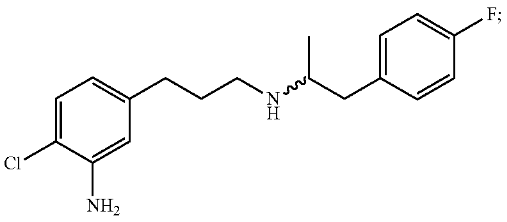
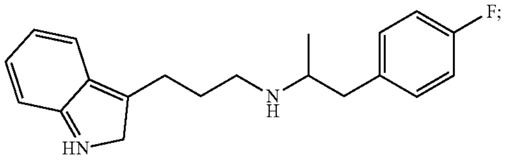
-continued
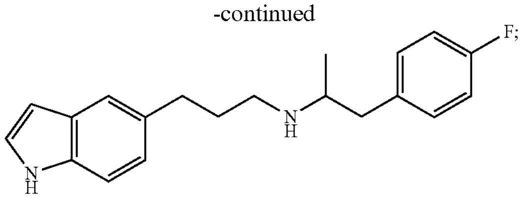
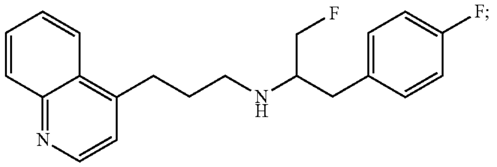
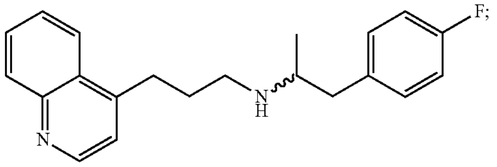
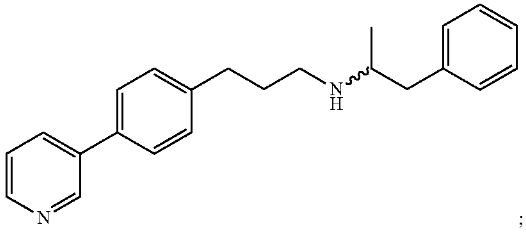
;
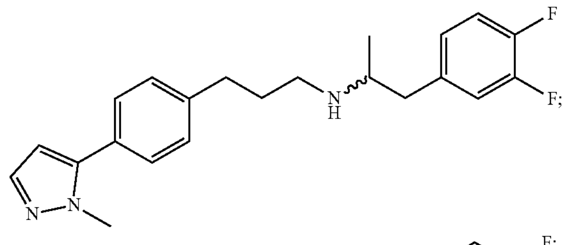
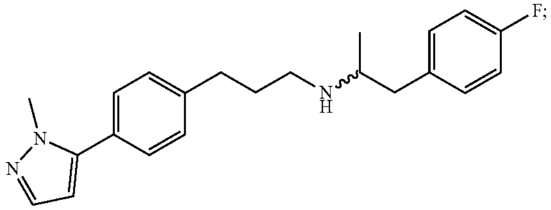
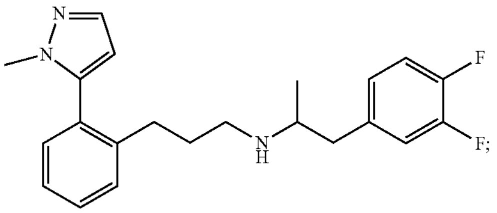
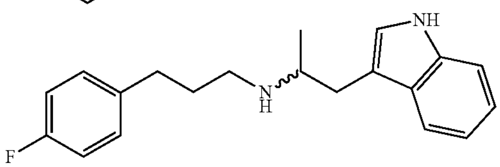
;
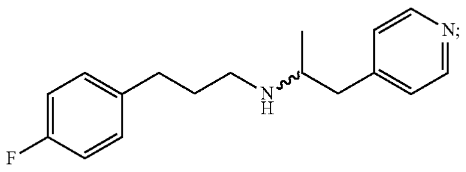

-continued
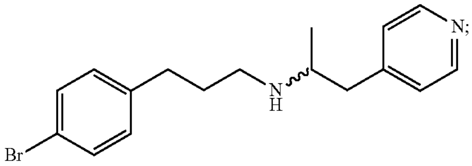
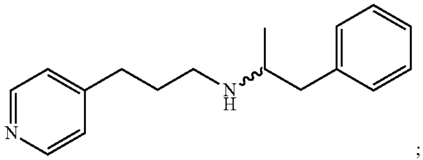
;
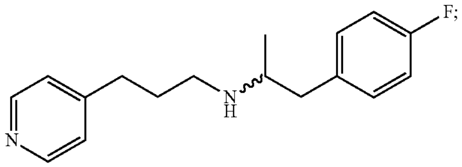
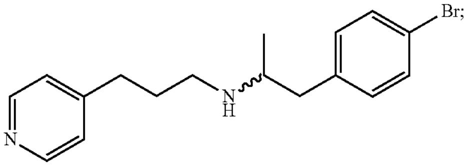
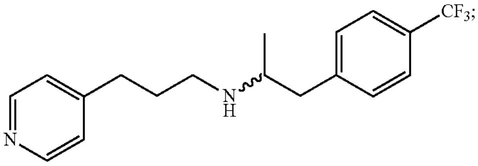
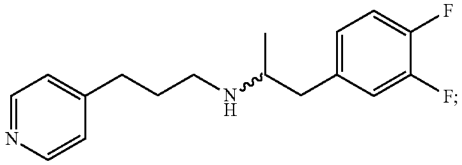
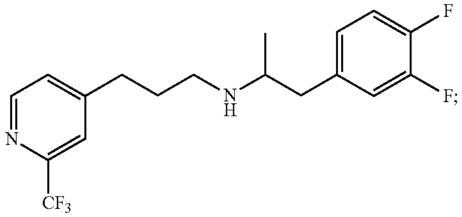
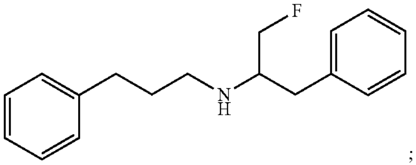
;
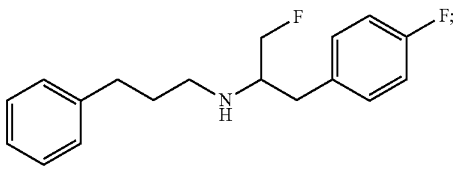
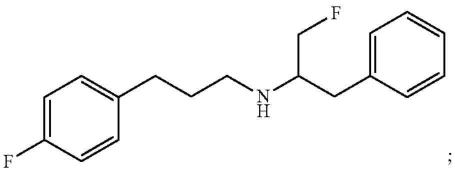
;
-continued
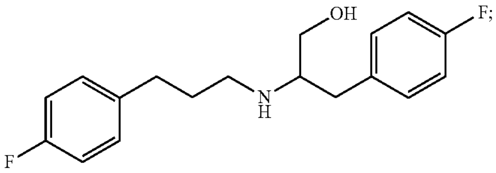
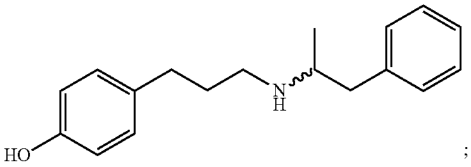
;
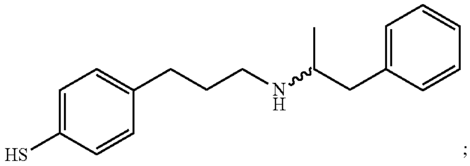
;
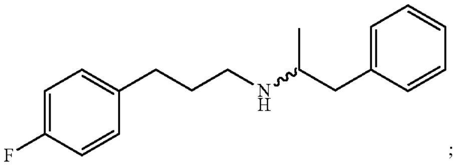
;
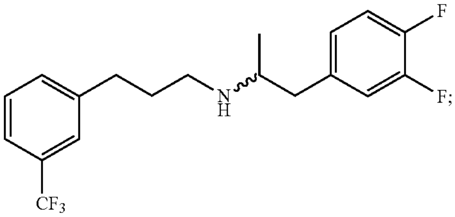
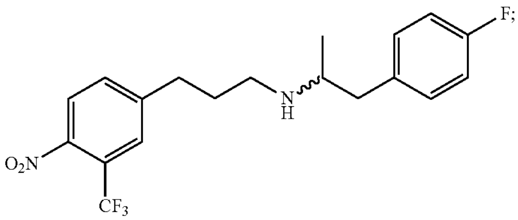
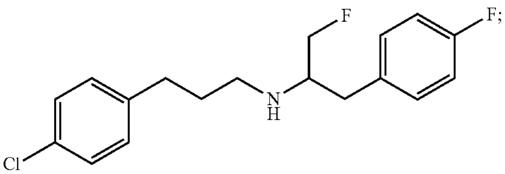
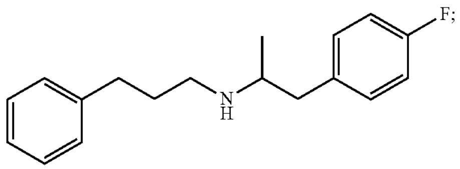
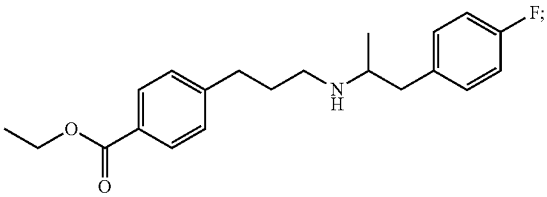

-continued
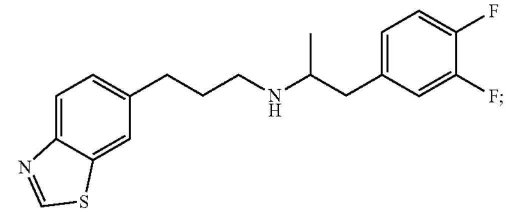
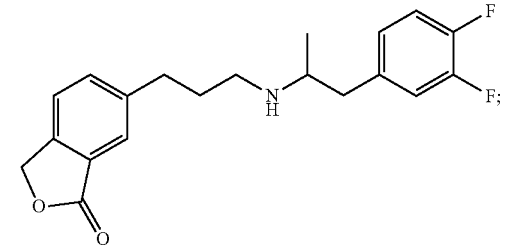
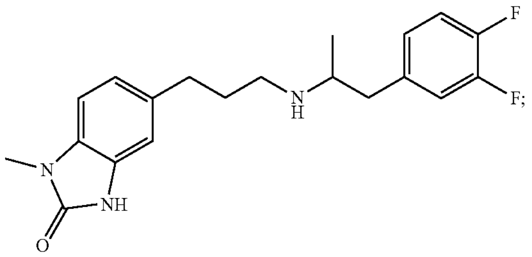
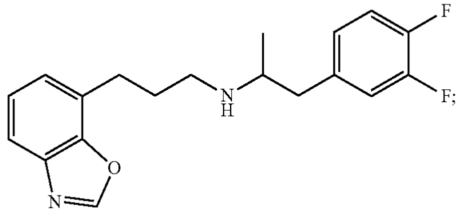
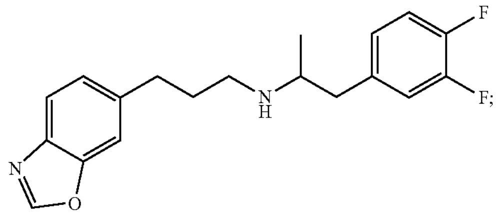
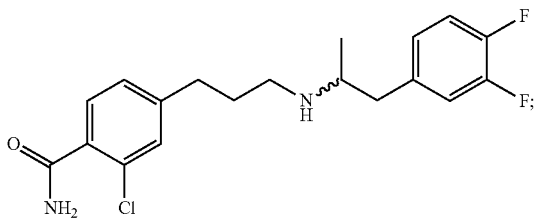
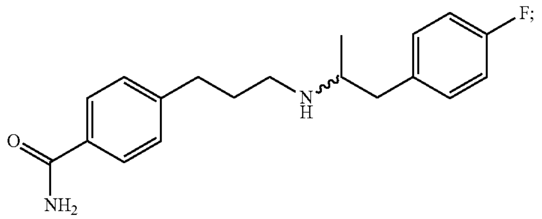
-continued
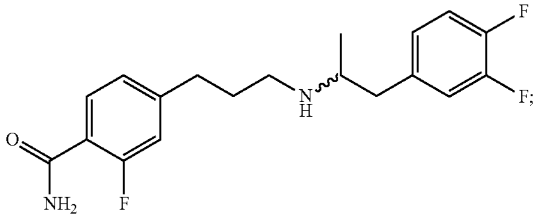
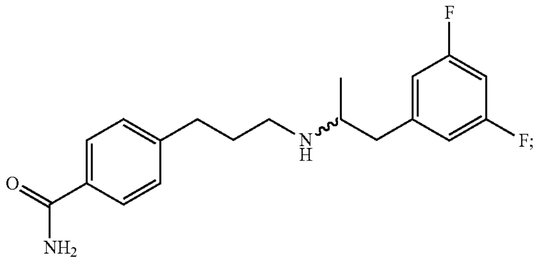
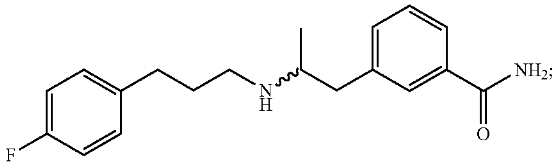
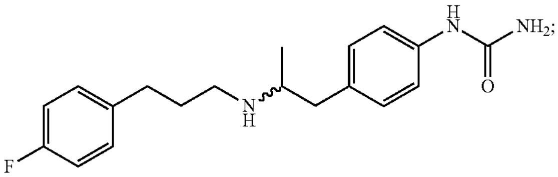
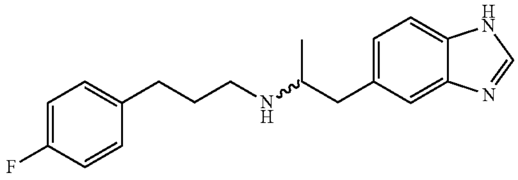
;
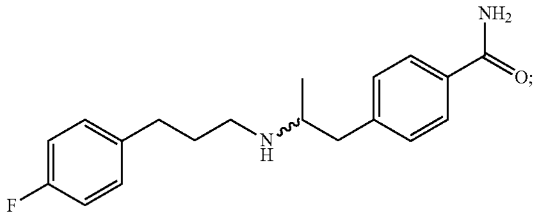
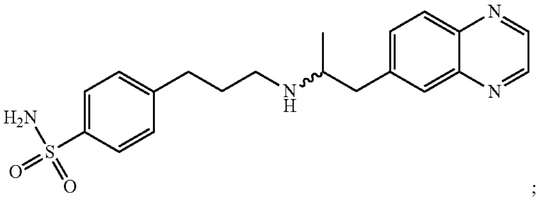
;
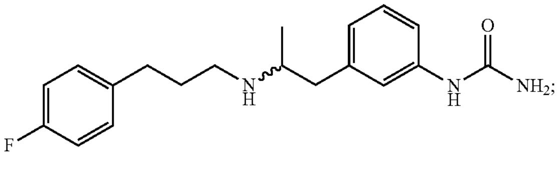

-continued

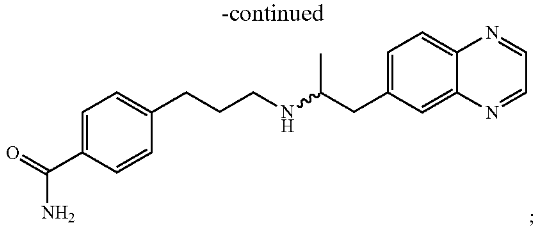

;

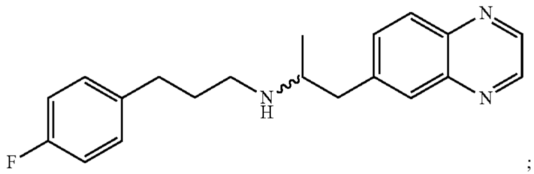

;

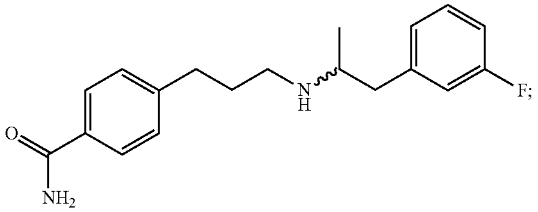

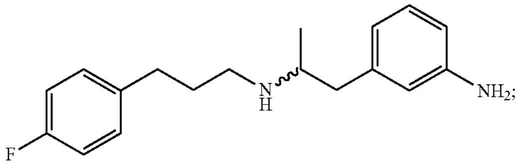

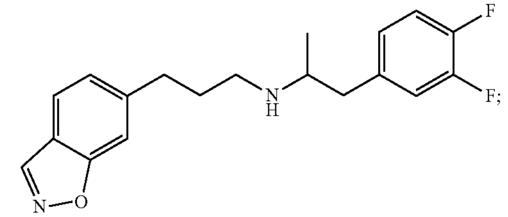

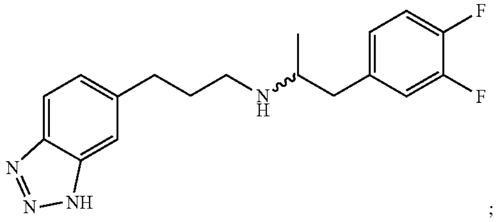

; and

-continued

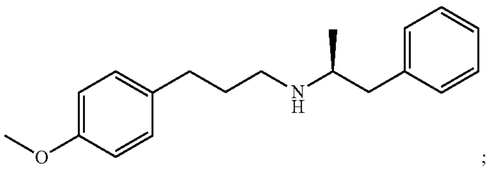

;

or an enantiomer; racemate; or pharmaceutically acceptable salt thereof.

19. The method of claim 18, wherein the compound is selected from the group consisting of:

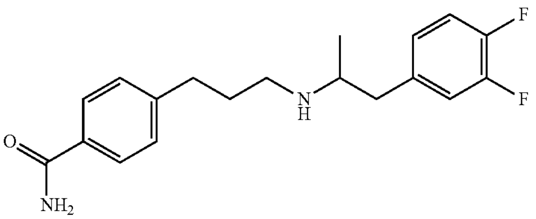

and

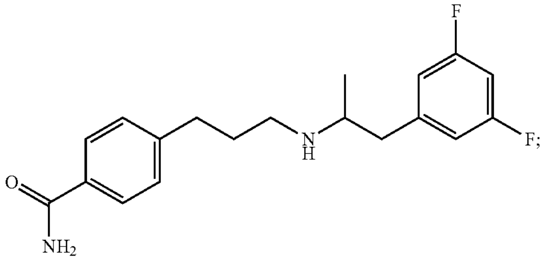

an enantiomer; racemate; or pharmaceutically acceptable salt thereof.

20. The method of claim 17, wherein the compound is administered to the individual intranasally; intrapulmonarily; topically; orally; intravenously as an infusion or injection; intramuscularly as an infusion or injection; subcutaneously as an infusion, injection, or depot formulation; transdermally; intraperitoneally; or rectally.

* * * * *